United States Patent [19]
Harris

[11] Patent Number: 5,837,497
[45] Date of Patent: Nov. 17, 1998

[54] DNAS ENCODING MAMMALIAN ZPC AND USES THEREOF

[75] Inventor: Jeffrey D. Harris, The Woodlands, Tex.

[73] Assignee: Zonagen, Inc., The Woodlands, Tex.

[21] Appl. No.: 484,993

[22] Filed: Jun. 7, 1995

Related U.S. Application Data

[60] Division of Ser. No. 149,223, Nov. 9, 1993, which is a continuation-in-part of Ser. No. 12,990, Jan. 29, 1993, abandoned, which is a continuation-in-part of Ser. No. 973,341, Nov. 9, 1992, abandoned.

[51] Int. Cl.$^6$ .............................. C12P 21/06; C12N 1/20; C12N 15/00; C07H 21/04
[52] U.S. Cl. ................. 435/693; 435/252.3; 435/254.11; 435/320.1; 435/325; 536/23.5
[58] Field of Search ................................. 435/69.1, 69.3, 435/240.2, 252.3, 254.11, 320.1, 325; 536/23.5, 24.1; 530/350

[56] References Cited

U.S. PATENT DOCUMENTS 4,996,297   2/1991   Dunbar ..................................... 530/395

FOREIGN PATENT DOCUMENTS 9015624   12/1990   WIPO .
WO 90/15624   12/1990   WIPO .
WO 92/03548   3/1992   WIPO .

OTHER PUBLICATIONS

Geneseq sequence alignment for SEQ ID No. 5, Oct. 1997.
Geneseq sequence alignment for SEQ ID No. 7, Oct. 1997.
Geneseq sequence alignment for SEQ ID No. 11, Oct. 1997.
Geneseq sequence alignment for SEQ ID No. 17, Oct. 1997.
Chamberlin et al. (1990) Proc. Natl. Acad. Sci. USA vol. 87: 6014–6018.
Yurewicz et al. (1986) J. Biol. Chem. 262(2):564–571.
Sacco et al. (1989) Biol. Reprod. 41:523–532.
Keenan et al. (1991) Biol of Reprod. 44:150–156.
Ringvette et al. (1988) Develop. Biol. 127:287–295.
Geneseq sequence alignment for SEQ ID No. 23, Oct. 1997.
Aitken et al., "Immuniztion against Zona Pellucida Antigens," *Immunilogical Aspects of Reproduction and Fertility Control*, Hearn, J., (ed.), MTP Press. Ltd. (1980).
Aitken et al., "The Influence of Anti–zona and Anti–sperm Antibodies on Sperm–egg Interactions," *J. Reprod. Fert.*, 62:597–606 (1981).
Bleil et al., "Identification of a Secondary Sperm Receptor in the Mouse Egg Zona Pellucida: Role in Maintenance of Binding of Acrosome–reacted Sperm to Eggs," *Developmental Biology*, 128:276–385 (1988).
Bleil et al., "Mammalian Sperm–Egg Interaction: Identification of a Glycoprotein in Mouse Egg Zonae Pellucidae Possessing Receptor Activity for Sperm," *Cell*, 20:873–882 (1980).
Bleil et al., "Structure and Function of the Zona Pellucida: Identification and Charaacterization of the Proteins of the Mouse Oocyte's Zona Pellucida," *Developmental Biology*, 76:185–202 (1980).

Chamberlin et al., "Genomic Organization of a Sex Specific Gene: The Primary Sperm Receptor of the Mouse Zona Pellucida," *Developmental Biology*, 131:207–214 (1989).
Chamberlin et al., "Human Homolog of the Sperm Receptor," *Developmental Biology*, 87:6014–6018 (1990).
Dunbar et al., "Proteolysis of Specific Porcine Zona Pellucida Glycoproteins by Boar Acrosin," *Biology of Reproduction*, 32:619–630 (1985).
Dunbar et al., "Identification of the Three Major Proteins of Porcine and Rabbit Zonae Pellucidae by High Resolution Two–Dimensional Gel Electrophoresis: Comparison with Serum, Follicular Fluid, and Ovarion Cell Proteins," *Biology of Reproduction*, 24:1111–1124 (1981).
Hedrick et al., "Isolation of the Zona Pellucida and Purification of Its Glycoprotein Families from Pig Oocytes," *Analytical Biochemistry*, 157:63–70 (1986).
Hedrick et al., "On the Macromolecular Composition of the Zona Pellucida from Porcine Oocytes," *Developmental Biology*, 121:478–488 (1987).
Jones et al., "Histology of Ovaries of Female Rabbits Immunized with Deglycosylated Zona Pellucida Macromolecules of Pigs," *J. Reprod. Fert.*, 95:513–525 (1992).
Keenan et al., "Endocrine Response in Rabbits Immunized with Native versus Deglycosylated Porcine Zona Pellucida Antigens, " *Biology of Reproduction*, 44:150–156 (1991).
Kinloch et al., "Primary Structure of the Mouse Sperm Receptor Polypeptide Determined by Genomic Cloning," *Proc. Natl. Acad. Sci., USA,* 85:6409–6413 (1988).
Kinloch et al., "Genomic Organization and Polypeptide Primary Structure of Zona Pellucida Glycoprotein hZP3, the Hamster Sperm Receptor," *Developmental Biology*, 142:414–421 (1990).
Liang et al., "Oocyte–Specific Expression of Mouse Zp–2: Developmental Regulation of the Zona Pellucida Genes," *Molecular and Cellular Biology*, 10(4): 1507–1515 (1990).
Mahi–Brown et al., "Fertility Control in the Bitch by Active Immunization with Porcine Zonae Pellucidae: Use of Different Adjuvants and Patterns of Estradiol and Progesterone Levels in Estrous Cycles," *Biology of Reproduction*, 32:761–722 (1985).
Maresh et al., "Antigenic Comparison of Five Species of Mammalian Zonae Pellucidae," *The Journal of Experimental Zoology*, 244:299–307 (1987).
Millar et al., "Vaccination with a Synthetic Zona Pellucida Peptide Produces Long–Term Contraception in Female Mice," *Science*, 246:935–938 (1989).

(List continued on next page.)

Primary Examiner—Frank C. Eisenschenk
Assistant Examiner—Patrick J. Nolan
Attorney, Agent, or Firm—Marshall, O'Toole, Gerstein, Murray & Borun

[57]  ABSTRACT

A method for specifically inducing transient infertility or permanent sterility in a host animal by selective vaccination with specific zona pellucida proteins or immunocontraceptively active fragments thereof. Novel zona pellucida DNA sequences encoding specific zona pellucida proteins are disclosed.

8 Claims, 6 Drawing Sheets

OTHER PUBLICATIONS

Ringuette et al., "Molecular Analysis of cDNA Coding for ZP3, a Sperm Binding Protein of the Mouse Zona Pellucida," *Developmental Biology*, 127:287–295 (1988).

Ringuette et al., "Oocyte–specific Gene Expression: Molecular Characterization of a cDNA Coding for ZP–3, the Sperm Receptor of the Mouse Zona Pellucida," *Proc. Natl. Acad. Sci., USA*, 83:4341–4345 (1986).

Sacco et al., "Application of a Radioimmunoassay (RIA) for Monitoring Immune Response to Porcine Zonae Pellucidae," *Proceedings of the Society for Experimental Biology and Medicine*, 167:318–326 (1981).

Sacco et al., "Carbohydrate Influenes the Immunogenic and Antigenic Characteristics of the ZP3 Macromolecule ($M_r$ 55 000) of the Pig Zona Pellucida," *J. Reprod. Fert.*, 76:575–586 (1986).

Schwoebel et al., "Isolation and Characteriztion of a Full–length cDNA Encoding the 55–kDa Rabbit Zona Pellucida Protein," *The Journal of Biological Chemistry.*, 266(11):7214–7219 (1991).

Skinner et al., "Species Variation in the Zona Pellucida" *Immunological Approaches to Contracption and to Promotion of Fertility*, GP Talwor, (Ed.), Plenum:New York, pp. 251–268 (1986).

Subramanian et al., "Specific Radioimmunoassay for the Detection of a Purified Porcine Zona Pellucida Antigen (PPZA)," *Biology of Reproduction*, 24:933–943 (1981).

Timmons et al., "Use of Specific Monoclonal and Polyclonal Antibodies to Define Distinct Antigens of the Porcine Zonae Pellucida, "*Antigen Biology of Reproduction*, :1275–187 (1987).

Timmons et al., "Perspectives in Immunoproduction: Conception and Contraception," Mathur, S. and Fredericks, C.M., (eds.), Hemisphere Publishing Co., New York, pp. 242–260 (1988).

Wasserman, "Zona Pellucida Glycoproteins," *Ann. Rev. Biochem.*, 57:415–442 (1988).

Wolgemuth et al., "Formation of the Rabbit Zona Pellucida and Its Relationship to Ovarian Follicular Development," *Developmental Biology*, 106:1–14 (1984).

Yurewicz et al., "Isolation and Preliminary Characterization of a Purified Pig Zona Antigen (PPZA) from Porcine Oocytes," *Biology of Reproduction*, 29:511–523 (1983).

Yurewicz et al., "Nucleotide Sequence of CDNA Encoding ZP3α, a Sperm–binding Glycoprotein from Zona Pellucida of Pig Oocyte," *Biochemica et Biophysica Acta.*, 1174:211–214 (1993).

Yurewicz et al., "Structural Characterization of the Mr=55, 000 Antigen (ZP3) of Porcine Oocyte Zona Pellucida," *The Journal of Biological Chemistry*, 262: (2):264–571 (1987).

Chamow and Dean, "Anti–Zona Pellucida Antibodies in Mice Immunized with Recombinant ZP3–β–Galactosidase Fusion Protein," *FED. Proc.*, 46 (6):2015 (1989).

East, I.J. "Scintigraphy of Normal Mouse Ovaries with Monoclonal Antibodies to ZP–2, the Major Zona Pellucida Protein," *Science*, 225:938–941 (Aug. 31, 1984).

Lou and Tung, "T Cell Peptide of a Self–Protein Elicits Autoantibody to the Protein Antigen," *J. of Immunology*, 151:5790–5798 (1993).

Paterson et al., "Analysis of the Contraceptive Potential of Antibodies against Native and Deglycosylated Porcine ZP3 in Vivo and in Vitro," *Biol. Reprod.*, 46 (4):523–534 (Apr. 1992).

Rhim et al., "Autoimmune Disease of the Ovary Induced by a ZP3 Peptide from the Mouse Zona Pellucida," *J. Clin. Invest.*, 89:28–35 (Jan., 1992).

Tung et al., "Autoimmune Disease of the Ovary: a Mechanism of Premature Ovarian Failure and a Complication of ZP3 Contraceptive Vaccine," *Reprod. Immunol.*,97:169–179 (1993).

Chamberlain and Dean, "Human Homolog of the Mouse Sperm Receptor," *Proc. Nat'l Acad. Sci., USA*, 87:6014–6018 (Aug., 1990).

Koyama et al., "Blocking of Human Sperm–Zona Interaction by Monoclonal Antibodies to a Glycoprotein Family (ZP4) of Porcine Zona Pellucida," *Biology of Reproduction*, 45:727–735 (1991).

Liu et al., "Contraception in Mares Heteroimmunized with a Pig Zonae Pellucidae," *J. Reprod. Fert.*, 85:19–29 (1989).

Henderson et al., "Contraceptive Potential of Antibodies to the Zona Pellucida," *Reprod. fert.*, 83–325–343 (1988).

ALIGNMENT OF HUMAN GENOMIC ZPB EcoRI INSERTS

SEQUENCE LISTING ( 1 ) GENERAL INFORMATION:

( i i i ) NUMBER OF SEQUENCES: 59

( 2 ) INFORMATION FOR SEQ ID NO:1:

( i ) SEQUENCE CHARACTERISTICS:
        ( A ) LENGTH: 2214 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Sus scrofa
        ( D ) DEVELOPMENTAL STAGE: Juvenile
        ( E ) HAPLOTYPE: Diploidy
        ( F ) TISSUE TYPE: Ovary
        ( G ) CELL TYPE: Oocyte ( i x ) FEATURE:

(A) NAME/KEY: sig_peptide
(B) LOCATION: 12..119

(ix) FEATURE:
(A) NAME/KEY: mat_peptide
(B) LOCATION: 120..2153

(ix) FEATURE:
(A) NAME/KEY: CDS
(B) LOCATION: 12..2153

(xi) SEQUENCE DESCRIPTION: SEQ ID NO:1:

```
GAATTCCGGG C AGG CAC AGA GGA GAC AGT GGG AGA CCC TTA AGC TGG CTC           50
            Arg His Arg Gly Asp Ser Gly Arg Pro Leu Ser Trp Leu
            -36 -35              -30                  -25

AGT GCA AGC TGG AGG TCA CTT CTT CTA TTT TTC CCC CTT GTG ACT TCA            98
Ser Ala Ser Trp Arg Ser Leu Leu Leu Phe Phe Pro Leu Val Thr Ser
        -20              -15                  -10

GTG AAC TCC ATA GGT GTC AAT CAG TTG GTG AAT ACT GCC TTC CCA GGT           146
Val Asn Ser Ile Gly Val Asn Gln Leu Val Asn Thr Ala Phe Pro Gly
        -5               1                5

ATT GTC ACT TGC CAT GAA AAT AGA ATG GTA GTG GAA TTT CCA AGA ATT           194
Ile Val Thr Cys His Glu Asn Arg Met Val Val Glu Phe Pro Arg Ile
10              15                  20                  25

CTT GGC ACT AAG ATA CAG TAC ACC TCT GTG GTG GAC CCT CTT GGT CTT           242
Leu Gly Thr Lys Ile Gln Tyr Thr Ser Val Val Asp Pro Leu Gly Leu
                30                  35                  40

GAA ATG ATG AAC TGT ACT TAT GTT CTG GAC CCA GAA AAC CTC ACC CTG           290
Glu Met Met Asn Cys Thr Tyr Val Leu Asp Pro Glu Asn Leu Thr Leu
            45                  50                  55

AAG GCC CCA TAT GAA GCC TGT ACC AAA AGA GTG CGT GGC CAT CAC CAA           338
Lys Ala Pro Tyr Glu Ala Cys Thr Lys Arg Val Arg Gly His His Gln
            60                  65                  70

ATG ACC ATC AGA CTC ATA GAT GAC AAT GCT GCT TTA AGA CAA GAG GCT           386
Met Thr Ile Arg Leu Ile Asp Asp Asn Ala Ala Leu Arg Gln Glu Ala
        75                  80                  85

CTC ATG TAT CAC ATC AGC TGT CCT GTT ATG GGA GCA GAA GGC CCT GAT           434
Leu Met Tyr His Ile Ser Cys Pro Val Met Gly Ala Glu Gly Pro Asp
90                  95                 100                 105

CAG CAT TCG GGA TCC ACA ATC TGC ATG AAA GAT TTC ATG TCT TTT ACC           482
Gln His Ser Gly Ser Thr Ile Cys Met Lys Asp Phe Met Ser Phe Thr
                110                 115                 120

TTT AAC TTT TTT CCC GGG ATG GCT GAC GAA AAT GTG AAA CGT GAG GAT           530
Phe Asn Phe Phe Pro Gly Met Ala Asp Glu Asn Val Lys Arg Glu Asp
            125                 130                 135

TCG AAG CAG CGC ATG GGA TGG AGC CTT GTA GTT GGT GAC GGT GAA AGA           578
Ser Lys Gln Arg Met Gly Trp Ser Leu Val Val Gly Asp Gly Glu Arg
        140                 145                 150

GCC CGA ACT CTG ACC TTT CAG GAG GCC ATG ACC CAA GGA TAT AAT TTC           626
Ala Arg Thr Leu Thr Phe Gln Glu Ala Met Thr Gln Gly Tyr Asn Phe
    155                 160                 165

CTG ATA GAG AAC CAG AAG ATG AAC ATC CAA GTG TCA TTC CAT GCC ACT           674
Leu Ile Glu Asn Gln Lys Met Asn Ile Gln Val Ser Phe His Ala Thr
170                 175                 180                 185

GGA GTG ACT CGC TAC TCG CAA GGT AAC AGT CAT CTC TAC ATG GTA CCT           722
Gly Val Thr Arg Tyr Ser Gln Gly Asn Ser His Leu Tyr Met Val Pro
                190                 195                 200

CTG AAG CTT AAA CAT GTA TCT CAT GGG CAG TCT CTC ATC TTA GCA TCA           770
Leu Lys Leu Lys His Val Ser His Gly Gln Ser Leu Ile Leu Ala Ser
            205                 210                 215

CAA CTC ATC TGT GTG GCA GAT CCT GTG ACC TGT AAT GCC ACA CAC GTG           818
Gln Leu Ile Cys Val Ala Asp Pro Val Thr Cys Asn Ala Thr His Val
        220                 225                 230
```

| | | | | | | | | | | | | | | | | |
|---|---|---|---|---|---|---|---|---|---|---|---|---|---|---|---|---|
| ACT | CTT | GCC | ATA | CCA | GAG | TTT | CCT | GGG | AAG | CTA | AAA | TCC | GTG | AAC | TTG | 866 |
| Thr | Leu | Ala | Ile | Pro | Glu | Phe | Pro | Gly | Lys | Leu | Lys | Ser | Val | Asn | Leu | |
| | | 235 | | | | 240 | | | | | 245 | | | | | |
| GGA | AGT | GGG | AAT | ATT | GCT | GTG | AGC | CAG | CTG | CAC | AAA | CAC | GGG | ATT | GAA | 914 |
| Gly | Ser | Gly | Asn | Ile | Ala | Val | Ser | Gln | Leu | His | Lys | His | Gly | Ile | Glu | |
| 250 | | | | | 255 | | | | | 260 | | | | | 265 | |
| ATG | GAA | ACA | ACA | AAC | GGC | CTG | AGG | TTG | CAT | TTC | AAC | CAA | ACT | CTT | CTC | 962 |
| Met | Glu | Thr | Thr | Asn | Gly | Leu | Arg | Leu | His | Phe | Asn | Gln | Thr | Leu | Leu | |
| | | | 270 | | | | | 275 | | | | | 280 | | | |
| AAA | ACA | AAT | GTC | TCT | GAA | AAA | TGC | CTA | CCA | CAT | CAG | TTG | TAC | TTA | TCT | 1010 |
| Lys | Thr | Asn | Val | Ser | Glu | Lys | Cys | Leu | Pro | His | Gln | Leu | Tyr | Leu | Ser | |
| | | | 285 | | | | 290 | | | | | 295 | | | | |
| TCA | CTC | AAG | CTG | ACT | TTT | CAC | AGT | CAA | CTA | GAG | GCA | GTA | TCC | ATG | GTG | 1058 |
| Ser | Leu | Lys | Leu | Thr | Phe | His | Ser | Gln | Leu | Glu | Ala | Val | Ser | Met | Val | |
| | | 300 | | | | | 305 | | | | | 310 | | | | |
| ATT | TAT | CCT | GAG | TGT | CTC | TGT | GAG | TCA | ACA | GTC | TCT | TTA | GTT | TCA | GAG | 1106 |
| Ile | Tyr | Pro | Glu | Cys | Leu | Cys | Glu | Ser | Thr | Val | Ser | Leu | Val | Ser | Glu | |
| 315 | | | | | 320 | | | | | 325 | | | | | | |
| GAG | CTA | TGC | ACT | CAG | GAT | GGG | TTT | ATG | GAC | GTC | AAG | GTC | CAC | AGC | CAC | 1154 |
| Glu | Leu | Cys | Thr | Gln | Asp | Gly | Phe | Met | Asp | Val | Lys | Val | His | Ser | His | |
| 330 | | | | | 335 | | | | | 340 | | | | | 345 | |
| CAA | ACA | AAA | CCA | GCT | CTC | AAC | TTG | GAT | ACC | CTC | AGG | GTG | GGA | GAC | TCA | 1202 |
| Gln | Thr | Lys | Pro | Ala | Leu | Asn | Leu | Asp | Thr | Leu | Arg | Val | Gly | Asp | Ser | |
| | | | | 350 | | | | | 355 | | | | | 360 | | |
| TCC | TGC | CAG | CCA | ACC | TTT | AAA | GCT | CCA | GCT | CAG | GGG | CTG | GTA | CAG | TTT | 1250 |
| Ser | Cys | Gln | Pro | Thr | Phe | Lys | Ala | Pro | Ala | Gln | Gly | Leu | Val | Gln | Phe | |
| | | | 365 | | | | | 370 | | | | | 375 | | | |
| CGC | ATA | CCC | CTG | AAT | GGA | TGT | GGA | ACA | AGA | CAT | AAG | TTC | AAG | AAT | GAC | 1298 |
| Arg | Ile | Pro | Leu | Asn | Gly | Cys | Gly | Thr | Arg | His | Lys | Phe | Lys | Asn | Asp | |
| | | 380 | | | | | 385 | | | | | 390 | | | | |
| AAA | GTC | ATC | TAT | GAA | AAT | GAA | ATA | CAT | GCT | CTC | TGG | GCA | GAT | CCT | CCA | 1346 |
| Lys | Val | Ile | Tyr | Glu | Asn | Glu | Ile | His | Ala | Leu | Trp | Ala | Asp | Pro | Pro | |
| | 395 | | | | | 400 | | | | | 405 | | | | | |
| AGC | GCC | GTT | TCC | AGA | GAT | AGT | GAG | TTC | AGA | ATG | ACA | GTG | AGG | TGC | TCT | 1394 |
| Ser | Ala | Val | Ser | Arg | Asp | Ser | Glu | Phe | Arg | Met | Thr | Val | Arg | Cys | Ser | |
| 410 | | | | | 415 | | | | | 420 | | | | | 425 | |
| TAC | AGC | AGC | AGC | AAC | ATG | CTA | ATA | AAT | ACC | AAT | GTT | GAA | AGT | CTT | CCT | 1442 |
| Tyr | Ser | Ser | Ser | Asn | Met | Leu | Ile | Asn | Thr | Asn | Val | Glu | Ser | Leu | Pro | |
| | | | | 430 | | | | | 435 | | | | | 440 | | |
| TCT | CCA | GAG | GCC | TCA | GTG | AAG | CCA | GGT | CCA | CTT | ACC | CTG | ACT | CTG | CAA | 1490 |
| Ser | Pro | Glu | Ala | Ser | Val | Lys | Pro | Gly | Pro | Leu | Thr | Leu | Thr | Leu | Gln | |
| | | | | 445 | | | | | 450 | | | | | 455 | | |
| ACC | TAC | CCA | GAT | AAC | GCC | TAC | CTG | CAG | CCT | TAT | GGG | GAC | AAG | GAG | TAC | 1538 |
| Thr | Tyr | Pro | Asp | Asn | Ala | Tyr | Leu | Gln | Pro | Tyr | Gly | Asp | Lys | Glu | Tyr | |
| | | 460 | | | | | 465 | | | | | 470 | | | | |
| CCT | GTG | GTG | AAA | TAT | CTC | CGC | CAA | CCA | ATT | TAC | CTA | GAA | GTG | AGA | ATC | 1586 |
| Pro | Val | Val | Lys | Tyr | Leu | Arg | Gln | Pro | Ile | Tyr | Leu | Glu | Val | Arg | Ile | |
| | 475 | | | | | 480 | | | | | 485 | | | | | |
| CTC | AAC | AGG | ACT | GAC | CCC | AAC | ATC | AAG | CTG | GTC | TTG | GAT | GAC | TGC | TGG | 1634 |
| Leu | Asn | Arg | Thr | Asp | Pro | Asn | Ile | Lys | Leu | Val | Leu | Asp | Asp | Cys | Trp | |
| 490 | | | | | 495 | | | | | 500 | | | | | 505 | |
| GCA | ACA | TCC | ACA | GAG | GAC | CCA | GCC | TCT | CTC | CCC | CAG | TGG | AAT | GTT | GTC | 1682 |
| Ala | Thr | Ser | Thr | Glu | Asp | Pro | Ala | Ser | Leu | Pro | Gln | Trp | Asn | Val | Val | |
| | | | | 510 | | | | | 515 | | | | | 520 | | |
| ATG | GAT | GGC | TGT | GAA | TAC | AAC | CTG | GAC | AAC | CAC | AGA | ACC | ACC | TTC | CAT | 1730 |
| Met | Asp | Gly | Cys | Glu | Tyr | Asn | Leu | Asp | Asn | His | Arg | Thr | Thr | Phe | His | |
| | | | 525 | | | | | 530 | | | | | 535 | | | |
| CCG | GTG | GGC | TCC | TCC | GTG | ACC | TAT | CCT | AAC | CAC | CAT | CAG | AGG | TTT | GAT | 1778 |
| Pro | Val | Gly | Ser | Ser | Val | Thr | Tyr | Pro | Asn | His | His | Gln | Arg | Phe | Asp | |
| | | 540 | | | | | 545 | | | | | 550 | | | | |

| | | | | | | | | | | | | | | | |
|---|---|---|---|---|---|---|---|---|---|---|---|---|---|---|---|
| GTG | AAG | ACC | TTT | GCC | TTT | GTG | TCA | GGG | GCC | CAA | GGG | GTC | TCT | CAA CTG | 1826 |
| Val | Lys | Thr | Phe | Ala | Phe | Val | Ser | Gly | Ala | Gln | Gly | Val | Ser | Gln Leu | |
| | 555 | | | | 560 | | | | | | 565 | | | | |
| GTC | TAC | TTC | CAC | TGC | AGT | GTC | TTC | ATC | TGC | AAT | CAA | CTC | TCT | CCC ACC | 1874 |
| Val | Tyr | Phe | His | Cys | Ser | Val | Phe | Ile | Cys | Asn | Gln | Leu | Ser | Pro Thr | |
| 570 | | | | | 575 | | | | 580 | | | | | 585 | |
| TTC | TCT | CTG | TGT | TCT | GTG | ACT | TGC | CAT | GGG | CCA | TCT | AGG | AGC | CGG CGA | 1922 |
| Phe | Ser | Leu | Cys | Ser | Val | Thr | Cys | His | Gly | Pro | Ser | Arg | Ser | Arg Arg | |
| | | | | 590 | | | | | 595 | | | | | 600 | |
| GCT | ACA | GGG | ACC | ACT | GAG | GAA | GAG | AAA | ATG | ATA | GTG | AGT | CTC | CCG GGC | 1970 |
| Ala | Thr | Gly | Thr | Thr | Glu | Glu | Glu | Lys | Met | Ile | Val | Ser | Leu | Pro Gly | |
| | | | 605 | | | | | 610 | | | | | 615 | | |
| CCC | ATC | CTG | CTG | TTG | TCA | GAT | GGC | TCT | TCA | CTC | AGA | GAT | GCT | GTG AAC | 2018 |
| Pro | Ile | Leu | Leu | Leu | Ser | Asp | Gly | Ser | Ser | Leu | Arg | Asp | Ala | Val Asn | |
| | | 620 | | | | | 625 | | | | | 630 | | | |
| TCT | AAA | GGA | TCC | AGA | ACC | AAC | GGA | TAT | GTT | GCT | TTT | AAA | ACT | ATG GTT | 2066 |
| Ser | Lys | Gly | Ser | Arg | Thr | Asn | Gly | Tyr | Val | Ala | Phe | Lys | Thr | Met Val | |
| | 635 | | | | 640 | | | | | 645 | | | | | |
| GCT | ATG | GTT | GCT | TCA | GCA | GGC | ATC | GTG | GCA | ACT | CTA | GGC | CTC | ATC AGC | 2114 |
| Ala | Met | Val | Ala | Ser | Ala | Gly | Ile | Val | Ala | Thr | Leu | Gly | Leu | Ile Ser | |
| 650 | | | | 655 | | | | | 660 | | | | | 665 | |
| TAC | CTG | CAC | AAA | AAA | AGA | ATC | ATG | ATG | TTA | AAT | CAC | TAATTTGGAT | | | 2160 |
| Tyr | Leu | His | Lys | Lys | Arg | Ile | Met | Met | Leu | Asn | His | | | | |
| | | | 670 | | | | | | 675 | | | | | | |

TTTCAAATAA AAGTGGAAGT AAGCCTCTTC TAAAAAAAAA AAAAACCGGA ATTC 2214

( 2 ) INFORMATION FOR SEQ ID NO:2:

( i ) SEQUENCE CHARACTERISTICS:
         ( A ) LENGTH: 713 amino acids
         ( B ) TYPE: amino acid
         ( D ) TOPOLOGY: linear ( i i ) MOLECULE TYPE: protein ( x i ) SEQUENCE DESCRIPTION: SEQ ID NO:2:

| | | | | | | | | | | | | | |
|---|---|---|---|---|---|---|---|---|---|---|---|---|---|
| Arg | His | Arg | Gly | Asp | Ser | Gly | Arg | Pro | Leu | Ser | Trp | Leu | Ser Ala Ser |
| -36 | -35 | | | | -30 | | | | | -25 | | | |
| Trp | Arg | Ser | Leu | Leu | Leu | Phe | Phe | Pro | Leu | Val | Thr | Ser | Val Asn Ser |
| -20 | | | | | -15 | | | | -10 | | | | -5 |
| Ile | Gly | Val | Asn | Gln | Leu | Val | Asn | Thr | Ala | Phe | Pro | Gly | Ile Val Thr |
| | | | | 1 | | | | 5 | | | | | 10 |
| Cys | His | Glu | Asn | Arg | Met | Val | Val | Glu | Phe | Pro | Arg | Ile | Leu Gly Thr |
| | | 15 | | | | | 20 | | | | | 25 | |
| Lys | Ile | Gln | Tyr | Thr | Ser | Val | Val | Asp | Pro | Leu | Gly | Leu | Glu Met Met |
| | 30 | | | | | 35 | | | | | 40 | | |
| Asn | Cys | Thr | Tyr | Val | Leu | Asp | Pro | Glu | Asn | Leu | Thr | Leu | Lys Ala Pro |
| 45 | | | | | 50 | | | | | 55 | | | | 60 |
| Tyr | Glu | Ala | Cys | Thr | Lys | Arg | Val | Arg | Gly | His | His | Gln | Met Thr Ile |
| | | | | 65 | | | | | 70 | | | | | 75 |
| Arg | Leu | Ile | Asp | Asp | Asn | Ala | Ala | Leu | Arg | Gln | Glu | Ala | Leu Met Tyr |
| | | | 80 | | | | | 85 | | | | | 90 | |
| His | Ile | Ser | Cys | Pro | Val | Met | Gly | Ala | Glu | Gly | Pro | Asp | Gln His Ser |
| | | 95 | | | | | 100 | | | | | 105 | | |
| Gly | Ser | Thr | Ile | Cys | Met | Lys | Asp | Phe | Met | Ser | Phe | Thr | Phe Asn Phe |
| | 110 | | | | | 115 | | | | | 120 | | | |
| Phe | Pro | Gly | Met | Ala | Asp | Glu | Asn | Val | Lys | Arg | Glu | Asp | Ser Lys Gln |
| 125 | | | | | 130 | | | | | 135 | | | | | 140 |

| Arg | Met | Gly | Trp | Ser | Leu | Val | Val | Gly | Asp | Gly | Glu | Arg | Ala | Arg | Thr |
|---|---|---|---|---|---|---|---|---|---|---|---|---|---|---|---|
| | | | | 145 | | | | | 150 | | | | | 155 | |

| Leu | Thr | Phe | Gln | Glu | Ala | Met | Thr | Gln | Gly | Tyr | Asn | Phe | Leu | Ile | Glu |
|---|---|---|---|---|---|---|---|---|---|---|---|---|---|---|---|
| | | | 160 | | | | 165 | | | | | 170 | | | |

| Asn | Gln | Lys | Met | Asn | Ile | Gln | Val | Ser | Phe | His | Ala | Thr | Gly | Val | Thr |
|---|---|---|---|---|---|---|---|---|---|---|---|---|---|---|---|
| | | 175 | | | | | 180 | | | | | 185 | | | |

| Arg | Tyr | Ser | Gln | Gly | Asn | Ser | His | Leu | Tyr | Met | Val | Pro | Leu | Lys | Leu |
|---|---|---|---|---|---|---|---|---|---|---|---|---|---|---|---|
| | 190 | | | | | 195 | | | | | 200 | | | | |

| Lys | His | Val | Ser | His | Gly | Gln | Ser | Leu | Ile | Leu | Ala | Ser | Gln | Leu | Ile |
|---|---|---|---|---|---|---|---|---|---|---|---|---|---|---|---|
| 205 | | | | | 210 | | | | | 215 | | | | | 220 |

| Cys | Val | Ala | Asp | Pro | Val | Thr | Cys | Asn | Ala | Thr | His | Val | Thr | Leu | Ala |
|---|---|---|---|---|---|---|---|---|---|---|---|---|---|---|---|
| | | | | 225 | | | | | 230 | | | | | 235 | |

| Ile | Pro | Glu | Phe | Pro | Gly | Lys | Leu | Lys | Ser | Val | Asn | Leu | Gly | Ser | Gly |
|---|---|---|---|---|---|---|---|---|---|---|---|---|---|---|---|
| | | | | 240 | | | | | 245 | | | | | 250 | |

| Asn | Ile | Ala | Val | Ser | Gln | Leu | His | Lys | His | Gly | Ile | Glu | Met | Glu | Thr |
|---|---|---|---|---|---|---|---|---|---|---|---|---|---|---|---|
| | | | 255 | | | | | 260 | | | | | 265 | | |

| Thr | Asn | Gly | Leu | Arg | Leu | His | Phe | Asn | Gln | Thr | Leu | Leu | Lys | Thr | Asn |
|---|---|---|---|---|---|---|---|---|---|---|---|---|---|---|---|
| | 270 | | | | | 275 | | | | | 280 | | | | |

| Val | Ser | Glu | Lys | Cys | Leu | Pro | His | Gln | Leu | Tyr | Leu | Ser | Ser | Leu | Lys |
|---|---|---|---|---|---|---|---|---|---|---|---|---|---|---|---|
| 285 | | | | | 290 | | | | | 295 | | | | | 300 |

| Leu | Thr | Phe | His | Ser | Gln | Leu | Glu | Ala | Val | Ser | Met | Val | Ile | Tyr | Pro |
|---|---|---|---|---|---|---|---|---|---|---|---|---|---|---|---|
| | | | | 305 | | | | | 310 | | | | | 315 | |

| Glu | Cys | Leu | Cys | Glu | Ser | Thr | Val | Ser | Leu | Val | Ser | Glu | Glu | Leu | Cys |
|---|---|---|---|---|---|---|---|---|---|---|---|---|---|---|---|
| | | | 320 | | | | | 325 | | | | | 330 | | |

| Thr | Gln | Asp | Gly | Phe | Met | Asp | Val | Lys | Val | His | Ser | His | Gln | Thr | Lys |
|---|---|---|---|---|---|---|---|---|---|---|---|---|---|---|---|
| | | 335 | | | | | 340 | | | | | 345 | | | |

| Pro | Ala | Leu | Asn | Leu | Asp | Thr | Leu | Arg | Val | Gly | Asp | Ser | Ser | Cys | Gln |
|---|---|---|---|---|---|---|---|---|---|---|---|---|---|---|---|
| | 350 | | | | | 355 | | | | | 360 | | | | |

| Pro | Thr | Phe | Lys | Ala | Pro | Ala | Gln | Gly | Leu | Val | Gln | Phe | Arg | Ile | Pro |
|---|---|---|---|---|---|---|---|---|---|---|---|---|---|---|---|
| 365 | | | | | 370 | | | | | 375 | | | | | 380 |

| Leu | Asn | Gly | Cys | Gly | Thr | Arg | His | Lys | Phe | Lys | Asn | Asp | Lys | Val | Ile |
|---|---|---|---|---|---|---|---|---|---|---|---|---|---|---|---|
| | | | | 385 | | | | | 390 | | | | | 395 | |

| Tyr | Glu | Asn | Glu | Ile | His | Ala | Leu | Trp | Ala | Asp | Pro | Pro | Ser | Ala | Val |
|---|---|---|---|---|---|---|---|---|---|---|---|---|---|---|---|
| | | | 400 | | | | | 405 | | | | | 410 | | |

| Ser | Arg | Asp | Ser | Glu | Phe | Arg | Met | Thr | Val | Arg | Cys | Ser | Tyr | Ser | Ser |
|---|---|---|---|---|---|---|---|---|---|---|---|---|---|---|---|
| | | 415 | | | | | 420 | | | | | 425 | | | |

| Ser | Asn | Met | Leu | Ile | Asn | Thr | Asn | Val | Glu | Ser | Leu | Pro | Ser | Pro | Glu |
|---|---|---|---|---|---|---|---|---|---|---|---|---|---|---|---|
| | 430 | | | | | 435 | | | | | 440 | | | | |

| Ala | Ser | Val | Lys | Pro | Gly | Pro | Leu | Thr | Leu | Thr | Leu | Gln | Thr | Tyr | Pro |
|---|---|---|---|---|---|---|---|---|---|---|---|---|---|---|---|
| 445 | | | | | 450 | | | | | 455 | | | | | 460 |

| Asp | Asn | Ala | Tyr | Leu | Gln | Pro | Tyr | Gly | Asp | Lys | Glu | Tyr | Pro | Val | Val |
|---|---|---|---|---|---|---|---|---|---|---|---|---|---|---|---|
| | | | | 465 | | | | | 470 | | | | | 475 | |

| Lys | Tyr | Leu | Arg | Gln | Pro | Ile | Tyr | Leu | Glu | Val | Arg | Ile | Leu | Asn | Arg |
|---|---|---|---|---|---|---|---|---|---|---|---|---|---|---|---|
| | | | 480 | | | | | 485 | | | | | 490 | | |

| Thr | Asp | Pro | Asn | Ile | Lys | Leu | Val | Leu | Asp | Asp | Cys | Trp | Ala | Thr | Ser |
|---|---|---|---|---|---|---|---|---|---|---|---|---|---|---|---|
| | | 495 | | | | | 500 | | | | | 505 | | | |

| Thr | Glu | Asp | Pro | Ala | Ser | Leu | Pro | Gln | Trp | Asn | Val | Val | Met | Asp | Gly |
|---|---|---|---|---|---|---|---|---|---|---|---|---|---|---|---|
| | 510 | | | | | 515 | | | | | 520 | | | | |

| Cys | Glu | Tyr | Asn | Leu | Asp | Asn | His | Arg | Thr | Thr | Phe | His | Pro | Val | Gly |
|---|---|---|---|---|---|---|---|---|---|---|---|---|---|---|---|
| 525 | | | | | 530 | | | | | 535 | | | | | 540 |

| Ser | Ser | Val | Thr | Tyr | Pro | Asn | His | His | Gln | Arg | Phe | Asp | Val | Lys | Thr |
|---|---|---|---|---|---|---|---|---|---|---|---|---|---|---|---|
| | | | | 545 | | | | | 550 | | | | | 555 | |

| Phe | Ala | Phe | Val | Ser | Gly | Ala | Gln | Gly | Val | Ser | Gln | Leu | Val | Tyr | Phe |
|---|---|---|---|---|---|---|---|---|---|---|---|---|---|---|---|
| | | | | 560 | | | | | 565 | | | | | 570 | |

| His | Cys | Ser | Val | Phe | Ile | Cys | Asn | Gln | Leu | Ser | Pro | Thr | Phe | Ser | Leu |
|---|---|---|---|---|---|---|---|---|---|---|---|---|---|---|---|
|   |   | 575 |   |   |   |   | 580 |   |   |   |   | 585 |   |   |   |
| Cys | Ser | Val | Thr | Cys | His | Gly | Pro | Ser | Arg | Ser | Arg | Arg | Ala | Thr | Gly |
|   |   | 590 |   |   |   |   | 595 |   |   |   |   | 600 |   |   |   |
| Thr | Thr | Glu | Glu | Glu | Lys | Met | Ile | Val | Ser | Leu | Pro | Gly | Pro | Ile | Leu |
| 605 |   |   |   |   | 610 |   |   |   |   | 615 |   |   |   |   | 620 |
| Leu | Leu | Ser | Asp | Gly | Ser | Ser | Leu | Arg | Asp | Ala | Val | Asn | Ser | Lys | Gly |
|   |   |   |   | 625 |   |   |   |   | 630 |   |   |   |   | 635 |   |
| Ser | Arg | Thr | Asn | Gly | Tyr | Val | Ala | Phe | Lys | Thr | Met | Val | Ala | Met | Val |
|   |   |   | 640 |   |   |   |   | 645 |   |   |   |   | 650 |   |   |
| Ala | Ser | Ala | Gly | Ile | Val | Ala | Thr | Leu | Gly | Leu | Ile | Ser | Tyr | Leu | His |
|   |   | 655 |   |   |   |   | 660 |   |   |   |   | 665 |   |   |   |
| Lys | Lys | Arg | Ile | Met | Met | Leu | Asn | His |
|   |   | 670 |   |   |   | 675 |   |   |

( 2 ) INFORMATION FOR SEQ ID NO:3:

( i ) SEQUENCE CHARACTERISTICS:
        ( A ) LENGTH: 1699 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Sus scrofa
        ( D ) DEVELOPMENTAL STAGE: Juvenile
        ( E ) HAPLOTYPE: Diploidy
        ( F ) TISSUE TYPE: Ovary
        ( G ) CELL TYPE: Oocyte ( i x ) FEATURE:
        ( A ) NAME/KEY: sig_peptide
        ( B ) LOCATION: 38..445

( i x ) FEATURE:
        ( A ) NAME/KEY: mat_peptide
        ( B ) LOCATION: 446..1648

( i x ) FEATURE:
        ( A ) NAME/KEY: CDS
        ( B ) LOCATION: 38..1648

( x i ) SEQUENCE DESCRIPTION: SEQ ID NO:3:

```
GAATTCCGGG  TGGAAGTACC  TGTTCTCCGC  AGGCGCT ATG  TGG  TTG  CGG  CCG  TCC          55
                                            Met  Trp  Leu  Arg  Pro  Ser
                                            -136                      -135

ATC  TGG  CTC  TGC  TTT  CCG  CTG  TGT  CTT  GCT  CTG  CCA  GGC  CAG  TCT  CAG   103
Ile  Trp  Leu  Cys  Phe  Pro  Leu  Cys  Leu  Ala  Leu  Pro  Gly  Gln  Ser  Gln
-130                -125                     -120                     -115

CCC  AAA  GCA  GCA  GAT  GAC  CTT  GGT  GGC  CTC  TAC  TGT  GGG  CCA  AGC  AGC   151
Pro  Lys  Ala  Ala  Asp  Asp  Leu  Gly  Gly  Leu  Tyr  Cys  Gly  Pro  Ser  Ser
               -110                -105                     -100

TTT  CAT  TTC  TCC  ATA  AAT  CTT  CTC  AGC  CAG  GAC  ACA  GCA  ACT  CCT  CCT   199
Phe  His  Phe  Ser  Ile  Asn  Leu  Leu  Ser  Gln  Asp  Thr  Ala  Thr  Pro  Pro
               -95                 -90                      -85

GCA  CTG  GTG  GTT  TGG  GAC  AGG  CGC  GGG  CGG  CTG  CAC  AAG  CTG  CAG  AAT   247
Ala  Leu  Val  Val  Trp  Asp  Arg  Arg  Gly  Arg  Leu  His  Lys  Leu  Gln  Asn
               -80                 -75                      -70

GAC  TCT  GGC  TGT  GGC  ACG  TGG  GTC  CAC  AAG  GGC  CCA  GGC  AGC  TCC  ATG   295
Asp  Ser  Gly  Cys  Gly  Thr  Trp  Val  His  Lys  Gly  Pro  Gly  Ser  Ser  Met
```

```
                -65                            -60                             -55
GGA  GTG  GAA  GCA  TCC  TAC  AGA  GGC  TGC  TAT  GTG  ACT  GAG  TGG  GAC  TCT    343
Gly  Val  Glu  Ala  Ser  Tyr  Arg  Gly  Cys  Tyr  Val  Thr  Glu  Trp  Asp  Ser
-50                           -45                           -40                 -35

CAC  TAC  CTC  ATG  CCC  ATT  GGA  CTT  GAA  GAA  GCA  GAT  GCA  GGT  GGA  CAC    391
His  Tyr  Leu  Met  Pro  Ile  Gly  Leu  Glu  Glu  Ala  Asp  Ala  Gly  Gly  His
                         -30                      -25                      -20

AGA  ACA  GTC  ACA  GAG  ACG  AAA  CTG  TTT  AAG  TGC  CCT  GTG  GAT  TTC  CTA    439
Arg  Thr  Val  Thr  Glu  Thr  Lys  Leu  Phe  Lys  Cys  Pro  Val  Asp  Phe  Leu
               -15                           -10                       -5

GCT  CTT  GAT  GTT  CCA  ACC  ATT  GGC  CTT  TGT  GAT  GCT  GTC  CCA  GTG  TGG    487
Ala  Leu  Asp  Val  Pro  Thr  Ile  Gly  Leu  Cys  Asp  Ala  Val  Pro  Val  Trp
          1                      5                           10

GAC  CGA  TTG  CCA  TGT  GCT  CCT  CCA  CCC  ATC  ACT  CAA  GGA  GAA  TGC  AAG    535
Asp  Arg  Leu  Pro  Cys  Ala  Pro  Pro  Pro  Ile  Thr  Gln  Gly  Glu  Cys  Lys
15                       20                       25                           30

CAG  CTT  GGC  TGC  TGC  TAC  AAC  TCG  GAA  GAG  GTC  CCT  TCT  TGT  TAC  TAT    583
Gln  Leu  Gly  Cys  Cys  Tyr  Asn  Ser  Glu  Glu  Val  Pro  Ser  Cys  Tyr  Tyr
                    35                      40                           45

GGA  AAC  ACA  GTG  ACC  TCA  CGC  TGT  ACC  CAA  GAT  GGC  CAC  TTC  TCC  ATC    631
Gly  Asn  Thr  Val  Thr  Ser  Arg  Cys  Thr  Gln  Asp  Gly  His  Phe  Ser  Ile
               50                           55                      60

GCT  GTG  TCT  CGC  AAT  GTG  ACC  TCA  CCT  CCA  CTG  CTC  TGG  GAT  TCT  GTG    679
Ala  Val  Ser  Arg  Asn  Val  Thr  Ser  Pro  Pro  Leu  Leu  Trp  Asp  Ser  Val
          65                           70                       75

CAC  CTG  GCC  TTC  AGA  AAT  GAC  AGT  GAA  TGT  AAA  CCT  GTG  ATG  GAA  ACA    727
His  Leu  Ala  Phe  Arg  Asn  Asp  Ser  Glu  Cys  Lys  Pro  Val  Met  Glu  Thr
               80                      85                      90

CAC  ACT  TTT  GTC  CTC  TTC  CGG  TTT  CCA  TTT  AGT  TCC  TGT  GGG  ACT  GCA    775
His  Thr  Phe  Val  Leu  Phe  Arg  Phe  Pro  Phe  Ser  Ser  Cys  Gly  Thr  Ala
95                       100                      105                         110

AAA  CGG  GTA  ACT  GGG  AAC  CAG  GCG  GTA  TAT  GAA  AAT  GAG  CTG  GTA  GCA    823
Lys  Arg  Val  Thr  Gly  Asn  Gln  Ala  Val  Tyr  Glu  Asn  Glu  Leu  Val  Ala
                    115                      120                      125

GCT  CGG  GAT  GTG  AGG  ACT  TGG  AGC  CAT  GGT  TCT  ATT  ACC  CGA  GAC  AGC    871
Ala  Arg  Asp  Val  Arg  Thr  Trp  Ser  His  Gly  Ser  Ile  Thr  Arg  Asp  Ser
               130                      135                      140

ATC  TTC  AGG  CTT  CGA  GTC  AGT  TGT  ATC  TAC  TCT  GTA  AGT  AGC  AGT  GCT    919
Ile  Phe  Arg  Leu  Arg  Val  Ser  Cys  Ile  Tyr  Ser  Val  Ser  Ser  Ser  Ala
          145                      150                      155

CTC  CCA  GTT  AAC  ATC  CAG  GTT  TTC  ACT  CTC  CCA  CCG  CTT  CCG  GAG         967
Leu  Pro  Val  Asn  Ile  Gln  Val  Phe  Thr  Leu  Pro  Pro  Leu  Pro  Glu
     160                      165                      170

ACC  CAC  CCT  GGA  CCT  CTT  ACT  CTG  GAG  CTT  CAG  ATT  GCC  AAA  GAT  GAA   1015
Thr  His  Pro  Gly  Pro  Leu  Thr  Leu  Glu  Leu  Gln  Ile  Ala  Lys  Asp  Glu
175                           180                     185                     190

CGC  TAT  GGC  TCC  TAC  TAC  AAT  GCT  AGT  GAC  TAC  CCG  GTG  GTG  AAA  TTG   1063
Arg  Tyr  Gly  Ser  Tyr  Tyr  Asn  Ala  Ser  Asp  Tyr  Pro  Val  Val  Lys  Leu
                    195                      200                      205

CTT  CGG  GAG  CCC  ATC  TAT  GTG  GAG  GTC  TCT  ATC  CGT  CAC  CGA  ACA  GAC   1111
Leu  Arg  Glu  Pro  Ile  Tyr  Val  Glu  Val  Ser  Ile  Arg  His  Arg  Thr  Asp
               210                      215                      220

CCC  AGT  CTC  GGG  CTG  CAC  CTG  CAC  CAG  TGC  TGG  GCC  ACA  CCC  GGC  ATG   1159
Pro  Ser  Leu  Gly  Leu  His  Leu  His  Gln  Cys  Trp  Ala  Thr  Pro  Gly  Met
          225                      230                      235

AGC  CCC  CTG  CTC  CAG  CCA  CAG  TGG  CCC  ATG  CTA  GTC  AAT  GGA  TGC  CCC   1207
Ser  Pro  Leu  Leu  Gln  Pro  Gln  Trp  Pro  Met  Leu  Val  Asn  Gly  Cys  Pro
     240                      245                      250

TAC  ACT  GGA  GAC  AAC  TAC  CAG  ACC  AAA  CTG  ATC  CCT  GTC  CAG  AAA  GCC   1255
Tyr  Thr  Gly  Asp  Asn  Tyr  Gln  Thr  Lys  Leu  Ile  Pro  Val  Gln  Lys  Ala
```

```
  255                          260                          265                          270
TCA  AAC  CTG  CTA  TTT  CCT  TCT  CAC  TAC  CAG  CGT  TTC  AGT  GTT  TCC  ACC    1303
Ser  Asn  Leu  Leu  Phe  Pro  Ser  His  Tyr  Gln  Arg  Phe  Ser  Val  Ser  Thr
               275                      280                     285

TTC  AGT  TTT  GTG  GAC  TCT  GTG  GCA  AAG  CAG  GCA  CTC  AAG  GGA  CCG  GTG    1351
Phe  Ser  Phe  Val  Asp  Ser  Val  Ala  Lys  Gln  Ala  Leu  Lys  Gly  Pro  Val
               290                      295                     300

TAT  CTG  CAT  TGT  ACT  GCA  TCG  GTC  TGC  AAG  CCT  GCA  GGG  GCA  CCG  ATC    1399
Tyr  Leu  His  Cys  Thr  Ala  Ser  Val  Cys  Lys  Pro  Ala  Gly  Ala  Pro  Ile
          305                           310                     315

TGT  GTG  ACA  ACC  TGT  CCT  GCT  GCC  AGA  CGA  AGA  AGA  AGT  TCT  GAC  ATC    1447
Cys  Val  Thr  Thr  Cys  Pro  Ala  Ala  Arg  Arg  Arg  Arg  Ser  Ser  Asp  Ile
          320                           325                     330

CAT  TTT  CAG  AAT  GGC  ACT  GCT  AGC  ATT  TCT  AGC  AAG  GGT  CCC  ATG  ATT    1495
His  Phe  Gln  Asn  Gly  Thr  Ala  Ser  Ile  Ser  Ser  Lys  Gly  Pro  Met  Ile
335                           340                      345                     350

CTA  CTC  CAA  GCC  ACT  CGG  GAC  TCT  TCA  GAA  AGG  CTC  CAT  AAA  TAC  TCA    1543
Leu  Leu  Gln  Ala  Thr  Arg  Asp  Ser  Ser  Glu  Arg  Leu  His  Lys  Tyr  Ser
                    355                      360                     365

AGG  CCT  CCT  GTA  GAC  TCC  CAT  GCT  CTG  TGG  GTG  GCT  GGC  CTC  TTG  GGA    1591
Arg  Pro  Pro  Val  Asp  Ser  His  Ala  Leu  Trp  Val  Ala  Gly  Leu  Leu  Gly
               370                      375                     380

AGC  TTA  ATT  ATT  GGA  GCC  TTG  TTA  GTG  TCC  TAC  CTG  GTC  TTC  AGG  AAA    1639
Ser  Leu  Ile  Ile  Gly  Ala  Leu  Leu  Val  Ser  Tyr  Leu  Val  Phe  Arg  Lys
          385                           390                     395

TGG  AGA  TGAGTTACTC  AGACCAAATG  TGTCAATAAA  ACCAATAAAA  CAAAACCGGA              1695
Trp  Arg
     400

ATTC                                                                              1699
```

( 2 ) INFORMATION FOR SEQ ID NO:4:

( i ) SEQUENCE CHARACTERISTICS:
        ( A ) LENGTH: 536 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met   Trp   Leu   Arg   Pro   Ser   Ile   Trp   Leu   Cys   Phe   Pro   Leu   Cys   Leu   Ala
-136  -135                    -130                        -125

Leu   Pro   Gly   Gln   Ser   Gln   Pro   Lys   Ala   Ala   Asp   Asp   Leu   Gly   Gly   Leu
-120                          -115                        -110                          -105

Tyr   Cys   Gly   Pro   Ser   Ser   Phe   His   Phe   Ser   Ile   Asn   Leu   Leu   Ser   Gln
                        -100                         -95                              -90

Asp   Thr   Ala   Thr   Pro   Pro   Ala   Leu   Val   Val   Trp   Asp   Arg   Arg   Gly   Arg
                  -85                          -80                          -75

Leu   His   Lys   Leu   Gln   Asn   Asp   Ser   Gly   Cys   Gly   Thr   Trp   Val   His   Lys
                  -70                          -65                          -60

Gly   Pro   Gly   Ser   Ser   Met   Gly   Val   Glu   Ala   Ser   Tyr   Arg   Gly   Cys   Tyr
            -55                          -50                          -45

Val   Thr   Glu   Trp   Asp   Ser   His   Tyr   Leu   Met   Pro   Ile   Gly   Leu   Glu   Glu
-40                           -35                          -30                         -25

Ala   Asp   Ala   Gly   Gly   His   Arg   Thr   Val   Thr   Glu   Thr   Lys   Leu   Phe   Lys
                        -20                          -15                         -10

Cys   Pro   Val   Asp   Phe   Leu   Ala   Leu   Asp   Val   Pro   Thr   Ile   Gly   Leu   Cys
                  -5                            1                             5

Asp   Ala   Val   Pro   Val   Trp   Asp   Arg   Leu   Pro   Cys   Ala   Pro   Pro   Pro   Ile
```

```
              10                        15                        20
Thr   Gln   Gly   Glu   Cys   Lys   Gln   Leu   Gly   Cys   Cys   Tyr   Asn   Ser   Glu   Glu
25                      30                        35                              40

Val   Pro   Ser   Cys   Tyr   Tyr   Gly   Asn   Thr   Val   Thr   Ser   Arg   Cys   Thr   Gln
                  45                        50                              55

Asp   Gly   His   Phe   Ser   Ile   Ala   Val   Ser   Arg   Asn   Val   Thr   Ser   Pro   Pro
                        60                        65                        70

Leu   Leu   Trp   Asp   Ser   Val   His   Leu   Ala   Phe   Arg   Asn   Asp   Ser   Glu   Cys
            75                        80                        85

Lys   Pro   Val   Met   Glu   Thr   His   Thr   Phe   Val   Leu   Phe   Arg   Phe   Pro   Phe
            90                        95                        100

Ser   Ser   Cys   Gly   Thr   Ala   Lys   Arg   Val   Thr   Gly   Asn   Gln   Ala   Val   Tyr
105                           110                       115                             120

Glu   Asn   Glu   Leu   Val   Ala   Ala   Arg   Asp   Val   Arg   Thr   Trp   Ser   His   Gly
                        125                       130                             135

Ser   Ile   Thr   Arg   Asp   Ser   Ile   Phe   Arg   Leu   Arg   Val   Ser   Cys   Ile   Tyr
                  140                         145                       150

Ser   Val   Ser   Ser   Ser   Ala   Leu   Pro   Val   Asn   Ile   Gln   Val   Phe   Thr   Leu
            155                       160                       165

Pro   Pro   Pro   Leu   Pro   Glu   Thr   His   Pro   Gly   Pro   Leu   Thr   Leu   Glu   Leu
170                           175                       180

Gln   Ile   Ala   Lys   Asp   Glu   Arg   Tyr   Gly   Ser   Tyr   Tyr   Asn   Ala   Ser   Asp
185                           190                       195                             200

Tyr   Pro   Val   Val   Lys   Leu   Leu   Arg   Glu   Pro   Ile   Tyr   Val   Glu   Val   Ser
                        205                       210                             215

Ile   Arg   His   Arg   Thr   Asp   Pro   Ser   Leu   Gly   Leu   His   Leu   His   Gln   Cys
                  220                         225                       230

Trp   Ala   Thr   Pro   Gly   Met   Ser   Pro   Leu   Leu   Gln   Pro   Gln   Trp   Pro   Met
            235                       240                       245

Leu   Val   Asn   Gly   Cys   Pro   Tyr   Thr   Gly   Asp   Asn   Tyr   Gln   Thr   Lys   Leu
      250                         255                       260

Ile   Pro   Val   Gln   Lys   Ala   Ser   Asn   Leu   Leu   Phe   Pro   Ser   His   Tyr   Gln
265                           270                       275                             280

Arg   Phe   Ser   Val   Ser   Thr   Phe   Ser   Phe   Val   Asp   Ser   Val   Ala   Lys   Gln
                        285                       290                             295

Ala   Leu   Lys   Gly   Pro   Val   Tyr   Leu   His   Cys   Thr   Ala   Ser   Val   Cys   Lys
                  300                         305                       310

Pro   Ala   Gly   Ala   Pro   Ile   Cys   Val   Thr   Thr   Cys   Pro   Ala   Ala   Arg   Arg
                  315                         320                       325

Arg   Arg   Ser   Ser   Asp   Ile   His   Phe   Gln   Asn   Gly   Thr   Ala   Ser   Ile   Ser
330                           335                       340

Ser   Lys   Gly   Pro   Met   Ile   Leu   Leu   Gln   Ala   Thr   Arg   Asp   Ser   Ser   Glu
345                           350                       355                             360

Arg   Leu   His   Lys   Tyr   Ser   Arg   Pro   Pro   Val   Asp   Ser   His   Ala   Leu   Trp
                  365                         370                             375

Val   Ala   Gly   Leu   Leu   Gly   Ser   Leu   Ile   Ile   Gly   Ala   Leu   Leu   Val   Ser
                  380                         385                       390

Tyr   Leu   Val   Phe   Arg   Lys   Trp   Arg
            395                       400
```

( 2 ) INFORMATION FOR SEQ ID NO:5:

( i ) SEQUENCE CHARACTERISTICS:
        ( A ) LENGTH: 1326 base pairs
        ( B ) TYPE: nucleic acid ( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
 ( A ) ORGANISM: Sus scrofa
 ( D ) DEVELOPMENTAL STAGE: Juvenile
 ( E ) HAPLOTYPE: Diploidy
 ( F ) TISSUE TYPE: Ovary
 ( G ) CELL TYPE: Oocyte ( i x ) FEATURE:
 ( A ) NAME/KEY: sig_peptide
 ( B ) LOCATION: 25..105

( i x ) FEATURE:
 ( A ) NAME/KEY: mat_peptide
 ( B ) LOCATION: 106..1290

( i x ) FEATURE:
 ( A ) NAME/KEY: CDS
 ( B ) LOCATION: 25..1290

( x i ) SEQUENCE DESCRIPTION: SEQ ID NO:5:

```
GAATTCCGGG GCCTTGTGAG TGCC ATG GCG CCG AGC TGG AGG TTC TTC GTC        51
                          Met Ala Pro Ser Trp Arg Phe Phe Val
                          -27         -25                 -20

TGC TTT CTG CTC TGG GGA GGT ACA GAG CTA TGC AGC CCG CAG CCC GTC        99
Cys Phe Leu Leu Trp Gly Gly Thr Glu Leu Cys Ser Pro Gln Pro Val
            -15             -10                     -5

TGG CAG GAC GAA GGC CAG CGC TTG AGG CCC TCA AAG CCA CCC ACC GTA       147
Trp Gln Asp Glu Gly Gln Arg Leu Arg Pro Ser Lys Pro Pro Thr Val
            1               5                   10

ATG GTG GAG TGT CAG GAG GCC CAG CTG GTG GTC ATT GTC AGC AAA GAC       195
Met Val Glu Cys Gln Glu Ala Gln Leu Val Val Ile Val Ser Lys Asp
15              20                  25                      30

CTT TTC GGT ACC GGG AAG CTC ATC AGG CCT GCA GAT CTC AGC CTG GGC       243
Leu Phe Gly Thr Gly Lys Leu Ile Arg Pro Ala Asp Leu Ser Leu Gly
                35              40                      45

CCT GCA AAG TGT GAG CCG CTG GTC TCT CAG GAC ACG GAC GCA GTG GTC       291
Pro Ala Lys Cys Glu Pro Leu Val Ser Gln Asp Thr Asp Ala Val Val
50              55                  60

AGG TTT GAG GTT GGG CTG CAC GAG TGT GGC AGC AGC TTG CAG GTG ACT       339
Arg Phe Glu Val Gly Leu His Glu Cys Gly Ser Ser Leu Gln Val Thr
            65                  70                  75

GAT GAT GCT CTG GTG TAC AGC ACC TTC CTG CGC CAT GAC CCC CGC CCT       387
Asp Asp Ala Leu Val Tyr Ser Thr Phe Leu Arg His Asp Pro Arg Pro
        80                  85                  90

GCA GGA AAC CTG TCC ATC CTG AGG ACG AAC CGT GCG GAG GTC CCC ATC       435
Ala Gly Asn Leu Ser Ile Leu Arg Thr Asn Arg Ala Glu Val Pro Ile
95              100                 105                     110

GAG TGT CAC TAC CCC AGG CAG GGC AAC GTG AGC AGC TGG GCC ATC CTG       483
Glu Cys His Tyr Pro Arg Gln Gly Asn Val Ser Ser Trp Ala Ile Leu
                115                 120                 125

CCC ACC TGG GTG CCC TTC AGG ACC ACG GTG TTC TCC GAG GAG AAG CTG       531
Pro Thr Trp Val Pro Phe Arg Thr Thr Val Phe Ser Glu Glu Lys Leu
            130                 135                 140

GTG TTC TCT CTG CGC CTG ATG GAG GAA AAC TGG AGT GCC GAG AAG ATG       579
Val Phe Ser Leu Arg Leu Met Glu Glu Asn Trp Ser Ala Glu Lys Met
        145                 150                 155

ACG CCC ACC TTC CAG CTG GGG GAC AGA GCC CAC CTC CAG GCC CAA GTC       627
Thr Pro Thr Phe Gln Leu Gly Asp Arg Ala His Leu Gln Ala Gln Val
```

|  |  |  | 160 |  |  |  | 165 |  |  |  | 170 |  |  |  |  |
|---|---|---|---|---|---|---|---|---|---|---|---|---|---|---|---|
| CAC | ACC | GGC | AGC | CAC | GTG | CCA | CTG | AGG | CTG | TTT | GTG | GAC | CAC | TGT | GTG | 675 |
| His | Thr | Gly | Ser | His | Val | Pro | Leu | Arg | Leu | Phe | Val | Asp | His | Cys | Val |
| 175 |  |  |  |  | 180 |  |  |  |  | 185 |  |  |  |  | 190 |

(CAC ACC GGC AGC CAC GTG CCA CTG AGG CTG TTT GTG GAC CAC TGT GTG  675
His Thr Gly Ser His Val Pro Leu Arg Leu Phe Val Asp His Cys Val
175             180                 185                 190

GCC ACG CTG ACG CCG GAC TGG AAC ACC TCC CCC TCT CAC ACC ATC GTG  723
Ala Thr Leu Thr Pro Asp Trp Asn Thr Ser Pro Ser His Thr Ile Val
                195                 200                 205

GAC TTC CAC GGC TGT CTC GTG GAC GGT CTC ACT GAG GCC TCA TCT GCT  771
Asp Phe His Gly Cys Leu Val Asp Gly Leu Thr Glu Ala Ser Ser Ala
            210                 215                 220

TTC AAA GCA CCT AGA CCT GGA CCA GAG ACG CTC CAG TTC ACC GTG GAT  819
Phe Lys Ala Pro Arg Pro Gly Pro Glu Thr Leu Gln Phe Thr Val Asp
        225                 230                 235

GTG TTC CAT TTT GCT AAT GAT TCC AGA AAC ACG ATC TAC ATC ACC TGC  867
Val Phe His Phe Ala Asn Asp Ser Arg Asn Thr Ile Tyr Ile Thr Cys
    240                 245                 250

CAT CTG AAG GTC ACT CCG GCT GAC CGA GTC CCG GAC CAA CTC AAC AAA  915
His Leu Lys Val Thr Pro Ala Asp Arg Val Pro Asp Gln Leu Asn Lys
255                 260                 265                 270

GCC TGT TCC TTC AGC AAG TCC TCC AAC AGG TGG TCC CCG GTG GAA GGG  963
Ala Cys Ser Phe Ser Lys Ser Ser Asn Arg Trp Ser Pro Val Glu Gly
                275                 280                 285

CCT GCT GTT ATC TGT CGT TGC TGT CAC AAG GGG CAG TGT GGT ACC CCA  1011
Pro Ala Val Ile Cys Arg Cys Cys His Lys Gly Gln Cys Gly Thr Pro
            290                 295                 300

AGC CTT TCC AGG AAG CTG TCT ATG CCG AAG AGA CAG TCT GCT CCC CGC  1059
Ser Leu Ser Arg Lys Leu Ser Met Pro Lys Arg Gln Ser Ala Pro Arg
        305                 310                 315

AGT CGC AGG CAC GTG ACA GAT GAA GCA GAT GTC ACA GTG GGG CCT CTG  1107
Ser Arg Arg His Val Thr Asp Glu Ala Asp Val Thr Val Gly Pro Leu
    320                 325                 330

ATC TTC CTG GGC AAG ACG AGT GAC CAC GGT GTG GAA GGG TCC ACC TCC  1155
Ile Phe Leu Gly Lys Thr Ser Asp His Gly Val Glu Gly Ser Thr Ser
335                 340                 345                 350

TCC CCC ACC TCG GTG ATG GTG GGC TTG GGC CTG GCC ACC GTG GTG ACC  1203
Ser Pro Thr Ser Val Met Val Gly Leu Gly Leu Ala Thr Val Val Thr
                355                 360                 365

TTG ACT CTG GCT ACC ATT GTC CTG GGT GTG CCC AGG AGG CGT CGG GCT  1251
Leu Thr Leu Ala Thr Ile Val Leu Gly Val Pro Arg Arg Arg Arg Ala
            370                 375                 380

GCT GCC CAC CTT GTG TGC CCC GTG TCT GCT TCC CAA TAAAAGGAGA  1297
Ala Ala His Leu Val Cys Pro Val Ser Ala Ser Gln
        385                 390

AACATGAAAA AAAAAAAAAA CCGGAATTC  1326

( 2 ) INFORMATION FOR SEQ ID NO:6:

( i ) SEQUENCE CHARACTERISTICS:
        ( A ) LENGTH: 421 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Met Ala Pro Ser Trp Arg Phe Phe Val Cys Phe Leu Leu Trp Gly Gly
-27         -25                 -20                 -15

Thr Glu Leu Cys Ser Pro Gln Pro Val Trp Gln Asp Glu Gly Gln Arg
        -10                 -5                  1                   5

Leu Arg Pro Ser Lys Pro Pro Thr Val Met Val Glu Cys Gln Glu Ala
                10                  15                  20

```
Gln  Leu  Val  Val  Ile  Val  Ser  Lys  Asp  Leu  Phe  Gly  Thr  Gly  Lys  Leu
               25                  30                       35

Ile  Arg  Pro  Ala  Asp  Leu  Ser  Leu  Gly  Pro  Ala  Lys  Cys  Glu  Pro  Leu
               40                  45                       50

Val  Ser  Gln  Asp  Thr  Asp  Ala  Val  Val  Arg  Phe  Glu  Val  Gly  Leu  His
          55                       60                       65

Glu  Cys  Gly  Ser  Ser  Leu  Gln  Val  Thr  Asp  Asp  Ala  Leu  Val  Tyr  Ser
70                            75                  80                           85

Thr  Phe  Leu  Arg  His  Asp  Pro  Arg  Pro  Ala  Gly  Asn  Leu  Ser  Ile  Leu
                    90                       95                      100

Arg  Thr  Asn  Arg  Ala  Glu  Val  Pro  Ile  Glu  Cys  His  Tyr  Pro  Arg  Gln
               105                 110                      115

Gly  Asn  Val  Ser  Ser  Trp  Ala  Ile  Leu  Pro  Thr  Trp  Val  Pro  Phe  Arg
               120                 125                      130

Thr  Thr  Val  Phe  Ser  Glu  Glu  Lys  Leu  Val  Phe  Ser  Leu  Arg  Leu  Met
     135                      140                      145

Glu  Glu  Asn  Trp  Ser  Ala  Glu  Lys  Met  Thr  Pro  Thr  Phe  Gln  Leu  Gly
150                           155                 160                          165

Asp  Arg  Ala  His  Leu  Gln  Ala  Gln  Val  His  Thr  Gly  Ser  His  Val  Pro
                    170                      175                     180

Leu  Arg  Leu  Phe  Val  Asp  His  Cys  Val  Ala  Thr  Leu  Thr  Pro  Asp  Trp
               185                 190                      195

Asn  Thr  Ser  Pro  Ser  His  Thr  Ile  Val  Asp  Phe  His  Gly  Cys  Leu  Val
          200                      205                      210

Asp  Gly  Leu  Thr  Glu  Ala  Ser  Ser  Ala  Phe  Lys  Ala  Pro  Arg  Pro  Gly
     215                           220                 225

Pro  Glu  Thr  Leu  Gln  Phe  Thr  Val  Asp  Val  Phe  His  Phe  Ala  Asn  Asp
230                      235                      240                         245

Ser  Arg  Asn  Thr  Ile  Tyr  Ile  Thr  Cys  His  Leu  Lys  Val  Thr  Pro  Ala
                    250                      255                     260

Asp  Arg  Val  Pro  Asp  Gln  Leu  Asn  Lys  Ala  Cys  Ser  Phe  Ser  Lys  Ser
               265                 270                      275

Ser  Asn  Arg  Trp  Ser  Pro  Val  Glu  Gly  Pro  Ala  Val  Ile  Cys  Arg  Cys
          280                      285                      290

Cys  His  Lys  Gly  Gln  Cys  Gly  Thr  Pro  Ser  Leu  Ser  Arg  Lys  Leu  Ser
     295                      300                      305

Met  Pro  Lys  Arg  Gln  Ser  Ala  Pro  Arg  Ser  Arg  Arg  His  Val  Thr  Asp
310                      315                      320                         325

Glu  Ala  Asp  Val  Thr  Val  Gly  Pro  Leu  Ile  Phe  Leu  Gly  Lys  Thr  Ser
                    330                      335                     340

Asp  His  Gly  Val  Glu  Gly  Ser  Thr  Ser  Ser  Pro  Thr  Ser  Val  Met  Val
               345                 350                      355

Gly  Leu  Gly  Leu  Ala  Thr  Val  Val  Thr  Leu  Thr  Leu  Ala  Thr  Ile  Val
          360                      365                      370

Leu  Gly  Val  Pro  Arg  Arg  Arg  Ala  Ala  Ala  His  Leu  Val  Cys  Pro
     375                      380                      385

Val  Ser  Ala  Ser  Gln
390
```

( 2 ) INFORMATION FOR SEQ ID NO:7:

( i ) SEQUENCE CHARACTERISTICS:
        ( A ) LENGTH: 1338 base pairs
        ( B ) TYPE: nucleic acid
        ( C ) STRANDEDNESS: double (D) TOPOLOGY: linear (ii) MOLECULE TYPE: cDNA (iii) HYPOTHETICAL: NO (iv) ANTI-SENSE: NO (vi) ORIGINAL SOURCE:
  (A) ORGANISM: Oryctolagus cuniculus
  (D) DEVELOPMENTAL STAGE: Juvenile
  (E) HAPLOTYPE: Diploidy
  (F) TISSUE TYPE: Ovary
  (G) CELL TYPE: Oocyte (ix) FEATURE:
  (A) NAME/KEY: CDS
  (B) LOCATION: 17..1261

(xi) SEQUENCE DESCRIPTION: SEQ ID NO:7:

```
GAATTCGCGG CCGGCC TAC GGG CTC TTC GTT TGC CTA CTG CTC TGG GGA          49
              Tyr Gly Leu Phe Val Cys Leu Leu Leu Trp Gly
               1               5                    10

GGC TCG GAG CTG TGC TGC CCC CAG CCG CTC TGG TTC TGG CAG GGC GGG        97
Gly Ser Glu Leu Cys Cys Pro Gln Pro Leu Trp Phe Trp Gln Gly Gly
          15              20                  25

ACC CGC CAG CCC GCG CCC TCC GTG ACG CCC GTG GTG GTG GAG TGT CTG       145
Thr Arg Gln Pro Ala Pro Ser Val Thr Pro Val Val Val Glu Cys Leu
         30              35                40

GAG GCC CGG CTC GTG GTC ACG GTC AGC AGG GAC CTT TTT GGC ACC GGG       193
Glu Ala Arg Leu Val Val Thr Val Ser Arg Asp Leu Phe Gly Thr Gly
 45              50              55

AAG CTC ATC CAG GAG GCC GAC CTC AGC CTG GGC CCC GAG GGC TGC GAG       241
Lys Leu Ile Gln Glu Ala Asp Leu Ser Leu Gly Pro Glu Gly Cys Glu
 60          65              70                      75

CCC CAG GCC TCC ACG GAC GCC GTG GTC AGG TTC GAG GTC GGG CTG CAT       289
Pro Gln Ala Ser Thr Asp Ala Val Val Arg Phe Glu Val Gly Leu His
              80              85                      90

GAA TGT GGT AAC AGC GTG CAG GTG ACT GAC GAC TCC CTG GTG TAC AGC       337
Glu Cys Gly Asn Ser Val Gln Val Thr Asp Asp Ser Leu Val Tyr Ser
              95              100                 105

TCC TTC CTG CTC CAC GAC CCC CGC CCC GCG GGA AAC CTG TCC ATC CTC       385
Ser Phe Leu Leu His Asp Pro Arg Pro Ala Gly Asn Leu Ser Ile Leu
         110                 115                 120

AGG ACC AAC CGC GCC GAG GTC CCC ATC GAG TGC CGC TAC CCC AGG CAG       433
Arg Thr Asn Arg Ala Glu Val Pro Ile Glu Cys Arg Tyr Pro Arg Gln
    125                  130                 135

GGC AAC GTG AGC AGC CGG GCG ATC CTG CCG ACC TGG GTG CCC TTC TGG       481
Gly Asn Val Ser Ser Arg Ala Ile Leu Pro Thr Trp Val Pro Phe Trp
140              145                 150                 155

ACC ACG GTA CTG TCA GAG GAG AGG CTG GTG TTC TCC CTG CGC CTC ATG       529
Thr Thr Val Leu Ser Glu Glu Arg Leu Val Phe Ser Leu Arg Leu Met
              160                 165                 170

GAG GAG AAC TGG AGC CGA GAA AAG ATG TCC CCC ACC TTC CAC CTG GGC       577
Glu Glu Asn Trp Ser Arg Glu Lys Met Ser Pro Thr Phe His Leu Gly
              175                 180                 185

GAC ACG GCC CAC CTG CAG GCA GAG GTC CGC ACG GGC AGC CAC CCG CCC       625
Asp Thr Ala His Leu Gln Ala Glu Val Arg Thr Gly Ser His Pro Pro
         190                 195                 200

CTG CTG CTG TTC GTG GAT CGC TGC GTG GCC ACC CCG ACA CGG GAC CAG       673
Leu Leu Leu Phe Val Asp Arg Cys Val Ala Thr Pro Thr Arg Asp Gln
    205                 210                 215

AGC GGC TCC CCC TAT CAC ACC ATC GTG GAC TTG CAC GGC TGT CTT GTG       721
Ser Gly Ser Pro Tyr His Thr Ile Val Asp Leu His Gly Cys Leu Val
220              225                 230                 235
```

```
GAT  GGC  CTC  TCC  GAT  GGG  GCT  TCC  AAG  TTC  AAA  GCC  CCC  AGG  CCG  AAG      769
Asp  Gly  Leu  Ser  Asp  Gly  Ala  Ser  Lys  Phe  Lys  Ala  Pro  Arg  Pro  Lys
               240                      245                      250

CCG  GAC  GTG  CTC  CAG  TTC  ATG  GTG  GCC  GTG  TTC  CAC  TTC  GCT  AAT  GAC      817
Pro  Asp  Val  Leu  Gln  Phe  Met  Val  Ala  Val  Phe  His  Phe  Ala  Asn  Asp
               255                      260                      265

TCC  AGG  CAC  ACG  GTC  TAC  ATC  ACG  TGT  CAC  CTG  AGG  GTC  ATT  CCT  GCC      865
Ser  Arg  His  Thr  Val  Tyr  Ile  Thr  Cys  His  Leu  Arg  Val  Ile  Pro  Ala
               270                      275                      280

CAG  CAA  GCC  CCG  GAC  CGG  CTC  AAC  AAG  GCT  TGT  TCT  TTC  AAC  CAG  TCC      913
Gln  Gln  Ala  Pro  Asp  Arg  Leu  Asn  Lys  Ala  Cys  Ser  Phe  Asn  Gln  Ser
     285                      290                      295

TCC  AGC  AGC  TGG  GCC  CCG  GTG  GAA  GGC  AGT  GCA  GAC  ATC  TGT  GAG  TGT      961
Ser  Ser  Ser  Trp  Ala  Pro  Val  Glu  Gly  Ser  Ala  Asp  Ile  Cys  Glu  Cys
300                      305                      310                      315

TGC  GGC  AAC  GGT  GAC  TGT  GAC  CTC  ATC  GCA  GGC  TCC  CCC  ATG  AAC  CAG     1009
Cys  Gly  Asn  Gly  Asp  Cys  Asp  Leu  Ile  Ala  Gly  Ser  Pro  Met  Asn  Gln
               320                      325                      330

AAC  CAT  GCT  GCC  CGG  TCC  TCT  CTG  CGA  AGC  CGC  AGG  CAC  GTG  ACG  GAA     1057
Asn  His  Ala  Ala  Arg  Ser  Ser  Leu  Arg  Ser  Arg  Arg  His  Val  Thr  Glu
               335                      340                      345

GAA  GCA  GAC  GTC  ACC  GTG  GGC  CCG  CTG  ATC  TTC  CTG  GGG  AAG  GCT  GGT     1105
Glu  Ala  Asp  Val  Thr  Val  Gly  Pro  Leu  Ile  Phe  Leu  Gly  Lys  Ala  Gly
               350                      355                      360

GAC  CCT  GCC  GGC  ACA  GAG  GGG  CTG  GCC  TCT  GCT  GCG  CAG  GCG  ACC  CTG     1153
Asp  Pro  Ala  Gly  Thr  Glu  Gly  Leu  Ala  Ser  Ala  Ala  Gln  Ala  Thr  Leu
     365                      370                      375

GTG  CTG  GGC  CTT  CGC  ATG  GCC  ACC  ATT  GTG  TTC  CTG  GCT  GTG  GCT  GCT     1201
Val  Leu  Gly  Leu  Arg  Met  Ala  Thr  Ile  Val  Phe  Leu  Ala  Val  Ala  Ala
380                      385                      390                      395

GTG  GTC  CTG  GGC  CTC  ACC  AGG  GGG  CGC  CAC  GCT  GCT  TCC  CAC  CCC  AGG     1249
Val  Val  Leu  Gly  Leu  Thr  Arg  Gly  Arg  His  Ala  Ala  Ser  His  Pro  Arg
               400                      405                      410

TCT  GCT  TCC  CAA  TAAAAAATCA  TGACTTCAAA  AAAAAAAAAA  AAAAAAAAA                   1301
Ser  Ala  Ser  Gln
               415

AAAAAAAAAA  AAAAAAAAAA  AAAGCGGCCG  CGAATTC                                         1338
```

( 2 ) INFORMATION FOR SEQ ID NO:8:

( i ) SEQUENCE CHARACTERISTICS:
        ( A ) LENGTH: 415 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Tyr  Gly  Leu  Phe  Val  Cys  Leu  Leu  Trp  Gly  Gly  Ser  Glu  Leu  Cys
 1              5                        10                       15

Cys  Pro  Gln  Pro  Leu  Trp  Phe  Trp  Gln  Gly  Gly  Thr  Arg  Gln  Pro  Ala
               20                       25                       30

Pro  Ser  Val  Thr  Pro  Val  Val  Val  Glu  Cys  Leu  Glu  Ala  Arg  Leu  Val
               35                       40                       45

Val  Thr  Val  Ser  Arg  Asp  Leu  Phe  Gly  Thr  Gly  Lys  Leu  Ile  Gln  Glu
     50                       55                       60

Ala  Asp  Leu  Ser  Leu  Gly  Pro  Glu  Gly  Cys  Glu  Pro  Gln  Ala  Ser  Thr
 65                       70                       75                       80

Asp  Ala  Val  Val  Arg  Phe  Glu  Val  Gly  Leu  His  Glu  Cys  Gly  Asn  Ser
               85                       90                       95
```

| Val | Gln | Val | Thr | Asp | Asp | Ser | Leu | Val | Tyr | Ser | Ser | Phe | Leu | Leu | His |
| | | | 100 | | | | | 105 | | | | | 110 | | |

| Asp | Pro | Arg | Pro | Ala | Gly | Asn | Leu | Ser | Ile | Leu | Arg | Thr | Asn | Arg | Ala |
| | | 115 | | | | 120 | | | | | | 125 | | | |

| Glu | Val | Pro | Ile | Glu | Cys | Arg | Tyr | Pro | Arg | Gln | Gly | Asn | Val | Ser | Ser |
| | 130 | | | | | 135 | | | | | 140 | | | | |

| Arg | Ala | Ile | Leu | Pro | Thr | Trp | Val | Pro | Phe | Trp | Thr | Thr | Val | Leu | Ser |
| 145 | | | | | 150 | | | | | 155 | | | | | 160 |

| Glu | Glu | Arg | Leu | Val | Phe | Ser | Leu | Arg | Leu | Met | Glu | Glu | Asn | Trp | Ser |
| | | | | 165 | | | | | 170 | | | | | 175 | |

| Arg | Glu | Lys | Met | Ser | Pro | Thr | Phe | His | Leu | Gly | Asp | Thr | Ala | His | Leu |
| | | | 180 | | | | | 185 | | | | | 190 | | |

| Gln | Ala | Glu | Val | Arg | Thr | Gly | Ser | His | Pro | Pro | Leu | Leu | Leu | Phe | Val |
| | | 195 | | | | | 200 | | | | | 205 | | | |

| Asp | Arg | Cys | Val | Ala | Thr | Pro | Thr | Arg | Asp | Gln | Ser | Gly | Ser | Pro | Tyr |
| | 210 | | | | | 215 | | | | | 220 | | | | |

| His | Thr | Ile | Val | Asp | Leu | His | Gly | Cys | Leu | Val | Asp | Gly | Leu | Ser | Asp |
| 225 | | | | | 230 | | | | | 235 | | | | | 240 |

| Gly | Ala | Ser | Lys | Phe | Lys | Ala | Pro | Arg | Pro | Lys | Pro | Asp | Val | Leu | Gln |
| | | | | 245 | | | | | 250 | | | | | 255 | |

| Phe | Met | Val | Ala | Val | Phe | His | Phe | Ala | Asn | Asp | Ser | Arg | His | Thr | Val |
| | | | 260 | | | | | 265 | | | | | 270 | | |

| Tyr | Ile | Thr | Cys | His | Leu | Arg | Val | Ile | Pro | Ala | Gln | Gln | Ala | Pro | Asp |
| | | 275 | | | | | 280 | | | | | 285 | | | |

| Arg | Leu | Asn | Lys | Ala | Cys | Ser | Phe | Asn | Gln | Ser | Ser | Ser | Ser | Trp | Ala |
| | 290 | | | | | 295 | | | | | 300 | | | | |

| Pro | Val | Glu | Gly | Ser | Ala | Asp | Ile | Cys | Glu | Cys | Cys | Gly | Asn | Gly | Asp |
| 305 | | | | | 310 | | | | | 315 | | | | | 320 |

| Cys | Asp | Leu | Ile | Ala | Gly | Ser | Pro | Met | Asn | Gln | Asn | His | Ala | Ala | Arg |
| | | | | 325 | | | | | 330 | | | | | 335 | |

| Ser | Ser | Leu | Arg | Ser | Arg | Arg | His | Val | Thr | Glu | Glu | Ala | Asp | Val | Thr |
| | | | 340 | | | | | 345 | | | | | 350 | | |

| Val | Gly | Pro | Leu | Ile | Phe | Leu | Gly | Lys | Ala | Gly | Asp | Pro | Ala | Gly | Thr |
| | | 355 | | | | | 360 | | | | | 365 | | | |

| Glu | Gly | Leu | Ala | Ser | Ala | Ala | Gln | Ala | Thr | Leu | Val | Leu | Gly | Leu | Arg |
| | 370 | | | | | 375 | | | | | 380 | | | | |

| Met | Ala | Thr | Ile | Val | Phe | Leu | Ala | Val | Ala | Ala | Val | Val | Leu | Gly | Leu |
| 385 | | | | | 390 | | | | | 395 | | | | | 400 |

| Thr | Arg | Gly | Arg | His | Ala | Ala | Ser | His | Pro | Arg | Ser | Ala | Ser | Gln | |
| | | | | 405 | | | | | 410 | | | | | 415 | |

( 2 ) INFORMATION FOR SEQ ID NO:9:

( i ) SEQUENCE CHARACTERISTICS:
        ( A ) LENGTH: 2381 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Canis familiaris
        ( D ) DEVELOPMENTAL STAGE: Juvenile
        ( E ) HAPLOTYPE: Diploidy (F) TISSUE TYPE: Ovary
(G) CELL TYPE: Oocyte (ix) FEATURE:
(A) NAME/KEY: CDS
(B) LOCATION: 206..2353

(xi) SEQUENCE DESCRIPTION: SEQ ID NO:9:

```
GAATTCCGGG AGCCCTGAAG GAAGCCGCAA GAACCCTGCC CGCACCTCCG CGACCTCAAG        60

ATGTCCACTC CACTGGAAGA CGGAGAATAC TGGATTGACC CCAACCAAGG ATGCAACCTG       120

ATGCCATCAA GGTTTTCTGC AACATGGAGA CAGGTGAGAC CTGCGTATAC CCACCTACCT       180

GGCTGATTTG GTGGTACGTT TGGCC ATG GCA TGC AAA CAG AAA GGA GAC AGT         232
                            Met Ala Cys Lys Gln Lys Gly Asp Ser
                              1               5

GGG AGT CCC TCA AGC AGG TTT AGT GCA GAT TGG AGC ACC TAC AGG TCA         280
Gly Ser Pro Ser Ser Arg Phe Ser Ala Asp Trp Ser Thr Tyr Arg Ser
 10              15                  20                      25

CTT TCT TTA TTC TTC ATC CTT GTG ACT TCA GTG AAC TCA GTA GGT GTT         328
Leu Ser Leu Phe Phe Ile Leu Val Thr Ser Val Asn Ser Val Gly Val
                     30                  35                  40

ATG CAG TTG GTG AAT CCC ATC TTC CCA GGT ACT GTC ATT TGC CAT GAA         376
Met Gln Leu Val Asn Pro Ile Phe Pro Gly Thr Val Ile Cys His Glu
             45                  50                  55

AAT AAA ATG ACA GTG GAA TTT CCA AGG GAT CTT GGC ACC AAA AAA TGG         424
Asn Lys Met Thr Val Glu Phe Pro Arg Asp Leu Gly Thr Lys Lys Trp
         60                  65                  70

CAT GCA TCT GTG GTG GAT CCA TTT AGT TTT GAA TTG TTG AAC TGT ACT         472
His Ala Ser Val Val Asp Pro Phe Ser Phe Glu Leu Leu Asn Cys Thr
     75                  80                  85

TCT ATC CTG GAC CCA GAA AAG CTC ACC CTG AAG GCC CCA TAT GAG ACC         520
Ser Ile Leu Asp Pro Glu Lys Leu Thr Leu Lys Ala Pro Tyr Glu Thr
 90                  95                 100                 105

TGT AGC AGG AGA GTG CTT GGC CAG CAT CAG ATG GCC ATC AGA CTC ACG         568
Cys Ser Arg Arg Val Leu Gly Gln His Gln Met Ala Ile Arg Leu Thr
                 110                 115                 120

GAC AAC AAT GCT GCT TCA AGA CAT AAG GCT TTC ATG TAT CAG ATC AGC         616
Asp Asn Asn Ala Ala Ser Arg His Lys Ala Phe Met Tyr Gln Ile Ser
             125                 130                 135

TGT CCA GTT ATG CAA ACA GAA GAA ACC CAT GAG CAT GCA GGA TCC ACA         664
Cys Pro Val Met Gln Thr Glu Glu Thr His Glu His Ala Gly Ser Thr
         140                 145                 150

ATC TGC ACA AAA GAT TCC ATG TCT TTT ACC TTT AAC ATT ATT CCT GGC         712
Ile Cys Thr Lys Asp Ser Met Ser Phe Thr Phe Asn Ile Ile Pro Gly
     155                 160                 165

ATG GCT GAT GAA AAT ACG AAT CCC AGT GGT GGG AAA TGG ATG ATG GAG         760
Met Ala Asp Glu Asn Thr Asn Pro Ser Gly Gly Lys Trp Met Met Glu
170                 175                 180                 185

GTT GAT GAT GCA AAA GCT CAA AAT CTG ACT CTT CGG GAG GCC TTG ATG         808
Val Asp Asp Ala Lys Ala Gln Asn Leu Thr Leu Arg Glu Ala Leu Met
                 190                 195                 200

CAA GGA TAT AAT TTC CTG TTT GAT AGC CAC AGG CTC AGT GTC CAA GTG         856
Gln Gly Tyr Asn Phe Leu Phe Asp Ser His Arg Leu Ser Val Gln Val
             205                 210                 215

TCA TTC AAT GCC ACT GGA GTC ACT CAC TAC ATG CAA GGT AAC AGT CAC         904
Ser Phe Asn Ala Thr Gly Val Thr His Tyr Met Gln Gly Asn Ser His
         220                 225                 230

CTC TAC ACA GTG CCT CTG AAG CTT ATA CAC ACA TCT CCT GGG CAG AAG         952
Leu Tyr Thr Val Pro Leu Lys Leu Ile His Thr Ser Pro Gly Gln Lys
     235                 240                 245

ATC ATC TTA ACA ACA CGA GTA CTT TGT ATG TCA GAT CCC GTG ACC TGT        1000
```

```
                Ile  Ile  Leu  Thr  Thr  Arg  Val  Leu  Cys  Met  Ser  Asp  Pro  Val  Thr  Cys
                250                 255                      260                      265

AAC  GCC  ACA  CAC  ATG  ACC  CTC  ACC  ATA  CCA  GAG  TTT  CCT  GGG  AAA  CTA             1048
Asn  Ala  Thr  His  Met  Thr  Leu  Thr  Ile  Pro  Glu  Phe  Pro  Gly  Lys  Leu
               270                 275                           280

CAG  TCT  GTG  AGA  TTT  GAA  AAC  ACG  AAC  TTT  CGT  GTA  AGC  CAG  CTG  CAC             1096
Gln  Ser  Val  Arg  Phe  Glu  Asn  Thr  Asn  Phe  Arg  Val  Ser  Gln  Leu  His
               285                      290                      295

AAC  CAT  GGG  ATT  GAT  AAA  GAA  GAA  TTA  AAC  GGC  TTG  AGG  TTA  CAC  TTC             1144
Asn  His  Gly  Ile  Asp  Lys  Glu  Glu  Leu  Asn  Gly  Leu  Arg  Leu  His  Phe
               300                 305                           310

AGC  AAA  TCT  CTT  CTC  AAA  ATG  AAC  TCC  TCT  GAA  AAA  TGC  CTA  CTC  TAT             1192
Ser  Lys  Ser  Leu  Leu  Lys  Met  Asn  Ser  Ser  Glu  Lys  Cys  Leu  Leu  Tyr
     315                      320                      325

CAG  TTC  TAC  TTA  GCA  TCT  CTC  AAG  CTG  ACC  TTT  GCC  TTT  GAA  CGG  GAC             1240
Gln  Phe  Tyr  Leu  Ala  Ser  Leu  Lys  Leu  Thr  Phe  Ala  Phe  Glu  Arg  Asp
330                      335                      340                      345

ACG  GTT  TCC  ACA  GTG  GTT  TAT  CCT  GAG  TGT  GTT  TGT  GAG  CCA  CCA  GTT             1288
Thr  Val  Ser  Thr  Val  Val  Tyr  Pro  Glu  Cys  Val  Cys  Glu  Pro  Pro  Val
               350                      355                      360

ACT  ATA  GTT  ACA  GGT  GAC  CTG  TGT  ACC  CAG  GAT  GGG  TTT  ATG  GAT  GTC             1336
Thr  Ile  Val  Thr  Gly  Asp  Leu  Cys  Thr  Gln  Asp  Gly  Phe  Met  Asp  Val
               365                      370                      375

AAG  GTC  TAC  AGC  CAC  CAA  ACA  AAA  CCA  GCT  CTA  AAC  TTG  GAT  ACC  CTC             1384
Lys  Val  Tyr  Ser  His  Gln  Thr  Lys  Pro  Ala  Leu  Asn  Leu  Asp  Thr  Leu
               380                      385                      390

AGA  GTG  GGA  GAC  TCC  TCC  TGC  CAA  CCT  ACT  TTC  AAG  GCT  CCA  TCA  CAA             1432
Arg  Val  Gly  Asp  Ser  Ser  Cys  Gln  Pro  Thr  Phe  Lys  Ala  Pro  Ser  Gln
     395                      400                      405

GGG  TTG  ACA  CTG  TTT  CAC  ATC  CCC  CTA  AAT  GGA  TGT  GGA  ACA  AGA  CTT             1480
Gly  Leu  Thr  Leu  Phe  His  Ile  Pro  Leu  Asn  Gly  Cys  Gly  Thr  Arg  Leu
410                      415                      420                      425

AAG  TTC  AAA  GGT  GAC  ACA  GTC  ATC  TAT  GAA  AAT  GAA  ATA  CAT  GCT  CTC             1528
Lys  Phe  Lys  Gly  Asp  Thr  Val  Ile  Tyr  Glu  Asn  Glu  Ile  His  Ala  Leu
                    430                      435                      440

TGG  ACA  GAT  CTC  CCT  CCA  AGC  ACA  ATT  TCC  AGA  GAT  AGT  GAA  TTC  AGA             1576
Trp  Thr  Asp  Leu  Pro  Pro  Ser  Thr  Ile  Ser  Arg  Asp  Ser  Glu  Phe  Arg
               445                      450                      455

ATG  ACT  GTG  AAG  TGC  CAT  TAC  AGC  AGA  GAT  GAC  CTG  CTG  ATA  AAT  ACC             1624
Met  Thr  Val  Lys  Cys  His  Tyr  Ser  Arg  Asp  Asp  Leu  Leu  Ile  Asn  Thr
               460                      465                      470

AAT  GTC  CAA  AGT  CTT  CCT  CCT  CCC  GTG  GCC  TCA  GTG  AGG  CCT  GGT  CCA             1672
Asn  Val  Gln  Ser  Leu  Pro  Pro  Pro  Val  Ala  Ser  Val  Arg  Pro  Gly  Pro
     475                      480                      485

CTT  GCC  TTA  ATC  CTG  CAA  ACC  TAC  CCA  GAT  AAA  TCC  TAT  TTG  CGA  CCC             1720
Leu  Ala  Leu  Ile  Leu  Gln  Thr  Tyr  Pro  Asp  Lys  Ser  Tyr  Leu  Arg  Pro
490                      495                      500                      505

TAT  GGG  GAT  AAG  GAG  TAT  CCT  GTG  GTG  AGA  TAC  CTC  CGC  CAA  CCA  ATT             1768
Tyr  Gly  Asp  Lys  Glu  Tyr  Pro  Val  Val  Arg  Tyr  Leu  Arg  Gln  Pro  Ile
               510                      515                      520

TAC  CTG  GAA  GTG  AAA  GTC  CTA  AAT  AGG  GCT  GAC  CCC  AAC  ATC  AAG  CTG             1816
Tyr  Leu  Glu  Val  Lys  Val  Leu  Asn  Arg  Ala  Asp  Pro  Asn  Ile  Lys  Leu
                    525                      530                      535

GTC  TTA  GAT  GAT  TGC  TGG  GCA  ACA  CCC  ACC  ATG  GAC  CCA  GCC  TCA  CTC             1864
Val  Leu  Asp  Asp  Cys  Trp  Ala  Thr  Pro  Thr  Met  Asp  Pro  Ala  Ser  Leu
               540                      545                      550

CCC  CAG  TGG  AAT  ATT  GTC  ATG  GAT  GGC  TGT  GAA  TAC  AAT  CTG  GAC  AAC             1912
Pro  Gln  Trp  Asn  Ile  Val  Met  Asp  Gly  Cys  Glu  Tyr  Asn  Leu  Asp  Asn
     555                      560                      565

TAC  AGA  ACG  ACC  TTC  CAT  CCA  GTT  GGC  TCC  TCT  GTG  ACC  TAC  CCT  ACT             1960
```

| | | | | | | | | | | | | | | | |
|---|---|---|---|---|---|---|---|---|---|---|---|---|---|---|---|
| Tyr | Arg | Thr | Thr | Phe | His | Pro | Val | Gly | Ser | Ser | Val | Thr | Tyr | Pro | Thr |
| 570 | | | | | 575 | | | | 580 | | | | | | 585 |

| CAC | TAT | CAG | AGG | TTT | GAT | GTG | AAG | ACC | TTT | GCC | TTT | ATA | TCA | GAG | GCC | 2008 |
|---|---|---|---|---|---|---|---|---|---|---|---|---|---|---|---|---|
| His | Tyr | Gln | Arg | Phe | Asp | Val | Lys | Thr | Phe | Ala | Phe | Ile | Ser | Glu | Ala | |
| | | | | 590 | | | | | 595 | | | | | 600 | | |

| CAA | GTG | CTT | TCT | AGC | CTG | GTC | TAC | TTC | CAC | TGC | ACC | GCA | TTA | ATC | TGC | 2056 |
|---|---|---|---|---|---|---|---|---|---|---|---|---|---|---|---|---|
| Gln | Val | Leu | Ser | Ser | Leu | Val | Tyr | Phe | His | Cys | Thr | Ala | Leu | Ile | Cys | |
| | | | | 605 | | | | | 610 | | | | | 615 | | |

| AAT | CGA | CTG | TCT | CCT | GAC | TCC | CCT | CTG | TGT | TCT | GTG | ACT | TGC | CCT | GTA | 2104 |
|---|---|---|---|---|---|---|---|---|---|---|---|---|---|---|---|---|
| Asn | Arg | Leu | Ser | Pro | Asp | Ser | Pro | Leu | Cys | Ser | Val | Thr | Cys | Pro | Val | |
| | | | 620 | | | | | 625 | | | | | 630 | | | |

| TCA | TCC | AGG | CAC | AGG | CGA | GCC | ACA | GGC | AGT | ACT | GAA | GAA | GAG | AAG | ATG | 2152 |
|---|---|---|---|---|---|---|---|---|---|---|---|---|---|---|---|---|
| Ser | Ser | Arg | His | Arg | Arg | Ala | Thr | Gly | Ser | Thr | Glu | Glu | Glu | Lys | Met | |
| | | 635 | | | | | 640 | | | | | 645 | | | | |

| ATA | GTA | AGT | CTC | CCG | GGA | CCC | ATC | CTC | CTG | TTG | GCA | GAC | AGC | TCT | TCA | 2200 |
|---|---|---|---|---|---|---|---|---|---|---|---|---|---|---|---|---|
| Ile | Val | Ser | Leu | Pro | Gly | Pro | Ile | Leu | Leu | Leu | Ala | Asp | Ser | Ser | Ser | |
| 650 | | | | | 655 | | | | | 660 | | | | | 665 | |

| CTC | AGA | GAT | GGT | GTG | GAC | TCA | AAA | GGG | CAC | AGG | GCT | GCT | GGA | TAT | GTT | 2248 |
|---|---|---|---|---|---|---|---|---|---|---|---|---|---|---|---|---|
| Leu | Arg | Asp | Gly | Val | Asp | Ser | Lys | Gly | His | Arg | Ala | Ala | Gly | Tyr | Val | |
| | | | | 670 | | | | | 675 | | | | | 680 | | |

| GCT | TTT | AAA | ACT | GTA | GTG | GCT | GTG | GCT | GCC | TTA | GCA | GGC | CTT | GTG | GCT | 2296 |
|---|---|---|---|---|---|---|---|---|---|---|---|---|---|---|---|---|
| Ala | Phe | Lys | Thr | Val | Val | Ala | Val | Ala | Ala | Leu | Ala | Gly | Leu | Val | Ala | |
| | | | 685 | | | | | 690 | | | | | 695 | | | |

| GCT | CTA | GGT | CTC | ATC | ATC | TAC | CTG | CGT | AAG | AAA | AGA | ACC | ATG | GTG | TTA | 2344 |
|---|---|---|---|---|---|---|---|---|---|---|---|---|---|---|---|---|
| Ala | Leu | Gly | Leu | Ile | Ile | Tyr | Leu | Arg | Lys | Lys | Arg | Thr | Met | Val | Leu | |
| | | 700 | | | | | 705 | | | | | 710 | | | | |

| AAT | CAC | TAAGGATTTT | CAAATAAAGT | GTCCGGAATT | C | 2381 |
|---|---|---|---|---|---|---|
| Asn | His | | | | | |
| | 715 | | | | | |

( 2 ) INFORMATION FOR SEQ ID NO:10:

( i ) SEQUENCE CHARACTERISTICS:
        ( A ) LENGTH: 715 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Met | Ala | Cys | Lys | Gln | Lys | Gly | Asp | Ser | Gly | Ser | Pro | Ser | Ser | Arg | Phe |
|---|---|---|---|---|---|---|---|---|---|---|---|---|---|---|---|
| 1 | | | | 5 | | | | | 10 | | | | | 15 | |

| Ser | Ala | Asp | Trp | Ser | Thr | Tyr | Arg | Ser | Leu | Ser | Leu | Phe | Phe | Ile | Leu |
|---|---|---|---|---|---|---|---|---|---|---|---|---|---|---|---|
| | | | 20 | | | | | 25 | | | | | 30 | | |

| Val | Thr | Ser | Val | Asn | Ser | Val | Gly | Val | Met | Gln | Leu | Val | Asn | Pro | Ile |
|---|---|---|---|---|---|---|---|---|---|---|---|---|---|---|---|
| | | 35 | | | | | 40 | | | | | 45 | | | |

| Phe | Pro | Gly | Thr | Val | Ile | Cys | His | Glu | Asn | Lys | Met | Thr | Val | Glu | Phe |
|---|---|---|---|---|---|---|---|---|---|---|---|---|---|---|---|
| | 50 | | | | | 55 | | | | | 60 | | | | |

| Pro | Arg | Asp | Leu | Gly | Thr | Lys | Lys | Trp | His | Ala | Ser | Val | Val | Asp | Pro |
|---|---|---|---|---|---|---|---|---|---|---|---|---|---|---|---|
| 65 | | | | | 70 | | | | | 75 | | | | | 80 |

| Phe | Ser | Phe | Glu | Leu | Leu | Asn | Cys | Thr | Ser | Ile | Leu | Asp | Pro | Glu | Lys |
|---|---|---|---|---|---|---|---|---|---|---|---|---|---|---|---|
| | | | | 85 | | | | | 90 | | | | | 95 | |

| Leu | Thr | Leu | Lys | Ala | Pro | Tyr | Glu | Thr | Cys | Ser | Arg | Arg | Val | Leu | Gly |
|---|---|---|---|---|---|---|---|---|---|---|---|---|---|---|---|
| | | | 100 | | | | | 105 | | | | | 110 | | |

| Gln | His | Gln | Met | Ala | Ile | Arg | Leu | Thr | Asp | Asn | Asn | Ala | Ala | Ser | Arg |
|---|---|---|---|---|---|---|---|---|---|---|---|---|---|---|---|
| | | | 115 | | | | | 120 | | | | | 125 | | |

| His | Lys | Ala | Phe | Met | Tyr | Gln | Ile | Ser | Cys | Pro | Val | Met | Gln | Thr | Glu |
|---|---|---|---|---|---|---|---|---|---|---|---|---|---|---|---|
| | | 130 | | | | | 135 | | | | | 140 | | | |

| Glu | Thr | His | Glu | His | Ala | Gly | Ser | Thr | Ile | Cys | Thr | Lys | Asp | Ser | Met |
|---|---|---|---|---|---|---|---|---|---|---|---|---|---|---|---|
| 145 | | | | | 150 | | | | | 155 | | | | | 160 |

```
Ser  Phe  Thr  Phe  Asn  Ile  Ile  Pro  Gly  Met  Ala  Asp  Glu  Asn  Thr  Asn
               165                      170                     175

Pro  Ser  Gly  Gly  Lys  Trp  Met  Met  Glu  Val  Asp  Asp  Ala  Lys  Ala  Gln
               180                      185                     190

Asn  Leu  Thr  Leu  Arg  Glu  Ala  Leu  Met  Gln  Gly  Tyr  Asn  Phe  Leu  Phe
               195                      200                     205

Asp  Ser  His  Arg  Leu  Ser  Val  Gln  Val  Ser  Phe  Asn  Ala  Thr  Gly  Val
          210                      215                     220

Thr  His  Tyr  Met  Gln  Gly  Asn  Ser  His  Leu  Tyr  Thr  Val  Pro  Leu  Lys
225                      230                     235                     240

Leu  Ile  His  Thr  Ser  Pro  Gly  Gln  Lys  Ile  Ile  Leu  Thr  Thr  Arg  Val
                    245                     250                     255

Leu  Cys  Met  Ser  Asp  Pro  Val  Thr  Cys  Asn  Ala  Thr  His  Met  Thr  Leu
                    260                     265                     270

Thr  Ile  Pro  Glu  Phe  Pro  Gly  Lys  Leu  Gln  Ser  Val  Arg  Phe  Glu  Asn
               275                      280                     285

Thr  Asn  Phe  Arg  Val  Ser  Gln  Leu  His  Asn  His  Gly  Ile  Asp  Lys  Glu
          290                      295                     300

Glu  Leu  Asn  Gly  Leu  Arg  Leu  His  Phe  Ser  Lys  Ser  Leu  Leu  Lys  Met
305                      310                     315                     320

Asn  Ser  Ser  Glu  Lys  Cys  Leu  Leu  Tyr  Gln  Phe  Tyr  Leu  Ala  Ser  Leu
                    325                     330                     335

Lys  Leu  Thr  Phe  Ala  Phe  Glu  Arg  Asp  Thr  Val  Ser  Thr  Val  Val  Tyr
               340                      345                     350

Pro  Glu  Cys  Val  Cys  Glu  Pro  Pro  Val  Thr  Ile  Val  Thr  Gly  Asp  Leu
          355                      360                     365

Cys  Thr  Gln  Asp  Gly  Phe  Met  Asp  Val  Lys  Val  Tyr  Ser  His  Gln  Thr
     370                      375                     380

Lys  Pro  Ala  Leu  Asn  Leu  Asp  Thr  Leu  Arg  Val  Gly  Asp  Ser  Ser  Cys
385                      390                     395                     400

Gln  Pro  Thr  Phe  Lys  Ala  Pro  Ser  Gln  Gly  Leu  Thr  Leu  Phe  His  Ile
               405                      410                     415

Pro  Leu  Asn  Gly  Cys  Gly  Thr  Arg  Leu  Lys  Phe  Lys  Gly  Asp  Thr  Val
               420                      425                     430

Ile  Tyr  Glu  Asn  Glu  Ile  His  Ala  Leu  Trp  Thr  Asp  Leu  Pro  Pro  Ser
          435                      440                     445

Thr  Ile  Ser  Arg  Asp  Ser  Glu  Phe  Arg  Met  Thr  Val  Lys  Cys  His  Tyr
     450                      455                     460

Ser  Arg  Asp  Asp  Leu  Leu  Ile  Asn  Thr  Asn  Val  Gln  Ser  Leu  Pro  Pro
465                      470                     475                     480

Pro  Val  Ala  Ser  Val  Arg  Pro  Gly  Pro  Leu  Ala  Leu  Ile  Leu  Gln  Thr
               485                      490                     495

Tyr  Pro  Asp  Lys  Ser  Tyr  Leu  Arg  Pro  Tyr  Gly  Asp  Lys  Glu  Tyr  Pro
               500                      505                     510

Val  Val  Arg  Tyr  Leu  Arg  Gln  Pro  Ile  Tyr  Leu  Glu  Val  Lys  Val  Leu
          515                      520                     525

Asn  Arg  Ala  Asp  Pro  Asn  Ile  Lys  Leu  Val  Leu  Asp  Asp  Cys  Trp  Ala
          530                      535                     540

Thr  Pro  Thr  Met  Asp  Pro  Ala  Ser  Leu  Pro  Gln  Trp  Asn  Ile  Val  Met
545                      550                     555                     560

Asp  Gly  Cys  Glu  Tyr  Asn  Leu  Asp  Asn  Tyr  Arg  Thr  Thr  Phe  His  Pro
               565                      570                     575

Val  Gly  Ser  Ser  Val  Thr  Tyr  Pro  Thr  His  Tyr  Gln  Arg  Phe  Asp  Val
```

|     |     |     |     |     |     |     |     |     |     |     |     |     |     |     |
| --- | --- | --- | --- | --- | --- | --- | --- | --- | --- | --- | --- | --- | --- | --- |
|     |     | 580 |     |     |     |     | 585 |     |     |     |     | 590 |     |     |
| Lys | Thr | Phe | Ala | Phe | Ile | Ser | Glu | Ala | Gln | Val | Leu | Ser | Ser | Leu | Val |
|     |     | 595 |     |     |     |     | 600 |     |     |     |     | 605 |     |     |
| Tyr | Phe | His | Cys | Thr | Ala | Leu | Ile | Cys | Asn | Arg | Leu | Ser | Pro | Asp | Ser |
|     |     | 610 |     |     |     |     | 615 |     |     |     |     | 620 |     |     |
| Pro | Leu | Cys | Ser | Val | Thr | Cys | Pro | Val | Ser | Ser | Arg | His | Arg | Arg | Ala |
| 625 |     |     |     |     | 630 |     |     |     |     | 635 |     |     |     |     | 640 |
| Thr | Gly | Ser | Thr | Glu | Glu | Glu | Lys | Met | Ile | Val | Ser | Leu | Pro | Gly | Pro |
|     |     |     |     | 645 |     |     |     |     | 650 |     |     |     |     | 655 |     |
| Ile | Leu | Leu | Leu | Ala | Asp | Ser | Ser | Ser | Leu | Arg | Asp | Gly | Val | Asp | Ser |
|     |     |     | 660 |     |     |     |     | 665 |     |     |     |     | 670 |     |     |
| Lys | Gly | His | Arg | Ala | Ala | Gly | Tyr | Val | Ala | Phe | Lys | Thr | Val | Val | Ala |
|     |     | 675 |     |     |     |     | 680 |     |     |     |     | 685 |     |     |
| Val | Ala | Ala | Leu | Ala | Gly | Leu | Val | Ala | Ala | Leu | Gly | Leu | Ile | Ile | Tyr |
|     | 690 |     |     |     |     | 695 |     |     |     |     | 700 |     |     |     |
| Leu | Arg | Lys | Lys | Arg | Thr | Met | Val | Leu | Asn | His |     |     |     |     |     |
| 705 |     |     |     |     | 710 |     |     |     |     | 715 |     |     |     |     |

( 2 ) INFORMATION FOR SEQ ID NO:11:

( i ) SEQUENCE CHARACTERISTICS:
        ( A ) LENGTH: 1325 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Canis familiaris
        ( D ) DEVELOPMENTAL STAGE: Juvenile
        ( E ) HAPLOTYPE: Diploidy
        ( F ) TISSUE TYPE: Ovary
        ( G ) CELL TYPE: Oocyte ( i x ) FEATURE:
        ( A ) NAME/KEY: CDS
        ( B ) LOCATION: 13..1293

( x i ) SEQUENCE DESCRIPTION: SEQ ID NO:11:

| | | | | | | | | | | | | | | |
| --- | --- | --- | --- | --- | --- | --- | --- | --- | --- | --- | --- | --- | --- | --- |
| GAATTCCGGG | CT | ATG | GGG | CTG | AGC | TAT | GGA | ATT | TTC | ATC | TGT | TTT | CTG | 48 |
| | | Met | Gly | Leu | Ser | Tyr | Gly | Ile | Phe | Ile | Cys | Phe | Leu | |
| | | 1 | | | | 5 | | | | | 10 | | | |
| CTC | CTG | GGA | GGC | ATG | GAG | CTG | TGC | TGC | CCC | CAG | ACC | ATC | TGG | CCA | ACT | 96 |
| Leu | Leu | Gly | Gly | Met | Glu | Leu | Cys | Cys | Pro | Gln | Thr | Ile | Trp | Pro | Thr |
| | | 15 | | | | | 20 | | | | | 25 | | |
| GAG | ACC | TAC | TAC | CCA | TTG | ACA | TCT | AGG | CCC | CCA | GTA | ATG | GTG | GAC | TGT | 144 |
| Glu | Thr | Tyr | Tyr | Pro | Leu | Thr | Ser | Arg | Pro | Pro | Val | Met | Val | Asp | Cys |
| | 30 | | | | | 35 | | | | | 40 | | | | |
| CTG | GAG | TCC | CAG | CTG | GTG | GTC | ACT | GTC | AGC | AAA | GAC | CTT | TTT | GGT | ACT | 192 |
| Leu | Glu | Ser | Gln | Leu | Val | Val | Thr | Val | Ser | Lys | Asp | Leu | Phe | Gly | Thr |
| 45 | | | | | 50 | | | | | 55 | | | | | 60 |
| GGG | AAG | CTC | ATC | AGG | CCA | GCA | GAC | CTC | ACC | CTG | GGT | CCA | GAG | AAC | TGT | 240 |
| Gly | Lys | Leu | Ile | Arg | Pro | Ala | Asp | Leu | Thr | Leu | Gly | Pro | Glu | Asn | Cys |
| | | | | 65 | | | | | 70 | | | | | 75 | |
| GAG | CCC | CTG | GTC | TCC | ATG | GAC | ACG | GAT | GAT | GTG | GTC | AGG | TTT | GAG | GTT | 288 |
| Glu | Pro | Leu | Val | Ser | Met | Asp | Thr | Asp | Asp | Val | Val | Arg | Phe | Glu | Val |
| | | | 80 | | | | | 85 | | | | | 90 | | |
| GGG | CTG | CAC | GAG | TGT | GGC | AGC | AGG | GTG | CAG | GTG | ACT | GAC | AAT | GCT | CTG | 336 |
| Gly | Leu | His | Glu | Cys | Gly | Ser | Arg | Val | Gln | Val | Thr | Asp | Asn | Ala | Leu |

|  |  |  |  |  |  |  |  |  |  |  |  |  |  |  |  |
|---|---|---|---|---|---|---|---|---|---|---|---|---|---|---|---|
|  |  | 95 |  |  |  |  | 100 |  |  |  |  | 105 |  |  |  |
| GTG | TAC | AGC | ACC | TTC | CTG | ATC | CAC | AGC | CCC | CGC | CCT | GCG | GGC | AAC | CTG | 384 |
| Val | Tyr | Ser | Thr | Phe | Leu | Ile | His | Ser | Pro | Arg | Pro | Ala | Gly | Asn | Leu |
|  | 110 |  |  |  | 115 |  |  |  |  | 120 |  |  |  |  |  |
| TCC | ATC | CTG | AGA | ACT | AAT | CGT | GCC | GAG | GTT | CCC | ATC | GAG | TGC | CAC | TAC | 432 |
| Ser | Ile | Leu | Arg | Thr | Asn | Arg | Ala | Glu | Val | Pro | Ile | Glu | Cys | His | Tyr |
| 125 |  |  |  |  | 130 |  |  |  |  | 135 |  |  |  |  | 140 |
| CCC | AGG | CAC | AGC | AAT | GTG | AGC | AGC | CAG | GCC | ATC | CTG | CCC | ACT | TGG | GTG | 480 |
| Pro | Arg | His | Ser | Asn | Val | Ser | Ser | Gln | Ala | Ile | Leu | Pro | Thr | Trp | Val |
|  |  |  |  | 145 |  |  |  |  | 150 |  |  |  |  | 155 |  |
| CCC | TTC | AGG | ACC | ACA | ATG | CTC | TTC | GAG | GAG | AAG | CTA | GTT | TTC | TCT | CTC | 528 |
| Pro | Phe | Arg | Thr | Thr | Met | Leu | Phe | Glu | Glu | Lys | Leu | Val | Phe | Ser | Leu |
|  |  |  | 160 |  |  |  |  | 165 |  |  |  |  | 170 |  |  |
| CGC | CTA | ATG | GAG | GAG | GAC | TGG | GGC | TCC | GAG | AAG | CAA | TCC | CCC | ACA | TTC | 576 |
| Arg | Leu | Met | Glu | Glu | Asp | Trp | Gly | Ser | Glu | Lys | Gln | Ser | Pro | Thr | Phe |
|  |  | 175 |  |  |  |  | 180 |  |  |  |  | 185 |  |  |  |
| CAG | CTG | GGA | GAC | ATA | GCC | CAC | CTC | CAG | GCT | GAA | GTC | CAC | ACT | GGC | AGC | 624 |
| Gln | Leu | Gly | Asp | Ile | Ala | His | Leu | Gln | Ala | Glu | Val | His | Thr | Gly | Ser |
|  | 190 |  |  |  |  | 195 |  |  |  |  | 200 |  |  |  |  |
| CAT | ATG | CCA | CTG | CGA | CTT | TTT | GTG | GAC | CAC | TGT | GTG | GCC | ACG | CTG | ACA | 672 |
| His | Met | Pro | Leu | Arg | Leu | Phe | Val | Asp | His | Cys | Val | Ala | Thr | Leu | Thr |
| 205 |  |  |  |  | 210 |  |  |  |  | 215 |  |  |  |  | 220 |
| CCA | GAT | CGG | AAT | GCC | TTC | CTT | CAT | CAC | AAA | ATT | GTG | GAC | TTC | CAT | GGC | 720 |
| Pro | Asp | Arg | Asn | Ala | Phe | Leu | His | His | Lys | Ile | Val | Asp | Phe | His | Gly |
|  |  |  |  | 225 |  |  |  |  | 230 |  |  |  |  | 235 |  |
| TGT | CTT | GTG | GAT | GGT | CTC | TAC | AAT | TCC | TCT | TCA | GCC | TTC | AAA | GCC | CCC | 768 |
| Cys | Leu | Val | Asp | Gly | Leu | Tyr | Asn | Ser | Ser | Ser | Ala | Phe | Lys | Ala | Pro |
|  |  |  | 240 |  |  |  |  | 245 |  |  |  |  | 250 |  |  |
| AGA | CCC | AGG | CCA | GAG | ACT | CTT | CAG | TTC | ACA | GTG | GAT | GTT | TTC | CAC | TTT | 816 |
| Arg | Pro | Arg | Pro | Glu | Thr | Leu | Gln | Phe | Thr | Val | Asp | Val | Phe | His | Phe |
|  |  | 255 |  |  |  |  | 260 |  |  |  |  | 265 |  |  |  |
| GCT | AAG | GAC | TCA | AGA | AAC | ACG | ATC | TAT | ATC | ACC | TGC | CAT | CTG | AAG | GTC | 864 |
| Ala | Lys | Asp | Ser | Arg | Asn | Thr | Ile | Tyr | Ile | Thr | Cys | His | Leu | Lys | Val |
|  | 270 |  |  |  |  | 275 |  |  |  |  | 280 |  |  |  |  |
| ACT | CCG | GCT | GAC | CGA | GTC | CCA | GAC | CAG | CTA | AAC | AAA | GCT | TGT | TCC | TTC | 912 |
| Thr | Pro | Ala | Asp | Arg | Val | Pro | Asp | Gln | Leu | Asn | Lys | Ala | Cys | Ser | Phe |
| 285 |  |  |  |  | 290 |  |  |  |  | 295 |  |  |  |  | 300 |
| ATC | AAG | TCT | ACC | AAG | AGG | TGG | TAC | CCT | GTA | GAA | GGC | TCG | GCT | GAT | ATT | 960 |
| Ile | Lys | Ser | Thr | Lys | Arg | Trp | Tyr | Pro | Val | Glu | Gly | Ser | Ala | Asp | Ile |
|  |  |  |  | 305 |  |  |  |  | 310 |  |  |  |  | 315 |  |
| TGT | CGC | TGT | TGT | AAC | AAA | GGC | AGC | TGT | GGC | CTT | CCA | GGC | CGG | TCC | AGG | 1008 |
| Cys | Arg | Cys | Cys | Asn | Lys | Gly | Ser | Cys | Gly | Leu | Pro | Gly | Arg | Ser | Arg |
|  |  |  | 320 |  |  |  |  | 325 |  |  |  |  | 330 |  |  |
| AGG | CTG | TCC | CAC | CTA | GAG | AGA | GGG | TGG | CGC | AAG | TCT | GTT | TCC | CAC | ACT | 1056 |
| Arg | Leu | Ser | His | Leu | Glu | Arg | Gly | Trp | Arg | Lys | Ser | Val | Ser | His | Thr |
|  |  | 335 |  |  |  |  | 340 |  |  |  |  | 345 |  |  |  |
| AGA | AAT | CGC | AGG | CAC | GTG | ACT | GAA | GAA | GCA | GAG | ATC | ACC | GTG | GGG | CCT | 1104 |
| Arg | Asn | Arg | Arg | His | Val | Thr | Glu | Glu | Ala | Glu | Ile | Thr | Val | Gly | Pro |
|  | 350 |  |  |  |  | 355 |  |  |  |  | 360 |  |  |  |  |
| CTG | ATC | TTC | CTG | GGA | AAG | GCT | AGT | GAT | CAT | GGT | ATA | GAG | GGG | TCA | ACC | 1152 |
| Leu | Ile | Phe | Leu | Gly | Lys | Ala | Ser | Asp | His | Gly | Ile | Glu | Gly | Ser | Thr |
| 365 |  |  |  |  | 370 |  |  |  |  | 375 |  |  |  |  | 380 |
| TCT | CCT | CAC | ACC | TCT | GTG | ATG | TTG | GGC | TTA | GGC | CTG | GCC | ACG | GTG | GTA | 1200 |
| Ser | Pro | His | Thr | Ser | Val | Met | Leu | Gly | Leu | Gly | Leu | Ala | Thr | Val | Val |
|  |  |  |  | 385 |  |  |  |  | 390 |  |  |  |  | 395 |  |
| TCC | CTG | ACT | CTA | GCT | ACC | ATT | GTC | CTG | GTC | CTT | GCC | AAG | AGG | CAT | CGT | 1248 |
| Ser | Leu | Thr | Leu | Ala | Thr | Ile | Val | Leu | Val | Leu | Ala | Lys | Arg | His | Arg |
|  |  |  | 400 |  |  |  |  | 405 |  |  |  |  | 410 |  |  |
| ACT | GCT | TCC | CAC | CCT | GTG | ATA | TGC | CCT | GCA | TCT | GTC | TCC | CAA | TAAAAGAATA | 1300 |
| Thr | Ala | Ser | His | Pro | Val | Ile | Cys | Pro | Ala | Ser | Val | Ser | Gln |  |  |

```
                              415                    420                     425
AGCAAAAAAA  AAAAAACCGG  AATTC                                                                           1325
```

(2) INFORMATION FOR SEQ ID NO:12:

(i) SEQUENCE CHARACTERISTICS:
        (A) LENGTH: 426 amino acids
        (B) TYPE: amino acid
        (D) TOPOLOGY: linear (ii) MOLECULE TYPE: protein (xi) SEQUENCE DESCRIPTION: SEQ ID NO:12:

```
Met  Gly  Leu  Ser  Tyr  Gly  Ile  Phe  Ile  Cys  Phe  Leu  Leu  Leu  Gly  Gly
 1              5                       10                           15

Met  Glu  Leu  Cys  Cys  Pro  Gln  Thr  Ile  Trp  Pro  Thr  Glu  Thr  Tyr  Tyr
               20                       25                      30

Pro  Leu  Thr  Ser  Arg  Pro  Pro  Val  Met  Val  Asp  Cys  Leu  Glu  Ser  Gln
          35                            40                 45

Leu  Val  Val  Thr  Val  Ser  Lys  Asp  Leu  Phe  Gly  Thr  Gly  Lys  Leu  Ile
     50                       55                      60

Arg  Pro  Ala  Asp  Leu  Thr  Leu  Gly  Pro  Glu  Asn  Cys  Glu  Pro  Leu  Val
 65                      70                       75                            80

Ser  Met  Asp  Thr  Asp  Asp  Val  Val  Arg  Phe  Glu  Val  Gly  Leu  His  Glu
                    85                      90                           95

Cys  Gly  Ser  Arg  Val  Gln  Val  Thr  Asp  Asn  Ala  Leu  Val  Tyr  Ser  Thr
                100                     105                      110

Phe  Leu  Ile  His  Ser  Pro  Arg  Pro  Ala  Gly  Asn  Leu  Ser  Ile  Leu  Arg
               115                      120                     125

Thr  Asn  Arg  Ala  Glu  Val  Pro  Ile  Glu  Cys  His  Tyr  Pro  Arg  His  Ser
     130                      135                     140

Asn  Val  Ser  Ser  Gln  Ala  Ile  Leu  Pro  Thr  Trp  Val  Pro  Phe  Arg  Thr
145                           150                     155                      160

Thr  Met  Leu  Phe  Glu  Glu  Lys  Leu  Val  Phe  Ser  Leu  Arg  Leu  Met  Glu
                    165                     170                     175

Glu  Asp  Trp  Gly  Ser  Glu  Lys  Gln  Ser  Pro  Thr  Phe  Gln  Leu  Gly  Asp
                180                     185                     190

Ile  Ala  His  Leu  Gln  Ala  Glu  Val  His  Thr  Gly  Ser  His  Met  Pro  Leu
               195                      200                     205

Arg  Leu  Phe  Val  Asp  His  Cys  Val  Ala  Thr  Leu  Thr  Pro  Asp  Arg  Asn
     210                      215                     220

Ala  Phe  Leu  His  His  Lys  Ile  Val  Asp  Phe  His  Gly  Cys  Leu  Val  Asp
225                           230                     235                      240

Gly  Leu  Tyr  Asn  Ser  Ser  Ala  Phe  Lys  Ala  Pro  Arg  Pro  Arg  Pro  Pro
                245                     250                     255

Glu  Thr  Leu  Gln  Phe  Thr  Val  Asp  Val  Phe  His  Phe  Ala  Lys  Asp  Ser
               260                      265                     270

Arg  Asn  Thr  Ile  Tyr  Ile  Thr  Cys  His  Leu  Lys  Val  Thr  Pro  Ala  Asp
     275                      280                     285

Arg  Val  Pro  Asp  Gln  Leu  Asn  Lys  Ala  Cys  Ser  Phe  Ile  Lys  Ser  Thr
     290                      295                     300

Lys  Arg  Trp  Tyr  Pro  Val  Glu  Gly  Ser  Ala  Asp  Ile  Cys  Arg  Cys  Cys
305                           310                     315                      320

Asn  Lys  Gly  Ser  Cys  Gly  Leu  Pro  Gly  Arg  Ser  Arg  Arg  Leu  Ser  His
                325                     330                     335

Leu  Glu  Arg  Gly  Trp  Arg  Lys  Ser  Val  Ser  His  Thr  Arg  Asn  Arg  Arg
```

|     |     |     | 340 |     |     |     | 345 |     |     |     | 350 |     |     |
| --- | --- | --- | --- | --- | --- | --- | --- | --- | --- | --- | --- | --- | --- |
| His | Val | Thr | Glu | Glu | Ala | Glu | Ile | Thr | Val | Gly | Pro | Leu | Ile | Phe | Leu |
|     |     | 355 |     |     |     |     | 360 |     |     |     |     | 365 |     |     |     |
| Gly | Lys | Ala | Ser | Asp | His | Gly | Ile | Glu | Gly | Ser | Thr | Ser | Pro | His | Thr |
|     | 370 |     |     |     |     | 375 |     |     |     |     | 380 |     |     |     |     |
| Ser | Val | Met | Leu | Gly | Leu | Gly | Leu | Ala | Thr | Val | Val | Ser | Leu | Thr | Leu |
| 385 |     |     |     |     | 390 |     |     |     |     | 395 |     |     |     |     | 400 |
| Ala | Thr | Ile | Val | Leu | Val | Leu | Ala | Lys | Arg | His | Arg | Thr | Ala | Ser | His |
|     |     |     |     | 405 |     |     |     |     | 410 |     |     |     |     | 415 |     |
| Pro | Val | Ile | Cys | Pro | Ala | Ser | Val | Ser | Gln |     |     |     |     |     |     |
|     |     |     | 420 |     |     |     |     | 425 |     |     |     |     |     |     |     |

( 2 ) INFORMATION FOR SEQ ID NO:13:

( i ) SEQUENCE CHARACTERISTICS:
        ( A ) LENGTH: 2236 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Felis domesticus
        ( D ) DEVELOPMENTAL STAGE: Juvenile
        ( E ) HAPLOTYPE: Diploidy
        ( F ) TISSUE TYPE: Ovary
        ( G ) CELL TYPE: Oocyte ( i x ) FEATURE:
        ( A ) NAME/KEY: CDS
        ( B ) LOCATION: 28..2175

( x i ) SEQUENCE DESCRIPTION: SEQ ID NO:13:

| GAATTCGCGG | CCGCGATACT | TTTGGCT | ATG | GCC | TCC | AGA | CAG | AAA | GGA | GAT | 51 |
| --- | --- | --- | --- | --- | --- | --- | --- | --- | --- | --- | --- |
|  |  |  | Met | Ala | Ser | Arg | Gln | Lys | Gly | Asp |  |
|  |  |  | 1 |  |  |  | 5 |  |  |  |  |

| AGT | GGG | AGT | CCT | TCA | AGC | TGG | TTT | AAT | GCA | GAT | TGG | AGC | ACC | TAC | AGG | 99 |
| --- | --- | --- | --- | --- | --- | --- | --- | --- | --- | --- | --- | --- | --- | --- | --- | --- |
| Ser | Gly | Ser | Pro | Ser | Ser | Trp | Phe | Asn | Ala | Asp | Trp | Ser | Thr | Tyr | Arg |  |
|  | 10 |  |  |  |  | 15 |  |  |  |  | 20 |  |  |  |  |  |

| TCA | CTT | TTT | CTA | CTC | TTT | ATC | CTC | GTG | ACT | TCA | GTG | AAT | TCC | ATA | GGT | 147 |
| --- | --- | --- | --- | --- | --- | --- | --- | --- | --- | --- | --- | --- | --- | --- | --- | --- |
| Ser | Leu | Phe | Leu | Leu | Phe | Ile | Leu | Val | Thr | Ser | Val | Asn | Ser | Ile | Gly |  |
| 25 |  |  |  |  | 30 |  |  |  |  | 35 |  |  |  |  | 40 |  |

| GTT | TTG | CAG | TTG | GTG | AAT | CCT | GTC | TTC | CCA | GGT | ACT | GTC | ACT | TGC | TAT | 195 |
| --- | --- | --- | --- | --- | --- | --- | --- | --- | --- | --- | --- | --- | --- | --- | --- | --- |
| Val | Leu | Gln | Leu | Val | Asn | Pro | Val | Phe | Pro | Gly | Thr | Val | Thr | Cys | Tyr |  |
|  |  |  |  | 45 |  |  |  |  | 50 |  |  |  |  | 55 |  |  |

| GAA | ACT | AGA | ATG | GCA | GTG | GAA | TTT | CCA | AGT | GAT | TTT | GGC | ACC | AAA | AAA | 243 |
| --- | --- | --- | --- | --- | --- | --- | --- | --- | --- | --- | --- | --- | --- | --- | --- | --- |
| Glu | Thr | Arg | Met | Ala | Val | Glu | Phe | Pro | Ser | Asp | Phe | Gly | Thr | Lys | Lys |  |
|  |  |  | 60 |  |  |  |  | 65 |  |  |  |  | 70 |  |  |  |

| TGG | CAT | ACA | TCT | GTG | GTG | GAT | CCC | TTT | AGT | TTT | GAA | TTG | TTG | AAC | TGC | 291 |
| --- | --- | --- | --- | --- | --- | --- | --- | --- | --- | --- | --- | --- | --- | --- | --- | --- |
| Trp | His | Thr | Ser | Val | Val | Asp | Pro | Phe | Ser | Phe | Glu | Leu | Leu | Asn | Cys |  |
|  |  | 75 |  |  |  |  | 80 |  |  |  |  | 85 |  |  |  |  |

| ACT | TAC | ATC | TTG | GAT | CCA | GAA | AAT | CTC | ACC | TTA | AAG | GCC | CCA | TAT | GAG | 339 |
| --- | --- | --- | --- | --- | --- | --- | --- | --- | --- | --- | --- | --- | --- | --- | --- | --- |
| Thr | Tyr | Ile | Leu | Asp | Pro | Glu | Asn | Leu | Thr | Leu | Lys | Ala | Pro | Tyr | Glu |  |
|  |  | 90 |  |  |  |  | 95 |  |  |  |  | 100 |  |  |  |  |

| ACC | TGT | ACC | AGA | AGA | ACG | CTT | GGC | CAG | CAC | CGG | ATG | ATC | ATC | AGA | CTC | 387 |
| --- | --- | --- | --- | --- | --- | --- | --- | --- | --- | --- | --- | --- | --- | --- | --- | --- |
| Thr | Cys | Thr | Arg | Arg | Thr | Leu | Gly | Gln | His | Arg | Met | Ile | Ile | Arg | Leu |  |
| 105 |  |  |  |  | 110 |  |  |  |  | 115 |  |  |  |  | 120 |  |

| AAG | GAC | CAC | AAT | GCT | GCT | TCA | AGA | CAT | AAC | AGT | TTG | ATG | TAT | CAG | ATC | 435 |
| --- | --- | --- | --- | --- | --- | --- | --- | --- | --- | --- | --- | --- | --- | --- | --- | --- |
| Lys | Asp | His | Asn | Ala | Ala | Ser | Arg | His | Asn | Ser | Leu | Met | Tyr | Gln | Ile |  |
|  |  |  |  | 125 |  |  |  |  | 130 |  |  |  |  | 135 |  |  |

| | | | | | | | | | | | | | | | | |
|---|---|---|---|---|---|---|---|---|---|---|---|---|---|---|---|---|
| AAC | TGT | CCA | GTT | ATG | CAA | GCA | GAA | GAA | ACC | CAT | GAG | CAT | GCA | GGA | TCC | 483 |
| Asn | Cys | Pro | Val | Met | Gln | Ala | Glu | Glu | Thr | His | Glu | His | Ala | Gly | Ser | |
| | | | 140 | | | | 145 | | | | | | 150 | | | |
| ACT | ATC | TGC | ACA | AAG | GAT | TCC | ATG | TCT | TTT | ACC | TTT | AAT | GTC | ATT | CCT | 531 |
| Thr | Ile | Cys | Thr | Lys | Asp | Ser | Met | Ser | Phe | Thr | Phe | Asn | Val | Ile | Pro | |
| | | 155 | | | | | 160 | | | | | 165 | | | | |
| GGC | CTG | GCT | GAT | GAA | AAT | ACG | GAT | ATC | AAG | AAT | CCG | ATG | GGA | TGG | AGC | 579 |
| Gly | Leu | Ala | Asp | Glu | Asn | Thr | Asp | Ile | Lys | Asn | Pro | Met | Gly | Trp | Ser | |
| | 170 | | | | | 175 | | | | | 180 | | | | | |
| ATT | GAG | GTT | GGT | GAT | GGT | ACA | AAA | GCC | AAA | ACT | CTG | ACT | CTT | CAG | GAT | 627 |
| Ile | Glu | Val | Gly | Asp | Gly | Thr | Lys | Ala | Lys | Thr | Leu | Thr | Leu | Gln | Asp | |
| 185 | | | | | 190 | | | | | 195 | | | | | 200 | |
| GTC | TTG | AGA | CAA | GGA | TAC | AAT | ATC | CTG | TTT | GAT | AAC | CAC | AAG | ATC | ACC | 675 |
| Val | Leu | Arg | Gln | Gly | Tyr | Asn | Ile | Leu | Phe | Asp | Asn | His | Lys | Ile | Thr | |
| | | | | 205 | | | | | 210 | | | | | 215 | | |
| TTC | CAG | GTG | TCA | TTC | AAT | GCC | ACT | GGA | GTG | ACT | CAC | TAC | ATG | CAA | GGT | 723 |
| Phe | Gln | Val | Ser | Phe | Asn | Ala | Thr | Gly | Val | Thr | His | Tyr | Met | Gln | Gly | |
| | | | 220 | | | | | 225 | | | | | 230 | | | |
| AAC | AGT | CAC | CTC | TAC | ATG | GTG | CCT | CTG | AAG | TTG | ATA | CAT | GAA | TCT | CTT | 771 |
| Asn | Ser | His | Leu | Tyr | Met | Val | Pro | Leu | Lys | Leu | Ile | His | Glu | Ser | Leu | |
| | | 235 | | | | | 240 | | | | | 245 | | | | |
| GGG | CAG | AAG | ATC | ATC | TTA | ACA | ACA | CGA | GTG | CTT | TGT | ATG | TCA | GAT | GCT | 819 |
| Gly | Gln | Lys | Ile | Ile | Leu | Thr | Thr | Arg | Val | Leu | Cys | Met | Ser | Asp | Ala | |
| | 250 | | | | | 255 | | | | | 260 | | | | | |
| GTG | ACC | TGT | AAT | GCC | ACA | CAT | GTG | ACT | CTG | ACC | ATA | CCA | GAG | TTT | CCT | 867 |
| Val | Thr | Cys | Asn | Ala | Thr | His | Val | Thr | Leu | Thr | Ile | Pro | Glu | Phe | Pro | |
| 265 | | | | | 270 | | | | | 275 | | | | | 280 | |
| GGG | AAG | TTA | AAA | TCT | GTG | AGC | TCT | GAA | AAT | AGG | AAC | TTT | GCT | GTA | AGC | 915 |
| Gly | Lys | Leu | Lys | Ser | Val | Ser | Ser | Glu | Asn | Arg | Asn | Phe | Ala | Val | Ser | |
| | | | | 285 | | | | | 290 | | | | | 295 | | |
| CAG | CTG | CAC | AAC | AAT | GGG | ATT | GAT | AAA | GAA | GAA | TCA | AGT | GGC | TTG | ACA | 963 |
| Gln | Leu | His | Asn | Asn | Gly | Ile | Asp | Lys | Glu | Glu | Ser | Ser | Gly | Leu | Thr | |
| | | | | 300 | | | | | 305 | | | | | 310 | | |
| TTG | CAC | TTC | AGC | AAA | ACT | CTT | CTC | AAA | ATG | GAA | TTC | TCT | GAA | AAA | TGC | 1011 |
| Leu | His | Phe | Ser | Lys | Thr | Leu | Leu | Lys | Met | Glu | Phe | Ser | Glu | Lys | Cys | |
| | | 315 | | | | | 320 | | | | | 325 | | | | |
| CTA | CCC | TAT | CAG | TTC | TAC | TTA | GCT | TCA | CTC | AAG | CTG | ACC | TTT | GCC | TTT | 1059 |
| Leu | Pro | Tyr | Gln | Phe | Tyr | Leu | Ala | Ser | Leu | Lys | Leu | Thr | Phe | Ala | Phe | |
| | 330 | | | | | 335 | | | | | 340 | | | | | |
| AAT | CAA | GAG | ACT | ATA | TCC | ACG | GTG | CTT | TAT | CCT | GAG | TGT | GTC | TGT | GAG | 1107 |
| Asn | Gln | Glu | Thr | Ile | Ser | Thr | Val | Leu | Tyr | Pro | Glu | Cys | Val | Cys | Glu | |
| 345 | | | | | 350 | | | | | 355 | | | | | 360 | |
| TCA | CCA | GTT | TCT | ATA | GTT | ACA | GGT | GAC | CTG | TGT | ACT | CAG | GAT | GGG | TTT | 1155 |
| Ser | Pro | Val | Ser | Ile | Val | Thr | Gly | Asp | Leu | Cys | Thr | Gln | Asp | Gly | Phe | |
| | | | | 365 | | | | | 370 | | | | | 375 | | |
| ATG | GAC | ATA | AAG | GTC | TAC | AGT | CAC | CAG | ACA | AAA | CCA | GCT | CTC | AAC | TTA | 1203 |
| Met | Asp | Ile | Lys | Val | Tyr | Ser | His | Gln | Thr | Lys | Pro | Ala | Leu | Asn | Leu | |
| | | | 380 | | | | | 385 | | | | | 390 | | | |
| GAA | ACC | CTA | AGG | GTG | GGA | GAC | TCA | TCC | TGC | CAA | CCT | ACC | TTC | CAG | GCT | 1251 |
| Glu | Thr | Leu | Arg | Val | Gly | Asp | Ser | Ser | Cys | Gln | Pro | Thr | Phe | Gln | Ala | |
| | | 395 | | | | | 400 | | | | | 405 | | | | |
| GCA | TCT | CAA | GGG | CTG | ATA | CTG | TTT | CAC | ATA | CCC | CTG | AAT | GGA | TGC | GGG | 1299 |
| Ala | Ser | Gln | Gly | Leu | Ile | Leu | Phe | His | Ile | Pro | Leu | Asn | Gly | Cys | Gly | |
| | 410 | | | | | 415 | | | | | 420 | | | | | |
| ACA | AGA | CAT | AAG | TTC | AAG | GAA | GGC | AAA | GTC | ATC | TAT | GAA | AAT | GAA | ATA | 1347 |
| Thr | Arg | His | Lys | Phe | Lys | Glu | Gly | Lys | Val | Ile | Tyr | Glu | Asn | Glu | Ile | |
| 425 | | | | 430 | | | | | 435 | | | | | | 440 | |
| CAT | GCT | GTC | TGG | GCG | GAT | CTT | CCT | CCA | AGC | ACA | ATT | TCT | AGA | GAT | AGT | 1395 |
| His | Ala | Val | Trp | Ala | Asp | Leu | Pro | Pro | Ser | Thr | Ile | Ser | Arg | Asp | Ser | |
| | | | | 445 | | | | | 450 | | | | | 455 | | |

```
GAA  TTC  AGA  ATG  ACA  GTG  CAG  TGC  CAT  TAC  AGC  AAA  GGT  GAC  CTG  CTA      1443
Glu  Phe  Arg  Met  Thr  Val  Gln  Cys  His  Tyr  Ser  Lys  Gly  Asp  Leu  Leu
               460                      465                      470

ATA  AAT  ACC  AGA  GTC  CAA  AGT  CTT  CCT  CCT  CTA  GAG  GCC  TCA  GTG  AGG      1491
Ile  Asn  Thr  Arg  Val  Gln  Ser  Leu  Pro  Pro  Leu  Glu  Ala  Ser  Val  Arg
          475                      480                      485

CCA  GGT  CCA  CTT  GCC  TTA  ATC  CTG  CAA  ACC  TAC  CCA  GAT  AAA  TCC  TAC      1539
Pro  Gly  Pro  Leu  Ala  Leu  Ile  Leu  Gln  Thr  Tyr  Pro  Asp  Lys  Ser  Tyr
     490                      495                      500

CTC  CAA  CCT  TAC  GGG  GAG  AAG  GAG  TAC  CCT  GTG  GTG  AGA  TAC  CTC  CGC      1587
Leu  Gln  Pro  Tyr  Gly  Glu  Lys  Glu  Tyr  Pro  Val  Val  Arg  Tyr  Leu  Arg
505                      510                      515                      520

CAA  CCA  ATT  TAT  CTG  GAA  GTG  AGA  GTC  CTA  AAT  AGG  TCT  GAC  CCC  AAC      1635
Gln  Pro  Ile  Tyr  Leu  Glu  Val  Arg  Val  Leu  Asn  Arg  Ser  Asp  Pro  Asn
               525                      530                      535

ATC  AAG  CTG  GTC  TTA  GAT  GAC  TGC  TGG  GCA  ACA  CCC  ACG  ATG  GAC  CCA      1683
Ile  Lys  Leu  Val  Leu  Asp  Asp  Cys  Trp  Ala  Thr  Pro  Thr  Met  Asp  Pro
          540                      545                      550

GCC  TCC  GTC  CCC  CAG  TGG  AAT  ATT  ATC  ATG  GAT  GGC  TGT  GAA  TAC  AAC      1731
Ala  Ser  Val  Pro  Gln  Trp  Asn  Ile  Ile  Met  Asp  Gly  Cys  Glu  Tyr  Asn
     555                      560                      565

CTG  GAC  AAC  CAC  AGA  ACC  ACC  TTC  CAT  CCA  GTT  GGC  TCC  TCT  GTG  ACC      1779
Leu  Asp  Asn  His  Arg  Thr  Thr  Phe  His  Pro  Val  Gly  Ser  Ser  Val  Thr
570                      575                      580

TAT  CCT  ACT  CAC  TAT  CGG  AGG  TTT  GAT  GTG  AAG  ACC  TTT  GCC  TTT  GTA      1827
Tyr  Pro  Thr  His  Tyr  Arg  Arg  Phe  Asp  Val  Lys  Thr  Phe  Ala  Phe  Val
               585                      590                      595                      600

TCA  GAG  GCC  CAA  GTG  CTT  TCT  AGT  CTG  GTC  TAC  TTC  CAC  TGC  AGT  GTC      1875
Ser  Glu  Ala  Gln  Val  Leu  Ser  Ser  Leu  Val  Tyr  Phe  His  Cys  Ser  Val
               605                      610                      615

TTA  ATC  TGC  AGT  CGA  CTG  TCT  GCT  GAC  TCC  CCT  CTG  TGT  TCC  GTG  ACT      1923
Leu  Ile  Cys  Ser  Arg  Leu  Ser  Ala  Asp  Ser  Pro  Leu  Cys  Ser  Val  Thr
               620                      625                      630

TGC  CCT  GTG  TCA  TTC  AGA  CAC  AGG  AGA  GCC  ACA  GGC  ACC  ACT  GAA  GAA      1971
Cys  Pro  Val  Ser  Phe  Arg  His  Arg  Arg  Ala  Thr  Gly  Thr  Thr  Glu  Glu
          635                      640                      645

GAG  AAA  ATG  ATA  GTG  AGT  CTT  CCA  GGA  CCC  ATC  CTC  CTG  CTG  TCA  GAT      2019
Glu  Lys  Met  Ile  Val  Ser  Leu  Pro  Gly  Pro  Ile  Leu  Leu  Leu  Ser  Asp
650                      655                      660

AGC  TCT  TCA  CTC  AGA  GAT  GTG  GTG  GAC  TCA  AAA  GGG  TAT  GGG  GCT  GCC      2067
Ser  Ser  Ser  Leu  Arg  Asp  Val  Val  Asp  Ser  Lys  Gly  Tyr  Gly  Ala  Ala
665                      670                      675                      680

GGA  TAT  GTT  GCT  TTT  AAG  ACT  GTG  GTA  GCT  GTG  GCT  GCC  TTA  GCA  GGC      2115
Gly  Tyr  Val  Ala  Phe  Lys  Thr  Val  Val  Ala  Val  Ala  Ala  Leu  Ala  Gly
                    685                      690                      695

CTC  GTG  GCA  ACG  CTA  GGC  TTC  ATC  ACC  TAC  CTG  CGC  AAG  AAC  AGA  ACC      2163
Leu  Val  Ala  Thr  Leu  Gly  Phe  Ile  Thr  Tyr  Leu  Arg  Lys  Asn  Arg  Thr
               700                      705                      710

ATG  ATA  AAT  CAC  TAAGGATTTT  CAAATAAAAT  GGTTGAAGTA  AAAAAAAAA             2215
Met  Ile  Asn  His
               715

AAAAAAAGCG  GCCGCGAATT  C                                                     2236
```

( 2 ) INFORMATION FOR SEQ ID NO:14:

( i ) SEQUENCE CHARACTERISTICS:
        ( A ) LENGTH: 716 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| Met | Ala | Ser | Arg | Gln | Lys | Gly | Asp | Ser | Gly | Ser | Pro | Ser | Ser | Trp | Phe |
| 1 | | | | 5 | | | | | 10 | | | | | 15 | |

| Asn | Ala | Asp | Trp | Ser | Thr | Tyr | Arg | Ser | Leu | Phe | Leu | Leu | Phe | Ile | Leu |
| | | | 20 | | | | | 25 | | | | | 30 | | |

| Val | Thr | Ser | Val | Asn | Ser | Ile | Gly | Val | Leu | Gln | Leu | Val | Asn | Pro | Val |
| | | 35 | | | | | 40 | | | | | 45 | | | |

| Phe | Pro | Gly | Thr | Val | Thr | Cys | Tyr | Glu | Thr | Arg | Met | Ala | Val | Glu | Phe |
| | 50 | | | | | 55 | | | | | 60 | | | | |

| Pro | Ser | Asp | Phe | Gly | Thr | Lys | Lys | Trp | His | Thr | Ser | Val | Val | Asp | Pro |
| 65 | | | | | 70 | | | | 75 | | | | | | 80 |

| Phe | Ser | Phe | Glu | Leu | Leu | Asn | Cys | Thr | Tyr | Ile | Leu | Asp | Pro | Glu | Asn |
| | | | | 85 | | | | | 90 | | | | | 95 | |

| Leu | Thr | Leu | Lys | Ala | Pro | Tyr | Glu | Thr | Cys | Thr | Arg | Arg | Thr | Leu | Gly |
| | | | 100 | | | | | 105 | | | | | 110 | | |

| Gln | His | Arg | Met | Ile | Ile | Arg | Leu | Lys | Asp | His | Asn | Ala | Ala | Ser | Arg |
| | | 115 | | | | | 120 | | | | | 125 | | | |

| His | Asn | Ser | Leu | Met | Tyr | Gln | Ile | Asn | Cys | Pro | Val | Met | Gln | Ala | Glu |
| | 130 | | | | | 135 | | | | | 140 | | | | |

| Glu | Thr | His | Glu | His | Ala | Gly | Ser | Thr | Ile | Cys | Thr | Lys | Asp | Ser | Met |
| 145 | | | | | 150 | | | | | 155 | | | | | 160 |

| Ser | Phe | Thr | Phe | Asn | Val | Ile | Pro | Gly | Leu | Ala | Asp | Glu | Asn | Thr | Asp |
| | | | | 165 | | | | | 170 | | | | | 175 | |

| Ile | Lys | Asn | Pro | Met | Gly | Trp | Ser | Ile | Glu | Val | Gly | Asp | Gly | Thr | Lys |
| | | | 180 | | | | | 185 | | | | | 190 | | |

| Ala | Lys | Thr | Leu | Thr | Leu | Gln | Asp | Val | Leu | Arg | Gln | Gly | Tyr | Asn | Ile |
| | | 195 | | | | | 200 | | | | | 205 | | | |

| Leu | Phe | Asp | Asn | His | Lys | Ile | Thr | Phe | Gln | Val | Ser | Phe | Asn | Ala | Thr |
| | 210 | | | | | 215 | | | | | 220 | | | | |

| Gly | Val | Thr | His | Tyr | Met | Gln | Gly | Asn | Ser | His | Leu | Tyr | Met | Val | Pro |
| 225 | | | | | 230 | | | | | 235 | | | | | 240 |

| Leu | Lys | Leu | Ile | His | Glu | Ser | Leu | Gly | Gln | Lys | Ile | Ile | Leu | Thr | Thr |
| | | | | 245 | | | | | 250 | | | | | 255 | |

| Arg | Val | Leu | Cys | Met | Ser | Asp | Ala | Val | Thr | Cys | Asn | Ala | Thr | His | Val |
| | | | 260 | | | | | 265 | | | | | 270 | | |

| Thr | Leu | Thr | Ile | Pro | Glu | Phe | Pro | Gly | Lys | Leu | Lys | Ser | Val | Ser | Ser |
| | | 275 | | | | | 280 | | | | | 285 | | | |

| Glu | Asn | Arg | Asn | Phe | Ala | Val | Ser | Gln | Leu | His | Asn | Asn | Gly | Ile | Asp |
| | 290 | | | | | 295 | | | | | 300 | | | | |

| Lys | Glu | Glu | Ser | Ser | Gly | Leu | Thr | Leu | His | Phe | Ser | Lys | Thr | Leu | Leu |
| 305 | | | | | 310 | | | | | 315 | | | | | 320 |

| Lys | Met | Glu | Phe | Ser | Glu | Lys | Cys | Leu | Pro | Tyr | Gln | Phe | Tyr | Leu | Ala |
| | | | | 325 | | | | | 330 | | | | | 335 | |

| Ser | Leu | Lys | Leu | Thr | Phe | Ala | Phe | Asn | Gln | Glu | Thr | Ile | Ser | Thr | Val |
| | | | 340 | | | | | 345 | | | | | 350 | | |

| Leu | Tyr | Pro | Glu | Cys | Val | Cys | Glu | Ser | Pro | Val | Ser | Ile | Val | Thr | Gly |
| | | 355 | | | | | 360 | | | | | 365 | | | |

| Asp | Leu | Cys | Thr | Gln | Asp | Gly | Phe | Met | Asp | Ile | Lys | Val | Tyr | Ser | His |
| | 370 | | | | | 375 | | | | | 380 | | | | |

| Gln | Thr | Lys | Pro | Ala | Leu | Asn | Leu | Glu | Thr | Leu | Arg | Val | Gly | Asp | Ser |
| 385 | | | | | 390 | | | | | 395 | | | | | 400 |

| Ser | Cys | Gln | Pro | Thr | Phe | Gln | Ala | Ala | Ser | Gln | Gly | Leu | Ile | Leu | Phe |
| | | | | 405 | | | | | 410 | | | | | 415 | |

His Ile Pro Leu Asn Gly Cys Gly Thr Arg His Lys Phe Lys Glu Gly
              420                     425                 430

Lys Val Ile Tyr Glu Asn Glu Ile His Ala Val Trp Ala Asp Leu Pro
          435                 440                 445

Pro Ser Thr Ile Ser Arg Asp Ser Glu Phe Arg Met Thr Val Gln Cys
      450                 455                 460

His Tyr Ser Lys Gly Asp Leu Leu Ile Asn Thr Arg Val Gln Ser Leu
465                 470                 475                     480

Pro Pro Leu Glu Ala Ser Val Arg Pro Gly Pro Leu Ala Leu Ile Leu
                485                     490                 495

Gln Thr Tyr Pro Asp Lys Ser Tyr Leu Gln Pro Tyr Gly Glu Lys Glu
              500                 505                 510

Tyr Pro Val Val Arg Tyr Leu Arg Gln Pro Ile Tyr Leu Glu Val Arg
          515                 520                 525

Val Leu Asn Arg Ser Asp Pro Asn Ile Lys Leu Val Leu Asp Asp Cys
    530                 535                 540

Trp Ala Thr Pro Thr Met Asp Pro Ala Ser Val Pro Gln Trp Asn Ile
545                     550                 555                 560

Ile Met Asp Gly Cys Glu Tyr Asn Leu Asp Asn His Arg Thr Thr Phe
              565                 570                     575

His Pro Val Gly Ser Ser Val Thr Tyr Pro Thr His Tyr Arg Arg Phe
              580                 585                 590

Asp Val Lys Thr Phe Ala Phe Val Ser Glu Ala Gln Val Leu Ser Ser
        595                 600                 605

Leu Val Tyr Phe His Cys Ser Val Leu Ile Cys Ser Arg Leu Ser Ala
        610                 615                 620

Asp Ser Pro Leu Cys Ser Val Thr Cys Pro Val Ser Phe Arg His Arg
625                 630                 635                     640

Arg Ala Thr Gly Thr Thr Glu Glu Glu Lys Met Ile Val Ser Leu Pro
              645                     650                 655

Gly Pro Ile Leu Leu Leu Ser Asp Ser Ser Ser Leu Arg Asp Val Val
          660                 665                 670

Asp Ser Lys Gly Tyr Gly Ala Ala Gly Tyr Val Ala Phe Lys Thr Val
        675                 680                 685

Val Ala Val Ala Ala Leu Ala Gly Leu Val Ala Thr Leu Gly Phe Ile
    690                 695                 700

Thr Tyr Leu Arg Lys Asn Arg Thr Met Ile Asn His
705                 710                 715

( 2 ) INFORMATION FOR SEQ ID NO:15:

( i ) SEQUENCE CHARACTERISTICS:
        ( A ) LENGTH: 1840 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Felis domesticus
        ( D ) DEVELOPMENTAL STAGE: Juvenile
        ( E ) HAPLOTYPE: Diploidy
        ( F ) TISSUE TYPE: Ovary
        ( G ) CELL TYPE: Oocyte (ix) FEATURE:
    (A) NAME/KEY: CDS
    (B) LOCATION: 57..1766

(xi) SEQUENCE DESCRIPTION: SEQ ID NO:15:

```
GAATTCCGCG GCCGCAAGTA CAGGTCTTGC AGCCAGTGGG GGCTCCCGAT GGCATC                              56

ATG TGG CTG CTG CAG CCC CTC TTG CTC TGT GTT CCC TTG TCT CTC GCT                           104
Met Trp Leu Leu Gln Pro Leu Leu Leu Cys Val Pro Leu Ser Leu Ala
 1               5                  10                  15

GTG CAT GGC CAG CAG AAG CCC CAG GTA CCA GAT TAT CCC GGT GAA CTC                           152
Val His Gly Gln Gln Lys Pro Gln Val Pro Asp Tyr Pro Gly Glu Leu
                20                  25                  30

CAT TGT GGG CTC CAG AGC CTT CAG TTT GCC ATA AAC CCG AGC CCC GGG                           200
His Cys Gly Leu Gln Ser Leu Gln Phe Ala Ile Asn Pro Ser Pro Gly
        35                  40                  45

AAA GCG ACT CCT GCA CTC ATA GTC TGG GAC AAT CGC GGG CTG CCA CAC                           248
Lys Ala Thr Pro Ala Leu Ile Val Trp Asp Asn Arg Gly Leu Pro His
 50                  55                  60

AAG CTG CAG AAC AAC TCT GGC TGC GGT ACC TGG GTA AGG GAG AGC CCG                           296
Lys Leu Gln Asn Asn Ser Gly Cys Gly Thr Trp Val Arg Glu Ser Pro
 65                  70                  75                  80

GGG GGC TCC GTG CTG TTA GAC GCC TCT TAC AGC AGC TGC TAT GTC AAC                           344
Gly Gly Ser Val Leu Leu Asp Ala Ser Tyr Ser Ser Cys Tyr Val Asn
                85                  90                  95

GAG TGG GTG AGC ACG ACC CAA TCC CCA GGA ACG TCG AGG CCC CCC ACC                           392
Glu Trp Val Ser Thr Thr Gln Ser Pro Gly Thr Ser Arg Pro Pro Thr
               100                 105                 110

CCA GCA TCC AGG GTG ACT CCC CAG GAC TCC CAC TAC GTC ATG ATA GTC                           440
Pro Ala Ser Arg Val Thr Pro Gln Asp Ser His Tyr Val Met Ile Val
            115                 120                 125

GGA GTT GAA GGC ACA GAT GCG GCT GGG CGC AGG GTT ACC AAC ACC AAG                           488
Gly Val Glu Gly Thr Asp Ala Ala Gly Arg Arg Val Thr Asn Thr Lys
        130                 135                 140

GTG CTC AGG TGT CCT AGG AAT CCC CCA GAC CAA GCT TTG GTG TCG AGC                           536
Val Leu Arg Cys Pro Arg Asn Pro Pro Asp Gln Ala Leu Val Ser Ser
145                 150                 155                 160

TTA AGT CCC TCT CCT CTT CAA AAC GTA GCA CTA GAA GCT CCA AAC GCT                           584
Leu Ser Pro Ser Pro Leu Gln Asn Val Ala Leu Glu Ala Pro Asn Ala
                165                 170                 175

GAC TTG TGT GAC TCT GTC CCA AAG TGG GAC AGG CTT CCG TGT GCT TCT                           632
Asp Leu Cys Asp Ser Val Pro Lys Trp Asp Arg Leu Pro Cys Ala Ser
            180                 185                 190

TCA CCC ATC ACT CAG GGA GAC TGC AAT AAG CTT GGT TGC TGC TAC AAA                           680
Ser Pro Ile Thr Gln Gly Asp Cys Asn Lys Leu Gly Cys Cys Tyr Lys
        195                 200                 205

TCA GAG GCA AAT TCC TGT TAC TAT GGA AAC ACA GTG ACC TCA CGC TGT                           728
Ser Glu Ala Asn Ser Cys Tyr Tyr Gly Asn Thr Val Thr Ser Arg Cys
210                 215                 220

ACC CAA GAC GGC CAC TTC TCC ATC GCC GTG TCT CGG AAC GTG ACC TCA                           776
Thr Gln Asp Gly His Phe Ser Ile Ala Val Ser Arg Asn Val Thr Ser
225                 230                 235                 240

CCC CCA CTG CTC TTA AAT TCT CTG CGC TTG GCC TTC GGG AAG GAC CGC                           824
Pro Pro Leu Leu Leu Asn Ser Leu Arg Leu Ala Phe Gly Lys Asp Arg
                245                 250                 255

GAA TGT AAC CCT GTG AAA GCA ACA CGT GCC TTT GCC CTG TTC TTT TTT                           872
Glu Cys Asn Pro Val Lys Ala Thr Arg Ala Phe Ala Leu Phe Phe Phe
            260                 265                 270

CCA TTT AAT TCC TGT GGC ACC ACG AGA TGG GTC ACT GGA GAC CAG GCA                           920
Pro Phe Asn Ser Cys Gly Thr Thr Arg Trp Val Thr Gly Asp Gln Ala
        275                 280                 285
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| GTA | TAT | GAA | AAT | GAG | CTG | GTG | GCA | GCT | AGA | GAT | GTG | AGA | ACT | TGG | AGC | 968 |
| Val | Tyr | Glu | Asn | Glu | Leu | Val | Ala | Ala | Arg | Asp | Val | Arg | Thr | Trp | Ser |   |
|     | 290 |     |     |     | 295 |     |     |     |     |     | 300 |     |     |     |     |   |
| CAT | GGT | TCT | ATT | ACC | CGT | GAC | AGT | ATC | TTC | AGG | CTT | CGA | GTT | AGC | TGC | 1016 |
| His | Gly | Ser | Ile | Thr | Arg | Asp | Ser | Ile | Phe | Arg | Leu | Arg | Val | Ser | Cys |   |
| 305 |     |     |     |     | 310 |     |     |     |     | 315 |     |     |     |     | 320 |   |
| AGC | TAC | TCT | GTA | AGG | AGT | AAT | GCC | TTC | CCG | CTT | AGC | GTT | CAG | GTG | TTT | 1064 |
| Ser | Tyr | Ser | Val | Arg | Ser | Asn | Ala | Phe | Pro | Leu | Ser | Val | Gln | Val | Phe |   |
|     |     |     |     | 325 |     |     |     |     | 330 |     |     |     |     | 335 |     |   |
| ACC | ATC | CCA | CCA | CCC | CAT | CTG | AAA | ACC | CAG | CAT | GGA | CCC | CTC | ACT | CTG | 1112 |
| Thr | Ile | Pro | Pro | Pro | His | Leu | Lys | Thr | Gln | His | Gly | Pro | Leu | Thr | Leu |   |
|     |     |     | 340 |     |     |     |     | 345 |     |     |     |     | 350 |     |     |   |
| GAA | CTC | AAG | ATT | GCC | AAA | GAT | AAG | CAC | TAT | GGC | TCC | TAC | TAC | ACT | ATT | 1160 |
| Glu | Leu | Lys | Ile | Ala | Lys | Asp | Lys | His | Tyr | Gly | Ser | Tyr | Tyr | Thr | Ile |   |
|     |     | 355 |     |     |     |     | 360 |     |     |     |     | 365 |     |     |     |   |
| GGT | GAC | TAC | CCA | GTG | GTA | AAG | TTG | CTT | CGG | GAT | CCC | ATT | TAT | GTG | GAG | 1208 |
| Gly | Asp | Tyr | Pro | Val | Val | Lys | Leu | Leu | Arg | Asp | Pro | Ile | Tyr | Val | Glu |   |
|     | 370 |     |     |     |     | 375 |     |     |     |     | 380 |     |     |     |     |   |
| GTC | TCT | ATC | CGC | CAC | AGA | ACG | GAC | CCC | TCC | CTG | GGG | CTG | CTC | CTC | CAT | 1256 |
| Val | Ser | Ile | Arg | His | Arg | Thr | Asp | Pro | Ser | Leu | Gly | Leu | Leu | Leu | His |   |
| 385 |     |     |     |     | 390 |     |     |     |     | 395 |     |     |     |     | 400 |   |
| AAC | TGT | TGG | GCC | ACA | CCC | GGC | AAG | AAC | TCC | CAG | AGT | CTG | TCC | CAG | TGG | 1304 |
| Asn | Cys | Trp | Ala | Thr | Pro | Gly | Lys | Asn | Ser | Gln | Ser | Leu | Ser | Gln | Trp |   |
|     |     |     |     | 405 |     |     |     |     | 410 |     |     |     |     | 415 |     |   |
| CCC | ATT | CTG | GTG | AAA | GGA | TGC | CCC | TAC | GTT | GGA | GAC | AAC | TAT | CAA | ACC | 1352 |
| Pro | Ile | Leu | Val | Lys | Gly | Cys | Pro | Tyr | Val | Gly | Asp | Asn | Tyr | Gln | Thr |   |
|     |     |     | 420 |     |     |     |     | 425 |     |     |     |     | 430 |     |     |   |
| CAG | CTG | ATC | CCT | GTC | CAG | AAG | GCT | CTG | GAT | ACA | CCA | TTT | CCA | TCT | TAC | 1400 |
| Gln | Leu | Ile | Pro | Val | Gln | Lys | Ala | Leu | Asp | Thr | Pro | Phe | Pro | Ser | Tyr |   |
|     |     | 435 |     |     |     |     | 440 |     |     |     |     | 445 |     |     |     |   |
| TAC | AAG | CGC | TTC | AGT | ATT | TTC | ACC | TTC | AGC | TTT | GTG | GAC | ACC | ATG | GCA | 1448 |
| Tyr | Lys | Arg | Phe | Ser | Ile | Phe | Thr | Phe | Ser | Phe | Val | Asp | Thr | Met | Ala |   |
|     | 450 |     |     |     |     | 455 |     |     |     |     | 460 |     |     |     |     |   |
| AAG | TGG | GCA | CTC | AGG | GGA | CCG | GTG | TAT | CTG | CAC | TGT | AAT | GTA | TCC | ATC | 1496 |
| Lys | Trp | Ala | Leu | Arg | Gly | Pro | Val | Tyr | Leu | His | Cys | Asn | Val | Ser | Ile |   |
| 465 |     |     |     |     | 470 |     |     |     |     | 475 |     |     |     |     | 480 |   |
| TGC | CAG | CCT | GCT | GGG | ACC | TCC | TCC | TGT | AGG | ATA | ACC | TGT | CCT | GTT | GCC | 1544 |
| Cys | Gln | Pro | Ala | Gly | Thr | Ser | Ser | Cys | Arg | Ile | Thr | Cys | Pro | Val | Ala |   |
|     |     |     |     | 485 |     |     |     |     | 490 |     |     |     |     | 495 |     |   |
| AGG | CGA | AGA | AGA | CAC | TCT | GAC | CTC | CAT | CAT | CAC | AGC | AGT | ACT | GCG | AGC | 1592 |
| Arg | Arg | Arg | Arg | His | Ser | Asp | Leu | His | His | His | Ser | Ser | Thr | Ala | Ser |   |
|     |     |     |     | 500 |     |     |     |     | 505 |     |     |     |     | 510 |     |   |
| ATC | TCT | AGC | AAG | GGT | CCC | ATG | ATT | CTA | CTC | CAA | GCC | ACT | ATG | GAC | TCT | 1640 |
| Ile | Ser | Ser | Lys | Gly | Pro | Met | Ile | Leu | Leu | Gln | Ala | Thr | Met | Asp | Ser |   |
|     |     | 515 |     |     |     |     | 520 |     |     |     |     | 525 |     |     |     |   |
| GCA | GAG | AAG | CTC | CAC | AAA | AAC | TCA | AGT | TCT | CCT | ATA | GAC | TCC | CAA | GCT | 1688 |
| Ala | Glu | Lys | Leu | His | Lys | Asn | Ser | Ser | Ser | Pro | Ile | Asp | Ser | Gln | Ala |   |
|     | 530 |     |     |     |     | 535 |     |     |     |     | 540 |     |     |     |     |   |
| CTG | TGG | ATG | GCA | GGC | CTT | TCC | GGG | ACC | CTA | ATC | TTT | GGA | TTC | TTG | TTA | 1736 |
| Leu | Trp | Met | Ala | Gly | Leu | Ser | Gly | Thr | Leu | Ile | Phe | Gly | Phe | Leu | Leu |   |
| 545 |     |     |     |     | 550 |     |     |     |     | 555 |     |     |     |     | 560 |   |
| GTG | TCC | TAC | TTG | GCT | ATC | AGG | AAA | CGG | AGG | TGAATTATTC | | CAGTTGTGTT | | | | 1786 |
| Val | Ser | Tyr | Leu | Ala | Ile | Arg | Lys | Arg | Arg |     |     |     |     |     |     |   |
|     |     |     |     | 565 |     |     |     | 570 |     |     |     |     |     |     |     |   |

AATAAAACCA GATTGCATTA CCAAAAAAAA AAAAAAAAAA GCGGCCGCGA ATTC          1840

( 2 ) INFORMATION FOR SEQ ID NO:16:

( i ) SEQUENCE CHARACTERISTICS:
        ( A ) LENGTH: 570 amino acids
        ( B ) TYPE: amino acid ( D ) TOPOLOGY: linear ( i i ) MOLECULE TYPE: protein ( x i ) SEQUENCE DESCRIPTION: SEQ ID NO:16:

| Met | Trp | Leu | Leu | Gln | Pro | Leu | Leu | Leu | Cys | Val | Pro | Leu | Ser | Leu | Ala |
|---|---|---|---|---|---|---|---|---|---|---|---|---|---|---|---|
| 1 | | | | 5 | | | | | 10 | | | | | 15 | |
| Val | His | Gly | Gln | Gln | Lys | Pro | Gln | Val | Pro | Asp | Tyr | Pro | Gly | Glu | Leu |
| | | | 20 | | | | 25 | | | | | 30 | | | |
| His | Cys | Gly | Leu | Gln | Ser | Leu | Gln | Phe | Ala | Ile | Asn | Pro | Ser | Pro | Gly |
| | | 35 | | | | 40 | | | | | 45 | | | | |
| Lys | Ala | Thr | Pro | Ala | Leu | Ile | Val | Trp | Asp | Asn | Arg | Gly | Leu | Pro | His |
| | 50 | | | | | 55 | | | | | 60 | | | | |
| Lys | Leu | Gln | Asn | Asn | Ser | Gly | Cys | Gly | Thr | Trp | Val | Arg | Glu | Ser | Pro |
| 65 | | | | | 70 | | | | | 75 | | | | | 80 |
| Gly | Gly | Ser | Val | Leu | Leu | Asp | Ala | Ser | Tyr | Ser | Ser | Cys | Tyr | Val | Asn |
| | | | | 85 | | | | | 90 | | | | | 95 | |
| Glu | Trp | Val | Ser | Thr | Thr | Gln | Ser | Pro | Gly | Thr | Ser | Arg | Pro | Pro | Thr |
| | | | 100 | | | | | 105 | | | | | 110 | | |
| Pro | Ala | Ser | Arg | Val | Thr | Pro | Gln | Asp | Ser | His | Tyr | Val | Met | Ile | Val |
| | | | 115 | | | | 120 | | | | | 125 | | | |
| Gly | Val | Glu | Gly | Thr | Asp | Ala | Ala | Gly | Arg | Arg | Val | Thr | Asn | Thr | Lys |
| | | 130 | | | | | 135 | | | | | 140 | | | |
| Val | Leu | Arg | Cys | Pro | Arg | Asn | Pro | Pro | Asp | Gln | Ala | Leu | Val | Ser | Ser |
| 145 | | | | | 150 | | | | | 155 | | | | | 160 |
| Leu | Ser | Pro | Ser | Pro | Leu | Gln | Asn | Val | Ala | Leu | Glu | Ala | Pro | Asn | Ala |
| | | | | 165 | | | | | 170 | | | | | 175 | |
| Asp | Leu | Cys | Asp | Ser | Val | Pro | Lys | Trp | Asp | Arg | Leu | Pro | Cys | Ala | Ser |
| | | | 180 | | | | | 185 | | | | | 190 | | |
| Ser | Pro | Ile | Thr | Gln | Gly | Asp | Cys | Asn | Lys | Leu | Gly | Cys | Cys | Tyr | Lys |
| | | 195 | | | | | 200 | | | | | 205 | | | |
| Ser | Glu | Ala | Asn | Ser | Cys | Tyr | Tyr | Gly | Asn | Thr | Val | Thr | Ser | Arg | Cys |
| | 210 | | | | | 215 | | | | | 220 | | | | |
| Thr | Gln | Asp | Gly | His | Phe | Ser | Ile | Ala | Val | Ser | Arg | Asn | Val | Thr | Ser |
| 225 | | | | | 230 | | | | | 235 | | | | | 240 |
| Pro | Pro | Leu | Leu | Leu | Asn | Ser | Leu | Arg | Leu | Ala | Phe | Gly | Lys | Asp | Arg |
| | | | | 245 | | | | | 250 | | | | | 255 | |
| Glu | Cys | Asn | Pro | Val | Lys | Ala | Thr | Arg | Ala | Phe | Ala | Leu | Phe | Phe | Phe |
| | | | 260 | | | | | 265 | | | | | 270 | | |
| Pro | Phe | Asn | Ser | Cys | Gly | Thr | Thr | Arg | Trp | Val | Thr | Gly | Asp | Gln | Ala |
| | | | 275 | | | | | 280 | | | | | 285 | | |
| Val | Tyr | Glu | Asn | Glu | Leu | Val | Ala | Ala | Arg | Asp | Val | Arg | Thr | Trp | Ser |
| | | 290 | | | | | 295 | | | | | 300 | | | |
| His | Gly | Ser | Ile | Thr | Arg | Asp | Ser | Ile | Phe | Arg | Leu | Arg | Val | Ser | Cys |
| 305 | | | | | 310 | | | | | 315 | | | | | 320 |
| Ser | Tyr | Ser | Val | Arg | Ser | Asn | Ala | Phe | Pro | Leu | Ser | Val | Gln | Val | Phe |
| | | | | 325 | | | | | 330 | | | | | 335 | |
| Thr | Ile | Pro | Pro | Pro | His | Leu | Lys | Thr | Gln | His | Gly | Pro | Leu | Thr | Leu |
| | | | 340 | | | | | 345 | | | | | 350 | | |
| Glu | Leu | Lys | Ile | Ala | Lys | Asp | Lys | His | Tyr | Gly | Ser | Tyr | Tyr | Thr | Ile |
| | | 355 | | | | | 360 | | | | | 365 | | | |
| Gly | Asp | Tyr | Pro | Val | Val | Lys | Leu | Leu | Arg | Asp | Pro | Ile | Tyr | Val | Glu |
| | | 370 | | | | 375 | | | | | 380 | | | | |
| Val | Ser | Ile | Arg | His | Arg | Thr | Asp | Pro | Ser | Leu | Gly | Leu | Leu | Leu | His |
| 385 | | | | | 390 | | | | | 395 | | | | | 400 |

| | | | | | | | | | | | | | | |
|---|---|---|---|---|---|---|---|---|---|---|---|---|---|---|
| Asn | Cys | Trp | Ala | Thr 405 | Pro | Gly | Lys | Asn | Ser 410 | Gln | Ser | Leu | Ser 415 | Gln | Trp |
| Pro | Ile | Leu | Val 420 | Lys | Gly | Cys | Pro | Tyr 425 | Val | Gly | Asp | Asn | Tyr 430 | Gln | Thr |
| Gln | Leu | Ile 435 | Pro | Val | Gln | Lys | Ala 440 | Leu | Asp | Thr | Pro | Phe 445 | Pro | Ser | Tyr |
| Tyr | Lys 450 | Arg | Phe | Ser | Ile | Phe 455 | Thr | Phe | Ser | Phe | Val 460 | Asp | Thr | Met | Ala |
| Lys 465 | Trp | Ala | Leu | Arg | Gly 470 | Pro | Val | Tyr | Leu | His 475 | Cys | Asn | Val | Ser | Ile 480 |
| Cys | Gln | Pro | Ala | Gly 485 | Thr | Ser | Ser | Cys | Arg 490 | Ile | Thr | Cys | Pro | Val 495 | Ala |
| Arg | Arg | Arg | Arg 500 | His | Ser | Asp | Leu | His 505 | His | His | Ser | Ser | Thr 510 | Ala | Ser |
| Ile | Ser | Ser 515 | Lys | Gly | Pro | Met | Ile 520 | Leu | Leu | Gln | Ala | Thr 525 | Met | Asp | Ser |
| Ala | Glu 530 | Lys | Leu | His | Lys | Asn 535 | Ser | Ser | Ser | Pro | Ile 540 | Asp | Ser | Gln | Ala |
| Leu 545 | Trp | Met | Ala | Gly | Leu 550 | Ser | Gly | Thr | Leu | Ile 555 | Phe | Gly | Phe | Leu | Leu 560 |
| Val | Ser | Tyr | Leu | Ala 565 | Ile | Arg | Lys | Arg 570 | Arg | | | | | | |

( 2 ) INFORMATION FOR SEQ ID NO:17:

( i ) SEQUENCE CHARACTERISTICS:
        ( A ) LENGTH: 1319 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Felis domesticus
        ( D ) DEVELOPMENTAL STAGE: Juvenile
        ( E ) HAPLOTYPE: Diploidy
        ( F ) TISSUE TYPE: Ovary
        ( G ) CELL TYPE: Oocyte ( i x ) FEATURE:
        ( A ) NAME/KEY: CDS
        ( B ) LOCATION: 26..1297

( x i ) SEQUENCE DESCRIPTION: SEQ ID NO:17:

| | | | | | | | | | | | | | |
|---|---|---|---|---|---|---|---|---|---|---|---|---|---|
| GAATTCGCGG | CCGCGCGTAG | GCCGC | ATG<br>Met<br>1 | GGG<br>Gly | CTG<br>Leu | AGC<br>Ser | TAC<br>Tyr<br>5 | GGG<br>Gly | CTT<br>Leu | TTC<br>Phe | ATC<br>Ile | | 52 |
| TGT<br>Cys<br>10 | TTT<br>Phe | CTG<br>Leu | CTT<br>Leu | TGG<br>Trp | GCA<br>Ala<br>15 | GGC<br>Gly | ACG<br>Thr | GGG<br>Gly | CTG<br>Leu | TGC<br>Cys<br>20 | TAT<br>Tyr | CCC<br>Pro | CCA<br>Pro | ACC<br>Thr | ACC<br>Thr<br>25 | 100 |
| ACC<br>Thr | GAG<br>Glu | GAT<br>Asp | AAG<br>Lys | ACC<br>Thr<br>30 | CAC<br>His | CCC<br>Pro | TCG<br>Ser | TTG<br>Leu | CCA<br>Pro<br>35 | TCA<br>Ser | AGC<br>Ser | CCC<br>Pro | TCT<br>Ser | GTG<br>Val<br>40 | GTG<br>Val | 148 |
| GTA<br>Val | GAG<br>Glu | TGT<br>Cys | CGG<br>Arg<br>45 | CAT<br>His | GCC<br>Ala | TGG<br>Trp | CTG<br>Leu | GTG<br>Val<br>50 | GTC<br>Val | AAC<br>Asn | GTC<br>Val | AGC<br>Ser | AAA<br>Lys<br>55 | AAC<br>Asn | CTT<br>Leu | 196 |
| TTT<br>Phe | GGT<br>Gly | ACT<br>Thr | GGG<br>Gly | AGG<br>Arg | CTT<br>Leu | GTG<br>Val | AGG<br>Arg | CCT<br>Pro | GCA<br>Ala | GAC<br>Asp | CTC<br>Leu | ACC<br>Thr | CTG<br>Leu | GGT<br>Gly | CCG<br>Pro | 244 |

-continued

|  |  |  |  |  | 60 |  |  |  |  | 65 |  |  |  |  | 70 |  |  |  |
|---|---|---|---|---|---|---|---|---|---|---|---|---|---|---|---|---|---|---|
| GAG | AAC | TGT | GAG | CCC | CTG | ATC | TCT | GGG | GAC | TCA | GAT | GAT | ACG | GTC | AGG | | | 292 |
| Glu | Asn | Cys | Glu | Pro | Leu | Ile | Ser | Gly | Asp | Ser | Asp | Asp | Thr | Val | Arg | | | |
| | 75 | | | | | | 80 | | | | | 85 | | | | | | |
| TTT | GAA | GTC | GAG | CTC | CAC | AAG | TGT | GGC | AAC | AGC | GTG | CAG | GTG | ACC | GAA | | | 340 |
| Phe | Glu | Val | Glu | Leu | His | Lys | Cys | Gly | Asn | Ser | Val | Gln | Val | Thr | Glu | | | |
| 90 | | | | | 95 | | | | | 100 | | | | | 105 | | | |
| GAT | GCC | CTG | GTG | TAT | AGC | ACC | TTC | CTG | CTC | CAC | AAC | CCC | CGC | CCC | ATG | | | 388 |
| Asp | Ala | Leu | Val | Tyr | Ser | Thr | Phe | Leu | Leu | His | Asn | Pro | Arg | Pro | Met | | | |
| | | | | 110 | | | | | 115 | | | | | 120 | | | | |
| GGA | AAC | CTG | TCC | ATC | CTG | AGG | ACC | AAC | CGC | GCG | GAA | GTT | CCC | ATT | GAG | | | 436 |
| Gly | Asn | Leu | Ser | Ile | Leu | Arg | Thr | Asn | Arg | Ala | Glu | Val | Pro | Ile | Glu | | | |
| | | | 125 | | | | | 130 | | | | | 135 | | | | | |
| TGC | CGT | TAC | CCC | AGG | CAT | AGC | AAC | GTG | AGC | AGC | GAG | GCC | ATC | CTG | CCC | | | 484 |
| Cys | Arg | Tyr | Pro | Arg | His | Ser | Asn | Val | Ser | Ser | Glu | Ala | Ile | Leu | Pro | | | |
| | | 140 | | | | | 145 | | | | | 150 | | | | | | |
| ACC | TGG | GTG | CCC | TTC | AGG | ACC | ACA | ATG | CTC | TCA | GAG | GAG | AAG | CTG | GCT | | | 532 |
| Thr | Trp | Val | Pro | Phe | Arg | Thr | Thr | Met | Leu | Ser | Glu | Glu | Lys | Leu | Ala | | | |
| | 155 | | | | | 160 | | | | | 165 | | | | | | | |
| TTC | TCT | CTG | CGC | CTG | ATG | GAG | GAG | GAC | TGG | GGC | TCC | GAG | AAG | CAG | TCC | | | 580 |
| Phe | Ser | Leu | Arg | Leu | Met | Glu | Glu | Asp | Trp | Gly | Ser | Glu | Lys | Gln | Ser | | | |
| 170 | | | | | 175 | | | | | 180 | | | | | 185 | | | |
| CCC | ACT | TTC | CAG | TTG | GGA | GAC | CTA | GCC | CAC | CTC | CAG | GCC | GAA | GTC | CAC | | | 628 |
| Pro | Thr | Phe | Gln | Leu | Gly | Asp | Leu | Ala | His | Leu | Gln | Ala | Glu | Val | His | | | |
| | | | | 190 | | | | | 195 | | | | | 200 | | | | |
| ACC | GGC | CGC | CAC | ATA | CCA | CTG | CGA | CTG | TTT | GTG | GAC | TAC | TGT | GTG | GCC | | | 676 |
| Thr | Gly | Arg | His | Ile | Pro | Leu | Arg | Leu | Phe | Val | Asp | Tyr | Cys | Val | Ala | | | |
| | | | 205 | | | | | 210 | | | | | 215 | | | | | |
| ACG | CTG | ACA | CCA | GAC | CAG | AAC | GCC | TCC | CCT | CAT | CAC | ACC | ATC | GTG | GAC | | | 724 |
| Thr | Leu | Thr | Pro | Asp | Gln | Asn | Ala | Ser | Pro | His | His | Thr | Ile | Val | Asp | | | |
| | | 220 | | | | | 225 | | | | | 230 | | | | | | |
| TTC | CAC | GGC | TGT | CTC | GTG | GAT | GGT | CTC | TCT | GAT | GCC | TCT | TCT | GCC | TTC | | | 772 |
| Phe | His | Gly | Cys | Leu | Val | Asp | Gly | Leu | Ser | Asp | Ala | Ser | Ser | Ala | Phe | | | |
| | 235 | | | | | 240 | | | | | 245 | | | | | | | |
| AAA | GCC | CCC | AGA | CCC | AGG | CCG | GAG | ACT | CTC | CAG | TTT | ACA | GTA | GAC | ACG | | | 820 |
| Lys | Ala | Pro | Arg | Pro | Arg | Pro | Glu | Thr | Leu | Gln | Phe | Thr | Val | Asp | Thr | | | |
| 250 | | | | | 255 | | | | | 260 | | | | | 265 | | | |
| TTC | CAC | TTT | GCT | AAT | GAC | CCC | AGA | AAC | ATG | ATC | TAT | ATC | ACC | TGC | CAT | | | 868 |
| Phe | His | Phe | Ala | Asn | Asp | Pro | Arg | Asn | Met | Ile | Tyr | Ile | Thr | Cys | His | | | |
| | | | | 270 | | | | | 275 | | | | | 280 | | | | |
| CTG | AAA | GTC | ACT | CCA | GCT | AGC | CGA | GTC | CCA | GAC | CAG | CTA | AAC | AAA | GCC | | | 916 |
| Leu | Lys | Val | Thr | Pro | Ala | Ser | Arg | Val | Pro | Asp | Gln | Leu | Asn | Lys | Ala | | | |
| | | | 285 | | | | | 290 | | | | | 295 | | | | | |
| TGT | TCC | TTC | ATC | AAG | TCT | TCT | AAC | AGG | TGG | TTC | CCA | GTA | GAA | GGC | CCT | | | 964 |
| Cys | Ser | Phe | Ile | Lys | Ser | Ser | Asn | Arg | Trp | Phe | Pro | Val | Glu | Gly | Pro | | | |
| | | 300 | | | | | 305 | | | | | 310 | | | | | | |
| GCT | GAC | ATC | TGT | AAC | TGT | TGT | AAC | AAA | GGT | AGC | TGT | GGC | CTT | CAG | GGC | | | 1012 |
| Ala | Asp | Ile | Cys | Asn | Cys | Cys | Asn | Lys | Gly | Ser | Cys | Gly | Leu | Gln | Gly | | | |
| | | 315 | | | | | 320 | | | | | 325 | | | | | | |
| CGT | TCC | TGG | AGG | CTG | TCC | CAC | CTA | GAC | AGA | CCG | TGG | CAC | AAG | ATG | GCT | | | 1060 |
| Arg | Ser | Trp | Arg | Leu | Ser | His | Leu | Asp | Arg | Pro | Trp | His | Lys | Met | Ala | | | |
| 330 | | | | | 335 | | | | | 340 | | | | | 345 | | | |
| TCC | CGA | AAT | CGC | AGG | CAT | GTG | ACC | GAA | GAA | GCG | GAT | ATC | ACC | GTG | GGG | | | 1108 |
| Ser | Arg | Asn | Arg | Arg | His | Val | Thr | Glu | Glu | Ala | Asp | Ile | Thr | Val | Gly | | | |
| | | | | 350 | | | | | 355 | | | | | 360 | | | | |
| CCT | CTG | ATC | TTC | CTG | GGA | AAG | GCT | GCC | GAT | CGT | GGT | GTG | GAG | GGG | TCG | | | 1156 |
| Pro | Leu | Ile | Phe | Leu | Gly | Lys | Ala | Ala | Asp | Arg | Gly | Val | Glu | Gly | Ser | | | |
| | | | 365 | | | | | 370 | | | | | 375 | | | | | |
| ACC | TCG | CCT | CAC | ACC | TCT | GTG | ATG | GTG | GGC | ATA | GGC | CTG | GCC | ACG | GTG | | | 1204 |
| Thr | Ser | Pro | His | Thr | Ser | Val | Met | Val | Gly | Ile | Gly | Leu | Ala | Thr | Val | | | |

```
                       380                           385                                  390
TTG  TCC  CTG  ACT  CTG  GCT  ACC  ATT  GTC  CTG  GGT  CTC  GCC  AGG  AGG  CAT            1252
Leu  Ser  Leu  Thr  Leu  Ala  Thr  Ile  Val  Leu  Gly  Leu  Ala  Arg  Arg  His
     395                      400                      405

CAC  ACT  GCT  TCC  CGT  CCT  ATG  ATC  TGC  CCT  GTG  TCT  GCT  TCC  CAA                 1297
His  Thr  Ala  Ser  Arg  Pro  Met  Ile  Cys  Pro  Val  Ser  Ala  Ser  Gln
410                      415                      420

TAAAAGAAGC  GGCCGCGAAT  TC                                                                1319
```

( 2 ) INFORMATION FOR SEQ ID NO:18:

( i ) SEQUENCE CHARACTERISTICS:
        ( A ) LENGTH: 424 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met  Gly  Leu  Ser  Tyr  Gly  Leu  Phe  Ile  Cys  Phe  Leu  Leu  Trp  Ala  Gly
 1                  5                      10                     15

Thr  Gly  Leu  Cys  Tyr  Pro  Pro  Thr  Thr  Thr  Glu  Asp  Lys  Thr  His  Pro
               20                      25                     30

Ser  Leu  Pro  Ser  Ser  Pro  Ser  Val  Val  Val  Glu  Cys  Arg  His  Ala  Trp
          35                      40                     45

Leu  Val  Val  Asn  Val  Ser  Lys  Asn  Leu  Phe  Gly  Thr  Gly  Arg  Leu  Val
     50                      55                     60

Arg  Pro  Ala  Asp  Leu  Thr  Leu  Gly  Pro  Glu  Asn  Cys  Glu  Pro  Leu  Ile
65                      70                      75                          80

Ser  Gly  Asp  Ser  Asp  Asp  Thr  Val  Arg  Phe  Glu  Val  Glu  Leu  His  Lys
                    85                      90                         95

Cys  Gly  Asn  Ser  Val  Gln  Val  Thr  Glu  Asp  Ala  Leu  Val  Tyr  Ser  Thr
                    100                     105                    110

Phe  Leu  Leu  His  Asn  Pro  Arg  Pro  Met  Gly  Asn  Leu  Ser  Ile  Leu  Arg
          115                     120                     125

Thr  Asn  Arg  Ala  Glu  Val  Pro  Ile  Glu  Cys  Arg  Tyr  Pro  Arg  His  Ser
     130                     135                     140

Asn  Val  Ser  Ser  Glu  Ala  Ile  Leu  Pro  Thr  Trp  Val  Pro  Phe  Arg  Thr
145                      150                     155                        160

Thr  Met  Leu  Ser  Glu  Glu  Lys  Leu  Ala  Phe  Ser  Leu  Arg  Leu  Met  Glu
                    165                     170                    175

Glu  Asp  Trp  Gly  Ser  Glu  Lys  Gln  Ser  Pro  Thr  Phe  Gln  Leu  Gly  Asp
               180                     185                     190

Leu  Ala  His  Leu  Gln  Ala  Glu  Val  His  Thr  Gly  Arg  His  Ile  Pro  Leu
          195                     200                     205

Arg  Leu  Phe  Val  Asp  Tyr  Cys  Val  Ala  Thr  Leu  Thr  Pro  Asp  Gln  Asn
     210                     215                     220

Ala  Ser  Pro  His  His  Thr  Ile  Val  Asp  Phe  His  Gly  Cys  Leu  Val  Asp
225                      230                     235                        240

Gly  Leu  Ser  Asp  Ala  Ser  Ser  Ala  Phe  Lys  Ala  Pro  Arg  Pro  Arg  Pro
                    245                     250                    255

Glu  Thr  Leu  Gln  Phe  Thr  Val  Asp  Thr  Phe  His  Phe  Ala  Asn  Asp  Pro
               260                     265                     270

Arg  Asn  Met  Ile  Tyr  Ile  Thr  Cys  His  Leu  Lys  Val  Thr  Pro  Ala  Ser
          275                     280                     285

Arg  Val  Pro  Asp  Gln  Leu  Asn  Lys  Ala  Cys  Ser  Phe  Ile  Lys  Ser  Ser
     290                     295                     300
```

| | | | | | | | | | | | | | | | |
|---|---|---|---|---|---|---|---|---|---|---|---|---|---|---|---|
| Asn | Arg | Trp | Phe | Pro | Val | Glu | Gly | Pro | Ala | Asp | Ile | Cys | Asn | Cys | Cys |
| 305 | | | | 310 | | | | | 315 | | | | | | 320 |
| Asn | Lys | Gly | Ser | Cys | Gly | Leu | Gln | Gly | Arg | Ser | Trp | Arg | Leu | Ser | His |
| | | | | 325 | | | | | 330 | | | | | 335 | |
| Leu | Asp | Arg | Pro | Trp | His | Lys | Met | Ala | Ser | Arg | Asn | Arg | Arg | His | Val |
| | | | 340 | | | | | 345 | | | | | 350 | | |
| Thr | Glu | Glu | Ala | Asp | Ile | Thr | Val | Gly | Pro | Leu | Ile | Phe | Leu | Gly | Lys |
| | | 355 | | | | | 360 | | | | | 365 | | | |
| Ala | Ala | Asp | Arg | Gly | Val | Glu | Gly | Ser | Thr | Ser | Pro | His | Thr | Ser | Val |
| | 370 | | | | | 375 | | | | | 380 | | | | |
| Met | Val | Gly | Ile | Gly | Leu | Ala | Thr | Val | Leu | Ser | Leu | Thr | Leu | Ala | Thr |
| 385 | | | | | 390 | | | | | 395 | | | | | 400 |
| Ile | Val | Leu | Gly | Leu | Ala | Arg | Arg | His | His | Thr | Ala | Ser | Arg | Pro | Met |
| | | | | 405 | | | | | 410 | | | | | 415 | |
| Ile | Cys | Pro | Val | Ser | Ala | Ser | Gln | | | | | | | | |
| | | | 420 | | | | | | | | | | | | |

( 2 ) INFORMATION FOR SEQ ID NO:19:

( i ) SEQUENCE CHARACTERISTICS:
        ( A ) LENGTH: 643 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Bos taurus
        ( D ) DEVELOPMENTAL STAGE: Juvenile
        ( E ) HAPLOTYPE: Diploidy
        ( F ) TISSUE TYPE: Ovary
        ( G ) CELL TYPE: Oocyte ( i x ) FEATURE:
        ( A ) NAME/KEY: CDS
        ( B ) LOCATION: 16..582

( x i ) SEQUENCE DESCRIPTION: SEQ ID NO:19:

| | | | | | | | | | | | | | | | | |
|---|---|---|---|---|---|---|---|---|---|---|---|---|---|---|---|---|
| GAATTCGCGG | CCGCC | CTA | AAC | AGG | ACT | GAC | CCC | AAC | ATC | AAG | TTG | GTC | TTA | | | 51 |
| | | Leu | Asn | Arg | Thr | Asp | Pro | Asn | Ile | Lys | Leu | Val | Leu | | | |
| | | 1 | | | | 5 | | | | | 10 | | | | | |
| GAT | GAT | TGC | TGG | GCA | ACA | TCC | ACC | ATG | GAC | CCA | GCC | TCT | CTC | CCT | CAG | 99 |
| Asp | Asp | Cys | Trp | Ala | Thr | Ser | Thr | Met | Asp | Pro | Ala | Ser | Leu | Pro | Gln | |
| | | 15 | | | | | 20 | | | | | 25 | | | | |
| TGG | AAT | ATT | ATC | GTG | GAT | GGC | TGT | GAA | TAC | AAC | TTG | GAC | AAC | CAC | AGA | 147 |
| Trp | Asn | Ile | Ile | Val | Asp | Gly | Cys | Glu | Tyr | Asn | Leu | Asp | Asn | His | Arg | |
| | | 30 | | | | 35 | | | | | 40 | | | | | |
| ACC | ACC | TTC | CAT | CCG | GTT | GGC | TCC | TCG | GTG | GCC | TAT | CCT | AAT | CAC | TAC | 195 |
| Thr | Thr | Phe | His | Pro | Val | Gly | Ser | Ser | Val | Ala | Tyr | Pro | Asn | His | Tyr | |
| 45 | | | | | 50 | | | | | 55 | | | | | 60 | |
| CAG | AGG | TTT | GCT | GTG | AAG | ACC | TTT | GCC | TTT | GTG | TCA | GAG | GAC | CCG | GCG | 243 |
| Gln | Arg | Phe | Ala | Val | Lys | Thr | Phe | Ala | Phe | Val | Ser | Glu | Asp | Pro | Ala | |
| | | | | 65 | | | | | 70 | | | | | 75 | | |
| TTC | TCT | CAC | TTG | GTC | TAC | TTC | CAC | TGC | AGC | GCC | TTA | ATC | TGC | GAT | CAA | 291 |
| Phe | Ser | His | Leu | Val | Tyr | Phe | His | Cys | Ser | Ala | Leu | Ile | Cys | Asp | Gln | |
| | | | 80 | | | | | 85 | | | | | 90 | | | |
| CTT | TCT | TCT | AAC | TTC | CCC | CTG | TGT | TCT | GCG | TCT | TGC | CTT | GTG | TCA | TCC | 339 |
| Leu | Ser | Ser | Asn | Phe | Pro | Leu | Cys | Ser | Ala | Ser | Cys | Leu | Val | Ser | Ser | |
| | | 95 | | | | 100 | | | | | 105 | | | | | |

| | | | | | | | | | | | | | | | | |
|---|---|---|---|---|---|---|---|---|---|---|---|---|---|---|---|---|
| AGA | AGC | AGG | CGA | GCC | ACA | GGG | GCC | ACT | GAG | GAA | GAG | AAG | ATG | ATA | GTG | 387 |
| Arg | Ser | Arg | Arg | Ala | Thr | Gly | Ala | Thr | Glu | Glu | Glu | Lys | Met | Ile | Val | |
| | 110 | | | | 115 | | | | | 120 | | | | | | |
| AGT | CTC | CCG | GGC | CCC | ATC | CTC | CTG | TTG | TCA | GAT | GGC | TCT | TCA | TTC | AGA | 435 |
| Ser | Leu | Pro | Gly | Pro | Ile | Leu | Leu | Leu | Ser | Asp | Gly | Ser | Ser | Phe | Arg | |
| 125 | | | | | 130 | | | | | 135 | | | | | 140 | |
| GAT | GCT | GTG | GAT | TCT | AAA | GGG | CAT | GGG | ACT | TCT | GGA | TAT | GCT | GCT | TTT | 483 |
| Asp | Ala | Val | Asp | Ser | Lys | Gly | His | Gly | Thr | Ser | Gly | Tyr | Ala | Ala | Phe | |
| | | | | 145 | | | | | 150 | | | | | 155 | | |
| AAA | ACT | ATG | GTT | GCT | GTA | GTT | GCC | TTA | GCA | GGT | GTT | GTG | GCA | ACT | CTA | 531 |
| Lys | Thr | Met | Val | Ala | Val | Val | Ala | Leu | Ala | Gly | Val | Val | Ala | Thr | Leu | |
| | | | 160 | | | | | 165 | | | | | 170 | | | |
| AGC | CTA | ATC | AGC | TAC | CTG | CGC | AAG | AAA | AGA | ATC | ACA | GTG | CTA | AAC | CAC | 579 |
| Ser | Leu | Ile | Ser | Tyr | Leu | Arg | Lys | Lys | Arg | Ile | Thr | Val | Leu | Asn | His | |
| | | 175 | | | | | | 180 | | | | | 185 | | | |

| | | | | |
|---|---|---|---|---|
| TAATTGGATT | TTCAATAAAA | TGTGGAAGTA | AAAAAAAAA | AAAAAAAAA GCGGCCGCGA | 639 |
| ATTC | | | | | 643 |

(2) INFORMATION FOR SEQ ID NO:20:

(i) SEQUENCE CHARACTERISTICS:
        (A) LENGTH: 188 amino acids
        (B) TYPE: amino acid
        (D) TOPOLOGY: linear (ii) MOLECULE TYPE: protein (xi) SEQUENCE DESCRIPTION: SEQ ID NO:20:

| | | | | | | | | | | | | | | |
|---|---|---|---|---|---|---|---|---|---|---|---|---|---|---|
| Leu | Asn | Arg | Thr | Asp | Pro | Asn | Ile | Lys | Leu | Val | Leu | Asp | Asp | Cys | Trp |
| 1 | | | | 5 | | | | | 10 | | | | | 15 | |
| Ala | Thr | Ser | Thr | Met | Asp | Pro | Ala | Ser | Leu | Pro | Gln | Trp | Asn | Ile | Ile |
| | | | 20 | | | | | 25 | | | | | 30 | | |
| Val | Asp | Gly | Cys | Glu | Tyr | Asn | Leu | Asp | Asn | His | Arg | Thr | Thr | Phe | His |
| | | | 35 | | | | | 40 | | | | | 45 | | |
| Pro | Val | Gly | Ser | Ser | Val | Ala | Tyr | Pro | Asn | His | Tyr | Gln | Arg | Phe | Ala |
| | | 50 | | | | | 55 | | | | | 60 | | | |
| Val | Lys | Thr | Phe | Ala | Phe | Val | Ser | Glu | Asp | Pro | Ala | Phe | Ser | His | Leu |
| 65 | | | | | 70 | | | | | 75 | | | | | 80 |
| Val | Tyr | Phe | His | Cys | Ser | Ala | Leu | Ile | Cys | Asp | Gln | Leu | Ser | Ser | Asn |
| | | | | 85 | | | | | 90 | | | | | 95 | |
| Phe | Pro | Leu | Cys | Ser | Ala | Ser | Cys | Leu | Val | Ser | Ser | Arg | Ser | Arg | Arg |
| | | | 100 | | | | | 105 | | | | | 110 | | |
| Ala | Thr | Gly | Ala | Thr | Glu | Glu | Glu | Lys | Met | Ile | Val | Ser | Leu | Pro | Gly |
| | | | 115 | | | | | 120 | | | | | 125 | | |
| Pro | Ile | Leu | Leu | Leu | Ser | Asp | Gly | Ser | Ser | Phe | Arg | Asp | Ala | Val | Asp |
| | | 130 | | | | | 135 | | | | | 140 | | | |
| Ser | Lys | Gly | His | Gly | Thr | Ser | Gly | Tyr | Ala | Ala | Phe | Lys | Thr | Met | Val |
| 145 | | | | | 150 | | | | | 155 | | | | | 160 |
| Ala | Val | Val | Ala | Leu | Ala | Gly | Val | Val | Ala | Thr | Leu | Ser | Leu | Ile | Ser |
| | | | | 165 | | | | | 170 | | | | | 175 | |
| Tyr | Leu | Arg | Lys | Lys | Arg | Ile | Thr | Val | Leu | Asn | His | | | | |
| | | | 180 | | | | | 185 | | | | | | | |

(2) INFORMATION FOR SEQ ID NO:21:

(i) SEQUENCE CHARACTERISTICS:
        (A) LENGTH: 1029 base pairs
        (B) TYPE: nucleic acid
        (C) STRANDEDNESS: double -continued ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
  ( A ) ORGANISM: Bos taurus
  ( D ) DEVELOPMENTAL STAGE: Juvenile
  ( E ) HAPLOTYPE: Diploidy
  ( F ) TISSUE TYPE: Ovary
  ( G ) CELL TYPE: Oocyte ( i x ) FEATURE:
  ( A ) NAME/KEY: CDS
  ( B ) LOCATION: 2..976

( x i ) SEQUENCE DESCRIPTION: SEQ ID NO:21:

```
G   AAT   TCT   GTA   CAC   TTG   GCC   TTC   AGG   AAT   GAC   AGC   GAA   TGT   AAA   CCT         46
    Asn   Ser   Val   His   Leu   Ala   Phe   Arg   Asn   Asp   Ser   Glu   Cys   Lys   Pro
    1                 5                             10                            15

GTG   ATG   GCA   ACA   CAC   ACT   TTT   GTT   CTG   TTC   CGG   TTT   CCA   TTT   ACT   ACT       94
Val   Met   Ala   Thr   His   Thr   Phe   Val   Leu   Phe   Arg   Phe   Pro   Phe   Thr   Thr
                        20                            25                            30

TGT   GGT   ACT   ACA   AAA   CAG   ATC   ACT   GGA   AAG   CAA   GCG   GTA   TAT   GAA   AAT       142
Cys   Gly   Thr   Thr   Lys   Gln   Ile   Thr   Gly   Lys   Gln   Ala   Val   Tyr   Glu   Asn
                  35                            40                            45

GAG   CTG   GTT   GCA   GCT   CGG   GAT   GTG   AGA   ACT   TGG   AGC   CGT   GGT   TCT   ATT       190
Glu   Leu   Val   Ala   Ala   Arg   Asp   Val   Arg   Thr   Trp   Ser   Arg   Gly   Ser   Ile
            50                            55                            60

ACC   CGA   GAC   AGT   ACC   TTC   AGG   CTC   CAA   GTC   AGT   TGT   AGC   TAC   TCT   GCA       238
Thr   Arg   Asp   Ser   Thr   Phe   Arg   Leu   Gln   Val   Ser   Cys   Ser   Tyr   Ser   Ala
      65                            70                            75

AGT   AGC   AGT   GCT   CTC   CCA   GTT   AAT   GTC   CAA   GTT   CTT   ACT   CTC   CCA   CCA       286
Ser   Ser   Ser   Ala   Leu   Pro   Val   Asn   Val   Gln   Val   Leu   Thr   Leu   Pro   Pro
80                            85                            90                            95

CCC   CTT   CCT   GAG   ACC   CTG   CCT   GGA   AAC   CTC   ACT   CTG   GAA   CTT   AAG   ATT       334
Pro   Leu   Pro   Glu   Thr   Leu   Pro   Gly   Asn   Leu   Thr   Leu   Glu   Leu   Lys   Ile
                        100                           105                           110

GCC   AAA   GAT   AAA   CCG   TAT   CGC   TCC   TAC   TAC   ACG   GCT   AGT   GAC   TAC   CCA       382
Ala   Lys   Asp   Lys   Pro   Tyr   Arg   Ser   Tyr   Tyr   Thr   Ala   Ser   Asp   Tyr   Pro
                  115                           120                           125

GTG   GTG   AAG   TTA   CTT   CGG   GAT   CCC   ATC   TAC   GTG   GAA   GTC   TCC   ATC   CAT       430
Val   Val   Lys   Leu   Leu   Arg   Asp   Pro   Ile   Tyr   Val   Glu   Val   Ser   Ile   His
            130                           135                           140

CAG   AGA   ACA   GAC   CCC   AGT   CTC   GAG   CTG   CGC   CTG   GAC   CAG   TGT   TGG   GCG       478
Gln   Arg   Thr   Asp   Pro   Ser   Leu   Glu   Leu   Arg   Leu   Asp   Gln   Cys   Trp   Ala
      145                           150                           155

ACA   CCT   GGT   GCA   GAT   GCC   CTG   CTC   CAG   CCC   CAG   TGG   CCC   TTG   CTT   GTG       526
Thr   Pro   Gly   Ala   Asp   Ala   Leu   Leu   Gln   Pro   Gln   Trp   Pro   Leu   Leu   Val
160                           165                           170                           175

AAT   GGG   TGC   CCC   TAC   ACA   GGA   GAC   AAC   TAT   CAG   ACA   AAA   CTG   ATC   CCT       574
Asn   Gly   Cys   Pro   Tyr   Thr   Gly   Asp   Asn   Tyr   Gln   Thr   Lys   Leu   Ile   Pro
                        180                           185                           190

GTC   TGG   GAA   GCC   TCA   GAC   CTG   CCG   TTT   CCT   TCT   CAC   TAC   CAG   CGC   TTC       622
Val   Trp   Glu   Ala   Ser   Asp   Leu   Pro   Phe   Pro   Ser   His   Tyr   Gln   Arg   Phe
                  195                           200                           205

AGC   ATT   TCC   ACC   TTC   AGC   TTT   GTG   GAC   TCA   GTG   GCA   AAG   CGG   GCC   CTC       670
Ser   Ile   Ser   Thr   Phe   Ser   Phe   Val   Asp   Ser   Val   Ala   Lys   Arg   Ala   Leu
            210                           215                           220

AAG   GGA   CCG   GTG   TAT   CTG   CAC   TGC   AGT   GCA   TCG   GTC   TGC   CAG   CCT   GCC       718
Lys   Gly   Pro   Val   Tyr   Leu   His   Cys   Ser   Ala   Ser   Val   Cys   Gln   Pro   Ala
      225                           230                           235
```

```
GGG  ACA  CCA  TCC  TGT  GTG  ACA  CTC  TGT  CCT  GCC  AGA  CGA  AGA  AGA  AGC         766
Gly  Thr  Pro  Ser  Cys  Val  Thr  Leu  Cys  Pro  Ala  Arg  Arg  Arg  Arg  Ser
240                      245                      250                      255

TCT  GAC  ATC  CAT  TTT  CAG  AAC  AAA  ACG  GCT  AGC  ATT  TCT  AGC  AAG  GGT         814
Ser  Asp  Ile  His  Phe  Gln  Asn  Lys  Thr  Ala  Ser  Ile  Ser  Ser  Lys  Gly
                    260                      265                      270

CCC  TTG  ATT  CTA  CTC  CAA  GCC  ATT  CAA  GAC  TCT  TCA  GAA  AAG  CTC  CAC         862
Pro  Leu  Ile  Leu  Leu  Gln  Ala  Ile  Gln  Asp  Ser  Ser  Glu  Lys  Leu  His
               275                      280                      285

AAA  TAC  TCA  AGG  TCT  CCT  GTA  GAC  TCT  CAA  GCT  TTG  TGG  GTG  GCT  GGC         910
Lys  Tyr  Ser  Arg  Ser  Pro  Val  Asp  Ser  Gln  Ala  Leu  Trp  Val  Ala  Gly
          290                      295                      300

CTA  TCT  GGA  ATC  TTA  ATC  GTT  GGA  GCC  TTG  TTC  ATG  TCC  TAC  CTG  GCC         958
Leu  Ser  Gly  Ile  Leu  Ile  Val  Gly  Ala  Leu  Phe  Met  Ser  Tyr  Leu  Ala
     305                      310                      315

ATT  AGG  AAA  TGG  AGA  TGAGTTGCTC  AGCCCAAATG  TGTTAATAAA  ACCAGATTGC               1013
Ile  Arg  Lys  Trp  Arg
320

AGCCGGCCGC  GAATTC                                                                   1029

( 2 ) INFORMATION FOR SEQ ID NO:22:

( i ) SEQUENCE CHARACTERISTICS:
            ( A ) LENGTH: 324 amino acids
            ( B ) TYPE: amino acid
            ( D ) TOPOLOGY: linear ( i i ) MOLECULE TYPE: protein ( x i ) SEQUENCE DESCRIPTION: SEQ ID NO:22:

Asn  Ser  Val  His  Leu  Ala  Phe  Arg  Asn  Asp  Ser  Glu  Cys  Lys  Pro  Val
 1                    5                      10                       15

Met  Ala  Thr  His  Thr  Phe  Val  Leu  Phe  Arg  Phe  Pro  Phe  Thr  Thr  Cys
                     20                      25                       30

Gly  Thr  Thr  Lys  Gln  Ile  Thr  Gly  Lys  Gln  Ala  Val  Tyr  Glu  Asn  Glu
               35                      40                       45

Leu  Val  Ala  Ala  Arg  Asp  Val  Arg  Thr  Trp  Ser  Arg  Gly  Ser  Ile  Thr
          50                      55                       60

Arg  Asp  Ser  Thr  Phe  Arg  Leu  Gln  Val  Ser  Cys  Ser  Tyr  Ser  Ala  Ser
65                       70                       75                       80

Ser  Ser  Ala  Leu  Pro  Val  Asn  Val  Gln  Val  Leu  Thr  Leu  Pro  Pro  Pro
                    85                       90                       95

Leu  Pro  Glu  Thr  Leu  Pro  Gly  Asn  Leu  Thr  Leu  Glu  Leu  Lys  Ile  Ala
               100                     105                     110

Lys  Asp  Lys  Pro  Tyr  Arg  Ser  Tyr  Tyr  Thr  Ala  Ser  Asp  Tyr  Pro  Val
          115                     120                     125

Val  Lys  Leu  Leu  Arg  Asp  Pro  Ile  Tyr  Val  Glu  Val  Ser  Ile  His  Gln
130                     135                     140

Arg  Thr  Asp  Pro  Ser  Leu  Glu  Leu  Arg  Leu  Asp  Gln  Cys  Trp  Ala  Thr
145                     150                     155                     160

Pro  Gly  Ala  Asp  Ala  Leu  Leu  Gln  Pro  Gln  Trp  Pro  Leu  Leu  Val  Asn
                    165                     170                     175

Gly  Cys  Pro  Tyr  Thr  Gly  Asp  Asn  Tyr  Gln  Thr  Lys  Leu  Ile  Pro  Val
               180                     185                     190

Trp  Glu  Ala  Ser  Asp  Leu  Pro  Phe  Pro  Ser  His  Tyr  Gln  Arg  Phe  Ser
          195                     200                     205

Ile  Ser  Thr  Phe  Ser  Phe  Val  Asp  Ser  Val  Ala  Lys  Arg  Ala  Leu  Lys
          210                     215                     220
```

| | | | | | | | | | | | | | | | |
|---|---|---|---|---|---|---|---|---|---|---|---|---|---|---|---|
| Gly | Pro | Val | Tyr | Leu | His | Cys | Ser | Ala | Ser | Val | Cys | Gln | Pro | Ala | Gly |
| 225 | | | | | 230 | | | | | 235 | | | | | 240 |
| Thr | Pro | Ser | Cys | Val | Thr | Leu | Cys | Pro | Ala | Arg | Arg | Arg | Arg | Ser | Ser |
| | | | | 245 | | | | | 250 | | | | | 255 | |
| Asp | Ile | His | Phe | Gln | Asn | Lys | Thr | Ala | Ser | Ile | Ser | Ser | Lys | Gly | Pro |
| | | | 260 | | | | | 265 | | | | | 270 | | |
| Leu | Ile | Leu | Leu | Gln | Ala | Ile | Gln | Asp | Ser | Ser | Glu | Lys | Leu | His | Lys |
| | | 275 | | | | | 280 | | | | | 285 | | | |
| Tyr | Ser | Arg | Ser | Pro | Val | Asp | Ser | Gln | Ala | Leu | Trp | Val | Ala | Gly | Leu |
| | 290 | | | | | 295 | | | | | 300 | | | | |
| Ser | Gly | Ile | Leu | Ile | Val | Gly | Ala | Leu | Phe | Met | Ser | Tyr | Leu | Ala | Ile |
| 305 | | | | | 310 | | | | | 315 | | | | | 320 |
| Arg | Lys | Trp | Arg | | | | | | | | | | | | |

( 2 ) INFORMATION FOR SEQ ID NO:23:

( i ) SEQUENCE CHARACTERISTICS:
        ( A ) LENGTH: 1457 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Bos taurus
        ( D ) DEVELOPMENTAL STAGE: Juvenile
        ( E ) HAPLOTYPE: Diploidy
        ( F ) TISSUE TYPE: Ovary
        ( G ) CELL TYPE: Oocyte ( i x ) FEATURE:
        ( A ) NAME/KEY: CDS
        ( B ) LOCATION: 149..1411

( x i ) SEQUENCE DESCRIPTION: SEQ ID NO:23:

```
CCCGGGCCTC CCTACTCTCA GGAAGGCACC CGCTCACCTC CTCAAGTTCT CGATCTCGGC        60

CGGGATGCTC TGAAGCTGGT TGCCGCCGAG GCTGAGGGTC TGCAGCGGCG CAGTCCAGCA       120

GCGAGGTGGG AGTGGCTTCG TGGGCACC ATG GGG CCG TGC TCT AGG CTG TTC         172
                              Met Gly Pro Cys Ser Arg Leu Phe
                                1               5
```

| GTC | TGC | TTT | CTG | CTC | TGG | GGA | AGC | ACA | GAG | CTC | TGC | AGC | CCC | CAG | CCC | 220 |
|---|---|---|---|---|---|---|---|---|---|---|---|---|---|---|---|---|
| Val | Cys | Phe | Leu | Leu | Trp | Gly | Ser | Thr | Glu | Leu | Cys | Ser | Pro | Gln | Pro | |
| | 10 | | | | | 15 | | | | | 20 | | | | | |

| TTC | TGG | GAT | GAT | GAA | ACC | GAG | CGC | TTC | AGG | CCA | TCA | AAG | CCG | CCC | GCC | 268 |
|---|---|---|---|---|---|---|---|---|---|---|---|---|---|---|---|---|
| Phe | Trp | Asp | Asp | Glu | Thr | Glu | Arg | Phe | Arg | Pro | Ser | Lys | Pro | Pro | Ala | |
| 25 | | | | | 30 | | | | | 35 | | | | | 40 | |

| GTG | ATG | GTG | GAG | TGT | CAG | GAG | GCC | CAG | CTG | GTG | GTC | ACA | GTC | GAC | AAA | 316 |
|---|---|---|---|---|---|---|---|---|---|---|---|---|---|---|---|---|
| Val | Met | Val | Glu | Cys | Gln | Glu | Ala | Gln | Leu | Val | Val | Thr | Val | Asp | Lys | |
| | | | | 45 | | | | | 50 | | | | | 55 | | |

| GAC | CTT | TTC | GGC | ACA | GGG | AAG | CTC | ATC | CGG | CCT | GCG | GAC | CTC | ACC | CTG | 364 |
|---|---|---|---|---|---|---|---|---|---|---|---|---|---|---|---|---|
| Asp | Leu | Phe | Gly | Thr | Gly | Lys | Leu | Ile | Arg | Pro | Ala | Asp | Leu | Thr | Leu | |
| | | | 60 | | | | | 65 | | | | | 70 | | | |

| GGC | CCC | GAC | AAC | TGT | GAG | CCG | CTG | GCC | TCC | GCG | GAC | ACG | GAT | GGC | GTG | 412 |
|---|---|---|---|---|---|---|---|---|---|---|---|---|---|---|---|---|
| Gly | Pro | Asp | Asn | Cys | Glu | Pro | Leu | Ala | Ser | Ala | Asp | Thr | Asp | Gly | Val | |
| | | 75 | | | | | 80 | | | | | 85 | | | | |

| GTT | AGG | TTT | GCG | GTC | GGG | CTG | CAC | GAG | TGT | GGC | AAC | ATC | TTG | CAG | GTG | 460 |
|---|---|---|---|---|---|---|---|---|---|---|---|---|---|---|---|---|
| Val | Arg | Phe | Ala | Val | Gly | Leu | His | Glu | Cys | Gly | Asn | Ile | Leu | Gln | Val | |
| | 90 | | | | | 95 | | | | | 100 | | | | | |

-continued

| | | | | | | | | | | | | | | | | |
|---|---|---|---|---|---|---|---|---|---|---|---|---|---|---|---|---|
| ACC | GAC | AAT | GCC | CTG | GTG | TAC | AGC | ACC | TTC | CTG | CTC | CAC | AAC | CCC | CGC | 508 |
| Thr | Asp | Asn | Ala | Leu | Val | Tyr | Ser | Thr | Phe | Leu | Leu | His | Asn | Pro | Arg | |
| 105 | | | | 110 | | | | | 115 | | | | | | 120 | |
| CCT | GCA | GGA | AAC | CTG | TCC | ATC | CTG | AGG | ACT | AAC | CGC | GCA | GAG | GTC | CCC | 556 |
| Pro | Ala | Gly | Asn | Leu | Ser | Ile | Leu | Arg | Thr | Asn | Arg | Ala | Glu | Val | Pro | |
| | | | | 125 | | | | | 130 | | | | | 135 | | |
| ATC | GAG | TGC | CAC | TAC | CCC | AGG | CAG | GGC | AAT | GTG | AGT | AGC | TGG | GCC | ATC | 604 |
| Ile | Glu | Cys | His | Tyr | Pro | Arg | Gln | Gly | Asn | Val | Ser | Ser | Trp | Ala | Ile | |
| | | | 140 | | | | | 145 | | | | | 150 | | | |
| CAG | CCC | ACC | TGG | GTG | CCA | TTC | AGG | ACC | ACA | GTG | TTC | TCG | GAG | GAG | AAG | 652 |
| Gln | Pro | Thr | Trp | Val | Pro | Phe | Arg | Thr | Thr | Val | Phe | Ser | Glu | Glu | Lys | |
| | | 155 | | | | | 160 | | | | | 165 | | | | |
| CTG | GTT | TTC | TCT | CTG | CGC | CTG | ATG | GAG | GAG | AAC | TGG | AGC | GCC | GAG | AAG | 700 |
| Leu | Val | Phe | Ser | Leu | Arg | Leu | Met | Glu | Glu | Asn | Trp | Ser | Ala | Glu | Lys | |
| | 170 | | | | | 175 | | | | | 180 | | | | | |
| ATG | ACG | CCC | ACC | TTC | CAG | CTG | GGA | GAC | AGA | GCC | CAC | CTC | CAG | GCC | CAA | 748 |
| Met | Thr | Pro | Thr | Phe | Gln | Leu | Gly | Asp | Arg | Ala | His | Leu | Gln | Ala | Gln | |
| 185 | | | | | 190 | | | | | 195 | | | | | 200 | |
| GTG | CAC | ACT | GGC | AGC | CAC | GTG | CCC | CTG | CGG | CTG | TTC | GTG | GAC | CAC | TGC | 796 |
| Val | His | Thr | Gly | Ser | His | Val | Pro | Leu | Arg | Leu | Phe | Val | Asp | His | Cys | |
| | | | | 205 | | | | | 210 | | | | | 215 | | |
| GTG | GCC | AGC | CTG | ACG | CCA | GAC | TGG | AGC | ACC | TCC | CCT | TAC | CAC | ACC | ATC | 844 |
| Val | Ala | Ser | Leu | Thr | Pro | Asp | Trp | Ser | Thr | Ser | Pro | Tyr | His | Thr | Ile | |
| | | | 220 | | | | | 225 | | | | | 230 | | | |
| GTG | GAC | TTC | CAT | GGT | TGT | CTC | GTC | GAT | GGT | CTC | ACC | GAT | GCC | TCC | TCT | 892 |
| Val | Asp | Phe | His | Gly | Cys | Leu | Val | Asp | Gly | Leu | Thr | Asp | Ala | Ser | Ser | |
| | | 235 | | | | | 240 | | | | | 245 | | | | |
| GCT | TTC | AAA | GCA | CCC | AGA | CCC | AGA | CCG | GAG | ATC | CTC | CAG | TTC | ACA | GTG | 940 |
| Ala | Phe | Lys | Ala | Pro | Arg | Pro | Arg | Pro | Glu | Ile | Leu | Gln | Phe | Thr | Val | |
| | 250 | | | | | 255 | | | | | 260 | | | | | |
| GAT | GTG | TTC | CGT | TTT | GCT | AAT | GAC | TCC | AGA | AAC | ATG | ATA | TAT | ATC | ACC | 988 |
| Asp | Val | Phe | Arg | Phe | Ala | Asn | Asp | Ser | Arg | Asn | Met | Ile | Tyr | Ile | Thr | |
| 265 | | | | | 270 | | | | | 275 | | | | | 280 | |
| TGC | CAC | CTG | AAG | GTC | ACT | CCG | GTT | GAC | CGA | GTC | CCG | GAC | CAA | CTA | AAC | 1036 |
| Cys | His | Leu | Lys | Val | Thr | Pro | Val | Asp | Arg | Val | Pro | Asp | Gln | Leu | Asn | |
| | | | | 285 | | | | | 290 | | | | | 295 | | |
| AAA | GCC | TGT | TCC | TTC | AGC | AAG | TCC | TCC | AAC | AGG | TGG | TCC | CCG | GTT | GAA | 1084 |
| Lys | Ala | Cys | Ser | Phe | Ser | Lys | Ser | Ser | Asn | Arg | Trp | Ser | Pro | Val | Glu | |
| | | | 300 | | | | | 305 | | | | | 310 | | | |
| GGC | CCC | ACT | GAC | ATC | TGT | CGA | TGC | TGT | AGC | AAG | GGG | CGC | TGT | GGC | ATT | 1132 |
| Gly | Pro | Thr | Asp | Ile | Cys | Arg | Cys | Cys | Ser | Lys | Gly | Arg | Cys | Gly | Ile | |
| | | 315 | | | | | 320 | | | | | 325 | | | | |
| TCA | GGC | CGT | TCC | ATG | AGG | CTG | TCC | CAC | CGG | GAG | GGC | AGG | CCT | GTT | CCC | 1180 |
| Ser | Gly | Arg | Ser | Met | Arg | Leu | Ser | His | Arg | Glu | Gly | Arg | Pro | Val | Pro | |
| | 330 | | | | | 335 | | | | | 340 | | | | | |
| CGA | AGT | CGC | AGG | CAC | GTG | ACG | GAG | GAA | GCA | GAT | GTC | ACC | GTG | GGG | CCG | 1228 |
| Arg | Ser | Arg | Arg | His | Val | Thr | Glu | Glu | Ala | Asp | Val | Thr | Val | Gly | Pro | |
| 345 | | | | | 350 | | | | | 355 | | | | | 360 | |
| TTG | ATC | TTC | CTG | AGG | AAG | ATG | AAT | GAC | CGT | GGC | GTG | GAA | GGG | CCC | ACC | 1276 |
| Leu | Ile | Phe | Leu | Arg | Lys | Met | Asn | Asp | Arg | Gly | Val | Glu | Gly | Pro | Thr | |
| | | | | 365 | | | | | 370 | | | | | 375 | | |
| TCC | TCT | CCC | CCT | CTG | GTG | ATG | CTG | GGC | TTA | GGC | CTG | GCT | ACT | GTG | ATG | 1324 |
| Ser | Ser | Pro | Pro | Leu | Val | Met | Leu | Gly | Leu | Gly | Leu | Ala | Thr | Val | Met | |
| | | | 380 | | | | | 385 | | | | | 390 | | | |
| ACC | TTG | ACT | CTG | GCT | GCC | ATT | GTC | CTG | GGT | CTC | ACT | GGG | AGG | CTT | CGG | 1372 |
| Thr | Leu | Thr | Leu | Ala | Ala | Ile | Val | Leu | Gly | Leu | Thr | Gly | Arg | Leu | Arg | |
| | | 395 | | | | | 400 | | | | | 405 | | | | |
| GCT | GCT | TCT | CAC | CCC | GTG | TGC | CCT | GTG | TCT | GCT | TCC | CAA | TAAAGAAGA | | | 1421 |
| Ala | Ala | Ser | His | Pro | Val | Cys | Pro | Val | Ser | Ala | Ser | Gln | | | | |
| | | 410 | | | | | 415 | | | | | 420 | | | | |

```
AAGTGAAAAA AAAAAAAAAA AAGCGGCCGC GAATTC                                                    1457
```

(2) INFORMATION FOR SEQ ID NO:24:

(i) SEQUENCE CHARACTERISTICS:
        (A) LENGTH: 421 amino acids
        (B) TYPE: amino acid
        (D) TOPOLOGY: linear (ii) MOLECULE TYPE: protein (xi) SEQUENCE DESCRIPTION: SEQ ID NO:24:

| Met 1 | Gly | Pro | Cys | Ser 5 | Arg | Leu | Phe | Val | Phe 10 | Phe | Leu | Leu | Trp | Gly 15 | Ser |
|---|---|---|---|---|---|---|---|---|---|---|---|---|---|---|---|
| Thr | Glu | Leu | Cys 20 | Ser | Pro | Gln | Pro | Phe 25 | Trp | Asp | Asp | Glu | Thr 30 | Glu | Arg |
| Phe | Arg | Pro 35 | Ser | Lys | Pro | Pro | Ala 40 | Val | Met | Val | Glu | Cys 45 | Gln | Glu | Ala |
| Gln | Leu 50 | Val | Val | Thr | Val | Asp 55 | Lys | Asp | Leu | Phe | Gly 60 | Thr | Gly | Lys | Leu |
| Ile 65 | Arg | Pro | Ala | Asp | Leu 70 | Thr | Leu | Gly | Pro | Asp 75 | Asn | Cys | Glu | Pro | Leu 80 |
| Ala | Ser | Ala | Asp | Thr 85 | Asp | Gly | Val | Val | Arg 90 | Phe | Ala | Val | Gly | Leu 95 | His |
| Glu | Cys | Gly | Asn 100 | Ile | Leu | Gln | Val | Thr 105 | Asp | Asn | Ala | Leu | Val 110 | Tyr | Ser |
| Thr | Phe | Leu 115 | Leu | His | Asn | Pro | Arg 120 | Pro | Ala | Gly | Asn | Leu 125 | Ser | Ile | Leu |
| Arg | Thr 130 | Asn | Arg | Ala | Glu | Val 135 | Pro | Ile | Glu | Cys | His 140 | Tyr | Pro | Arg | Gln |
| Gly 145 | Asn | Val | Ser | Ser | Trp 150 | Ala | Ile | Gln | Pro | Thr 155 | Trp | Val | Pro | Phe | Arg 160 |
| Thr | Thr | Val | Phe | Ser 165 | Glu | Glu | Lys | Leu | Val 170 | Phe | Ser | Leu | Arg | Leu 175 | Met |
| Glu | Glu | Asn | Trp 180 | Ser | Ala | Glu | Lys | Met 185 | Thr | Pro | Thr | Phe | Gln 190 | Leu | Gly |
| Asp | Arg | Ala 195 | His | Leu | Gln | Ala | Gln 200 | Val | His | Thr | Gly | Ser 205 | His | Val | Pro |
| Leu | Arg 210 | Leu | Phe | Val | Asp | His 215 | Cys | Val | Ala | Ser | Leu 220 | Thr | Pro | Asp | Trp |
| Ser 225 | Thr | Ser | Pro | Tyr | His 230 | Thr | Ile | Val | Asp | Phe 235 | His | Gly | Cys | Leu | Val 240 |
| Asp | Gly | Leu | Thr | Asp 245 | Ala | Ser | Ser | Ala | Phe 250 | Lys | Ala | Pro | Arg | Pro 255 | Arg |
| Pro | Glu | Ile | Leu 260 | Gln | Phe | Thr | Val | Asp 265 | Val | Phe | Arg | Phe | Ala 270 | Asn | Asp |
| Ser | Arg | Asn 275 | Met | Ile | Tyr | Ile | Thr 280 | Cys | His | Leu | Lys | Val 285 | Thr | Pro | Val |
| Asp | Arg 290 | Val | Pro | Asp | Gln | Leu 295 | Asn | Lys | Ala | Cys | Ser 300 | Phe | Ser | Lys | Ser |
| Ser 305 | Asn | Arg | Trp | Ser | Pro 310 | Val | Glu | Gly | Pro | Thr 315 | Asp | Ile | Cys | Arg | Cys 320 |
| Cys | Ser | Lys | Gly | Arg 325 | Cys | Gly | Ile | Ser | Gly 330 | Arg | Ser | Met | Arg | Leu 335 | Ser |
| His | Arg | Glu | Gly | Arg 340 | Pro | Val | Pro | Arg | Ser 345 | Arg | Arg | His | Val 350 | Thr | Glu |

| Glu | Ala | Asp | Val | Thr | Val | Gly | Pro | Leu | Ile | Phe | Leu | Arg | Lys | Met | Asn |
|-----|-----|-----|-----|-----|-----|-----|-----|-----|-----|-----|-----|-----|-----|-----|-----|
|     |     | 355 |     |     |     |     | 360 |     |     |     |     |     | 365 |     |     |

| Asp | Arg | Gly | Val | Glu | Gly | Pro | Thr | Ser | Ser | Pro | Pro | Leu | Val | Met | Leu |
|-----|-----|-----|-----|-----|-----|-----|-----|-----|-----|-----|-----|-----|-----|-----|-----|
|     | 370 |     |     |     |     | 375 |     |     |     |     | 380 |     |     |     |     |

| Gly | Leu | Gly | Leu | Ala | Thr | Val | Met | Thr | Leu | Thr | Leu | Ala | Ala | Ile | Val |
|-----|-----|-----|-----|-----|-----|-----|-----|-----|-----|-----|-----|-----|-----|-----|-----|
| 385 |     |     |     |     | 390 |     |     |     |     | 395 |     |     |     |     | 400 |

| Leu | Gly | Leu | Thr | Gly | Arg | Leu | Arg | Ala | Ala | Ser | His | Pro | Val | Cys | Pro |
|-----|-----|-----|-----|-----|-----|-----|-----|-----|-----|-----|-----|-----|-----|-----|-----|
|     |     |     |     | 405 |     |     |     |     | 410 |     |     |     |     | 415 |     |

| Val | Ser | Ala | Ser | Gln |
|-----|-----|-----|-----|-----|
|     |     |     | 420 |     |

( 2 ) INFORMATION FOR SEQ ID NO:25:

( i ) SEQUENCE CHARACTERISTICS:
        ( A ) LENGTH: 125 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

| AGTTCGTGCT | TATCTGAACA | TGTCTTGAGG | GATTAGTATG | TGTGCTCATT | TGGGTTCTTT | 60 |
|---|---|---|---|---|---|---|
| CCGCTGTATG | CTAGGCGTAT | CTAGATGCAT | TAGCTTGTTA | ACACCTCATG | TGGAGTAAAA | 120 |
| GATGT | | | | | | 125 |

( 2 ) INFORMATION FOR SEQ ID NO:26:

( i ) SEQUENCE CHARACTERISTICS:
        ( A ) LENGTH: 111 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

| CAGGCGTAGG | CGTGGACTGA | AGTTCAAAGC | CATGCGCCCG | TTCTGATAGC | ATACGTTTGA | 60 |
|---|---|---|---|---|---|---|
| AATGTCATTG | TAGTTGCATG | GCTGTATAAG | CCAGTCTCAT | AGATAAGGGA | A | 111 |

( 2 ) INFORMATION FOR SEQ ID NO:27:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

| GCGGTCGGTC | ATGTGATGCT | GCGTATAGTA | CGATTTTGAA | TGCATTATGC | GAAATTATTC | 60 |
|---|---|---|---|---|---|---|
| TAACGACCCG | CGATATGGAG | GTTGGATTAA | GTTACA | | | 96 |

( 2 ) INFORMATION FOR SEQ ID NO:28:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

ATGGARAGRT GYCAMGARG 19

( 2 ) INFORMATION FOR SEQ ID NO:29:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

GATCTAAGGA AGATCTATGG ATCC 24

( 2 ) INFORMATION FOR SEQ ID NO:30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

GATCTAAGGA GGTTGTATGG ATCC 24

( 2 ) INFORMATION FOR SEQ ID NO:31:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

GATCTATGAC CATGATTACG GATTCGCGTA GCCGTCGTCC TGCAGCGTCG CGACT 55

( 2 ) INFORMATION FOR SEQ ID NO:32:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

GGGAAAACCC GGGCGTTACC CAACTTAATC GATTAGCAGC ACATCCCCCT TCGCCAG 57

( 2 ) INFORMATION FOR SEQ ID NO:33:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

TTTTCCCAGT CGCGCTGCAG AACGACGGCT AGCGAATCCG TAATCATGGT CATA 54

( 2 ) INFORMATION FOR SEQ ID NO:34:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

```
CTGGCCAAAG GGGGATGTGG CTGCTAATCG ATTAAGTTGG GTAACGCCCG GG          52
```

( 2 ) INFORMATION FOR SEQ ID NO:35:

( i ) SEQUENCE CHARACTERISTICS:
        ( A ) LENGTH: 220 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:35:

```
GATCTATGAC CATGATTACG GATTCGCTAG CCGTCGTTCT GCAGCGTCGC GACTGGGAAA  60
ATACTGGTAC TAATGCCTAA GCGATCGGCA GCAAGACGTC GGAGCGCTGAC CCTTTACCC  120
GGGCGTTACC CAACTTAATC GATTAGCAGC ACATCCCCCT TTCGCCAGTGG GCCCGCAAT  180
CCCTTGAATT AGCAAATCGT CGTGTAGGGG GAAAGCGGTC                       220
```

( 2 ) INFORMATION FOR SEQ ID NO:36:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

```
GCGAAGCTTC CGACACCATC GAACGGCGC                                   29
```

( 2 ) INFORMATION FOR SEQ ID NO:37:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

```
GCGCACAATG TGCCTAATGA GTGAGCTAAC                                  30
```

( 2 ) INFORMATION FOR SEQ ID NO:38:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:38:

```
CGCGGATCCG GACGAAGGCC AGCGCTTG                                    28
```

( 2 ) INFORMATION FOR SEQ ID NO:39:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:39:

```
GCGGTCGACT  CATTAATGAT  GATGATGATG  ATGCGGGCTC  GAGGTGGACC  CTTCCACC              58
```

( 2 ) INFORMATION FOR SEQ ID NO:40:

( i ) SEQUENCE CHARACTERISTICS:
        ( A ) LENGTH: 1701 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1698

( x i ) SEQUENCE DESCRIPTION: SEQ ID NO:40:

```
ATG  TGG  CTG  CTG  CGG  TGC  GTT  TTG  CTG  TGT  GTT  TCA  TTA  TCT  CTT  GCT    48
Met  Trp  Leu  Leu  Arg  Cys  Val  Leu  Leu  Cys  Val  Ser  Leu  Ser  Leu  Ala
  1              5                        10                       15

GTG  AGT  GGC  CAG  CAT  AAG  CCT  GAG  GCA  CCA  GAT  TAT  TCC  AGT  GTG  CTC    96
Val  Ser  Gly  Gln  His  Lys  Pro  Glu  Ala  Pro  Asp  Tyr  Ser  Ser  Val  Leu
             20                        25                       30

CAC  TGT  GGG  CCG  TGG  AGC  TTC  CAG  TTT  GCT  GTA  AAC  CTC  AAC  CAG  GAG   144
His  Cys  Gly  Pro  Trp  Ser  Phe  Gln  Phe  Ala  Val  Asn  Leu  Asn  Gln  Glu
         35                        40                       45

GCA  ACG  TCT  CCT  CCT  GTA  CTA  ATA  GCT  TGG  GAC  AAC  CAA  GGG  CTG  CTG   192
Ala  Thr  Ser  Pro  Pro  Val  Leu  Ile  Ala  Trp  Asp  Asn  Gln  Gly  Leu  Leu
     50                        55                       60

CAC  GAG  CTG  CAG  AAT  GAC  TCC  GAC  TGT  GGC  ACC  TGG  ATA  AGA  AAA  GGT   240
His  Glu  Leu  Gln  Asn  Asp  Ser  Asp  Cys  Gly  Thr  Trp  Ile  Arg  Lys  Gly
 65                        70                       75                       80

CCA  GGC  AGC  TCC  GTG  GTG  TTG  GAG  GCA  ACC  TAT  AGC  AGC  TGC  TAT  GTC   288
Pro  Gly  Ser  Ser  Val  Val  Leu  Glu  Ala  Thr  Tyr  Ser  Ser  Cys  Tyr  Val
                 85                        90                       95

ACT  GAG  TGG  GTG  AGT  ATG  ACC  CAA  TGG  CCA  GGG  AGA  CTG  TGT  GAA  GCG   336
Thr  Glu  Trp  Val  Ser  Met  Thr  Gln  Trp  Pro  Gly  Arg  Leu  Cys  Glu  Ala
            100                       105                      110

CCT  CAT  GCT  ACC  ATC  CAG  GCT  GAC  CCC  CAA  GGC  CTG  TCT  CTC  CAG  GAC   384
Pro  His  Ala  Thr  Ile  Gln  Ala  Asp  Pro  Gln  Gly  Leu  Ser  Leu  Gln  Asp
        115                       120                      125

TCC  CAC  TAC  ATC  ATG  CCA  GTT  GGA  GTT  GAA  GGA  GCA  GGC  GCG  GCT  GAA   432
Ser  His  Tyr  Ile  Met  Pro  Val  Gly  Val  Glu  Gly  Ala  Gly  Ala  Ala  Glu
    130                       135                      140

CAC  AAG  GTG  GTT  ACA  GAG  AGG  AAG  CTG  CTC  AAG  TGT  CCT  ATG  GAT  CTT   480
His  Lys  Val  Val  Thr  Glu  Arg  Lys  Leu  Leu  Lys  Cys  Pro  Met  Asp  Leu
145                       150                      155                      160

CTA  GAT  GCT  CCA  GAT  ACT  GAC  TGG  TGT  GAC  TCC  ATC  CCA  GCA  CGG  GAC   528
Leu  Asp  Ala  Pro  Asp  Thr  Asp  Trp  Cys  Asp  Ser  Ile  Pro  Ala  Arg  Asp
                     165                      170                      175

AGA  CTG  CCA  TGT  GCA  CCT  TCA  CCC  ATC  TCT  CGA  GGA  GAC  TGT  GAA  GGG   576
Arg  Leu  Pro  Cys  Ala  Pro  Ser  Pro  Ile  Ser  Arg  Gly  Asp  Cys  Glu  Gly
                 180                      185                      190
```

| | | | | | | | | | | | | | | | | |
|---|---|---|---|---|---|---|---|---|---|---|---|---|---|---|---|---|
| CTA | GGC | TGT | TGT | TAT | AGC | TCT | GAA | GAG | GTG | AAT | TCC | TGC | TAC | TAT | GGA | 624 |
| Leu | Gly | Cys | Cys | Tyr | Ser | Ser | Glu | Glu | Val | Asn | Ser | Cys | Tyr | Tyr | Gly | |
| | | 195 | | | | | 200 | | | | | 205 | | | | |
| AAC | ACT | GTG | ACC | TTG | CAT | TGT | ACC | CGA | GAG | GGC | CAT | TTC | TCT | ATT | GCT | 672 |
| Asn | Thr | Val | Thr | Leu | His | Cys | Thr | Arg | Glu | Gly | His | Phe | Ser | Ile | Ala | |
| | 210 | | | | | 215 | | | | | 220 | | | | | |
| GTG | TCT | CGG | AAC | GTG | ACC | TCG | CCA | CCA | CTG | CTC | TTG | GAT | TCT | GTG | CGC | 720 |
| Val | Ser | Arg | Asn | Val | Thr | Ser | Pro | Pro | Leu | Leu | Leu | Asp | Ser | Val | Arg | |
| 225 | | | | | 230 | | | | | 235 | | | | | 240 | |
| TTG | GCC | CTT | AGG | AAT | GAC | AGT | GCG | TGT | AAC | CCT | GTG | ATG | GCA | ACA | CAA | 768 |
| Leu | Ala | Leu | Arg | Asn | Asp | Ser | Ala | Cys | Asn | Pro | Val | Met | Ala | Thr | Gln | |
| | | | | 245 | | | | | 250 | | | | | 255 | | |
| GCT | TTT | GTT | CTG | TTC | CAG | TTT | CCA | TTT | ACT | TCC | TGT | GGC | ACC | ACA | AGA | 816 |
| Ala | Phe | Val | Leu | Phe | Gln | Phe | Pro | Phe | Thr | Ser | Cys | Gly | Thr | Thr | Arg | |
| | | | 260 | | | | | 265 | | | | | 270 | | | |
| CAG | ATC | ACT | GGA | GAC | CGA | GCA | GTA | TAT | GAA | AAT | GAA | CTG | GTG | GCA | ACT | 864 |
| Gln | Ile | Thr | Gly | Asp | Arg | Ala | Val | Tyr | Glu | Asn | Glu | Leu | Val | Ala | Thr | |
| | | 275 | | | | | 280 | | | | | 285 | | | | |
| AGG | GAT | GTG | AAA | AAT | GGG | AGC | CGT | GGC | TCT | GTC | ACT | CGT | GAC | AGC | ATC | 912 |
| Arg | Asp | Val | Lys | Asn | Gly | Ser | Arg | Gly | Ser | Val | Thr | Arg | Asp | Ser | Ile | |
| | 290 | | | | | 295 | | | | | 300 | | | | | |
| TTC | AGG | CTC | CAT | GTC | AGC | TGC | AGC | TAC | TCA | GTA | AGT | AGC | AAC | TCT | CTC | 960 |
| Phe | Arg | Leu | His | Val | Ser | Cys | Ser | Tyr | Ser | Val | Ser | Ser | Asn | Ser | Leu | |
| 305 | | | | | 310 | | | | | 315 | | | | | 320 | |
| CCA | ATC | AAT | GTC | CAG | GTT | TTC | ACT | CTC | CCA | CCA | CCC | TTT | CCT | GAG | ACC | 1008 |
| Pro | Ile | Asn | Val | Gln | Val | Phe | Thr | Leu | Pro | Pro | Pro | Phe | Pro | Glu | Thr | |
| | | | | 325 | | | | | 330 | | | | | 335 | | |
| CAG | CCT | GGA | CCC | CTC | ACT | CTG | GAA | CTT | CAG | ATT | GCC | AAA | GAT | AAA | AAC | 1056 |
| Gln | Pro | Gly | Pro | Leu | Thr | Leu | Glu | Leu | Gln | Ile | Ala | Lys | Asp | Lys | Asn | |
| | | | 340 | | | | | 345 | | | | | 350 | | | |
| TAT | GGC | TCT | TAC | TAC | GGT | GTT | GGT | GAC | TAC | CCA | GTG | GTG | AAG | TTG | CTT | 1104 |
| Tyr | Gly | Ser | Tyr | Tyr | Gly | Val | Gly | Asp | Tyr | Pro | Val | Val | Lys | Leu | Leu | |
| | | 355 | | | | | 360 | | | | | 365 | | | | |
| CGG | GAT | CCC | ATT | TAC | GTG | GAG | GTC | TCC | ATC | CTT | CAC | AGA | ACA | GAC | CCC | 1152 |
| Arg | Asp | Pro | Ile | Tyr | Val | Glu | Val | Ser | Ile | Leu | His | Arg | Thr | Asp | Pro | |
| | 370 | | | | | 375 | | | | | 380 | | | | | |
| TAC | CTG | GGG | CTG | CTC | CTA | CAA | CAG | TGT | TGG | GCA | ACA | CCC | AGC | ACT | GAC | 1200 |
| Tyr | Leu | Gly | Leu | Leu | Leu | Gln | Gln | Cys | Trp | Ala | Thr | Pro | Ser | Thr | Asp | |
| 385 | | | | | 390 | | | | | 395 | | | | | 400 | |
| CCC | CTG | AGT | CAG | CCA | CAG | TGG | CCC | ATC | CTG | GTA | AAG | GGC | TGC | CCC | TAC | 1248 |
| Pro | Leu | Ser | Gln | Pro | Gln | Trp | Pro | Ile | Leu | Val | Lys | Gly | Cys | Pro | Tyr | |
| | | | | 405 | | | | | 410 | | | | | 415 | | |
| ATT | GGA | GAC | AAC | TAT | CAG | ACC | CAG | CTG | ATC | CCT | GTC | CAG | AAA | GCC | TTG | 1296 |
| Ile | Gly | Asp | Asn | Tyr | Gln | Thr | Gln | Leu | Ile | Pro | Val | Gln | Lys | Ala | Leu | |
| | | | 420 | | | | | 425 | | | | | 430 | | | |
| GAT | CTT | CCA | TTT | CCC | TCT | CAC | CAC | CAG | CGC | TTC | AGC | ATC | TTC | ACC | TTC | 1344 |
| Asp | Leu | Pro | Phe | Pro | Ser | His | His | Gln | Arg | Phe | Ser | Ile | Phe | Thr | Phe | |
| | | 435 | | | | | 440 | | | | | 445 | | | | |
| AGC | TTT | GTG | AAC | CCT | ACA | GTG | GAG | AAA | CAG | GCC | CTC | AGG | GGA | CCG | GTG | 1392 |
| Ser | Phe | Val | Asn | Pro | Thr | Val | Glu | Lys | Gln | Ala | Leu | Arg | Gly | Pro | Val | |
| | 450 | | | | | 455 | | | | | 460 | | | | | |
| CAT | CTG | CAC | TGC | AGC | GTG | TCA | GTC | TGC | CAG | CCT | GCT | GAG | ACA | CCA | TCC | 1440 |
| His | Leu | His | Cys | Ser | Val | Ser | Val | Cys | Gln | Pro | Ala | Glu | Thr | Pro | Ser | |
| 465 | | | | | 470 | | | | | 475 | | | | | 480 | |
| TGT | GTG | GTG | ACC | TGT | CCT | GAT | CTC | AGT | CGA | AGA | AGA | AAT | TTT | GAC | AAC | 1488 |
| Cys | Val | Val | Thr | Cys | Pro | Asp | Leu | Ser | Arg | Arg | Arg | Asn | Phe | Asp | Asn | |
| | | | | 485 | | | | | 490 | | | | | 495 | | |
| AGT | TCT | CAG | AAC | ACT | ACT | GCT | AGT | GTT | TCT | AGC | AAA | GGC | CCC | ATG | ATT | 1536 |
| Ser | Ser | Gln | Asn | Thr | Thr | Ala | Ser | Val | Ser | Ser | Lys | Gly | Pro | Met | Ile | |
| | | | 500 | | | | | 505 | | | | | 510 | | | |

| | | | | | | | | | | | | | | | | |
|---|---|---|---|---|---|---|---|---|---|---|---|---|---|---|---|---|
| CTA | CTC | CAA | GCC | ACT | AAG | GAC | CCT | CCA | GAA | AAG | CTC | CGT | GTT | CCT | GTA | 1584 |
| Leu | Leu | Gln | Ala | Thr | Lys | Asp | Pro | Pro | Glu | Lys | Leu | Arg | Val | Pro | Val | |
| | | 515 | | | | 520 | | | | | 525 | | | | | |
| GAC | TCG | AAA | GTT | CTG | TGG | GTG | GCA | GGC | CTT | TCT | GGG | ACC | TTA | ATC | CTT | 1632 |
| Asp | Ser | Lys | Val | Leu | Trp | Val | Ala | Gly | Leu | Ser | Gly | Thr | Leu | Ile | Leu | |
| | 530 | | | | 535 | | | | | 540 | | | | | | |
| GGA | GCC | TTG | TTA | GTA | TCC | TAC | TTG | GCT | GTC | AAG | AAA | CAG | AAG | AGT | TGC | 1680 |
| Gly | Ala | Leu | Leu | Val | Ser | Tyr | Leu | Ala | Val | Lys | Lys | Gln | Lys | Ser | Cys | |
| 545 | | | | | 550 | | | | | 555 | | | | | 560 | |
| CCA | GAC | CAA | ATG | TGT | CAA | TAA | | | | | | | | | | 1701 |
| Pro | Asp | Gln | Met | Cys | Gln | | | | | | | | | | | |
| | | | | 565 | | | | | | | | | | | | |

( 2 ) INFORMATION FOR SEQ ID NO:41:

( i ) SEQUENCE CHARACTERISTICS:
        ( A ) LENGTH: 566 amino acids
        ( B ) TYPE: amino acid
        ( D ) TOPOLOGY: linear ( i i ) MOLECULE TYPE: protein ( x i ) SEQUENCE DESCRIPTION: SEQ ID NO:41:

| | | | | | | | | | | | | | | |
|---|---|---|---|---|---|---|---|---|---|---|---|---|---|---|
| Met | Trp | Leu | Leu | Arg | Cys | Val | Leu | Leu | Cys | Val | Ser | Leu | Ser | Leu | Ala |
| 1 | | | | 5 | | | | | 10 | | | | | 15 | |
| Val | Ser | Gly | Gln | His | Lys | Pro | Glu | Ala | Pro | Asp | Tyr | Ser | Ser | Val | Leu |
| | | | 20 | | | | | 25 | | | | | 30 | | |
| His | Cys | Gly | Pro | Trp | Ser | Phe | Gln | Phe | Ala | Val | Asn | Leu | Asn | Gln | Glu |
| | | 35 | | | | | 40 | | | | | 45 | | | |
| Ala | Thr | Ser | Pro | Pro | Val | Leu | Ile | Ala | Trp | Asp | Asn | Gln | Gly | Leu | Leu |
| | | 50 | | | | 55 | | | | | 60 | | | | |
| His | Glu | Leu | Gln | Asn | Asp | Ser | Asp | Cys | Gly | Thr | Trp | Ile | Arg | Lys | Gly |
| 65 | | | | | 70 | | | | | 75 | | | | | 80 |
| Pro | Gly | Ser | Ser | Val | Val | Leu | Glu | Ala | Thr | Tyr | Ser | Ser | Cys | Tyr | Val |
| | | | | 85 | | | | | 90 | | | | | 95 | |
| Thr | Glu | Trp | Val | Ser | Met | Thr | Gln | Trp | Pro | Gly | Arg | Leu | Cys | Glu | Ala |
| | | | 100 | | | | 105 | | | | | 110 | | | |
| Pro | His | Ala | Thr | Ile | Gln | Ala | Asp | Pro | Gln | Gly | Leu | Ser | Leu | Gln | Asp |
| | | 115 | | | | 120 | | | | | 125 | | | | |
| Ser | His | Tyr | Ile | Met | Pro | Val | Gly | Val | Glu | Gly | Ala | Gly | Ala | Ala | Glu |
| | 130 | | | | | 135 | | | | | 140 | | | | |
| His | Lys | Val | Val | Thr | Glu | Arg | Lys | Leu | Leu | Lys | Cys | Pro | Met | Asp | Leu |
| 145 | | | | | 150 | | | | | 155 | | | | | 160 |
| Leu | Asp | Ala | Pro | Asp | Thr | Asp | Trp | Cys | Asp | Ser | Ile | Pro | Ala | Arg | Asp |
| | | | | 165 | | | | | 170 | | | | | 175 | |
| Arg | Leu | Pro | Cys | Ala | Pro | Ser | Pro | Ile | Ser | Arg | Gly | Asp | Cys | Glu | Gly |
| | | | 180 | | | | | 185 | | | | | 190 | | |
| Leu | Gly | Cys | Cys | Tyr | Ser | Ser | Glu | Glu | Val | Asn | Ser | Cys | Tyr | Tyr | Gly |
| | | | 195 | | | | | 200 | | | | | 205 | | |
| Asn | Thr | Val | Thr | Leu | His | Cys | Thr | Arg | Glu | Gly | His | Phe | Ser | Ile | Ala |
| | | 210 | | | | | 215 | | | | | 220 | | | |
| Val | Ser | Arg | Asn | Val | Thr | Ser | Pro | Pro | Leu | Leu | Leu | Asp | Ser | Val | Arg |
| 225 | | | | | 230 | | | | | 235 | | | | | 240 |
| Leu | Ala | Leu | Arg | Asn | Asp | Ser | Ala | Cys | Asn | Pro | Val | Met | Ala | Thr | Gln |
| | | | | 245 | | | | | 250 | | | | | 255 | |
| Ala | Phe | Val | Leu | Phe | Gln | Phe | Pro | Phe | Thr | Ser | Cys | Gly | Thr | Thr | Arg |
| | | | 260 | | | | | 265 | | | | | 270 | | |
| Gln | Ile | Thr | Gly | Asp | Arg | Ala | Val | Tyr | Glu | Asn | Glu | Leu | Val | Ala | Thr |

|        |        |        |        |        | 275    |        |        |        |        | 280    |        |        |        |        | 285    |        |        |
|--------|--------|--------|--------|--------|--------|--------|--------|--------|--------|--------|--------|--------|--------|--------|--------|--------|--------|

Arg Asp Val Lys Asn Gly Ser Arg Gly Ser Val Thr Arg Asp Ser Ile
290                     295                     300

Phe Arg Leu His Val Ser Cys Ser Tyr Ser Val Ser Ser Asn Ser Leu
305             310             315                     320

Pro Ile Asn Val Gln Val Phe Thr Leu Pro Pro Phe Pro Glu Thr
            325             330             335

Gln Pro Gly Pro Leu Thr Leu Glu Leu Gln Ile Ala Lys Asp Lys Asn
            340             345             350

Tyr Gly Ser Tyr Tyr Gly Val Gly Asp Tyr Pro Val Val Lys Leu Leu
        355             360             365

Arg Asp Pro Ile Tyr Val Glu Val Ser Ile Leu His Arg Thr Asp Pro
370                     375             380

Tyr Leu Gly Leu Leu Leu Gln Gln Cys Trp Ala Thr Pro Ser Thr Asp
385             390             395                     400

Pro Leu Ser Gln Pro Gln Trp Pro Ile Leu Val Lys Gly Cys Pro Tyr
            405             410             415

Ile Gly Asp Asn Tyr Gln Thr Gln Leu Ile Pro Val Gln Lys Ala Leu
            420             425             430

Asp Leu Pro Phe Pro Ser His His Gln Arg Phe Ser Ile Phe Thr Phe
        435             440             445

Ser Phe Val Asn Pro Thr Val Glu Lys Gln Ala Leu Arg Gly Pro Val
    450             455             460

His Leu His Cys Ser Val Ser Val Cys Gln Pro Ala Glu Thr Pro Ser
465             470             475                     480

Cys Val Val Thr Cys Pro Asp Leu Ser Arg Arg Arg Asn Phe Asp Asn
            485             490             495

Ser Ser Gln Asn Thr Thr Ala Ser Val Ser Ser Lys Gly Pro Met Ile
            500             505             510

Leu Leu Gln Ala Thr Lys Asp Pro Glu Lys Leu Arg Val Pro Val
        515             520             525

Asp Ser Lys Val Leu Trp Val Ala Gly Leu Ser Gly Thr Leu Ile Leu
    530             535             540

Gly Ala Leu Leu Val Ser Tyr Leu Ala Val Lys Lys Gln Lys Ser Cys
545             550             555             560

Pro Asp Gln Met Cys Gln
            565

( 2 ) INFORMATION FOR SEQ ID NO:42:

( i ) SEQUENCE CHARACTERISTICS:
        ( A ) LENGTH: 2266 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..2235

( x i ) SEQUENCE DESCRIPTION: SEQ ID NO:42:

ATG GCG TGC AGG CAG AGA GGA GGC TCT TGG AGT CCC TCA GGC TGG TTC    48
Met Ala Cys Arg Gln Arg Gly Gly Ser Trp Ser Pro Ser Gly Trp Phe
1               5                   10                  15

AAT GCA GGC TGG AGC ACC TAC AGG TCG ATT TCT CTC TTC TTC GCC CTT    96
Asn Ala Gly Trp Ser Thr Tyr Arg Ser Ile Ser Leu Phe Phe Ala Leu
            20                  25                  30

| | | | | | | | | | | | | | | | | |
|---|---|---|---|---|---|---|---|---|---|---|---|---|---|---|---|---|
| GTG | ACT | TCA | GGG | AAC | TCC | ATA | GAT | GTT | TCT | CAG | TTG | GTA | AAT | CCT | GCC | 144 |
| Val | Thr | Ser | Gly | Asn | Ser | Ile | Asp | Val | Ser | Gln | Leu | Val | Asn | Pro | Ala | |
| | | 35 | | | | 40 | | | | | 45 | | | | | |
| TTT | CCA | GGC | ACT | GTC | ACT | TGC | GAT | GAA | AGG | GAA | ATA | ACA | GTG | GAG | TTC | 192 |
| Phe | Pro | Gly | Thr | Val | Thr | Cys | Asp | Glu | Arg | Glu | Ile | Thr | Val | Glu | Phe | |
| | 50 | | | | 55 | | | | | 60 | | | | | | |
| CCA | AGC | AGT | CCT | GGC | ACC | AAG | AAA | TGG | CAT | GCA | TCT | GTG | GTG | GAT | CCT | 240 |
| Pro | Ser | Ser | Pro | Gly | Thr | Lys | Lys | Trp | His | Ala | Ser | Val | Val | Asp | Pro | |
| 65 | | | | | 70 | | | | | 75 | | | | | 80 | |
| CTT | GGT | CTC | GAC | ATG | CCG | AAC | TGC | ACT | TAC | ATC | CTG | GAC | CCA | GAA | AAG | 288 |
| Leu | Gly | Leu | Asp | Met | Pro | Asn | Cys | Thr | Tyr | Ile | Leu | Asp | Pro | Glu | Lys | |
| | | | | 85 | | | | | 90 | | | | | 95 | | |
| CTC | ACC | CTG | AGG | GCT | ACC | TAT | GAT | AAC | TGT | ACC | AGG | AGA | GTG | CAT | GGT | 336 |
| Leu | Thr | Leu | Arg | Ala | Thr | Tyr | Asp | Asn | Cys | Thr | Arg | Arg | Val | His | Gly | |
| | | | 100 | | | | | 105 | | | | | 110 | | | |
| GGA | CAC | CAG | ATG | ACC | ATC | AGA | GTC | ATG | AAC | AAC | AGT | GCT | GCC | TTA | AGA | 384 |
| Gly | His | Gln | Met | Thr | Ile | Arg | Val | Met | Asn | Asn | Ser | Ala | Ala | Leu | Arg | |
| | | 115 | | | | | 120 | | | | | 125 | | | | |
| CAC | GGA | GCT | GTC | ATG | TAT | CAG | TTC | TTC | TGT | CCA | GCT | ATG | CAA | GTA | GAA | 432 |
| His | Gly | Ala | Val | Met | Tyr | Gln | Phe | Phe | Cys | Pro | Ala | Met | Gln | Val | Glu | |
| | 130 | | | | | 135 | | | | | 140 | | | | | |
| GAG | ACC | CAG | GGG | CTT | TCA | GCA | TCT | ACA | ATC | TGC | CAG | AAG | GAT | TTC | ATG | 480 |
| Glu | Thr | Gln | Gly | Leu | Ser | Ala | Ser | Thr | Ile | Cys | Gln | Lys | Asp | Phe | Met | |
| 145 | | | | | 150 | | | | | 155 | | | | | 160 | |
| TCT | TTT | TCC | TTG | CCA | CGG | GTC | TTC | TCT | GGC | TTG | GCT | GAC | GAC | AGT | AAG | 528 |
| Ser | Phe | Ser | Leu | Pro | Arg | Val | Phe | Ser | Gly | Leu | Ala | Asp | Asp | Ser | Lys | |
| | | | | 165 | | | | | 170 | | | | | 175 | | |
| GGG | ACC | AAA | GTT | CAG | ATG | GGA | TGG | AGC | ATT | GAG | GTT | GGT | GAT | GGT | GCA | 576 |
| Gly | Thr | Lys | Val | Gln | Met | Gly | Trp | Ser | Ile | Glu | Val | Gly | Asp | Gly | Ala | |
| | | | 180 | | | | | 185 | | | | | 190 | | | |
| AGA | GCC | AAA | ACT | CTG | ACC | CTG | CCA | GAG | GCC | ATG | AAG | GAA | GGC | TTC | AGC | 624 |
| Arg | Ala | Lys | Thr | Leu | Thr | Leu | Pro | Glu | Ala | Met | Lys | Glu | Gly | Phe | Ser | |
| | | 195 | | | | | 200 | | | | | 205 | | | | |
| CTC | TTG | ATT | GAC | AAC | CAC | AGG | ATG | ACC | TTC | CAT | GTG | CCA | TTC | AAT | GCC | 672 |
| Leu | Leu | Ile | Asp | Asn | His | Arg | Met | Thr | Phe | His | Val | Pro | Phe | Asn | Ala | |
| | 210 | | | | | 215 | | | | | 220 | | | | | |
| ACT | GGA | GTG | ACT | CAC | TAT | GTG | CAA | GGT | AAC | AGT | CAT | CTC | TAC | ATG | GTG | 720 |
| Thr | Gly | Val | Thr | His | Tyr | Val | Gln | Gly | Asn | Ser | His | Leu | Tyr | Met | Val | |
| 225 | | | | | 230 | | | | | 235 | | | | | 240 | |
| TCT | CTG | AAG | CTT | ACA | TTT | ATA | TCT | CCT | GGA | CAG | AAG | GTG | ATC | TTC | TCT | 768 |
| Ser | Leu | Lys | Leu | Thr | Phe | Ile | Ser | Pro | Gly | Gln | Lys | Val | Ile | Phe | Ser | |
| | | | | 245 | | | | | 250 | | | | | 255 | | |
| TCA | CAA | GCT | ATT | TGT | GCA | CCA | GAT | CCT | GTG | ACC | TGC | AAT | GCC | ACA | CAC | 816 |
| Ser | Gln | Ala | Ile | Cys | Ala | Pro | Asp | Pro | Val | Thr | Cys | Asn | Ala | Thr | His | |
| | | | 260 | | | | | 265 | | | | | 270 | | | |
| ATG | ACT | CTC | ACC | ATA | CCA | GAG | TTT | CCT | GGG | AAG | CTT | AAG | TCT | GTG | AGC | 864 |
| Met | Thr | Leu | Thr | Ile | Pro | Glu | Phe | Pro | Gly | Lys | Leu | Lys | Ser | Val | Ser | |
| | | 275 | | | | | 280 | | | | | 285 | | | | |
| TTT | GAA | AAC | CAG | AAC | ATT | GAT | GTG | AGC | CAG | CTG | CAT | GAC | AAT | GGA | ATT | 912 |
| Phe | Glu | Asn | Gln | Asn | Ile | Asp | Val | Ser | Gln | Leu | His | Asp | Asn | Gly | Ile | |
| | 290 | | | | | 295 | | | | | 300 | | | | | |
| GAT | CTA | GAA | GCA | ACA | AAT | GGC | ATG | AAA | TTG | CAT | TTC | AGC | AAA | ACT | CTG | 960 |
| Asp | Leu | Glu | Ala | Thr | Asn | Gly | Met | Lys | Leu | His | Phe | Ser | Lys | Thr | Leu | |
| 305 | | | | | 310 | | | | | 315 | | | | | 320 | |
| CTC | AAA | ACG | AAA | TTA | TCT | GAA | AAA | TGC | CTA | CTC | CAT | CAG | TTC | TAC | TTA | 1008 |
| Leu | Lys | Thr | Lys | Leu | Ser | Glu | Lys | Cys | Leu | Leu | His | Gln | Phe | Tyr | Leu | |
| | | | | 325 | | | | | 330 | | | | | 335 | | |
| GCT | TCA | CTC | AAG | CTG | ACC | TTT | CTC | CTT | CGG | CCA | GAG | ACA | GTA | TCC | ATG | 1056 |
| Ala | Ser | Leu | Lys | Leu | Thr | Phe | Leu | Leu | Arg | Pro | Glu | Thr | Val | Ser | Met | |
| | | | 340 | | | | | 345 | | | | | 350 | | | |

```
GTG  ATC  TAT  CCT  GAG  TGT  CTC  TGT  GAG  TCA  CCC  GTT  TCT  ATA  GTT  ACA   1104
Val  Ile  Tyr  Pro  Glu  Cys  Leu  Cys  Glu  Ser  Pro  Val  Ser  Ile  Val  Thr
          355                     360                    365

GGG  GAG  CTG  TGC  ACC  CAG  GAT  GGG  TTT  ATG  GAC  GTC  GAG  GTC  TAC  AGC   1152
Gly  Glu  Leu  Cys  Thr  Gln  Asp  Gly  Phe  Met  Asp  Val  Glu  Val  Tyr  Ser
     370                     375                    380

TAC  CAA  ACA  CAA  CCA  GCT  CTT  GAC  CTG  GGT  ACT  CTG  AGG  GTG  GGA  AAC   1200
Tyr  Gln  Thr  Gln  Pro  Ala  Leu  Asp  Leu  Gly  Thr  Leu  Arg  Val  Gly  Asn
385                     390                    395                         400

TCA  TCC  TGC  CAG  CCT  GTC  TTT  GAG  GCT  CAG  TCT  CAG  GGG  CTG  GTA  CGG   1248
Ser  Ser  Cys  Gln  Pro  Val  Phe  Glu  Ala  Gln  Ser  Gln  Gly  Leu  Val  Arg
               405                     410                         415

TTC  CAC  ATA  CCC  CTG  AAT  GGA  TGT  GGA  ACG  AGA  TAT  AAG  TTC  GAA  GAT   1296
Phe  His  Ile  Pro  Leu  Asn  Gly  Cys  Gly  Thr  Arg  Tyr  Lys  Phe  Glu  Asp
               420                     425                    430

GAT  AAA  GTC  GTC  TAT  GAA  AAC  GAA  ATA  CAT  GCT  CTC  TGG  ACG  GAT  TTT   1344
Asp  Lys  Val  Val  Tyr  Glu  Asn  Glu  Ile  His  Ala  Leu  Trp  Thr  Asp  Phe
          435                     440                    445

CCT  CCA  AGC  AAA  ATA  TCT  AGA  GAC  AGT  GAG  TTC  AGA  ATG  ACA  GTG  AAG   1392
Pro  Pro  Ser  Lys  Ile  Ser  Arg  Asp  Ser  Glu  Phe  Arg  Met  Thr  Val  Lys
     450                     455                    460

TGT  TCT  TAT  AGC  AGG  AAT  GAC  ATG  CTA  CTA  AAC  ATC  AAC  GTT  GAA  AGC   1440
Cys  Ser  Tyr  Ser  Arg  Asn  Asp  Met  Leu  Leu  Asn  Ile  Asn  Val  Glu  Ser
465                     470                    475                         480

CTT  ACT  CCT  CCA  GTG  GCC  TCA  GTG  AAG  TTG  GGT  CCA  TTT  ACC  TTG  ATC   1488
Leu  Thr  Pro  Pro  Val  Ala  Ser  Val  Lys  Leu  Gly  Pro  Phe  Thr  Leu  Ile
               485                     490                    495

CTG  CAA  AGC  TAC  CCA  GAT  AAT  TCC  TAC  CAA  CAA  CCT  TAT  GGG  GAA  AAC   1536
Leu  Gln  Ser  Tyr  Pro  Asp  Asn  Ser  Tyr  Gln  Gln  Pro  Tyr  Gly  Glu  Asn
               500                     505                         510

GAG  TAC  CCT  CTA  GTG  AGA  TTC  CTC  CGC  CAA  CCA  ATT  TAC  ATG  GAA  GTG   1584
Glu  Tyr  Pro  Leu  Val  Arg  Phe  Leu  Arg  Gln  Pro  Ile  Tyr  Met  Glu  Val
          515                     520                    525

AGA  GTC  CTA  AAC  AGG  GAT  GAC  CCC  AAC  ATC  AAG  CTG  GTC  TTA  GAT  GAC   1632
Arg  Val  Leu  Asn  Arg  Asp  Asp  Pro  Asn  Ile  Lys  Leu  Val  Leu  Asp  Asp
     530                     535                    540

TGC  TGG  GCG  ACG  TCC  ACC  ATG  GAT  CCA  GAC  TCT  TTC  CCC  CAG  TGG  AAC   1680
Cys  Trp  Ala  Thr  Ser  Thr  Met  Asp  Pro  Asp  Ser  Phe  Pro  Gln  Trp  Asn
545                     550                    555                         560

GTT  GTC  GTG  GAT  GGC  TGT  GCA  TAT  GAC  CTG  GAC  AAC  TAC  CAG  ACC  ACC   1728
Val  Val  Val  Asp  Gly  Cys  Ala  Tyr  Asp  Leu  Asp  Asn  Tyr  Gln  Thr  Thr
               565                     570                    575

TTC  CAT  CCA  GTC  GGC  TCC  TCT  GTG  ACC  CAT  CCT  GAT  CAC  TAT  CAG  AGG   1776
Phe  His  Pro  Val  Gly  Ser  Ser  Val  Thr  His  Pro  Asp  His  Tyr  Gln  Arg
               580                     585                    590

TTT  GAC  ATG  AAG  GCT  TTT  GCC  TTT  GTA  TCA  GAA  GCC  CAC  GTG  CTC  TCT   1824
Phe  Asp  Met  Lys  Ala  Phe  Ala  Phe  Val  Ser  Glu  Ala  His  Val  Leu  Ser
          595                     600                    605

AGC  CTG  GTC  TAC  TTC  CAC  TGC  AGT  GCC  TTA  ATC  TGT  AAT  CGA  CTC  TCC   1872
Ser  Leu  Val  Tyr  Phe  His  Cys  Ser  Ala  Leu  Ile  Cys  Asn  Arg  Leu  Ser
     610                     615                    620

CCT  GAC  TCC  CCA  CTG  TGT  TCT  GTG  ACC  TGC  CCT  GTG  TCC  TCT  AGG  CAC   1920
Pro  Asp  Ser  Pro  Leu  Cys  Ser  Val  Thr  Cys  Pro  Val  Ser  Ser  Arg  His
625                     630                    635                         640

AGG  CGA  GCC  ACA  GGG  GCC  ACT  GAA  GCA  GAG  AAA  ATG  ACA  GTC  AGC  CTC   1968
Arg  Arg  Ala  Thr  Gly  Ala  Thr  Glu  Ala  Glu  Lys  Met  Thr  Val  Ser  Leu
               645                     650                    655

CCA  GGA  CCC  ATT  CTC  CTG  TTG  TCA  GAT  GAC  TCC  TCA  TTC  AGA  GGT  GTC   2016
Pro  Gly  Pro  Ile  Leu  Leu  Leu  Ser  Asp  Asp  Ser  Ser  Phe  Arg  Gly  Val
               660                     665                    670
```

| | | | | | | | | | | | | | | | | |
|---|---|---|---|---|---|---|---|---|---|---|---|---|---|---|---|---|
| GGC | TCA | TCT | GAT | CTA | AAA | GCA | AGT | GGG | AGC | AGT | GGG | GAG | AAG | AGT | AGG | 2064 |
| Gly | Ser | Ser | Asp | Leu | Lys | Ala | Ser | Gly | Ser | Ser | Gly | Glu | Lys | Ser | Arg | |
| | | 675 | | | | | 680 | | | | | 685 | | | | |
| AGT | GAA | ACA | GGG | GAG | GAG | GTT | GGC | TCA | CGA | GGT | GCT | ATG | GAC | ACC | AAA | 2112 |
| Ser | Glu | Thr | Gly | Glu | Glu | Val | Gly | Ser | Arg | Gly | Ala | Met | Asp | Thr | Lys | |
| | 690 | | | | | 695 | | | | | 700 | | | | | |
| GGG | CAC | AAG | ACT | GCT | GGA | GAT | GTT | GGT | TCC | AAA | GCT | GTG | GCT | GCT | GTG | 2160 |
| Gly | His | Lys | Thr | Ala | Gly | Asp | Val | Gly | Ser | Lys | Ala | Val | Ala | Ala | Val | |
| 705 | | | | | 710 | | | | | 715 | | | | | 720 | |
| GCT | GCC | TTT | GCA | GGT | GTG | GTG | GCA | ACT | CTA | GGC | TTC | ATC | TAC | TAC | CTG | 2208 |
| Ala | Ala | Phe | Ala | Gly | Val | Val | Ala | Thr | Leu | Gly | Phe | Ile | Tyr | Tyr | Leu | |
| | | | | 725 | | | | | 730 | | | | | 735 | | |
| TAC | GAG | AAA | AGG | ACT | GTG | TCA | AAT | CAC | TAAATGGGCT | | TCTAAATAAA | | | | | 2255 |
| Tyr | Glu | Lys | Arg | Thr | Val | Ser | Asn | His | | | | | | | | |
| | | | 740 | | | | | 745 | | | | | | | | |
| GCAGTCAAAA T | | | | | | | | | | | | | | | | 2266 |

( 2 ) INFORMATION FOR SEQ ID NO:43:

( i ) SEQUENCE CHARACTERISTICS:
        ( A ) LENGTH: 745 amino acids
        ( B ) TYPE: amino acid
        ( D ) TOPOLOGY: linear ( i i ) MOLECULE TYPE: protein ( x i ) SEQUENCE DESCRIPTION: SEQ ID NO:43:

| | | | | | | | | | | | | | | |
|---|---|---|---|---|---|---|---|---|---|---|---|---|---|---|
| Met | Ala | Cys | Arg | Gln | Arg | Gly | Gly | Ser | Trp | Ser | Pro | Ser | Gly | Trp | Phe |
| 1 | | | | 5 | | | | | 10 | | | | | 15 | |
| Asn | Ala | Gly | Trp | Ser | Thr | Tyr | Arg | Ser | Ile | Ser | Leu | Phe | Phe | Ala | Leu |
| | | | 20 | | | | | 25 | | | | | 30 | | |
| Val | Thr | Ser | Gly | Asn | Ser | Ile | Asp | Val | Ser | Gln | Leu | Val | Asn | Pro | Ala |
| | | | 35 | | | | 40 | | | | | 45 | | | |
| Phe | Pro | Gly | Thr | Val | Thr | Cys | Asp | Glu | Arg | Glu | Ile | Thr | Val | Glu | Phe |
| | | 50 | | | | 55 | | | | | 60 | | | | |
| Pro | Ser | Ser | Pro | Gly | Thr | Lys | Lys | Trp | His | Ala | Ser | Val | Val | Asp | Pro |
| 65 | | | | | 70 | | | | 75 | | | | | | 80 |
| Leu | Gly | Leu | Asp | Met | Pro | Asn | Cys | Thr | Tyr | Ile | Leu | Asp | Pro | Glu | Lys |
| | | | | 85 | | | | | 90 | | | | | 95 | |
| Leu | Thr | Leu | Arg | Ala | Thr | Tyr | Asp | Asn | Cys | Thr | Arg | Arg | Val | His | Gly |
| | | | 100 | | | | | 105 | | | | | 110 | | |
| Gly | His | Gln | Met | Thr | Ile | Arg | Val | Met | Asn | Asn | Ser | Ala | Ala | Leu | Arg |
| | | 115 | | | | | 120 | | | | | 125 | | | |
| His | Gly | Ala | Val | Met | Tyr | Gln | Phe | Phe | Cys | Pro | Ala | Met | Gln | Val | Glu |
| | 130 | | | | | 135 | | | | | 140 | | | | |
| Glu | Thr | Gln | Gly | Leu | Ser | Ala | Ser | Thr | Ile | Cys | Gln | Lys | Asp | Phe | Met |
| 145 | | | | | 150 | | | | | 155 | | | | | 160 |
| Ser | Phe | Ser | Leu | Pro | Arg | Val | Phe | Ser | Gly | Leu | Ala | Asp | Asp | Ser | Lys |
| | | | | 165 | | | | | 170 | | | | | 175 | |
| Gly | Thr | Lys | Val | Gln | Met | Gly | Trp | Ser | Ile | Glu | Val | Gly | Asp | Gly | Ala |
| | | | 180 | | | | | 185 | | | | | 190 | | |
| Arg | Ala | Lys | Thr | Leu | Thr | Leu | Pro | Glu | Ala | Met | Lys | Glu | Gly | Phe | Ser |
| | | 195 | | | | | 200 | | | | | 205 | | | |
| Leu | Leu | Ile | Asp | Asn | His | Arg | Met | Thr | Phe | His | Val | Pro | Phe | Asn | Ala |
| | 210 | | | | | 215 | | | | | 220 | | | | |
| Thr | Gly | Val | Thr | His | Tyr | Val | Gln | Gly | Asn | Ser | His | Leu | Tyr | Met | Val |
| 225 | | | | | 230 | | | | | 235 | | | | | 240 |

```
Ser  Leu  Lys  Leu  Thr  Phe  Ile  Ser  Pro  Gly  Gln  Lys  Val  Ile  Phe  Ser
               245                      250                      255

Ser  Gln  Ala  Ile  Cys  Ala  Pro  Asp  Pro  Val  Thr  Cys  Asn  Ala  Thr  His
               260                      265                      270

Met  Thr  Leu  Thr  Ile  Pro  Glu  Phe  Pro  Gly  Lys  Leu  Lys  Ser  Val  Ser
               275                      280                      285

Phe  Glu  Asn  Gln  Asn  Ile  Asp  Val  Ser  Gln  Leu  His  Asp  Asn  Gly  Ile
          290                      295                      300

Asp  Leu  Glu  Ala  Thr  Asn  Gly  Met  Lys  Leu  His  Phe  Ser  Lys  Thr  Leu
305                      310                      315                      320

Leu  Lys  Thr  Lys  Leu  Ser  Glu  Lys  Cys  Leu  Leu  His  Gln  Phe  Tyr  Leu
               325                      330                      335

Ala  Ser  Leu  Lys  Leu  Thr  Phe  Leu  Leu  Arg  Pro  Glu  Thr  Val  Ser  Met
               340                      345                      350

Val  Ile  Tyr  Pro  Glu  Cys  Leu  Cys  Glu  Ser  Pro  Val  Ser  Ile  Val  Thr
               355                      360                      365

Gly  Glu  Leu  Cys  Thr  Gln  Asp  Gly  Phe  Met  Asp  Val  Glu  Val  Tyr  Ser
               370                      375                      380

Tyr  Gln  Thr  Gln  Pro  Ala  Leu  Asp  Leu  Gly  Thr  Leu  Arg  Val  Gly  Asn
385                      390                      395                      400

Ser  Ser  Cys  Gln  Pro  Val  Phe  Glu  Ala  Gln  Ser  Gln  Gly  Leu  Val  Arg
                    405                      410                      415

Phe  His  Ile  Pro  Leu  Asn  Gly  Cys  Gly  Thr  Arg  Tyr  Lys  Phe  Glu  Asp
               420                      425                      430

Asp  Lys  Val  Val  Tyr  Glu  Asn  Glu  Ile  His  Ala  Leu  Trp  Thr  Asp  Phe
          435                      440                      445

Pro  Pro  Ser  Lys  Ile  Ser  Arg  Asp  Ser  Glu  Phe  Arg  Met  Thr  Val  Lys
     450                      455                      460

Cys  Ser  Tyr  Ser  Arg  Asn  Asp  Met  Leu  Leu  Asn  Ile  Asn  Val  Glu  Ser
465                      470                      475                      480

Leu  Thr  Pro  Pro  Val  Ala  Ser  Val  Lys  Leu  Gly  Pro  Phe  Thr  Leu  Ile
               485                      490                      495

Leu  Gln  Ser  Tyr  Pro  Asp  Asn  Ser  Tyr  Gln  Gln  Pro  Tyr  Gly  Glu  Asn
               500                      505                      510

Glu  Tyr  Pro  Leu  Val  Arg  Phe  Leu  Arg  Gln  Pro  Ile  Tyr  Met  Glu  Val
          515                      520                      525

Arg  Val  Leu  Asn  Arg  Asp  Asp  Pro  Asn  Ile  Lys  Leu  Val  Leu  Asp  Asp
530                      535                      540

Cys  Trp  Ala  Thr  Ser  Thr  Met  Asp  Pro  Asp  Ser  Phe  Pro  Gln  Trp  Asn
545                      550                      555                      560

Val  Val  Val  Asp  Gly  Cys  Ala  Tyr  Asp  Leu  Asp  Asn  Tyr  Gln  Thr  Thr
               565                      570                      575

Phe  His  Pro  Val  Gly  Ser  Ser  Val  Thr  His  Pro  Asp  His  Tyr  Gln  Arg
               580                      585                      590

Phe  Asp  Met  Lys  Ala  Phe  Ala  Phe  Val  Ser  Glu  Ala  His  Val  Leu  Ser
               595                      600                      605

Ser  Leu  Val  Tyr  Phe  His  Cys  Ser  Ala  Leu  Ile  Cys  Asn  Arg  Leu  Ser
          610                      615                      620

Pro  Asp  Ser  Pro  Leu  Cys  Ser  Val  Thr  Cys  Pro  Val  Ser  Ser  Arg  His
625                      630                      635                      640

Arg  Arg  Ala  Thr  Gly  Ala  Thr  Glu  Ala  Glu  Lys  Met  Thr  Val  Ser  Leu
               645                      650                      655

Pro  Gly  Pro  Ile  Leu  Leu  Leu  Ser  Asp  Asp  Ser  Ser  Phe  Arg  Gly  Val
               660                      665                      670
```

```
Gly Ser Ser Asp Leu Lys Ala Ser Gly Ser Ser Gly Glu Lys Ser Arg
        675                 680                 685
Ser Glu Thr Gly Glu Glu Val Gly Ser Arg Gly Ala Met Asp Thr Lys
    690                 695                 700
Gly His Lys Thr Ala Gly Asp Val Gly Ser Lys Ala Val Ala Ala Val
705                 710                 715                 720
Ala Ala Phe Ala Gly Val Val Ala Thr Leu Gly Phe Ile Tyr Tyr Leu
                725                 730                 735
Tyr Glu Lys Arg Thr Val Ser Asn His
                740                 745
```

( 2 ) INFORMATION FOR SEQ ID NO:44:

( i ) SEQUENCE CHARACTERISTICS:
    ( A ) LENGTH: 560 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 15..506

( x i ) SEQUENCE DESCRIPTION: SEQ ID NO:44:

```
GAATTCGCGG CCGC TCC TCT GTG ACC CAT CCT GAT CAC TAT CAG AGG TTT        50
               Ser Ser Val Thr His Pro Asp His Tyr Gln Arg Phe
                1               5                      10

GAC ATG AAG GCT TTT GCC TTT GTA TCA GAG GCC CAT GTG CTC TCT AGC        98
Asp Met Lys Ala Phe Ala Phe Val Ser Glu Ala His Val Leu Ser Ser
        15                  20                  25

CTG GTC TAC TTC CAC TGC AGT GCC TTA ATC TGC AAT CGA CTC TCT CCA       146
Leu Val Tyr Phe His Cys Ser Ala Leu Ile Cys Asn Arg Leu Ser Pro
        30                  35                  40

GAC TCC CCT CTG TGT TCT GTG ACC TGC CCT GTG TCA TCT AGG CAC AGG       194
Asp Ser Pro Leu Cys Ser Val Thr Cys Pro Val Ser Ser Arg His Arg
45                  50                  55                  60

CGA GCC ACA GGG GCC ACT GAA GCA GAG AAA ATG ACA GTC AGC CTC CCA       242
Arg Ala Thr Gly Ala Thr Glu Ala Glu Lys Met Thr Val Ser Leu Pro
                65                  70                  75

GGA CCC ATT CTC CTG TTG TCA GAC GAC TCC TCA TTC AGA GGT GTT GGC       290
Gly Pro Ile Leu Leu Leu Ser Asp Asp Ser Ser Phe Arg Gly Val Gly
                80                  85                  90

TCA TCT GAT CTA AAA GCA AGT GGG AGC AGT GGG GAG AAC AGT AGG AGC       338
Ser Ser Asp Leu Lys Ala Ser Gly Ser Ser Gly Glu Asn Ser Arg Ser
        95                  100                 105

GAA ACA GGG GAG GAG GTT GGC TCA CGA GAT GTT ATG GAC ACC AAA GGG       386
Glu Thr Gly Glu Glu Val Gly Ser Arg Asp Val Met Asp Thr Lys Gly
    110                 115                 120

CAC AGG ACT GCT GGA GAT GTT GGT TCC AAA GCT GTG GCT GCT GTG GCT       434
His Arg Thr Ala Gly Asp Val Gly Ser Lys Ala Val Ala Ala Val Ala
125                 130                 135                 140

GCC TTG GCA GGT GTG GTG GCA ACT CTA GGC TTC ATC TGT TAC CTG TAT       482
Ala Leu Ala Gly Val Val Ala Thr Leu Gly Phe Ile Cys Tyr Leu Tyr
                145                 150                 155

AAG AAA AGG ACT GTG TCA AAT CAC TAAATGGGCT TCTAAATAAA GCAGTCAAAA       536
Lys Lys Arg Thr Val Ser Asn His
                160

TAAAAAAAAA GCGGCCGCGA ATTC                                              560
```

(2) INFORMATION FOR SEQ ID NO:45:

(i) SEQUENCE CHARACTERISTICS:
  (A) LENGTH: 164 amino acids
  (B) TYPE: amino acid
  (D) TOPOLOGY: linear (ii) MOLECULE TYPE: protein (xi) SEQUENCE DESCRIPTION: SEQ ID NO:45:

```
Ser Ser Val Thr His Pro Asp His Tyr Gln Arg Phe Asp Met Lys Ala
 1               5                  10                 15
Phe Ala Phe Val Ser Glu Ala His Val Leu Ser Ser Leu Val Tyr Phe
            20                  25                 30
His Cys Ser Ala Leu Ile Cys Asn Arg Leu Ser Pro Asp Ser Pro Leu
            35                  40                 45
Cys Ser Val Thr Cys Pro Val Ser Ser Arg His Arg Arg Ala Thr Gly
        50                  55                 60
Ala Thr Glu Ala Glu Lys Met Thr Val Ser Leu Pro Gly Pro Ile Leu
65                  70                  75                     80
Leu Leu Ser Asp Asp Ser Ser Phe Arg Gly Val Gly Ser Ser Asp Leu
                85                  90                 95
Lys Ala Ser Gly Ser Ser Gly Glu Asn Ser Arg Ser Glu Thr Gly Glu
            100                 105                110
Glu Val Gly Ser Arg Asp Val Met Asp Thr Lys Gly His Arg Thr Ala
            115                 120                125
Gly Asp Val Gly Ser Lys Ala Val Ala Ala Val Ala Ala Leu Ala Gly
        130                 135                 140
Val Val Ala Thr Leu Gly Phe Ile Cys Tyr Leu Tyr Lys Lys Arg Thr
145                 150                 155                    160
Val Ser Asn His
```

(2) INFORMATION FOR SEQ ID NO:46:

(i) SEQUENCE CHARACTERISTICS:
  (A) LENGTH: 866 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: CDS
  (B) LOCATION: 12..821

(xi) SEQUENCE DESCRIPTION: SEQ ID NO:46:

```
GAATTCGCGG C CGC CGT GGC TCT GTC ACT CGT GAC AGC ATC TTC AGG CTC       50
             Arg Arg Gly Ser Val Thr Arg Asp Ser Ile Phe Arg Leu
              1               5                      10
CAT GTC AGC TGC AGC TAC TCA GTA AGT AGC AAC TCT CTC CCA ATC AAG        98
His Val Ser Cys Ser Tyr Ser Val Ser Ser Asn Ser Leu Pro Ile Lys
            15                  20                  25
GTC CAG GTT TTT ACT CTC CCA CCA CCC TTT CCT GAG ACC CAG CCT GGA       146
Val Gln Val Phe Thr Leu Pro Pro Pro Phe Pro Glu Thr Gln Pro Gly
 30                  35                  40                  45
CCC CTC ACT CTG GAA CTT CAG ATT GCC AAA GAT AAA AAC TAT GGC TCC       194
Pro Leu Thr Leu Glu Leu Gln Ile Ala Lys Asp Lys Asn Tyr Gly Ser
                50                  55                  60
TAC TAT GGT GTT GGT GAC TAC CCC GTG GTG AAG TTG CTT CGG GAT CCC       242
Tyr Tyr Gly Val Gly Asp Tyr Pro Val Val Lys Leu Leu Arg Asp Pro
            65                  70                  75
```

| | | | | | | | | | | | | | | | | |
|---|---|---|---|---|---|---|---|---|---|---|---|---|---|---|---|---|
| ATC | TAT | GTG | GAG | GTC | TCC | ATC | CTT | CAC | AGA | ACA | GAC | CCC | TCC | CTG | GGG | 290 |
| Ile | Tyr | Val | Glu | Val | Ser | Ile | Leu | His | Arg | Thr | Asp | Pro | Ser | Leu | Gly | |
| | | 80 | | | | 85 | | | | | | 90 | | | | |
| CTG | CTC | CTA | CAT | CAG | TGT | TGG | GCA | ACA | CCC | AGC | ACA | GAC | CCA | CTG | AGT | 338 |
| Leu | Leu | Leu | His | Gln | Cys | Trp | Ala | Thr | Pro | Ser | Thr | Asp | Pro | Leu | Ser | |
| | 95 | | | | 100 | | | | | 105 | | | | | | |
| CAG | CCA | CAG | TGG | CCC | ATC | CTG | GTA | AAG | GGC | TGC | CCC | TAC | ATT | GGA | GAC | 386 |
| Gln | Pro | Gln | Trp | Pro | Ile | Leu | Val | Lys | Gly | Cys | Pro | Tyr | Ile | Gly | Asp | |
| 110 | | | | 115 | | | | | 120 | | | | | | 125 | |
| AAC | TAT | CAG | ACC | CAG | CTG | ATC | CCT | GTC | CAG | AAA | GCC | TTG | GAT | CTT | CCA | 434 |
| Asn | Tyr | Gln | Thr | Gln | Leu | Ile | Pro | Val | Gln | Lys | Ala | Leu | Asp | Leu | Pro | |
| | | | | 130 | | | | | 135 | | | | | 140 | | |
| TTT | CCC | TCT | CAC | TAC | CAG | CGC | TTC | AGC | ATC | TTC | ACC | TTC | AGC | TTT | GTG | 482 |
| Phe | Pro | Ser | His | Tyr | Gln | Arg | Phe | Ser | Ile | Phe | Thr | Phe | Ser | Phe | Val | |
| | | | 145 | | | | | 150 | | | | | 155 | | | |
| GAC | CCT | ACA | GCG | GAG | AAA | CAG | GCC | CTC | AGG | GGA | CCG | GTG | CAT | CTG | CAC | 530 |
| Asp | Pro | Thr | Ala | Glu | Lys | Gln | Ala | Leu | Arg | Gly | Pro | Val | His | Leu | His | |
| | | 160 | | | | | 165 | | | | | 170 | | | | |
| TGC | AGT | GTG | TCA | GTC | TGC | CAG | CCT | GCT | GAG | ACA | CCA | TCC | TGT | GCG | GTA | 578 |
| Cys | Ser | Val | Ser | Val | Cys | Gln | Pro | Ala | Glu | Thr | Pro | Ser | Cys | Ala | Val | |
| | 175 | | | | | 180 | | | | | 185 | | | | | |
| ACC | TGT | CCT | GAT | CTC | AGT | CGA | AGA | AAT | TCA | GGC | ACC | ATT | TTT | CAG | AAC | 626 |
| Thr | Cys | Pro | Asp | Leu | Ser | Arg | Arg | Asn | Ser | Gly | Thr | Ile | Phe | Gln | Asn | |
| 190 | | | | | 195 | | | | | 200 | | | | | 205 | |
| ACT | ACT | GCT | AGT | GTT | TCT | AGC | AAA | GGC | CCC | ATG | ATT | CTA | CTC | CAA | GCC | 674 |
| Thr | Thr | Ala | Ser | Val | Ser | Ser | Lys | Gly | Pro | Met | Ile | Leu | Leu | Gln | Ala | |
| | | | | 210 | | | | | 215 | | | | | 220 | | |
| ACT | AAG | GAC | CCT | CCA | GAA | AAG | CTC | CGT | GCT | CCT | GTA | GAC | TCA | AAA | GTT | 722 |
| Thr | Lys | Asp | Pro | Pro | Glu | Lys | Leu | Arg | Ala | Pro | Val | Asp | Ser | Lys | Val | |
| | | | 225 | | | | | 230 | | | | | 235 | | | |
| CTG | TGG | GTG | GCA | GGC | CTT | TCT | GGG | ACC | TTA | ATC | CTT | GGA | GGC | TTA | GTA | 770 |
| Leu | Trp | Val | Ala | Gly | Leu | Ser | Gly | Thr | Leu | Ile | Leu | Gly | Gly | Leu | Val | |
| | | 240 | | | | | 245 | | | | | 250 | | | | |
| GTA | TCC | TAC | TTG | GCT | ATC | AAA | CAG | CTG | AAT | TGT | CCA | GAC | CAA | ACA | TGT | 818 |
| Val | Ser | Tyr | Leu | Ala | Ile | Lys | Gln | Leu | Asn | Cys | Pro | Asp | Gln | Thr | Cys | |
| | 255 | | | | | 260 | | | | | 265 | | | | | |
| CAA | TAAAACCAGA | CTGTACTCCC | AAAAAAAAAA | AGCGGCCGCG | AATTC | | | | | | | | | | | 866 |
| Gln | | | | | | | | | | | | | | | | |
| 270 | | | | | | | | | | | | | | | | |

( 2 ) INFORMATION FOR SEQ ID NO:47:

( i ) SEQUENCE CHARACTERISTICS:
        ( A ) LENGTH: 270 amino acids
        ( B ) TYPE: amino acid
        ( D ) TOPOLOGY: linear ( i i ) MOLECULE TYPE: protein ( x i ) SEQUENCE DESCRIPTION: SEQ ID NO:47:

| | | | | | | | | | | | | | | |
|---|---|---|---|---|---|---|---|---|---|---|---|---|---|---|
| Arg | Arg | Gly | Ser | Val | Thr | Arg | Asp | Ser | Ile | Phe | Arg | Leu | His | Val | Ser |
| 1 | | | | 5 | | | | | 10 | | | | | 15 | |
| Cys | Ser | Tyr | Ser | Val | Ser | Ser | Asn | Ser | Leu | Pro | Ile | Lys | Val | Gln | Val |
| | | | 20 | | | | | 25 | | | | | 30 | | |
| Phe | Thr | Leu | Pro | Pro | Pro | Phe | Pro | Glu | Thr | Gln | Pro | Gly | Pro | Leu | Thr |
| | | | 35 | | | | | 40 | | | | | 45 | | |
| Leu | Glu | Leu | Gln | Ile | Ala | Lys | Asp | Lys | Asn | Tyr | Gly | Ser | Tyr | Tyr | Gly |
| | | 50 | | | | | 55 | | | | | 60 | | | |
| Val | Gly | Asp | Tyr | Pro | Val | Val | Lys | Leu | Leu | Arg | Asp | Pro | Ile | Tyr | Val |
| 65 | | | | | 70 | | | | | 75 | | | | | 80 |
| Glu | Val | Ser | Ile | Leu | His | Arg | Thr | Asp | Pro | Ser | Leu | Gly | Leu | Leu | Leu |

|  |  |  |  |  |  |  | 85 |  |  |  |  | 90 |  |  |  |  | 95 |  |  |
|---|---|---|---|---|---|---|---|---|---|---|---|---|---|---|---|---|---|---|---|

His Gln Cys Trp Ala Thr Pro Ser Thr Asp Pro Leu Ser Gln Pro Gln
            100                 105                 110

Trp Pro Ile Leu Val Lys Gly Cys Pro Tyr Ile Gly Asp Asn Tyr Gln
        115                 120                 125

Thr Gln Leu Ile Pro Val Gln Lys Ala Leu Asp Leu Pro Phe Pro Ser
    130                 135                 140

His Tyr Gln Arg Phe Ser Ile Phe Thr Phe Ser Phe Val Asp Pro Thr
145                 150                 155                 160

Ala Glu Lys Gln Ala Leu Arg Gly Pro Val His Leu His Cys Ser Val
                165                 170                 175

Ser Val Cys Gln Pro Ala Glu Thr Pro Ser Cys Ala Val Thr Cys Pro
            180                 185                 190

Asp Leu Ser Arg Arg Asn Ser Gly Thr Ile Phe Gln Asn Thr Thr Ala
        195                 200                 205

Ser Val Ser Ser Lys Gly Pro Met Ile Leu Leu Gln Ala Thr Lys Asp
    210                 215                 220

Pro Pro Glu Lys Leu Arg Ala Pro Val Asp Ser Lys Val Leu Trp Val
225                 230                 235                 240

Ala Gly Leu Ser Gly Thr Leu Ile Leu Gly Gly Leu Val Val Ser Tyr
                245                 250                 255

Leu Ala Ile Lys Gln Leu Asn Cys Pro Asp Gln Thr Cys Gln
            260                 265                 270

(2) INFORMATION FOR SEQ ID NO:48:

(i) SEQUENCE CHARACTERISTICS:
    (A) LENGTH: 722 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 15..683

(xi) SEQUENCE DESCRIPTION: SEQ ID NO:48:

```
GAATTCGCGG CCGC ATC CAC ACT GGC AGC CAC GTG CCA CTG CGG TTG TTT         50
               Ile His Thr Gly Ser His Val Pro Leu Arg Leu Phe
                 1               5                  10

GTG GAC CAC TGC GTG GCC ACA CCA ACA CCA GAC CAG AAT GCC TCC CCT         98
Val Asp His Cys Val Ala Thr Pro Thr Pro Asp Gln Asn Ala Ser Pro
            15                  20                  25

TAT CAC ACC ATC GTG GAC TTC CAT GGC TGT CTT GTC GAT GGT CTC ACT        146
Tyr His Thr Ile Val Asp Phe His Gly Cys Leu Val Asp Gly Leu Thr
        30                  35                  40

GAT GCC TCT TCT GCG TTC AAA GTT CCT CGA CCC GGG CCA GAT ACA CTC        194
Asp Ala Ser Ser Ala Phe Lys Val Pro Arg Pro Gly Pro Asp Thr Leu
45                  50                  55                  60

CAG TTC ACA GTG GAT GTC TTC CAC TTT GCT AAT GAC TCC AGA AAC ATG        242
Gln Phe Thr Val Asp Val Phe His Phe Ala Asn Asp Ser Arg Asn Met
                65                  70                  75

ATA TAC ATC ACC TGC CAC CTG AAG GCC ATC CCA GCT GAG CAG GAA CCA        290
Ile Tyr Ile Thr Cys His Leu Lys Ala Ile Pro Ala Glu Gln Glu Pro
            80                  85                  90

GAC GAA CTC AAC AAA GCC TGT TCC TTC AGC AAG TCT TCC AAC AGC TGG        338
Asp Glu Leu Asn Lys Ala Cys Ser Phe Ser Lys Ser Ser Asn Ser Trp
        95                  100                 105
```

| | | | | | | | | | | | | | | | |
|---|---|---|---|---|---|---|---|---|---|---|---|---|---|---|---|
| TTC | CCA | GTG | GAA | GGC | CCA | GCT | GAC | ATC | TGT | CAA | TGC | TGT | AGC | AAG | GGT | 386
| Phe | Pro | Val | Glu | Gly | Pro | Ala | Asp | Ile | Cys | Gln | Cys | Cys | Ser | Lys | Gly
| | 110 | | | | 115 | | | | | 120 | | | | |
| GAC | TGT | GGC | ACT | CCA | AGC | CAT | TCC | AGG | AGG | CAG | CCC | CAT | GTC | GTG | AGC | 434
| Asp | Cys | Gly | Thr | Pro | Ser | His | Ser | Arg | Arg | Gln | Pro | His | Val | Val | Ser
| 125 | | | | | 130 | | | | | 135 | | | | | 140
| CAG | TGG | TCC | AGG | TCT | GCT | TCT | CGT | AAC | CGC | AGG | CAT | GTG | ACA | GAA | GAA | 482
| Gln | Trp | Ser | Arg | Ser | Ala | Ser | Arg | Asn | Arg | Arg | His | Val | Thr | Glu | Glu
| | | | | 145 | | | | | 150 | | | | | 155 |
| GCA | GAT | ATC | ACC | GTG | GGG | CCA | CTG | ATC | TTC | CTG | GAC | AGG | AGT | GCT | GAC | 530
| Ala | Asp | Ile | Thr | Val | Gly | Pro | Leu | Ile | Phe | Leu | Asp | Arg | Ser | Ala | Asp
| | | | 160 | | | | | 165 | | | | | 170 | |
| TAT | GAA | GTA | GAA | CAG | TGG | GCC | TTG | CCG | ACT | GAC | ACC | TCC | GTG | CTG | CTG | 578
| Tyr | Glu | Val | Glu | Gln | Trp | Ala | Leu | Pro | Thr | Asp | Thr | Ser | Val | Leu | Leu
| | | 175 | | | | | | 180 | | | | | 185 | |
| CTG | GGC | ATA | GGC | CTG | GCC | GTG | GTG | GCA | TCT | CTG | ACT | CTG | ACC | GCT | GTT | 626
| Leu | Gly | Ile | Gly | Leu | Ala | Val | Val | Ala | Ser | Leu | Thr | Leu | Thr | Ala | Val
| | | 190 | | | | | 195 | | | | | 200 | | |
| ATC | CTG | ATT | TTC | ACC | AGG | AGG | TGG | CGC | ACT | GCC | TCC | CGC | CCT | GTG | TCT | 674
| Ile | Leu | Ile | Phe | Thr | Arg | Arg | Trp | Arg | Thr | Ala | Ser | Arg | Pro | Val | Ser
| 205 | | | | | 210 | | | | | 215 | | | | | 220
| GTT | TCC | CAA | TAAAAGAAGA | AAGCAGTAAA | AAAAAGCGGC | CGCGAATTC | | | | | | | | | | 722
| Val | Ser | Gln | | | | | | | | | | | | | |

(2) INFORMATION FOR SEQ ID NO:49:

(i) SEQUENCE CHARACTERISTICS:
        (A) LENGTH: 223 amino acids
        (B) TYPE: amino acid
        (D) TOPOLOGY: linear (ii) MOLECULE TYPE: protein (xi) SEQUENCE DESCRIPTION: SEQ ID NO:49:

| | | | | | | | | | | | | | | |
|---|---|---|---|---|---|---|---|---|---|---|---|---|---|---|
| Ile | His | Thr | Gly | Ser | His | Val | Pro | Leu | Arg | Leu | Phe | Val | Asp | His | Cys
| 1 | | | | 5 | | | | | 10 | | | | | 15 |
| Val | Ala | Thr | Pro | Thr | Pro | Asp | Gln | Asn | Ala | Ser | Pro | Tyr | His | Thr | Ile
| | | | 20 | | | | | 25 | | | | | 30 | |
| Val | Asp | Phe | His | Gly | Cys | Leu | Val | Asp | Gly | Leu | Thr | Asp | Ala | Ser | Ser
| | | | 35 | | | | | 40 | | | | | 45 | |
| Ala | Phe | Lys | Val | Pro | Arg | Pro | Gly | Pro | Asp | Thr | Leu | Gln | Phe | Thr | Val
| | 50 | | | | | 55 | | | | | 60 | | | | |
| Asp | Val | Phe | His | Phe | Ala | Asn | Asp | Ser | Arg | Asn | Met | Ile | Tyr | Ile | Thr
| 65 | | | | | 70 | | | | | 75 | | | | | 80
| Cys | His | Leu | Lys | Ala | Ile | Pro | Ala | Glu | Gln | Glu | Pro | Asp | Glu | Leu | Asn
| | | | | 85 | | | | | 90 | | | | | 95 |
| Lys | Ala | Cys | Ser | Phe | Ser | Lys | Ser | Ser | Asn | Ser | Trp | Phe | Pro | Val | Glu
| | | | | 100 | | | | | 105 | | | | | 110 |
| Gly | Pro | Ala | Asp | Ile | Cys | Gln | Cys | Cys | Ser | Lys | Gly | Asp | Cys | Gly | Thr
| | | | 115 | | | | | 120 | | | | | 125 | |
| Pro | Ser | His | Ser | Arg | Arg | Gln | Pro | His | Val | Val | Ser | Gln | Trp | Ser | Arg
| | | | 130 | | | | | 135 | | | | | 140 | |
| Ser | Ala | Ser | Arg | Asn | Arg | Arg | His | Val | Thr | Glu | Glu | Ala | Asp | Ile | Thr
| 145 | | | | | 150 | | | | | 155 | | | | | 160
| Val | Gly | Pro | Leu | Ile | Phe | Leu | Asp | Arg | Ser | Ala | Asp | Tyr | Glu | Val | Glu
| | | | | 165 | | | | | 170 | | | | | 175 |
| Gln | Trp | Ala | Leu | Pro | Thr | Asp | Thr | Ser | Val | Leu | Leu | Leu | Gly | Ile | Gly
| | | | 180 | | | | | 185 | | | | | 190 | |
| Leu | Ala | Val | Val | Ala | Ser | Leu | Thr | Leu | Thr | Ala | Val | Ile | Leu | Ile | Phe

|     | 195 |     |     | 200 |     |     | 205 |     |     |
|-----|-----|-----|-----|-----|-----|-----|-----|-----|-----|
| Thr Arg Arg Trp Arg Thr Ala Ser Arg Pro Val Ser Val Ser Gln |
|     | 210 |     |     | 215 |     |     | 220 |     |     |

( 2 ) INFORMATION FOR SEQ ID NO:50:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:50:

CGCCCTTCCC AGCAACTGCA CCATCACCAC CATGGG            36

( 2 ) INFORMATION FOR SEQ ID NO:51:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:51:

GATCCCCATG GTGGTGGTGA TGGTGCAGTT GCTGGGAAGG GCGAT       45

( 2 ) INFORMATION FOR SEQ ID NO:52:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:52:

GATCCCTCGA GCCACCATCA CCACCATCAT G              31

( 2 ) INFORMATION FOR SEQ ID NO:53:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:53:

AATTCATGAT GGTGGTGATG GTGGCTCGAG G              31

( 2 ) INFORMATION FOR SEQ ID NO:54:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:54:

CCCGGATCCG CAGACCATCT GGCCAACTGA G              31

(2) INFORMATION FOR SEQ ID NO:55:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:55:

GCGCTCGAGG GCATATGGCT GCCAGTGTG    29

(2) INFORMATION FOR SEQ ID NO:56:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:56:

CGCGCTAGCA GATCTATGGC GCCGAGCTGG AGGTTC    36

(2) INFORMATION FOR SEQ ID NO:57:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:57:

CGCGGATCCT ATTAATGGTG GTGATGGTGG TGACTAGTGG ACCCTTCCA    49

(2) INFORMATION FOR SEQ ID NO:58:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:58:

CCCGCTAGCA GATCTATGGG GCTGAGCTAT GGAATTTTC    39

(2) INFORMATION FOR SEQ ID NO:59:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:59:

CGCACTAGTT GACCCCTCTA TACCATGATC ACTA    34

DNAS ENCODING MAMMALIAN ZPC AND USES THEREOF

CROSS REFERENCE TO RELATED APPLICATION

This is a divisional of U.S. application Ser. No. 08/149,223, filed Nov. 9, 1993, pending; which is a continuation-in-part of U.S. application Ser. No. 08/012,990, filed Jan. 29, 1993, now abandoned; which is a continuation-in-part of U.S. application Ser. No. 07/973,341, filed Nov. 9, 1992, now abandoned.

FIELD OF THE INVENTION

This invention relates generally to the production and use of zona pellucida proteins, and more particularly to novel DNA sequences encoding zona pellucida proteins, to recombinant materials and methods for producing such proteins and to materials and methods for selectively effecting either transient infertility or permanent sterility in mammals through use of naturally occurring and recombinant zona pellucida proteins.

BACKGROUND OF THE INVENTION

The present invention relates to a method for inducing reproducible transient infertility or sterility in a mammal by inducing in that mammal antibodies directed to proteins found in the zona pellucida of that mammal's oocytes. The invention also relates to purified, isolated DNA sequences encoding the zona pellucida proteins herein designated "ZPA" and "ZPB" and "ZPC" from various mammalian species. The invention is further directed to pharmaceutical compositions capable of inducing antibody production in a subject mammal.

The zona pellucida (ZP) is a complex matrix surrounding the mammalian oocyte, formed of glycoproteins secreted by ovarian cells. Zona pellucida glycoproteins perform a variety of functions. For example, the mouse ZP proteins previously designated ZP2 and ZP3 are complexed into long filaments which are cross-linked by the protein designated ZP1 in the ZP matrix providing structural integrity to the matrix. Wassarman, P. M., *Annu. Rev. Biochem.* 57:415–442 (1988). In addition to its structural role, mouse ZP3 has been shown to be a sperm receptor in the ZP matrix. Bleil, J. P. and Wassarman, P. M., *Cell* 20: 873–882 (1980). Following binding of sperm to ZP3 and the subsequent induction of the sperm acrosome reaction on the surface of the ZP, ZP2 acts as a secondary sperm receptor that is necessary for the maintenance of sperm binding to the egg. Bleil et al., *Dev. Biol.* 128: 376–385 (1988). Because of its role in the maintenance of the oocyte and in sperm-oocyte interactions, the ZP represents a logical target for design of contraceptive agents which interfere with the fertilization process.

Various groups have undertaken an immunological approach in attempts to interfere with ZP functions and thus to decrease fertility in immunized animals. See, Dunbar et al. In: *International Congress on Reproductive Immunology.* T. Wegman and T. Gills (eds.). London: Oxford Press, pp. 505–528 (1983); and Dunbar et al. In: *Mechanisms and Control of Animal Fertilization.* J. Hartman (ed.) Academic Press, New York, pp. 139–166 (1983). These studies showed that active immunization of mammals with ovarian homogenates decreased fertility. However, the large number of components in such homogenates made the identification of antigens responsible for the decrease in fertility nearly impossible. In addition, the use of such a complex mixture creates a potential for unwanted and potentially harmful side-effects.

Research by various investigators using chromatographic methods including SDS polyacrylamide gel electrophoresis (PAGE) and high pressure liquid chromatography (HPLC) have resulted in the identification of numerous zona pellucida proteins from a variety of mammalian species. Data compiled by Timmons and Dunbar in "*Perspectives in Immunoreproduction: Conception and Contraception*"; pp. 242–260, Mathur, S. and Fredericks, C. M. eds.; New York, Hemisphere Publishing Co (1988), as described below, illustrate examples of zona pellucida proteins that have been characterized.

Zona pellucida proteins isolated from pig include: PZI, a 40–110 kD protein isolated by Dunbar et al., *Biol. Reprod.* 24:1111 (1981); PZII, a 70–110 kD protein, PZIII, a 95–118 kD protein, and PZIV, an 18–25 kD protein, all isolated by Dunbar et al., *Biol. Reprod.* 32:619 (1985); 90K, a 89–119 kD protein, 65K, a 61–83 kD protein, 55K, a 47–66 kD protein, and 25K, an 18–26 kD protein, all isolated by Hedrick, J. L. and Wardrip, N. J. *Biochem.* 157: 63 (1986); ZP1, an 82–118 kD protein, ZP2, a 58–96 kD protein, ZP3 (PPZA), a 40–74 kD protein, and ZP4, a 21 kD protein, all isolated by Subramanian et al., *Biol. Reprod.* 24:933 (1981); 87K (ZP1/ZP2), a 77–97 kD protein, 58K, a 40–70 kD protein both isolated by Yurewicz et al., *Biol. Reprod.* 29: 511 (1983); deglycosylated PZI, a 35 kD protein; PZII, a 55 kD protein; and PZIII, an 80 kD protein all isolated by Skinner and Dunbar as described in *Immunological Approaches to Contraception and the Promotion of Fertility,* G. P. Talwar (ed.) New York: Plenum pp. 251–268 (1986); and deglycosylated ZP3 having a molecular weight of 45 kD isolated by Sacco et al., *J. Reprod. Fertil.* 76:575 (1986).

Isolated rabbit zona pellucida proteins include: RZI, RZII, and RZIII, having molecular weights of 68–125 kD, 80–100.5 kD, and 100–132 kD respectively, all isolated by Dunbar et al., *Biol. Reprod.* 24:1111 (1986); ZP1, ZP2, and ZP3 having molecular weights of 100–118 kD, 83–110 kD, and 80–92 kD respectively, all isolated by Sacco et al., *Proc. Soc. Exp. Biol. Med.* 167:318 (1981); deglycosylated RZI, and RZII having molecular weights of 65 kD, and 80 kD respectively, both isolated by Skinner and Dunbar and described in *Immunological Approaches to Contraception and Promotion of Fertility.* G. P. Talwar (ed.). New York: Plenum, pp. 251–268 (1986); and deglycosylated RZIII, a 90 kD protein isolated by Timmons and Dunbar, *Biol. Reprod.* 36: 1275 (1987).

A number of mouse zona pellucida proteins have been isolated including: ZP1, ZP2, and ZP3 having molecular weights of 200 kD, 120 kD, and 83 kD respectively, all isolated by Bleil and Wassarman *Dev. Biol.* 76:185 (1980); and ZP1 and ZP2 having molecular weights of 166–122 kD and 90–92 kD respectively, isolated by Sacco et al., *Proc. Soc. Exp. Biol. Med.* 167: 318 (1981). The differences in the molecular weights of mouse ZP1 and ZP2 as reported by Bleil et al. and Sacco et al. may be due to the fact that Bleil used 2D-PAGE under non-reducing conditions while Sacco used 2D-PAGE under reducing conditions.

The cat zona pellucida proteins CZI and CZII were isolated by Maresh and Dunbar *J. Exp. Zool.* 244:299 (1987) and have molecular weights of 50–110 kD and 90–110 kD respectively.

Maresh and Dunbar *J. Exp. Zool.* 244:299 (1987), have also isolated the dog zona pellucida proteins DZI, DZII, and DZIII which have molecular weights of 50–110 kD, 70–95 kD, and 90–100 kD respectively.

Sacco et al., *Proc. Soc. Exp. Biol. Med.* 167:318 (1981) described squirrel monkey ZP1, ZP2, ZP3, and ZP4 having molecular weights of 63–78 kD, 63–70 kD, 47–51 kD, and 43–47 kD respectively. In the same publication Sacco et al. described human ZP1, ZP2, and ZP3 having molecular weights of 80–120 kD, 73 kD, and 59–65 kD respectively.

To date, few mammalian zona pellucida genes or proteins have been isolated and sequenced. None has been successfully used to produce an effective immunocontraceptive. A lack of consensus among those of skill in the art regarding the number and characteristics (e.g. molecular weight) of proteins present in the zona pellucida of various mammalian species, and difficulties in purifying these heavily glycosylated proteins have hampered attempts to utilize zona pellucida proteins to produce an effective immunocontraceptive with predictable function.

A number of groups have had success in cloning cDNAs or genes encoding various mammalian zona pellucida proteins.

Ringuette et al., *Dev. Biol.*, 127:287–295 (1988) and Liang et al., *Mol. Cell. Biol.*, 10:1507–1515 (1990), reported cloning of mouse DNA encoding zona pellucida proteins ZP3 and ZP2, respectively. The clones were obtained by screening mouse cDNA libraries with anti-ZP3 and anti-ZP2 antibodies. No sequence homology was found between mouse ZP3 and ZP2.

Ringuette et al., *Proc. Natl. Acad. Sci. U.S.A.*, 83:4341–4345 (1986), reported isolation of a partial cDNA clone for mouse ZP3, which clone hybridized with total genomic DNA of mouse, rat, dog, cow, and human, but not with pig or rabbit genomic DNA unless the hybridization was performed at very low stringency. The full length ZP3 cDNA characterized by Ringuette *Dev. Biol.* 127:287–295 (1988) represents a germ-line specific mRNA having relatively short 5' and 3' untranslated regions and an open reading frame of about 1317 nucleotides with an additional 200–300 nucleotide poly-A tail. Ringuette also found that rat, rabbit, dog, and cow ovary transcribes mRNA which hybridized to the mouse ZP3 cDNA and that the ZP3 transcripts had similar molecular weights. Liang et al. *Mol. Cell. Biol.*, 10:1507–1515 (1990), showed that the nucleic acid and deduced amino acid sequence of ZP2 is distinctly different from that of ZP3 although it had the same short motif of 5' and 3' untranslated regions. The ZP2 mRNA is reported to have single open reading frame of 2,139 nucleotides which codes for a polypeptide of 80,217 Daltons representing 713 amino acids.

Chamberlin and Dean, *Dev. Biol.* 131:207–214 (1989) and Kinloch, R. A. et al., *Proc. Nat. Acad. Sci. U.S.A.*, 85:6409–6413 (1988) have reported the cloning of the mouse ZP3 gene. The mouse ZP3 gene is reported to have 8 exons and 7 introns in a transcription unit of 8.6 kbp.

Kinloch et al., *Dev. Biol.* 142:414–421 (1990), reported cloning of hamster genomic ZP3 DNA from a hamster genomic DNA library screened with mouse ZP3 DNA as a probe. The hamster ZP3 gene has a transcription unit of 7900 nucleotides and was found to contain 7 introns and 8 exons. The hamster ZP3 protein is approximately 81% homologous to mouse ZP3 protein. The hamster transcript contained 1266 nucleotides, six less than mouse ZP3 mRNA.

Chamberlain and Dean, *Proc. Natl. Acad. Sci. U.S.A.* 87:6014–6018 (1990), reported the cloning of human ZP3 from a human genomic DNA library using mouse ZP3 cDNA as a probe. The human ZP3 gene is composed of 8 exons in a transcription unit of 18.3 kbp. The exons are almost identical in size to the eight exons of mouse ZP3 and the nucleotide sequence of the coding region is 74% homologous. The human ZP3 transcript is very similar to mouse ZP3 mRNA. Both have short 5' and 3' untranslated regions, and both have a single open reading frame of 1272 nucleotides that encodes a 424-amino acid protein.

U.S. Pat. No. 4,996,297, to Dunbar, reported the isolation of three rabbit zona pellucida clones encoding rabbit ZP1 and ZP2 proteins, using anti-ZP1 and anti-ZP2 antibodies as screening probes. The sequences designated as P2 and P3 in FIG. 4 of the Dunbar patent represent rabbit ZP cDNAs of 812 and 1705 nucleotides respectively.

Schwoebel et al., *J. Biol. Chem.* 266:7214–7219 (1991), isolated and characterized a full length cDNA (designated rc 55) encoding the 55-kD rabbit zona pellucida protein using cross-species affinity purified antisera. The protein encoded by this cDNA has some similarity to the mouse ZP2 protein described by Liang. However, comparisons of rc 55 with the mouse ZP3 protein revealed no homology.

The functional activities of the cloned ZP DNAs and their encoded proteins have not been fully characterized and neither has their potential use as immunocontraceptives been demonstrated.

In order to develop a useful zona pellucida product for use in fertility control, particularly in the form of a vaccine, it is highly desirable to purify, isolate, and characterize zona pellucida proteins from a species of an animal of interest. Because of factors such as the purity of such proteins needed for vaccine production, and the high cost and numerous problems associated with purification of these proteins, it would be highly desirable to ascertain the DNA and amino acid sequences of zona pellucida proteins of a specific species of interest. Having such known, isolated and characterized zona pellucida proteins, the function of each zona pellucida protein may be understood and a fertility control product may be designed based upon the specific functional characteristics of a particular zona pellucida protein and for a particular mammalian species.

It would be thus highly useful and desirable to provide isolated, purified, sequenced, and characterized recombinant zona pellucida proteins which would permit the development of fertility control products possessing specific reproducible effects in eliciting transient and/or permanent infertility. Such products, where used to elicit transient infertility, would desirably have long lasting effects so as to minimize the number of times the immunocontraceptive agent must be administered to maintain infertility.

SUMMARY OF THE INVENTION

The present invention provides novel methods and materials for inducing either reproducible transient or permanent infertility effects in female mammals, including humans, by selective administration of homologous and/or heterologous mammalian species ZP proteins or immunocontraceptively active fragments thereof hereinafter designated as ZPA, ZPB and ZPC. By "reproducible" is meant that, unlike prior art attempts to induce transient infertility by administration of ZP proteins (in the form of mixtures of such proteins), this invention achieves its transient infertility effects by the administration of ZPA and/or ZPB in a form such that the duration of transient infertility is controllable and can be maintained in an on or off condition in a controllable and/or predictable fashion. This is achieved primarily through administration of the highly pure ZPA and ZPB proteins or immunocontraceptively active fragments thereof of this invention, e.g., in recombinant form and thus essentially devoid of ZPC. By immunocontraceptively active fragments is meant a ZP protein fragment capable of inducing infertility.

In one of its aspects, the present invention provides methods for inducing reproducible transient infertility in a mammal by administering to a subject female mammal a zona pellucida protein (or fragment thereof) selected from the group consisting of mammalian ZPA, and ZPB, and combinations thereof in doses effective to stimulate production in said mammal of antibodies which recognize ZPA or ZPB proteins of said mammal. It is presently preferred that mammalian ZPA and ZPB for use in such methods be derived from the same mammalian species as the subject mammal although the use of heterologous species proteins is also contemplated. Use of purified isolates of mammalian ZPA or ZPB protein such as obtained by chromatographic separatory procedures is contemplated. Use of proteins produced by recombinant methods is expected to be most preferred.

According to another aspect of the invention, methods are provided for inducing permanent sterility in a female mammal by administering to a subject female mammal a recombinant mammalian ZPC protein (or fragment thereof) in a form essentially devoid of ZPA and/or ZPB, in a dose effective to stimulate production in said female mammal of antibodies which recognize the ZPC protein of said mammal. As is the case with induction of transient infertility, use of homologous species ZPC is preferred, but not required, and the protein may be derived from natural sources or produced by recombinant methods. Modified ZPC proteins including but not limited to palmitylated and chitosan modified proteins are also contemplated by the present invention.

Presently preferred ZPA, ZPB, and ZPC proteins for veterinary application of the transient infertility and sterility inducing methods include porcine, rabbit, canine, feline, bovine, and cynomolgus monkey ZP proteins.

In another of its aspects, the present invention provides pharmaceutical compositions for use in inducing reproducible transient infertility in a female mammal (including humans) comprising an effective dose of a zona pellucida protein (or fragment thereof) selected from the group consisting of mammalian ZPA, and ZPB (substantially free of ZPC), in combination with one or more pharmaceutically acceptable carriers, diluents and adjuvants. Modified ZPA and ZPB proteins (for example, palmitylated or chitosan modified) are also contemplated by the present invention.

According to another aspect of the present invention, novel purified and isolated DNA sequences are provided which encode porcine ZPA, ZPB, and ZPC, as illustrated by the DNA sequences set out in SEQ ID NOS. 1, 3, and 5. Also, provided are purified and isolated DNA sequences encoding: rabbit ZPC, as illustrated by the DNA sequence set out in SEQ ID NO. 7; canine ZPA and ZPC, as illustrated by the DNA sequences set out in SEQ ID NOS. 9 and 11; feline ZPA, ZPB, and ZPC, as illustrated by the DNA sequences set out in SEQ ID NOS. 13, 15, and 17; bovine ZPA, ZPB, and ZPC, as illustrated by the DNA sequences set out in SEQ ID NOS. 19, 21, and 23; human ZPA and ZPB as illustrated by sequences set out in SEQ ID NO. 42 and 40, respectively, and as contained as human DNA inserts in lambda phage clones A1 and A4, (ZPA) and as contained in human DNA inserts in lambda phage clones 1-1 and 4-9 (ZPB).

Polynucleotide sequences of the invention are useful for the production of ZPA, ZPB and ZPC proteins by recombinant methods and as probes for the isolation of heterologous species polynucleotides encoding corresponding zona pellucida proteins by hybridization methods.

Also provided by the present invention are novel host cells, especially unicellular eucaryotic and procaryotic cells, stably transformed or transfected with polynucleotides of the invention in a manner allowing expression of the ZP proteins (or immunologically significant fragments thereof) in the host cells. Host cells expressing such ZP products, when grown in a suitable culture medium, and particularly useful for large scale production processes wherein the desired polypeptide products, in glycosylated or non-glycosylated form are isolated from the cells or the medium in which the cells are grown.

Recombinant polypeptides provided by the invention thus comprise ZPA, ZPB and ZPC, and full equivalents of such zona pellucida proteins including both glycosylated and non-glycosylated forms, variants and immunologically active fragments thereof which retain substantial biological activity, i.e., at least one of the biological activities of the zona pellucida protein discussed herein, e.g., the ability to stimulate the production of antibodies as discussed herein upon administration to a mammal. Such immunologically active fragments may be defined as containing at least one epitope effective to stimulate the production of antibodies upon administration to a mammal in accordance with this invention.

In another aspect of the invention, a method is provided for the isolation of nucleic acid sequences encoding other mammalian ZPA, ZPB, and ZPC proteins by hybridization under stringent conditions of heterologous species ZPA, ZPB, and/or ZPC probes to cDNA or genomic DNA libraries, derived from the mammalian species of interest.

More particularly, it is an aspect of the invention to provide a method for the isolation of nucleic acid sequences encoding human ZPA and ZPB by hybridization under stringent conditions of sequences encoding ZPA and/or ZPB from heterologous species.

Other aspects and advantages of the present invention will be readily understood upon consideration of the following detailed description of presently preferred embodiments thereof, reference being made to the figures wherein:

DETAILED DESCRIPTION OF THE INVENTION

Figure 1:
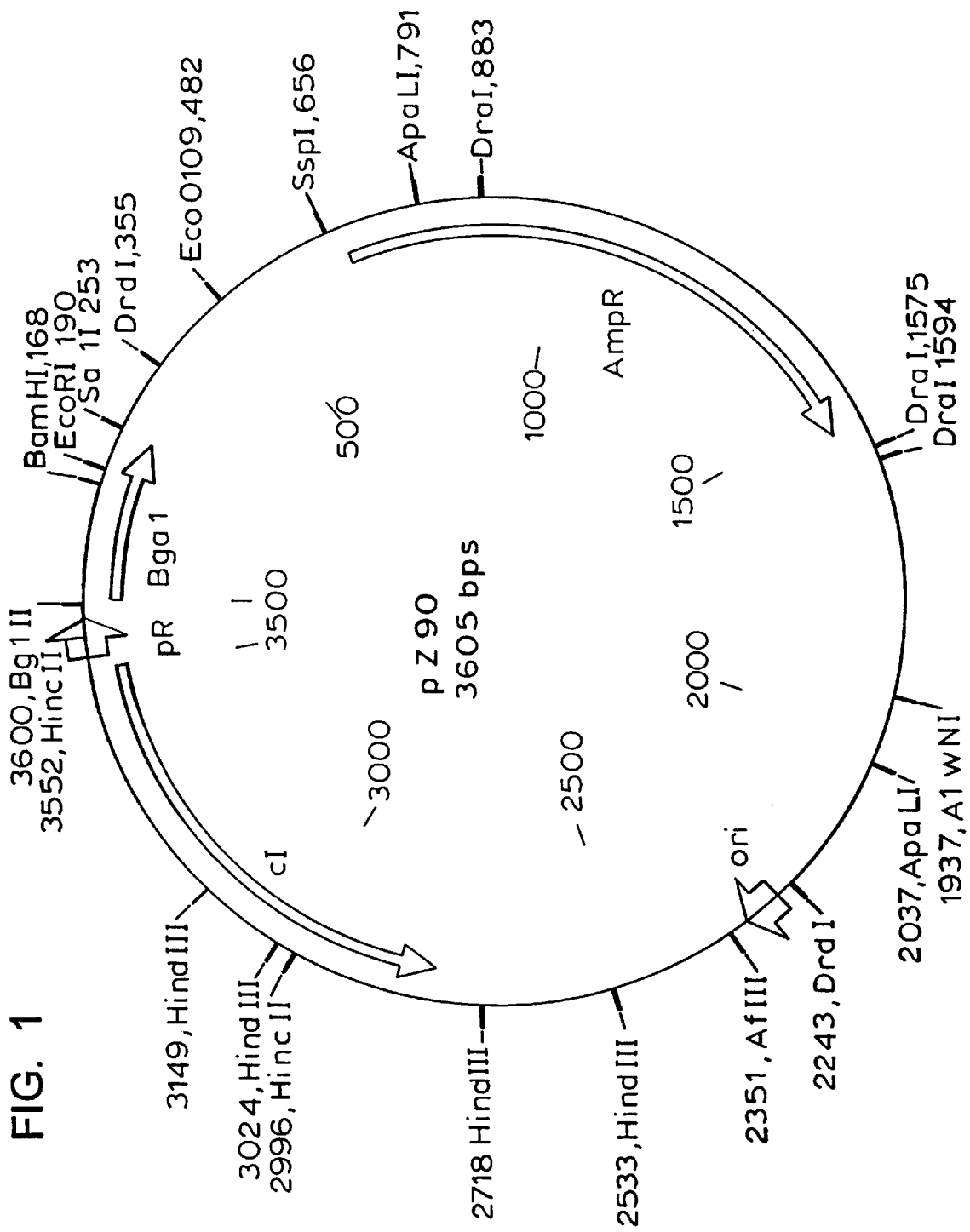
FIG. 1 is a diagrammatic representation of the plasmid vector pZ90.

The present invention is directed to mammalian zona pellucida proteins characterized in three major classes: ZPA, ZPB, and ZPC. This classification scheme has resulted from repetitive screening of various mammalian ovarian cDNA libraries and retrieval of clones which encode proteins showing significant homology in three distinct groups, designated herein as ZPA, ZPB and ZPC. Although similarity is seen between DNA sequences encoding ZPA, ZPB, or ZPC between animal species, very little homology is found between the individual species' ZPA, ZPB, and ZPC proteins.

DNA sequences encoding zona pellucida proteins A, B, and C and their deduced amino acid sequences for various mammalian species ZPs are presented in SEQ ID NOS. 1–24. It is understood that the DNA sequence of a particular animal may vary slightly due to the phenomenon of allelic variation. Small differences in the precise DNA sequence between animals or slight errors due to the inefficiency of sequencing procedures are to be expected. Such variants are included within the scope of the present invention.

The zona pellucida DNA sequences described above were obtained from ovarian cDNA libraries screened with specific zona pellucida antibodies or known zona pellucida DNA probes. Comparison of isolated sequences to published protein or DNA sequences and with other clones as they were isolated was used to classify and identify the clones as described above.

The term "zona pellucida protein" is meant to include full length proteins ZPA, ZPB, and ZPC, as well as expected variants, immunologically active fragments or peptides contained within these proteins. The term "zona pellucida DNA" is meant to include those nucleic acid sequences encoding zona pellucida protein or fragments thereof.

The three major classes of mammalian zona pellucida proteins have been determined on the basis of homology within the DNAs encoding ZP proteins of a variety of mammalian species. ZPA includes those peptides previously, variously described in the literature as ZP1, ZP2, and ZP4; ZPB includes those peptides previously, variously described as ZP3α and rc 55; and ZPC includes those peptides previously variously described as ZP3β and ZP3.

The homology of various species of zona pellucida proteins within a specific class as compared with a consensus sequence for each class is shown in Table 1. The consensus sequence was derived using the Microgenie® Sequence Analysis Program (Beckman Instruments, Inc. Spinco Division, Palo Alto, Calif.). The minimum percent of aligned sequences which must have the same residue at a given position for that residue to be included in the consensus sequence was 50%. The DNA sequences corresponding to the amino acid consensus sequences for ZPA, ZPB, and ZPC proteins are set out in SEQ ID NOS 25, 26, and 27, respectively.

TABLE 1

HOMOLOGY OF DEDUCED ZP PROTEINS AMINO ACIDS

|  | ZPA | ZPB | ZPC |
|---|---|---|---|
| DOG | 78.9% | — | 77.3% |
| CAT | 78.4% | 70.9% | 77.5% |
| COW | 77.2% | 80.4% | 77.2% |
| PIG | 73.0% | 77.8% | 79.0% |
| RABBIT | 70.1% | 74.6% | 71.3% |
| MOUSE | 61.6% | — | 69.6% |
| HUMAN | — | — | 76.9% |
| HAMSTER | — | — | 70.5% |

The deduced amino acid sequences of the various species of zona pellucida proteins suggest approximate unglycosylated molecular weights of 75 kD, 55 kD, and 45 kD for ZPA, ZPB, and ZPC, respectively. A more detailed analysis of both DNA sequence homology and deduced amino acid sequence homology is set out as Examples 13, 14, and 15.

It has surprisingly been found that administration of a specific class of zona pellucida protein to a host animal results in a specific immunocontraceptive effect and that selection of the appropriate ZP protein for administration allows induction of desired contraceptive results, in terms of permanent sterility or transient infertility. For example, vaccination of an animal with zona pellucida protein C induces antibody titers in that animal which recognize endogenous ZPC resulting in loss of oocytes from the animal's ovary, thereby causing permanent sterility. In contrast, vaccination of an animal with zona pellucida protein A, B or combinations thereof induces antibody titers which do not recognize ZPC, but recognize ZPA and/or ZPB. This results in cycling, infertile animals for the time period during which anti-ZPA and/or anti-ZPB antibody titers remain high. When such antibody titers fall, the infertility effect is diminished, and the animal regains fertility.

Vaccination with the purified, isolated, and characterized ZPA, ZPB, or ZPC proteins is seen to exert a specific effect on the immunized animal if an autoimmune response is triggered wherein the autoantibodies generated specifically recognize the immunized animals' own specific zona pellucida protein. This self-recognition for antibodies induced according to the present invention may be defined and characterized by the ability of serum antibodies to recognize at least one epitope present on a homologous species zona pellucida protein.

In the preferred method of the invention, an animal is immunized with a recombinant ZPA, ZPB, or ZPC or fragments thereof. The recombinant protein or peptide may be of homologous species or derived from a heterologous species zona pellucida which shares common epitopic determinants, with the proviso that such common epitopic determinants function to induce the desired autoimmune response.

The recombinant protein or peptide fragment may be chemically conjugated to immune enhancing agents such as Keyhole Limpet Hemocyanin (KLH), and Muramyl dipeptide (MDP), and the like, or alternatively may be provided in the form of a fusion protein, e.g., with foreign protein amino acids at the amino and/or carboxy terminus. Fully conventional methods for stimulating the production of antibodies upon administration of the proteins or fragments of this invention are well known; similarly, passive immunization techniques involving administration of antibodies per se, e.g., anti-ZPA antibodies, anti-ZPB antibodies, or anti-ZPC antibodies, to the zona pellucida proteins or fragments of this invention is also within the scope of the invention. For details, see Dean, PCT Application WO90/15624 whose disclosure is entirely incorporated by reference herein.

Thus, to induce permanent sterility in a dog, recombinant canine ZPC may be employed which is expressed as a bacterial fusion protein (or conjugated to immune enhancing agents) wherein active canine ZPC protein is conserved and available for interaction with antigen presenting cells. The expressed protein is then administered to a host dog and induces an autoimmune response in which generated antibodies recognize canine zona pellucida protein C. This autoimmune effect, which specifically recognizes dog ZPC protein or its aggregates, induces permanent sterility in the vaccinated dog, which sterility is associated with a loss of oocytes from the dog's ovary.

Alternately, a non-homologous species ZPC, such as recombinant porcine ZPC or peptides thereof which are cross-reactive with canine ZPC, can be administered to a dog to achieve similar sterilizing effects. The sterilizing effect, however, is only realized when antibodies capable of recognizing the host's own native zona pellucida are induced (or administered in the context of passive immunization).

In an alternative embodiment of the present invention, the administration of a host species' own A and/or B class zona pellucida protein, or a related A and/or B protein from another species which induce antibodies against the host's ZPA and/or ZPB proteins results in an infertility effect which is distinct from that produced by ZPC class antigens. The physiological effect of vaccination with the ZPA and ZPB proteins is a transient one. "Transient infertility" is herein defined as infertility which is maintained when antibodies against self-zona pellucida proteins are sustained in the host animal's circulation at a contraceptively effective concentration (e.g., at titers of approximately 1:250 in the dog) and which infertility is diminished when antibodies against self fall below a contraceptively effective lower limit. The reduction in antibodies against self-zona pellucida results in restoration of fertility without evidence of major physiological changes in the ovary. Typically, the reduction in antibody titers occur by natural processes in the mammalian host, but other methods of reducing antibody titers are within the scope of the invention.

Contraceptively effective antibody titers against self zona pellucida proteins A and B required to maintain infertility will vary with the species of vaccinated animal as well as with the species of recombinant ZPA or ZPB peptide administered, but may readily be determined, for example, by testing a panel of the desired animal species with varying doses of the specific antigen, measuring the induced titer of anti-self antibodies by known ELISA techniques, and correlating the titers with reproductive indicators, e.g., cycling, hormone levels, and the like. In general, antibody titers greater than 1:250 are contraceptively effective.

Based on amino acid sequence homologies, it is expected that all zona pellucida proteins of a particular class contain functional epitopes which are cross-reactive between mammalian species. However, absent characterization and identification of such functional cross-reactive epitopes, a preferred, selective contraceptive agent is a homologous species zona pellucida protein or antibody thereto.

The present invention will be more completely understood upon consideration of the following illustrative examples of the practice thereof wherein: Example 1 addresses the isolation of DNAs encoding porcine species ZPA, ZPB and ZPC; Example 2 relates to isolation of rabbit ZPC DNA; Example 3 relates to isolation of DNAs encoding canine ZPA and ZPC; Example 4 addresses isolation of feline DNAs encoding ZPA, ZPB and ZPC; Example 5 relates to cloning and isolation of DNAs encoding bovine species ZPA, ZPB and ZPC; Examples 6 and 7 describe immunocontraceptive treatment of dogs with naturally-derived porcine zona pellucida proteins; Example 8 relates to serochemical studies on animals treated in Examples 6, and 7; and Examples 9 and 10 address recombinant production of a canine ZPC fusion protein and its immunocontraceptive use in dogs. Example 11 relates to the isolation of DNAs encoding human ZPA and ZPB by methods described herein. Example 12 relates to the isolation and sequencing of DNAs encoding cynomolgus monkey ZPA, ZPB and ZPC. Examples 13–15 relate to the comparison of the DNA sequence and the deduced amino acid sequence of mammalian ZPA, ZPB, and ZPC, respectively. Example 16 relates to the immunization of cynomolgus monkey using HSPZ and fractionated HZPC. Example 17 relates to the mapping of mammalian zona pellucida protein epitopes. Example 18 describes the immunization of dogs using recombinant ZPC proteins. Example 19 relates to the vaccination of cows and cats with recombinant ZP proteins.

EXAMPLE 1

Isolation of DNA Sequences Encoding Porcine Zona Pellucida Proteins ZPA, ZPB, and ZPC A cDNA library in λgt11 was commercially prepared by Clone Tech, Palo Alto, Calif., from an ovary isolated from a 14 week old pig and was screened using an anti-ZP3, antibody obtained from E. C. Yurewicz and described in Keenan et al., *Biol. Reprod.*, 44:150–156 (1991). Eight candidate clones were identified.

A degenerate DNA oligonucleotide probe (19 bps) was constructed to represent all possible sequences of a short portion of the N-terminus porcine ZP3α as described in Yurewicz et al., *J. Biol. Chem.*, 262:564–571, (1987). The degenerate probe sequence is set out in SEQ ID NO. 28.

Southern analysis of the eight candidate clones isolated by expression screening with the degenerate DNA oligonucleotide probe resulted in hybridization with two of the eight candidates. The two clones recognized by the degenerate probe were then subcloned into the pBS KS plasmid (STRATAGENE Cloning Systems, La Jolla, Calif.) for sequence analysis using the sequence enzyme and the protocol described in the SEQUENASE® Manual (U.S. Biochemical, Cleveland, Ohio). One of the clones, B-8, having an insert size of approximately 1200 base pairs, included a sequence homologous to the N-terminal sequence of mouse ZP3, previously identified by Ringuette et al., *Dev. Biol.*, 127:287–295, (1988). The remaining clone, B-6, had an insert size of approximately 1000 base pairs. Neither hybridizing clone contained the C-terminal portion of the gene, as suggested by the lack of homology to the mouse ZP3 gene in this region.

The 14-week porcine ovarian library was then rescreened by DNA hybridization. Approximately 150,000 PFUs were plated on agar plates with *E. coli* Y1090. After overnight incubation at 37° C., nylon membrane lifts of plaques were prepared and screened using the B6 and B8 clones derived above isolated by screening with the degenerate oligonucleotide probe set out in SEQ ID NO. 28.

Filters were prehybridized in a solution containing 5×saline, sodium phosphate, EDTA buffer (SSPE), 5×Denhardt's Reagent, 100 μg/ml salmon sperm DNA, 30% formamide and 0.5% SDS for three hours at 42° C. Approximately 50 ml of the prehybridization solution was used for 12 filters (132 mm). After prehybridization, 10 ng of freshly radiolabeled DNA probe in 30% formamide, 5×SSPE was added. The probes were heat denatured at 95° C. for 3–5 minutes and hybridization with the DNA probes continued overnight at 42° C. The hybridized filters were then washed twice with 100 ml of 5×SSPE at 55° C., for approximately one hour each wash. The filters were then rinsed with 250 ml of 5×SSPE at room temperature and allowed to air dry. The dried filters were exposed to x-ray film at −70° C. using intensifier screens for at least eight hours and the films were developed for visual analysis.

Among the additional clones isolated were two clones including the C-terminal portion of the porcine ZP3β gene. One clone, λ5-1, was subcloned into plasmid pBS KS and sequenced. This plasmid, termed pZ57, contained a ZP DNA insert having 1266 base pairs and appeared to encode the full length amino acid sequence of porcine ZP3β as compared with known mouse ZP3. Alignment of the deduced amino acid sequence of the clone with the known N-terminal amino acid sequence of ZP3β reported by Yurewicz et al., *J. Biol. Chem.*, 262:564–571 (1987), and an internal peptide sequence of ZP3β corresponding to amino acids 255–274 as provided by E. C. Yurewicz confirmed the identity of this clone as encoding porcine ZP3β.

The DNA sequence of this clone, termed porcine ZPC, is set out in SEQ ID NO. 5 and its deduced amino acid sequence is set out in SEQ ID NO. 6.

The 14-week porcine ovarian cDNA library was further screened using rabbit zona pellucida rc 55 cDNA as a probe [described in Schwoebel et al., *J. Biol. Chem*, 266:7214–7219, (1991)].

One candidate clone of approximately 1700 base pairs, λ2-1, was isolated and was transferred into the sequencing plasmid pBS KS. The DNA sequence and deduced amino acid sequence of the porcine DNA insert was determined using the method described in the SEQUENASE® manual (US Biochemical Corporation, Cleveland, Ohio). The sequenced clone contained 1620 base pairs and included a full length copy of the porcine ZP3α gene as confirmed by alignment of the deduced amino acid sequence with portions of the known protein sequence of porcine ZP3α provided by E. C. Yurewicz between amino acids 206–222, 271–279, and 328–344. The DNA sequence of this clone, termed porcine ZPB, is set out in SEQ ID NO. 3. Its deduced amino acid set out in SEQ ID NO. 4.

The 14-week porcine ovarian library was further screened using the procedure described above and using a DNA probe encoding canine ZPA protein (as obtained in Example 3 below, SEQ ID NO. 9). A single clone, λ3-5 having approximately 1300 base pairs, was obtained representing the N-terminal 60% of the theoretical porcine ZPA gene as estimated by the size of the clone in relation to the ZP2 gene isolated from mouse by Liang et al., *Mol. Cell. Biol.* 10: 1507–1515 (1990), and rabbit by Dunbar, U.S. Pat. No. 4,996,297, and dog (see Example 3 below).

This clone was then used to rescreen the porcine ovarian library. Three additional clones were obtained, two small clones and one clone large enough to contain the full length sequence. The large candidate clone, λB, having approximately 2200 base pairs, was sequenced, and the data showed this ZPA clone to lack only approximately seven base pairs of the full length sequence including the ATG start codon when aligned with the mouse ZP2 gene and the canine ZPA gene described in Example 3. The DNA sequence of this clone, termed porcine ZPA, is set out in SEQ ID NO. 1. Its deduced amino acid sequence is set out in SEQ ID NO. 2.

This isolated porcine clone included sequences corresponding to published sequences of three identified porcine zona pellucida proteins, ZP1 (80 kD), ZP2 (62 kD) as disclosed in U.S. Pat. No. 4,996,297 to Dunbar and ZP4 (21 kD) as disclosed by Hasegawa et al., Abst. No. 382, *Meeting Soc. Study Reprod.* July, 1991. These results suggest that a singular clone encodes one zona pellucida protein which previously had been thought to exist as three separate proteins, i.e., ZP1, ZP2, and ZP4. This further suggests that only three major porcine zona pellucida genes encode three major zona pellucida proteins which here are termed ZPA, ZPB, and ZPC. ZPA includes those proteins previously identified as ZP1, ZP2, and ZP4. ZPB corresponds to ZP3α and ZPC corresponds to previously identified ZP3β. Yurewicz et al. *J. Biol. Chem.*, 262:564–571, (1987).

EXAMPLE 2

Isolation and Purification of DNA Sequences Encoding Rabbit ZPC Protein

Ovaries were removed from five week old rabbits and mRNA was prepared using the Fast Track™ mRNA isolation kit in accordance with the procedure described in the Fast Tracks instruction manual, version 3.1, catalog No. K1593-02 (Invitrogen, San Diego, Calif.). A Lambda Librarian™ kit (Invitrogen, San Diego, Calif.) was used to prepare cDNA and to clone cDNAs into λgt10 according to the manufacturer's instructions. Approximately 150,000 PFUs were plated on agar plates with *E. coli* Y1090. After overnight incubation at 370° C., nylon membrane lifts of colonies were prepared and screened with a porcine ZPC DNA probe using the screening procedures described for Example 1. The probe used was the porcine ZPC sequence as set out in SEQ ID NO. 5.

Two positive clones, λR4 and λR5, hybridized with the porcine ZPC DNA. The size of each of these clones as estimated in agarose gels was approximately 1300 base pairs. Both λR4 and λR5 were sequenced as described for Example 1. The sequences were identical except that λR5 contained four additional nucleotides at the 5' end. The determined DNA sequence was approximately 75% homologous to the DNA sequence encoding porcine ZPC.

The DNA sequence encoding rabbit ZPC protein is set out in SEQ ID NO. 7. Its deduced amino acid sequence is set out in SEQ ID NO. 8.

Rabbit ZPA and ZPB proteins have been previously identified by Dunbar in U.S. Pat. No. 4,996,297 as P2 and P3, respectively.

EXAMPLE 3

Isolation of DNA Sequences Encoding Canine Zona Pellucida Proteins ZPA and ZPC

A 16 week canine ovarian cDNA expression library was commercially prepared by Clone Tech, Palo Alto, Calif., in λgt11 generally following the methods described in Example 1. The canine ovarian cDNA library was screened using antibodies raised against heat solubilized canine zona pellucida. Heat solubilized canine zona pellucida (HSDZ) was prepared generally following the procedures described in Dunbar et al. *Biochemistry*, 19:356–365, (1980) except ganged razor blades were used to mince the ovaries.

Rabbits were immunized with 250 μg HSDZ and 250 μg MDP. Two additional boosts followed at approximately three week intervals. The resultant rabbit serum was used to screen the canine ovarian cDNA expression library. Seven candidate clones were obtained. Cross-hybridization experiments were performed by Southern blot analysis as follows. The largest clone, λ26-1, having approximately 1300 base pairs, was first used as a probe against all of the other clones in Southern blots. Three other clones were identified. The largest of the remaining clones, λ20-1 and λ7-1, having approximately 800 and 1000 base pairs respectively, were then used as probes in Southern blots. These probes identified no additional clones. This cross hybridization analysis of the seven candidate clones to each other indicated that four of these clones were related, e.g. four clones hybridized to λ26-1 while the remaining three λ20-1, λ7-1, and λ19-3 were independent.

The largest of the four related clones, λ26-1, was subcloned into pBS KS plasmid for sequence analysis according to the procedure described in Example 1. The analyzed sequence demonstrated the presence of a long open reading frame of 1278 base pairs encoding a protein of approximately 426 amino acids. Comparison of the deduced amino acid sequence of this clone with the sequences of known zona pellucida proteins, indicated this clone encoded a protein related to mouse ZP3 (ZPC) as reported by Ringuette et al., *Dev. Biol.* 127:287–295 (1988), hamster ZP3 as reported by Kinloch et al., *Dev. Biol.,* 142:414–421 (1990), human ZP3 as reported by Chamberlin et al., *Proc. Natl. Acad. Sci. U.S.A.* 87:6014–6018 (1990) and porcine ZPC protein (see Example 1). The DNA sequence of this clone, termed canine ZPC, is set out in SEQ ID NO. 11. Its deduced amino acid sequence is set out in SEQ ID NO. 12.

The remaining three independent candidate clones were subcloned into the pBS KS plasmid for sequence analysis as described above. The determined sequence of the 800 base pair clone, λ20-1, was compared with known ZP sequences by computer analysis as described above and was found to be related to the mouse ZP2 (ZPA) [Liang et al., *Mol. Cell. Biol.* 10:1507–1515 (1990)] and porcine ZPA (see Example 1).

The 800 base pair fragment from λ20-1, was then used as a hybridization probe to rescreen the canine cDNA library. Two additional candidate clones were identified, the larger of which, λ7A, having approximately 2800 base pairs, was subcloned into pBS KS plasmid for sequence analysis. Comparison of this sequence with known sequences encoding zona pellucida proteins suggested the candidate clone λ7A contained a full length ZPA sequence, but an incorrect N-terminal sequence, e.g., the clone contained an additional 600 base pairs as determined by alignment with known mouse ZP2 and rabbit ZPA sequences referenced in Example 1. The second candidate clone, λ9-2, having approximately 1000 base pairs, was then subcloned into the plasmid pBS KS and sequenced. The sequence of the second clone indicated the presence of a correct N-terminal sequence, but included only approximately the N-terminal 40% of the full length clone as determined by alignment with the mouse ZP2 and rabbit ZPA genes. Overlap of the two cDNA clones, however, provided the full length sequence.

The appropriate pieces of each clone were subcloned as follows to generate the correct full length zona pellucida clone containing a 2028 base pair open reading frame encoding a protein of approximately 676 amino acids. The λ7A DNA was digested with Eco RI to yield two insert fragments (2000 bps and 800 bps). These two fragments were each subcloned into pBS KS yielding pZ36 and pZ37, respectively. Plasmid pZ37 carried the C-terminal portion of this sequence. The λ9-2 DNA insert was removed from the λ vector and subcloned into pBS KS to yield pZ38. Plasmid pZ36 was digested with Hind III to remove approximately 1350 bps of the N-terminal portion of the λ7A gene fragment (about 850 bps of nonsense DNA and 500 bps of coding sequence). This digestion also removed one of the Eco RI insert ends and left a single Eco RI site. The pZ37 Eco RI insert was then moved into the single remaining Eco RI site in the modified pZ36 (pZ36 Δ1) to reestablish the relative DNA structure orientation that existed in the λ7A insert (1450/2800 bps). This combined plasmid was then opened with Hind III and the Hind III fragment from pZ38 carrying the N-terminal ZP DNA sequence was inserted to create plasmid pZ39 which is a pBS KS carrying the full length canine ZPA sequence. The DNA sequence of this canine ZPA gene is set out in SEQ ID NO. 9. Its deduced amino acid sequence set out in SEQ ID NO. 10.

EXAMPLE 4

Isolation of DNA Sequences Encoding Feline Zona Pellucida Proteins ZPA, ZPB, and ZPC Ovaries were isolated from five cats approximately three to four months in age. Messenger RNA was isolated from six ovaries using the Fast Track™ mRNA Isolation Kit (Invitrogen, San Diego, Calif., Catalog No. K1593-02) using the protocol provided with the kit. cDNA was prepared using the protocol and cloned into λgt10 as described in Example 2.

Approximately 150,000 plaque forming units (PFUs) were plated on agar plates with *E. coli* Y1090. After overnight incubation at 37° C., nylon transfer membranes were used to prepare and screen plaque lifts. Plaques were screened using a mixture of DNA probes in equal proportions encoding porcine ZPA, ZPB, and ZPC proteins and using the hybridization procedure as described for Example 2. A total of 81 positive clones were identified. Twelve of these clones were plaque-purified. Southern analysis of these clones using porcine ZPA, ZPB, and ZPC DNAs individually as probes indicated that seven of these clones encoded ZPC proteins and one clone encoded a ZPA protein. Four of the clones contained inserts which could not be separated by Eco RI digestion Five of the ZPC clones were between 1200–1350 base pairs in length. One clone, λC-112, having approximately 1350 base pairs was subjected to sequence analysis as described above and its deduced amino acid sequence was found to be approximately 70% homologous to the canine ZPC protein obtained in Example 3. The DNA sequence of this feline ZPC clone is set out in SEQ ID NO. 17. Its deduced amino acid sequence is set out in SEQ ID NO. 18.

The single feline ZPA clone, λC-116, was sequenced and found to be approximately 2215 base pairs in length. The deduced amino acid sequence was approximately 75% homologous to the canine ZPA protein characterized in Example 5. The DNA sequence of this feline ZPA clone is set out in SEQ ID NO. 13. Its deduced amino acid sequence is set out in SEQ ID NO. 14.

The remaining 69 positive clones were rescreened using porcine ZPB DNA as a probe (SEQ ID NO. 3). Ten positive clones were obtained. The largest clone, λC-1, contained approximately 1.7 kilobases as determined by agarose gel electrophoresis. This clone was sequenced, and its deduced amino acid sequence was found to be approximately 80% homologous to the porcine ZPB protein described in Example 1. The DNA sequence of this feline ZPB clone is set out in SEQ ID NO. 15. Its deduced amino acid sequence is set out in SEQ ID NO. 16.

EXAMPLE 5

Isolation of DNA Sequences Encoding Bovine Zona Pellucida-Proteins ZPA, ZPB, and ZPC A cDNA library was constructed from a five month bovine ovary by the method described in Example 2. The bovine ovarian library was screened with DNA hybridization probes representing each of the classes of zona pellucida proteins using a mixture of equal proportions of porcine DNA probes encoding ZPA (SEQ ID NO. 1), ZPB (SEQ ID NO. 3), and ZPC (SEQ ID NO. 5) proteins, as described for Example 2 and using the procedures described for Example 1. Initial screening yielded three candidate clones. Southern analysis of these clones with individual porcine ZPA, ZPB, and ZPC DNA probes used in the initial screening indicated that one of the clones, λB2, having approximately 650 base pairs, encoded ZPA. A second clone, λB-1 having approximately 1000 base pairs encoded ZPB. A third clone, λB14, having approximately 1200 base pairs, encoded ZPC.

The bovine ovarian library was then rescreened with the mixed porcine ZP DNA probes. Two additional clones were obtained and identified by Southern analysis as encoding ZPC.

The Eco RI inserts of the ZPA, ZPB, and largest ZPC clone were subcloned and their DNA sequences analyzed. The sequences encoding these bovine ZPA, ZPB and ZPC fragments were set out in SEQ ID NOS. 19, 21, and 23, respectively. Their deduced amino acid sequences are set out in SEQ ID NOS. 20, 22, and 24, respectively.

EXAMPLE 6

Immunization of Dogs with Heat-Solubilized Fractionated Porcine Zona Pellucida Heat-solubilized, porcine zona pellucida (HSPZ) was prepared generally following the procedures described by Dunbar et al. *Biochemistry,* 19:356–365, (1980) but using a hand powered meat grinder instead of the Zonamatic described. Following isolation, the zona pellucida protein was solubilized in 0.1M sodium carbonate buffer, pH 9.6, and was dialyzed extensively against 6M urea. The resultant solution, a volume of 2–3ml containing approximately 12 μg of HSPZ, was subjected to isoelectric-focusing in a BIO-RAD Rotofor isoelectric-focusing chamber as follows. An isoelectric gradient was established using 1% ampholytes having a pI range of 3–10. The zona pellucida protein was introduced into the mid-range chamber (pI 7.0) and allowed to focus for approximately four hours at 4° C. or until. the voltage stabilized.

Twenty isoelectrically focused fractions were collected and analyzed by SDS PAGE and Western blot analysis for pig zona pellucida proteins. Acidic fractions having a pI range of approximately 3.5–5.5 and which contained the porcine zona pellucida proteins were combined. The fractions were dialyzed into 0.1M carbonate buffer, pH 9.6 and concentrated to approximately 3 mg/ml. This antigenic preparation was used to vaccinate animals as described below. Analysis of this antigenic preparation by two-dimensional gel electrophoresis indicated the presence of ZPA and ZPB protein. However, ZPC was not revealed to be present in this preparation.

The HSPZ antigenic preparation was added to a 50/50 water oil emulsion with incomplete Freund's adjuvant (Sigma, St. Louis, Mo.) containing 250 μg of MDP per dose. One ml of the 50/50 water oil emulsion contained 0.425 ml paraffin oil, 0.075 ml mannide monooleate, and 0.5 ml PBS containing 250 μg threonyl-MDP (SYNTEX Corporation) and the amount of HSPZ described in Table 3 below.

Four random breed dogs aged 10–12 weeks were immunized with HSPZ using the regimen described in Table 2.

TABLE 2

|  |  | mg HSPZ |
| --- | --- | --- |
| Prime | Time 0 | 0.1 |
| Boost #1 | Week 4 | 1.0 |
| Boost #2 | Week 8 | 0.25 |
| Boost #3 | Week 12 | 0.2 |
| Boost #4 | Week 16 | 1.0 |
| Boost #5 | Week 36 | 1.0 |

The antisera produced by these animals was monitored via ELISA methodology. By week 17 antibody titers against self, e.g. against canine zona pellucida proteins, had reached a maximum (8–16K by ELISA) and thereafter began to drop.

At week 36, one animal was unilaterally ovariectomized and the removed ovary was sectioned and stained with periodic acid schiff stain (PAS) for histological examination. The ovary appeared normal, as evidenced by the presence of follicles in all stages of development. At week 52, two of the four test animals were observed to exhibit estrus behavior. The remaining two test animals exhibited estrus behavior at approximately one and a half years when the first two test animals experienced their second heat. All test animals were bred repeatedly with competent males and by artificial insemination, however, none became pregnant. During this same period, animals in various test regimens in which no self titers were obtained, as described in Example 10, became pregnant when presented with the same males or artificial insemination techniques.

Two weeks following the breeding sessions, e.g. at 54 weeks, the two early cycling animals were unilaterally ovariectomized and the removed ovaries were sectioned for histological examination. The ovaries appeared normal for this stage of follicular activity despite the functional infertility demonstrated.

EXAMPLE 7

Vaccination With Porcine ZPC Protein

A purified porcine ZPC protein (ZP3β) was obtained from E. Yurewicz, prepared as described in *J. Biol. Chem.,* 262:564–571, (1987).

Vaccines were prepared by adding 167 μg purified porcine ZPC protein (ZP3β) to a 50/50 water-oil emulsion with complete Freund's adjuvant (Sigma No. F5881, St. Louis Mo.), for the priming dose or with Incomplete Freund's Adjuvant (Sigma No. F5506, St. Louis, Mo.) containing MDP as described in Example 6 for the booster doses.

Five random breed dogs of approximately 10–12 weeks of age were injected with the ZPC vaccine preparation described above using the regimen described in Table 3.

TABLE 3

|  |  | mg of ZPC |
| --- | --- | --- |
| Prime | Time 0 | 0.167 |
| Boost | Week 3 | 0.167 |
| Boost | Week 6 | 0.167 |
| Boost | Week 28 | 0.167 |

Each animal's antibody titer versus self- zona proteins, e.g., versus canine zona pellucida proteins, was monitored by ELISA, using the method described in Dunbar, *Two Dimensional Gel Electrophoresis and Immunological Techniques,* 1987. ELISA microtiter plates were coated with HSDZ in antigen-coating buffer (0.1M sodium carbonate, pH 9.6). Biotinylated rabbit-antidog IgG was used as the second antibody. ABC reagent (Avidin-biotinylated peroxidase complex) and O-phenylene diamine dihydrochloride with a peroxide substrate was used for visualization. Only two animals produced antibodies versus self achieving peak self-antibody titers of 16K by week 4. The other three animals produced no self-antibody titers but achieved peak antibody titers of 4K against porcine zona pellucida protein. During the period of time between week 20 and week 36, all dogs were observed to exhibit estrous behavior. The animals were bred repeatedly with proven males. Only the two animals having antibody titers versus self zona pellucida proteins remained infertile. All other animals in the study became pregnant.

Two weeks after estrous and breeding the two infertile dogs exhibiting self-antibody titers were unilaterally ovariectomized and the removed ovaries were sectioned and stained with PAS for histological examination. The histological examination revealed abnormal morphology in the ovaries of the infertile dogs. No evidence of ongoing folliculogenesis was seen and the ovaries were depleted of oocyte-containing follicles. In addition, no primordial oocytes were seen.

EXAMPLE 8

Western Analysis of Antisera Produced by Vaccinated Animals

In an attempt to better understand the immune response and different physiological effects obtained in the two studies described in Examples 6 and 7, antisera produced in each test group was analyzed by Western Analysis against a variety of antigens including natural porcine ZPC, heat-solubilized dog zona pellucida (HSDZ), recombinant dog ZPA and ZPC, and recombinant pig ZPC. Western blots were probed with antiserum obtained from the test animals of Example 6, e.g., animals immunized with isoelectric focused, heat-solubilized porcine zona pellucida, and with antiserum obtained from the two test animals of Example 7 which contained antibodies against self-zona proteins.

The data demonstrate no recognition of recombinant porcine or canine ZPC by antisera from infertile, but cycling dogs immunized with heat solubilized porcine zona pellucida which contained no demonstrable ZPC by PAGE analysis, however, natural ZPC, HSDZ and recombinant canine ZPA were recognized. In contrast, antisera obtained from infertile dogs whose ovaries were depleted of oocytes recognized recombinant ZPC protein, i.e., the polypeptide backbone.

A key difference in the antibody recognition of antigen was that only the antisera obtained from dogs having ovaries devoid of oocytes appeared to recognize the recombinant dog ZPC antigen. Infertile dogs whose antisera strongly recognized natural ZPC, HSDZ, and recombinant dog ZPA demonstrated no recognition of recombinant dog ZPC.

Given that autoimmunity is essential for a contraceptive effect, these data suggest that infertility without histologically evident ovarian dysfunction can be obtained in dogs via an autoimmune response against dog ZPA antigens. In contrast, histologically confirmed ovarian dysfunction, i.e., loss of oocytes, which would result in permanent sterility, requires the generation of antibodies which specifically recognize homologous species ZPC protein.

EXAMPLE 9

Expression of Recombinant ZP Proteins

I. Construction of Expression Vectors

The plasmid vector pZ90 shown in FIG. 1 was constructed from fragments of the plasmids pUC9 (Vierra & Messing, *Gene* 19:259–268 (1982)) and pβgal2 (Queen, *J. Mol. App. Gen.* 2:1–10 (1983)). The single Pvu II restriction site present in pβgal2 was converted to a Sal I site using a Sal I polylinker adaptor purchased from New England Biolabs. The DNA sequences between the new Sal I site and a pre-existing Sal I site were excised by digestion with Sal I, religated and screened for the reduced size plasmid.

A Cla 1—Nde I fragment of the modified pβgal2 plasmid which carried the λCI repressor gene, the λpR promoter and the Lac Z gene (β-galactosidase) was inserted into pUC9 between its Acc I and Nde I restriction sites. The pUC9 plasmid carries the ampicillin resistance ($Amp^R$) gene and col EI replication origin (ori) needed to maintain the plasmid in *E. coli* cells. The combination plasmid was further modified to convert the Bam HI site 3' of the ATG initiation codon (ATG GAT CCN) to a Bgl II site 5' of the ATG initiation codon (AGATCTATG). This was accomplished by partially digesting the plasmid with Rsa I. One of the several digestion points was about 20 bps 5' of the Bam HI restriction site. When the partially digested plasmid was digested with Bam HI, some of the plasmids produced were nearly full length. A synthetic oligomer (GTACTAAGGAAGATCTATGGATCC) (SEQ ID NO. 29) was produced to replace the sequence that had been removed (GTACTAAGGAGGTTGTATGGATCC) (SEQ ID NO. 30). The net effect of this replacement was the substitution of 3 bps to create the Bgl II restriction site. A DNA fragment containing approximately 3000 base pairs of the Lac Z gene was then excised by restriction digestion with Bgl I and Ban II and was followed by insertion of a synthetic oligomer containing a Bam HI site. The plasmid was cut with Bgl I and Ban II, and then treated with nuclease S1 to create blunt ends. A Bam HI linker (New England Biolabs) was inserted at the blunt ends of the digested plasmid. Next a Pvu II restriction site between the λCI repressor gene and the ori sequence was converted to a Hind III site using a synthetic linker. The Pvu II restriction site was cut with Pvu II, and a Hind III linker (New England Biolabs) was ligated to the blunted ends. Because the remaining lac Z sequence was missing the first 8 codons of the natural sequence, these 8 codons were replaced by synthesizing a synthetic oligomer that began with a Bgl II site and encoded the lac Z wild type gene product (βgal) N-terminal sequence.

The synthetic oligomer was prepared by synthesizing four oligomers having the sequences set out in SEQ ID NO. 31 (oligomer 1), SEQ ID NO. 32 (oligomer 2), SEQ ID NO. 33 (oligomer 3), and SEQ ID NO. 34 (Oligomer 4). Oligomers 2 and 3 were phosphorylated by treating with kinase and ATP to add phosphate to the 5' end. Oligomers 1 and 2 were then hybridized to oligomers 3 and 4, respectively, by incubation at 100° C. followed by a slow cooling in 200 $\mu$M NaCl. The resultant oligomer had the sequence set out in SEQ ID NO. 35. The synthetic oligomer as set out in SEQ ID No. 35 had Bgl II-Pvu II ends and was substituted for the Bgl II-Pvu II sequence of the plasmid by restriction digestion of the plasmid and ligation with the oligomer.

Figure 2:
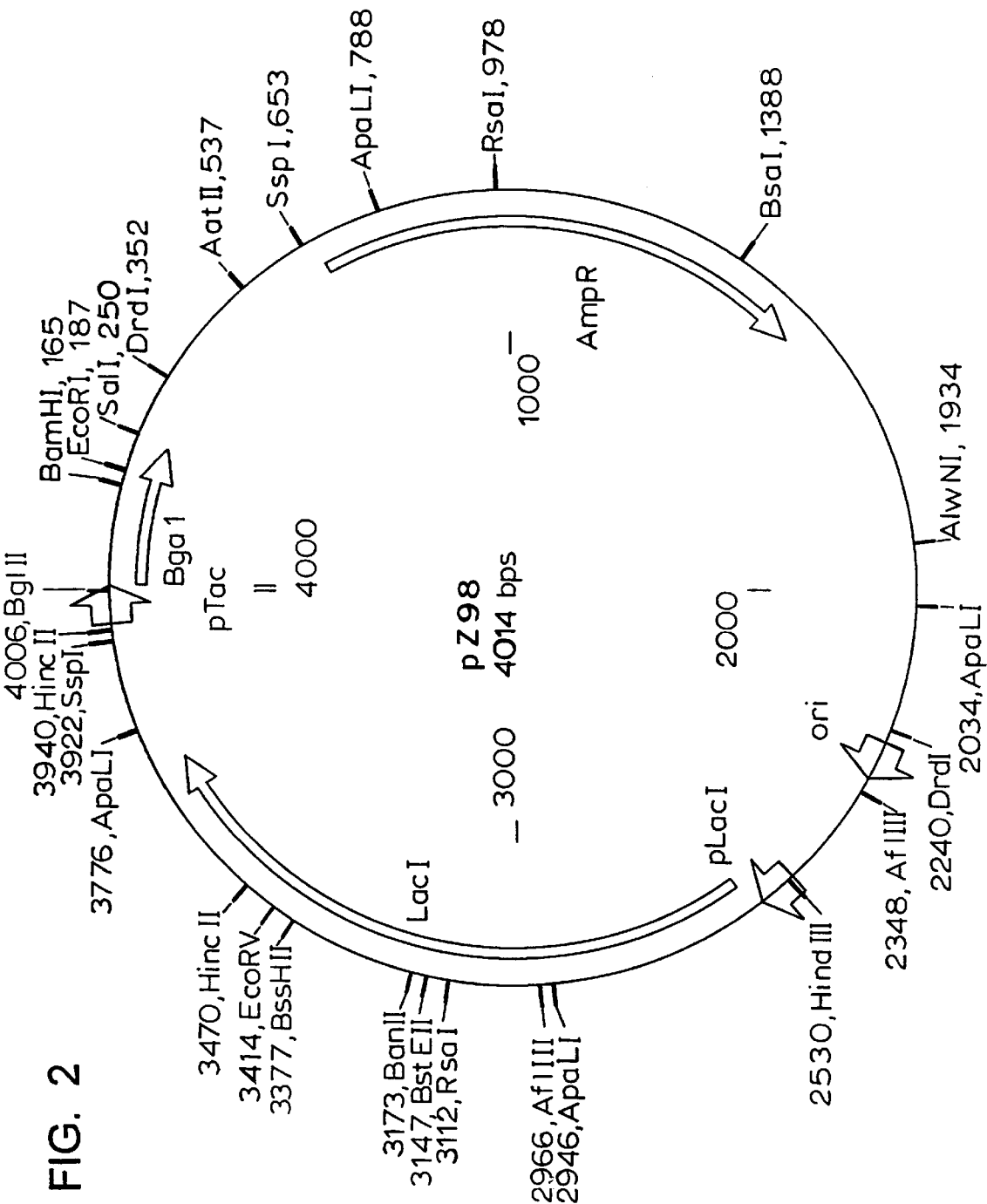
FIG. 2 is a diagrammatic representation of the plasmid vector pZ98.

The resultant plasmid was termed pZ90 and is shown in FIG. 1. The plasmid pZ90 can be used to express recombinant proteins by heat induction, using the heat labile λCI repressor. The heat-inducible repressor and promoter of pZ90 was next replaced with the chemically inducible promoter ptac (Amann et al., *Gene* 25:167–178 (1983)). The ptac promoter is controlled by the lac repressor, a product of the lac I gene (Farabaugh, *Nature* 279:765–769 (1978)). The Lac I gene was obtained from pMC9 (Miller et al., *The EMBO Journal* 3:3117–3121 (1984)) by use of PCR methodology as described by Innis and Gelfand, In: *PCR Protocols: A Guide to Methods and Applications,* Innis, M. A., Gelfand, D. H., Sninsky, J. J. and White, T. J. (eds)., pgs 1–12, Academic Press, Inc., San Diego, Calif. The primers used were complimentary to the Lac I promoter at one end and the Lac I gene termination codon at the opposite end. The N-terminal primer carried a Hind III site and the C-terminal primer carried a tac promoter sequence followed by a Bgl II site. The N-terminal primer had the sequence set out in SEQ ID NO. 36. The C-terminal primer had the sequence as set out in SEQ ID NO. 37 which includes a Dra 3 site having the sequence 5'-CACAATGTG-3'. The resulting lac I—ptac DNA fragment having Hind III and Bgl II restriction sites at its respective ends was then used to replace the Hind III—Bgl II fragment of pZ90 which carried the λCI repressor and λpR promotor. This replacement yielded the plasmid pZ98 shown in FIG. 2.

II. Insertion of Recombinant ZP DNA

DNA sequences encoding porcine ZPC were prepared by the PCR procedures described above (Innis & Gelfand) from the plasmid pZ57 prepared in Example 1, which contains the full length porcine ZPC sequence obtained from λgt11 clone 5-1 described for Example 1. During the PCR procedure the porcine ZPC gene was modified by using primers that did not include the leader sequence and the hydrophobic tail. The N-terminal primer used had the sequence set out in SEQ ID NO. 38 which included an internal Bam HI restriction site having the sequence 5'-GGATCC-3'. The C-terminal primer used had the sequence as set in SEQ ID NO. 39 includes a Sal I restriction site having the sequence 5'-CTCGAG-3' and an internal Xho I restriction site having the sequence 5'-CTCGAG-3'. The modified ZPC gene contained base pairs 105 to 1154 encoding ZPC amino acids 1–350.

Figure 3:
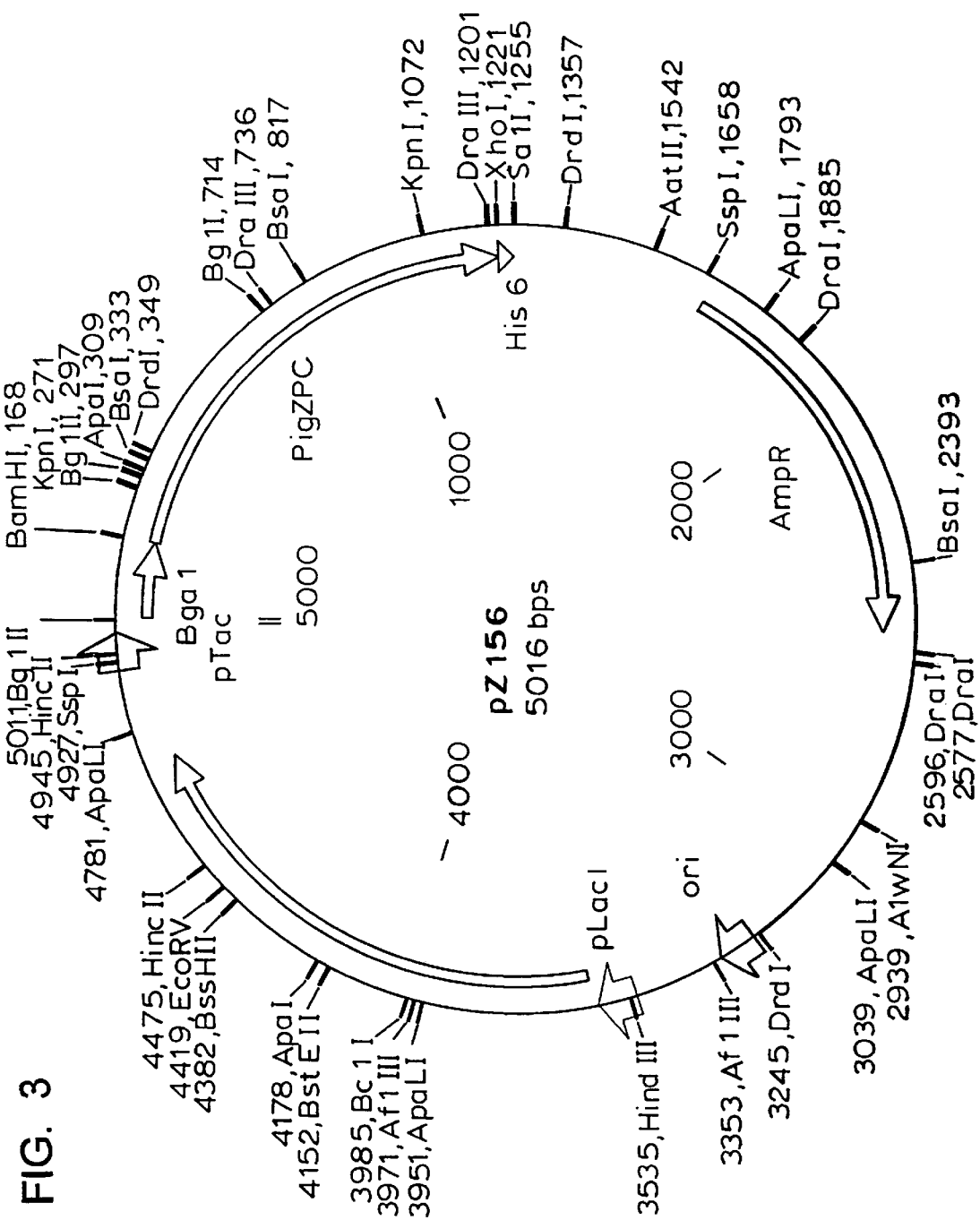
FIG. 3 is a diagrammatic representation of the plasmid vector pZ156.

To the 5' end of the modified porcine ZPC gene was added a Bam HI restriction site, and to the 3' end was added an Xho I site, a Hexa-CAT-codon sequence $(CAT)_6$, a termination codon, and a Sal I restriction site. This modified porcine ZPC gene was inserted into the Bam HI—Sal I restriction site of pZ98 to yield the porcine ZPC expression vector, plasmid pZ156 shown in FIG. 3. The $(CAT)_6$ sequence produces a C-terminal hexahistidine $(His_6)$ amino acid sequence in the recombinant fusion protein which permits purification of the fusion protein by immobilized metal in affinity chromatography.

In a similar manner as described above, the plasmid pZ156 when digested with Bam HI and Xho I, may be used to receive any other recombinant ZP gene or gene fragment for expression as a βgal fusion protein which can be purified by metal ion affinity chromatography.

III. Expression of Porcine ZPC Fusion Protein in *E. coli*

The expression vector pZ156 (FIG. 3) was transformed into *E. coli* strain Top 10F' (*Invitrogen*, San Diego, Calif.) by the procedure of Chung et al., *Proc. Natl. Acad. Sci. U.S.A.* 86: 2172–2175 (1989). The transformed *E. coli* cell line was termed Strain ZI 156, and was used to express recombinant porcine ZPC-βgal fusion protein.

Bacterial cultures of ZI 156 were grown in Luria Broth (LB) containing 100 μg/ml ampicillin at 30° C. until the cell density reached an $OD^{600}$ of approximately 1.5. Isopropyl beta-D-thiogalactopyranoside (IPTG) (3 ml of 100 mM solution/1 media) was added to induce expression from the tac promoter, and the cells were further incubated at 30° C. for 2–3 hours. The cells were harvested by centrifugation, and the resulting cell pellet was frozen at −70° C.

The frozen cell pellets were suspended in 10 mM EDTA (1 g/2–2.5 ml) and twice sonicated at 50% power for 3 minutes, cooling in an ice bath between each sonication. The cell lysate was then centrifuged at 3300×g for one hour and the hard pellet was retained. This lysis procedure was repeated using the hard pellets.

In order to remove residual EDTA, the final hard cellular pellet was dispersed in a small volume of water by a brief burst of sonication, the suspension was centrifuged, and the supernatant discarded. The washed pellet was thoroughly resuspended in Buffer A, (6M guanidine hydrochloride (GuHCl), 100 mM Na $H_2PO_4$, 10 mM TRIS pH 8, at approximately 0.5 ml per original gram of cell pellet). The suspension was centrifuged at 10,000×g for 45 seconds and the supernatant was retained while the pellet was discarded.

The retained supernatant was loaded onto a Ni column (in Buffer A) and the column was washed with 10 column volumes of Buffer A. The column was next washed with 5 volumes each Buffers B–D, each containing 8M urea, 100 mM $NaH_2PO_4$, and 10 mM TRIS, and having successively reduced pH values of 8, 6.3, 5.9 for Buffers B, C, and D, respectively. The recombinant pZPC-βgal fusion protein eluted with Buffer E, at pH 4.5 as shown by screening by Western Blot analysis using rabbit anti-HSDZ and anti-HSPZ as probes. Further elution may be accomplished using Buffer F (pH 2.5) (8M $GuHCl_2$ 200 mM Acetic Acid).

The fusion protein obtained by this protocol was prepared in its final dose for injection into a host animal by adjusting the final volume to 0.5 ml in 8M urea, and adding it to 0.5 ml adjuvant as described above. Each dose was injected subcutaneously into a test animal.

EXAMPLE 10

Vaccination of Dogs with Recombinant ZPC-β gal Fusion Protein

Eleven mixed breed dogs approximately 5–6 months of age were randomly selected from test animals previously treated at approximately 2 months of age with heat solubilized porcine zona pellucida or chromatographically purified porcine ZP3β in combination with various biopolymers as adjuvants and drug releasing vehicles. Six weeks post first injection, i.e., three and a half months of age, all test animals had achieved antibody titers versus HSPZ in the range of 2–16K as determined by ELISA. However, none of the test animals achieved antibody titers against self-antigen, e. g., HSDZ.

At 5–6 months of age, five of the test animals were then injected with a loading dose of the porcine ZPC-β gal fusion protein prepared as described for Example 9. The recombinant ZPC-β gal fusion protein produced in Example 9 was adjusted to the desired dose in a final volume of 0.5 ml 8M urea and combined with 0.5 ml adjuvant. The adjuvant, N-acetyl-D-glucosaminyl-β(1,4)-N-acetyl muramyl-L-alanyl-D-isoglutamine (GMDP), 250 μg, was dispersed in 0.42 ml mineral oil, 0.157 ml L-121 block polymers, and 0.02 ml Tween 80. Each dose was injected subcutaneously into the five test animals. The remaining 6 animals were maintained as controls.

Following a total of four injections given at 2–3 week intervals, antibody titers versus self antigen, e.g., HSDZ, were obtained in all test animals, with peaks in the range of 2–8 K as measured by ELISA.

Some of the control animals began to cycle beginning at approximately 9 months of age, and by 11 months of age, 4 of 6 control animals had experienced their first estrus. In contrast, none of the 5 test animals which had received recombinant ZPC-β gal fusion protein had cycled during this same time period. However, although the first estrus was delayed for several months in the test animals, they eventually began to cycle. Two of the five vaccinated dogs became pregnant during their second estrus after immunization while a third dog became pregnant during its third estrus after immunization; however, the two remaining test animals remain infertile through three estrus cycles and nearly two years after vaccination.

EXAMPLE 11

Isolation of Human DNA Sequences Encoding Human Zona Pellucida Proteins ZPA and ZPB A human genomic DNA library purchased from Stratagene (catalog no. 946203) was used for the isolation of DNA sequences encoding human ZP proteins. The library consisted of 9–23 kb inserts of human DNA (from placenta tissue of a male caucasian) cloned into the Lambda Fix™II vector (Stratagene). Approximately 40,000 pfus were plated on *E. coli* strain LE 392 (Stratagene, catalog no. 200266), as described in the Stratagene protocol, but replacing $MgSO_4$ with $MgCl_2$. After overnight incubation, nylon membrane lifts of the plaques were prepared and screened with $^{32}P$-labelled porcine ZPA cDNA (SEQ ID NO. 1) and with $^{32}P$-labelled porcine ZPB cDNA (SEQ ID NO. 3) as described in Example 2.

Three clones 1-1, 2-2, and 4-9 were shown to hybridize to the porcine ZPB cDNA (SEQ ID NO. 3). Clones 1-1 and 4-9 were deposited with the American Type Culture Collection, (ATCC) 12301 Parklawn Drive, Rockville, Md., on Jan. 27, 1993 under ATCC Accession Nos. 75406 and 75405, respectively. Human DNA inserts were isolated from these clones and analyzed by restriction endonuclease digestion with Eco RI and Southern blot analysis as described in Example 1. Table 4 shows the results of Eco RI digestion of these clones.

TABLE 4

HUMAN GENOMIC ZPB EcoRI INSERTS

| Fragment | 1-1 | 2-2 | 4-9 |
| --- | --- | --- | --- |
| A |  | 2.8 kb | 2.8 kb |
| B | 2.2 kb |  |  |
| C | 2.0 kb |  |  |
| D | 1.5 kb |  | 1.5 kb |
| E | 0.2 kb |  | 0.2 kb |
| F | 3.2 kb | 3.2 kb | 3.2 kb |
| G | 0.7 kb |  |  |

Southern blot analysis revealed four Eco RI fragments which were judged to carry ZPB coding sequences based on hybridization to the porcine ZPB cDNA (SEQ ID NO. 3). Clone 1-1 DNA included a 2.2 kb, 2.0 kb, and 1.5 kb Eco RI fragments which so hybridized. Clone 2-2 DNA included a 2.8 kb Eco RI hybridizing fragment. Clone 4-9 DNA included a 2.8 kb and a 1.5 kb Eco RI fragment which hybridized to the porcine ZPB cDNA probe. All inserts additionally included a 3.2 kb non-hybridizing Eco RI fragment; inserts from clones 1-1 and 4-9 both provided 0.2 kb non-hybridizing fragments; and clone 1-1 additionally provided a 0.7 kb non-hybridizing fragment.

Figure 4:
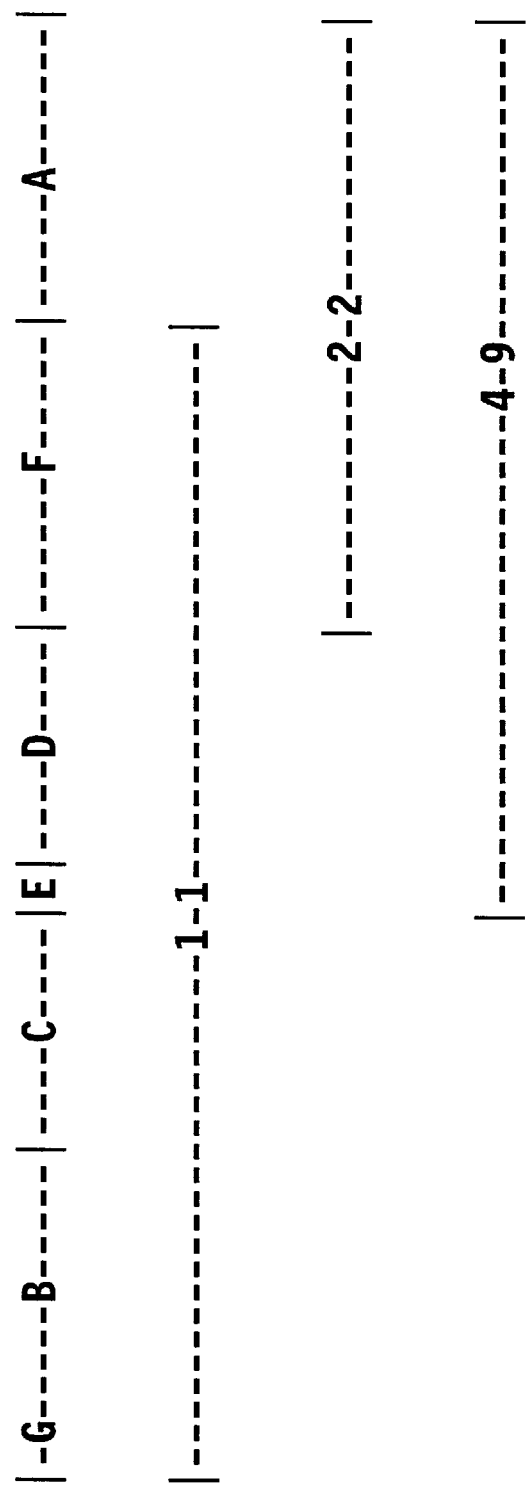
FIG. 4 is a diagrammatic representation of the alignment of the Eco R1 fragments encoding human ZPB.

Further restriction analysis revealed the fragment alignment shown in FIG. 4. Six of the fragments (A–F) were subcloned into pBSKS for sequence analysis, as described in Example 1. Preliminary sequence analysis confirmed the fragment alignment shown in FIG. 4, and suggested that the complete coding sequence of the human ZPB gene may be from clones 1-1 and 4-9. This was confirmed by nucleotide sequence analysis of the inserts, and comparison of the sequences with the feline ZPB sequence (SEQ ID NO. 15) and porcine ZPB sequence (SEQ ID NO. 3). The DNA sequence and deduced amino acid sequences for human ZPB are set out as SEQ ID NO. 40 and 41, respectively.

Clones hybridizing to the porcine ZPA cDNA (SEQ ID NO. 1) under the conditions described in Example 1 were also isolated. Two positive clones, A1 and A4 were identified. The clones were deposited with the American Type Culture Collection, 12301 Parklawn Drive, Rockville, Md. 20852, on Jan. 27, 1993 under ATCC Accession Nos. 75404 and 75403 respectively. Southern blot analysis revealed that these clones contain all or part of the human ZPA gene. DNA was isolated from these clones and was analyzed by Bgl II, Hind III, and Not I restriction endonuclease digestion and Southern blot analysis as described in Example 1. The size of the A1 clone DNA insert is approximately 11.6 kb, and that of the A4 clone is approximately 13.2 kb. Two of the Bgl II fragments which hybridized with the porcine ZPA cDNA (SEQ ID NO 1) were subcloned into pBSKS for sequence analysis, as described in Example 1. Sequence analysis revealed that A1 and A4 collectively contain the human ZPA gene as supported by comparison to sequences with the porcine ZPA cDNA (SEQ ID. NO. 1) and the canine ZPA cDNA (SEQ ID NO. 11). The complete DNA sequence and the deduced amino acid sequence are set out as SEQ ID NOS. 42 and 43, respectively.

EXAMPLE 12

Isolation and Sequencing of DNA Encoding Cynomolgus Monkey ZPA, ZPB, and ZPC Cynomolgus monkey cDNA libraries were constructed in $\lambda$gt10 as described below. Briefly, a set of ovaries were collected from two female cynomolgus monkeys aged 1.5 years and 2 years, and a second set from three females aged 3 years, 4 years, and 14 years of age. Messenger RNA was isolated using the Fast Track™ mRNA isolation kit following the manufacturer's instructions. The cDNA was prepared using the Lambda Librarian™ (Invitrogen, as described in Example 2) kit following the protocol provided with the kit. The cDNA was packaged into lambda phage heads using the Protoclone® (Promega, Madison, Wis.) $\lambda$gt10 EcoRI arms plus the Packagene® (Promega) lambda DNA packaging system following the manufacturer's instructions. This procedure generally produced libraries with a titer of greater than $1 \times 10^6$ pfu/ml. The monkey cDNA library was then screened using porcine ZPA, ZPB, and ZPC probes isolated from the porcine cDNA as described in Example 1. Screening was accomplished by preparing duplicate plaque lifts using Nytran® nylon filters (0.2 $\mu$M pore size). The filters were prehybridized in a solution of 5×SSPE (43.83 g/l of NaCl, 6.9 g/l of $NaH_2PO_4$, $H_2O$, 1.85 g/l of EDTA, pH 7.4), 5×Denhardts Reagent (1 g/l of Ficoll [type 400], 1 g/l of polyvinylpyrrolidone and 1 g/l bovine serum albumin), 100 $\mu$g/ml sonicated, denatured salmon sperm testes DNA, 30% formamide, and 0.5% SDS, for 3 hrs. at 42° C. Radio-labelled probes were prepared using [$\alpha$-$^{32}P$]-dATP and the Prime-a-Gene® (Promega) labelling system. After prehybridization, 10 ng of freshly radio-labelled probe was heat denatured at 95° C. for 5 minutes in 50% formamide and 100 $\mu$g/ml sonicated, denatured salmon testes DNA, and was added to the filters. The hybridization was carried out at 42° C. for 15–24 hours. The hybridized filters were then washed twice with 100 ml of 5×SSPE at 55° C., for approximately one hour each wash. The filters were then rinsed in 250 ml of 5×SSPE at 55° C. and allowed to air dry. The dried filters were exposed to x-ray film (Kodak XAR5, Eastman Kodak, Rochester N.Y.) at −70° C. using two intensifying screens (Kodak X-OMATIC™) for at least eight hours. The film was then developed for visual analysis.

Exhaustive screening of the two cynomolgus monkey ovarian cDNA libraries using all of the porcine probes yielded a total of 12 candidate clones. Southern hybridization revealed that only one of these clones ($\lambda$ CM 4-2)

hybridized to the porcine ZPA probe. This clone contained an insert of 560 bp. Sequencing of the insert was performed using the Sequenase® Version 2 kit (U.S. Biochemicals, Cleveland, Ohio) according to the manufacturer's instructions. Sequencing revealed that the 560 bp insert was homologous to the 3' end of other mammalian ZPA genes. The 560 bp fragment represents just under 25% bp of the full-length sequence and contains an open reading frame of 492 bp which would encode a protein of 164 amino acids. The DNA sequence and the deduced amino acid sequence of the cynomolgus monkey ZPA cDNA is set out as SEQ ID NOS. 44 and 45, respectively.

Exhaustive screening of the cynomolgus monkey ovarian cDNA libraries with the porcine ZPB probe yielded a single ZPB candidate clone having an insert of 866 bp. Sequence analysis suggests that the insert includes the C-terminal 50% of the expected full-length sequence. The DNA sequence and deduced amino acid sequence of the monkey ZPB insert are set out as SEQ ID NOS. 46 and 47, respectively. Screening of monkey ovarian cDNA libraries with the porcine ZPC DNA probe yielded only partial ZPC clones, the largest (λ CM1-1) having an insert of approximately 1300 bp which contains just over 50% of the C-terminal portion of the full-length sequence based on comparison to known ZPC clones, (particularly the human ZPC clone). The clone contains an open reading frame of 672 bp which would encode a protein of 224 amino acids. The clone also contains stop codons immediately 5' to the coding sequence in all three reading frames. The DNA sequence and the deduced amino acid sequence of the cynomolgus monkey ZPC clones are set out as sequence ID NOS 48 and 49 respectively.

EXAMPLE 13

Comparison of ZPA DNA and Deduced Amino Acid Sequences

Table 5 shows a comparison of the DNA and deduced amino acid sequence of mammalian ZPAs.

a variety of mammalian species, implies a great deal of structural similarity in the ZP layers of these species. However, post-translational modification differences such as glycosylation and others, could represent a potential source of variation.

One protein processing site that all of these ZPA proteins have in common is a furin cleavage site (R-X-R/K-R; Hosaka et al. *J. Biol. Chem*, 266:12127 (1991)) near the C-terminal end of the protein. In fact, with only a few exceptions, all ZP proteins contain a furin processing site near the C-terminus This furin site could serve to cleave off a putative membrane anchor sequence which would allow the processed proteins to move toward the outer edge of the growing ZP layer.

The human ZPA gene contains an exon near the 3' end that is present in the cynomolgus monkey ZPA sequence, but not present in the ZPA genes from other species. This extra exon codes for an amino acid sequence that occurs after the furin processing site, which suggests that the C-terminal fragment generated by furin cleavage might still be important to the function of the ZP layer or to the oocyte in some way.

There are 20 conserved cysteine residues and one or two non-conserved cysteine residues in each of the full-length ZPA sequences. The non-conserved cysteine residues occur either in the N-terminal leader sequence region, or in the extreme C-terminal region of the sequence, where a large amount of the variation between the ZPA sequences occurs. The high degree of homology and the large number of conserved cysteine residues suggests that the tertiary structures of the ZPA proteins are similar.

It has been noted previously that there are regions of homology between the ZPA and ZPB class proteins (Schwoebel et al. *J. Biol. Chem.*, 266:7214 (1991); Lee et al. *J. Biol. Chem*, 268: 12412 (1993); Yurewicz et al. *Biochem. Biophys. Acta* 1174:211 (1993)). Comparison of the human ZPA genomic structure with the human ZPB genomic structure shows these regions to be confined to exons 12, 13, and 14 of the human ZPA gene and exons 5, 6, and 7 of the human ZPB gene. This suggests that this homology might be

TABLE 5

|  | | | ZPA HOMOLOGY | | | PROTEIN HOMOLOGY | | |
| --- | --- | --- | --- | --- | --- | --- | --- | --- |
|  | Mouse | Rabbit | Pig | Cow | Dog | Cat | Monkey | Human |
| Mouse | — | 61.0% | 54.2% | 60.8% | 57.9% | 56.9% | 57.2% | 58.9% |
| Rabbit | 73.0% | — | 63.0% | 69.8% | 66.2% | 64.6% | 65.1% | 68.9% |
| Pig | 69.0% | 75.6% | — | 79.9% | 69.6% | 70.2% | 56.9% | 63.9% |
| Cow | 70.5% | 79.0% | 86.2% | — | 78.3% | 77.8% | 59.0% | 63.6% |
| Dog | 70.4% | 77.2% | 80.4% | 84.8% | — | 83.1% | 66.9% | 67.5% |
| Cat | 69.6% | 77.5% | 81.3% | 84.7% | 88.9% | — | 65.5% | 67.4% |
| Monkey | 56.7% | 59.6% | 56.6% | 57.0% | 59.2% | 58.4% | — | 95.8% |
| Human | 68.4% | 74.6% | 73.7% | 63.1% | 74.4% | 75.3% | 96.3% | — |
| | | | DNA HOMOLOGY | | | | | |

Data is presented as a cross-wise comparison of the ZPA protein and DNA sequences. The comparison of the protein sequences are shown in the upper right hand side of the table, above the diagonal dashed lines. The comparison of the DNA sequences are shown in the lower left hand side of the table, below the diagonal dashed lines. The ZPA DNA and deduced amino acid sequences are highly homologous between species. The homology is highest between members of the same order within the class *mammalia*. For example, the human and cynomolgus monkey (*primata*), the pig and cow (*ungulata*), and the cat and dog (*carnivora*) sequences have the most similarity. The high degree of homology between the ZPA genes, as well as between the ZPB (see Example 14) and ZPC (Example 15) genes from due to a partial ancestral gene duplication. The ZPB proteins contain 21 conserved cysteine residues. The first 11 of these do not align with those in the ZPA proteins, but the last 10 match well. This extends the homology to approximately 270 amino acids, covering exons 11–16 of the ZPA gene and exons 4–9 of the ZPB gene, although the overall homology of the expanded region is slightly lower (approximately 43%). The remainder of the ZPA and ZPB genes show very little homology with each other, and the ZPC genes also show no extensive homology to the ZPA genes. In addition, the ZPA gene has no extensive sequence similarity to non-ZP nucleic acid and protein sequences in Genbank and the SwissProt data banks.

EXAMPLE 14

Comparison of ZPB DNA and of Deduced Amino Acid Sequences

Table 6 shows the comparison of the six known ZPB DNA and protein sequences (the bovine and cynomolgus cDNA fragments are only compared to the corresponding regions of the other full-length ZPB sequences).

TABLE 6

|  | ZPB HOMOLOGY | | | | PROTEIN HOMOLOGY | |
|---|---|---|---|---|---|---|
|  | Rabbit | Bovine | Porcine | Feline | C. Monkey | Human |
| Rabbit | — | 75.3% | 65.3% | 60.1% | 70.2% | 65.2% |
| Bovine | 78.8% | — | 82.3% | 71.2% | 69.9% | 69.6% |
| Porcine | 74.2% | 86.2% | — | 63.7% | 63.6% | 63.1% |
| Feline | 69.5% | 78.7% | 72.9% | — | 70.3% | 64.6% |
| C. Monkey | 78.9% | 78.5% | 78.2% | 78.6% | — | 92.3% |
| Human | 74.3% | 80.8% | 73.3% | 74.2% | 95% | — |
| DNA HOMOLOGY | | | | | | |

The data are presented as cross-wise comparison of the ZPB protein and DNA sequences. The comparison of the protein sequences are shown in the upper right hand side of the table, above the diagonal dashed lines. The comparison of the DNA sequences are shown in the lower left hand side of the table, below the diagonal dashed lines.

The data shows considerable ZPB homology among members of different mammalian species. As was the case with ZPA, this homology is most pronounced between members of the same order within the class *mammalia*. For example, the human and cynomolgus monkey sequences (*primata*) and the pig and cow sequences (*ungulata*) have the most homology to each other. With only a few exceptions (noted below), the ZPB sequences show no homology to other DNA or protein sequences in the GenBank or SwissProt databases. Hybridization experiments suggest that the ZPB transcripts are ovary specific.

Comparisons of the deduced amino acid sequences of the ZPB clones show more divergence within this genetic group than within the ZPA and ZPC groups. Comparison of the rabbit ZPB and porcine ZPB shows the sequences to be predominantly collinear (74% homologous) except that the rabbit has an additional upstream ATG codon which adds six codons to the rabbit sequence.

The feline ZPB sequence has two additional amino acid inserts, which total 38 additional codons, in the first quarter of the gene, compared to the porcine and rabbit sequences. Both inserts occur just after cysteine residues, which suggests that if the cysteines are involved in disulfide bridges, these regions might form unique epitopes. However, the feline gene is still 73% homologous to porcine gene and 70% homologous to the rabbit gene.

The human gene has a sequence homologous to the first of the inserts in the cat sequence, but not the second. However, there are consensus splice site donor and acceptor sequences adjacent to this extra region in the human sequence, which if used would leave the coding sequence in frame. Therefore, the sequence representing exon 2 could actually be two small exons (122 and 103 bp) separated by a small intron (84 bp). This would make the human sequence in this region identical to the pig sequence. The first extra region in the cat sequence is also flanked by in frame splice site donor and acceptor signals. If the extra region was removed from the cat sequence, it would differ from the pig sequence by only a single amino acid. However, the cat sequence was obtained from a cDNA clone made from an mRNA that appears to be fully processed. The second extra region in the cat sequence does not contain in frame splice site donor or acceptor signals, and therefore is probably not due to the presence of an unprocessed intron.

The cynomolgus monkey and human sequences have an additional seven codons at the C-terminus when compared to the other ZPB sequences. In the cynomolgus monkey, this is due to a two-base pair deletion, which causes a frameshift mutation which puts the termination codon used by the other species out of frame. The human sequence also contains this deletion, but in addition, there is also a base change that eliminates this termination codon.

There are 21 conserved cysteine residues in the ZPB proteins, the final 10 of which occur in a region that has homology to the ZPA proteins. This homology was noted previously (Schwoebel et al., supra; Lee et al. supra, 1993; Yurewicz et al. supra, 1993), but examination of the genomic structure of the human ZPA and ZPB genes allowed the homology to be extended to approximately 270 amino acids. This homology could be due to a partial ancestral gene duplication. In addition to the conserved cysteine residues, the pig ZPB protein contains one additional cysteine residue in the putative leader sequence, and the human sequence contains four additional cysteine residues. The first of these is in the putative leader sequence (in a different location than pig), the second is in the region containing the additional insert, and the last two are in the C-terminal extension caused by the mutated termination codon. These last two extra cysteine residues are conserved in the cynomolgus monkey sequence.

All of the ZP proteins contain a putative transmembrane domain near the C-terminus. However, the canonical furin proteolytic processing signal (R-X-R/K-R, Hosaka et al. supra, 1991), which occurs just prior to the transmembrane domain in all of the ZPA and ZPC proteins, is altered in the human (S-R-R-R), cynomolgus monkey (S-R-R-N) and rabbit (S-R-R-R) ZPB sequences. The significance of this is unknown, but it may indicate that these proteins are processed by a related system with specificity for di- or tribasic sequences, since the release of the putative transmembrane domain would be necessary for the ZPB protein to move as the ZP layer grows. There appears to be a great deal of proteolytic processing of the pig ZPA and ZPB (Yurewicz et al. supra,) proteins. There is no data concerning the post-translational modification of the ZPB proteins of cat, cow, cynomolgus monkey or human. The physiologic significance of this processing is unknown, but differential processing would present an avenue of variation among species of the highly conserved ZP proteins.

There is a question of whether humans actually transcribe the ZPB gene. Since the amount of human ovarian mRNA recovered was so small, there was not enough RNA to both construct a cDNA library and perform a Northern analysis. However, since cynomolgus monkey transcribes the ZPB gene, it is probable that the highly homologous human ZPB gene is also transcribed.

The apparent lack of a ZPB cDNA in the dog cDNA library is another puzzle. All of the libraries screened which contained any zona pellucida gene contained all three genes, except the dog. However, mRNA isolated from the ovary of a six-month old dog (the library was made from the ovary of a four-month old dog), includes a ZPB mRNA that comigrates with the porcine and cynomolgus monkey ZPB mRNA on a Northern blot. One possibility to explain the lack of a canine ZPB cDNA is that the transcriptional timing of the three ZP genes is spread out, and since the ovary used to make the library was young, the transcription of the ZPB gene occurs later than the ZPA and ZPC genes (Andersen and Simpson, 1973).

EXAMPLE 15

Comparison of ZPC DNA and Deduced Amino Acid Sequences

Table 7 shows the comparison of the DNA and deduced amino acid sequences from all of the ZPC cDNAs and genes.

TABLE 7

|  | Mouse | Hamster | Rabbit | ZPC HOMOLOGY Pig | Cow | Dog | PROTEIN HOMOLOGY Cat | Monkey | Human |
|---|---|---|---|---|---|---|---|---|---|
| Mouse | — | 78.8% | 65.9% | 65.6% | 64.0% | 64.7% | 63.3% | 64.4% | 67.0% |
| Hamster | 84.7% | — | 65.9% | 65.6% | 63.5% | 65.1% | 63.6% | 68.2% | 68.0% |
| Rabbit | 70.1% | 71.3% | — | 68.2% | 68.5% | 65.3% | 64.1% | 59.4% | 68.5% |
| Pig | 71.5% | 72.0% | 74.6% | — | 83.6% | 75.7% | 72.8% | 69.2% | 73.7% |
| Cow | 70.5% | 71.4% | 74.5% | 86.5% | — | 74.5% | 72.8% | 67.4% | 71.1% |
| Dog | 70.1% | 71.9% | 71.5% | 79.8% | 80.3% | — | 79.2% | 66.5% | 70.1% |
| Cat | 70.9% | 71.6% | 73.0% | 79.3% | 80.0% | 84.3% | — | 71.1% | 70.5% |
| Monkey | 72.4% | 74.1% | 71.3% | 76.6% | 77.2% | 73.8% | 77.8% | — | 90.6% |
| Human | 74.1% | 75.0% | 76.2% | 80.0% | 79.6% | 77.7% | 78.8% | 94.4% | — |
|  |  |  |  | DNA HOMOLOGY |  |  |  |  |  |

The data are presented as a cross-wise comparison of the ZPC protein and DNA sequences. The comparison of the protein sequences are shown in the upper right hand side of the table, above the diagonal dashed lines. The comparison of the DNA sequences are shown in the lower left hand side of the table, below the diagonal dashed lines.

ZPC proteins and DNA sequences show a higher degree of homology than the ZPA and ZPB DNAs and proteins. As was the case with ZPA and ZPB, the homology is most pronounced in members of the same order within the class *mammalia;* the human and cynomolgus monkey sequences (*primata*), the cat and dog sequences (*carnivora*), the pig and cow sequences (*ungulata*), and the mouse and hamster sequences (*rodenta*). The ZPC transcripts are ovary specific, based on Northern blot analysis and comparison to the sequences in the GenBank and SwissProt databases detects no significant non-ZP homology. Comparison of the deduced amino acid sequences of the known ZPC genes detects three regions that contain large numbers of non-consensus sequences. These regions are: the putative leader sequences and the first 20–25 amino acids of the mature protein; the region containing the peptide that was identified as a sperm-binding region in the mouse (Millar et al. *Science* 216:935–938 (1989)); and the C-terminal region of the proteins that might be removed from the mature protein at the furin processing site (see below).

The epitope identified as a putative sperm-binding site (Millar et al. supra, 1989) occurs immediately before a furin proteolytic cleavage site (Hosaka et al., 1991). The furin site (R-X-R/K-R) is highly conserved in all of the ZPC sequences. However, it should be noted that the canine ZPC sequence contains a second furin site, 19 amino acids upstream from the first furin site. Also as is the case with ZPA and ZPB, cleavage by furin of the ZPC proteins would remove a putative membrane anchor sequence (Klein et al., 1985), which would allow the processed ZPC protein to move toward the outer layer of the expanding oocyte. Therefore, this sperm-binding site probably represents the C-terminus of the mature proteins. However, there is very little homology (even between hamster and mouse) in the regions of the ZPC proteins corresponding to this epitope. This might indicate that this region contributes to the species specificity of sperm-egg binding.

The variation that is seen at the C-terminus of the ZPC proteins occurs in the putative transmembrane region. This variation could indicate that this amino acid sequence is less important than the overall hydrophobicity of the amino acids in this region, similar to the lack of homology seen in leader sequences. However, it is also possible that this variation signifies a species-specific function for this region.

Each ZPC sequence contains 14 conserved cysteine residues, but each sequence also has one or two extra cysteine residues that are shared only with one or a few other sequences. These extra cysteine residues are near the N- or C-terminus of the proteins, where the greatest sequence variation exists. However, the large number of conserved cysteine residues probably indicates that the overall structure of the central core of all of these proteins is quite conserved.

EXAMPLE 16

Immunization of Cynomolgus Monkeys With HSPZ

A sexually mature cynomolgus monkey was immunized with HSPZ to test the ability of HSPZ to induce infertility. HSPZ was prepared as described in Example 6. HSPZ was mixed with the following GMDP/oil adjuvant. 50 $\mu$g GMDP (N-acetyl-D-glucosaminyl-($\beta$1–4)-N-acetylmuramyl-D-isoglutamine) (CC. Biotech, Poway, Calif.); 42.1 of mineral oil, 15.8% pluronic VC-121 (block polymer polyols, BASF-Wyandotte, Parsippany, N.J.). The animal received a series of 4 subcutaneous injections of 1 mg of HSPZ in the GMDP/oil adjuvant beginning with a priming dose followed four weeks later by a booster dose, which was followed by two booster doses five weeks apart which were followed six weeks later by a final dose. This dosage regimen resulted in an anovulatory monkey having antibody titers against its cynomolgus monkey heat-solubilized zona pellucida prepared as described for HSPZ. The peak antibody titers to cynomolgus monkey HSPZ were 1:8000–1:16,000.

A fractionated preparation of HSPZ which is essentially native porcine ZPA and ZPB was prepared by isoelectric focusing, as described in Example 6 and was used to vaccinate cynomolgus monkeys using 1 mg of fractionated HSPZ in GMDP/oil injected subcutaneously according to the following schedule: a priming dose was given followed approximately 6 weeks later by a booster dose followed by a final booster dose 11 weeks after the previous booster dose. The immunized monkeys achieved peak antibody titers of 1:4,000–1:8,000 against monkey heat-solubilized zona pellucida while maintaining a regular ovulatory cycle. However, despite maintaining a regular ovulatory cycle, the monkeys remained infertile until their antibody titers to monkey heat-solubilized zona pellucida fell below 1:500 after which the animals became pregnant upon breeding.

Immunization of cynomolgus monkeys with recombinant baculovirus produced canine ZPC and porcine ZPC (prepared as described in Example 18) failed to induce infertility despite inducing antibody production against monkey heat-solubilized zona pellucida. One possible explanation for this is that the glycosylation pattern of ZP proteins produced in the baculovirus system may prevent recognition of the epitopes responsible for induction of infertility.

Bacterially produced porcine ZPA, ZPB, and ZPC described above administered to cynomolgus monkeys failed to induce detectable antibody titers against cynomolgus monkey heat-solubilized zona pellucida even though antibody titers against the presented antigens were produced.

EXAMPLE 17

Mapping of Mammalian Zona Pellucida Protein Epitopes

A Pin Technology™ Epitope Scanning Kit purchased from Chiron Mimotopes U.S., Emeryville, Calif. (Catalog No. PT-02-20000A) was used for mapping epitopes in Zona Pellucida proteins. The procedures described in the kit manual were followed, with the exception of modifications in the ELISA testing procedure (described below).

Briefly, Pin Technology software was installed in a United Business Machines 486/33 computer according to the manufacturer's instructions. The protein sequence was entered into the computer program, the desired peptide length, and degree of overlap between peptides were selected, and a protocol containing the daily requirements of activated protected amino acid derivatives and their location in the coupling tray wells was printed. Prior to use, the pins were first washed once with dimethylformamide (DMF), and then with methanol three times, each wash lasting for two minutes. The pin block was air dried and the pins were deprotected by agitation in a 20% mixture of piperidine in DMF at room temperature for 30 minutes. The pins were washed again as described above, except that the washes were for 5 minutes each, and the pin block was then air dried. The required amino acid derivative solutions were prepared and dispensed into the wells of the synthesis tray according to the protocol for the current cycle. The dried mimotope pins were washed once more in a DMF bath for 5 minutes and then positioned appropriately in the wells of the synthesis tray. The assembly was then sealed in a plastic bag and incubated at 30° C. for approximately 22 hours. On the following day, the pin block was removed from the coupling tray and subjected to the same cycle of washing, deprotection, and coupling steps as outlined above; however, using the amino acid derivatives and their tray location appropriate to the next cycle. The foregoing cycle of washing, deprotection, washing, and coupling was repeated until the peptide sequences were completed.

After coupling the terminal amino acids of the peptides, the pin block was washed, air dried, deprotected, washed and air dried as before. The terminal amino groups of the peptides were then acetylated by immersion of the pins in a mixture containing 5 parts DMF, 2 parts acetic anhydride, and 1 part triethylamine, by volume, dispensed in the wells of a polypropylene coupling tray, and incubating at 30° C. for 90 minutes. The pin block was removed, subjected to another washing sequence as before, and air dried.

Side chain deprotection of the peptides was performed by agitating the pin block in a mixture containing 95 parts trifluoroacetic acid, 2.5 parts anisole, and 2.5 parts ethanedithiol, by volume, at room temperature for 4 hours. The pin block was then air dried for approximately 10 minutes, sonicated in a bath containing 0.1% hydrochloric acid in a mixture containing equal parts of methanol and deionized water, by volume, for 15 minutes, and finally air dried.

Prior to ELISA testing, the pins were subjected to a disruption procedure involving sonication in a bath consisting of a mixture containing 39 parts sodium dihydrogen orthophosphate, 25 parts sodium dodecyl sulfate, 0.1 part 2-mercaptoethanol, and 2500 parts deionized water, by weight, adjusted to pH 7.2 with 50% sodium hydroxide solution. The sonication was performed at 55° to 60° C. for approximately 45 minutes. The pin block was then washed by immersion with gentle agitation in three sequential baths of deionized water at 60 degrees for three minutes each. Finally, the pin block was immersed in gently boiling methanol for approximately 4 minutes and then air dried.

Preparation of Antisera

Antisera directed against zona pellucida proteins was prepared by immunizing the appropriate animals with the appropriate zona pellucida protein using procedures well known in the art and described in E. Harlow and D. Lane in Antibodies, A Laboratory Manual, Chapter 5, Cold Spring Harbor Laboratory, 1988 which is incorporated herein by reference. Biotinylated antisera was prepared by a modification of the procedure described in Harlow supra (page 314). Briefly, to a solution containing between 1 and 3 mg per ml of the selected antibody IgG fraction in phosphate buffer with saline (PBS) at pH 7.2 was added a solution containing 25 to 250 micrograms biotinamidocaproate, N-hydroxysuccinimide ester (Sigma, Cat No. B2643) in dimethyl sulfoxide at a concentration of 10 mg/ml. The mixture was mixed well and then incubated at room temperature for 4 hours. One molar ammonium chloride solution in the amount corresponding to 20 microliters per 250 micrograms biotin ester was added, and the resulting mixture was incubated at room temperature for 10 minutes. Unreacted biotin ester was then removed by extensive diafiltration with PBS using a Centricon-30 (TM) microconcentrator devices (Amicon Division, W.R. Grace & Co., Inc., Beverly Mass.). The dilution factor for the resulting conjugate was determined by ELISA titration against the appropriate native protein.

ELISA Testing

A modification of the procedure described in the Epitope Scanning Kit manual was employed.

After disruption, the mimotope pins were blocked by incubation with "supercocktail" (10 g ovalbumin, 10 g bovine serum albumin, and 1 ml Tween 20 detergent per liter of PBS) at room temperature for 1 hour. This was followed by incubation at room temperature for 2 hours with appropriately diluted biotinylated antisera. The pins were washed 4 times with PBS containing 0.5% Tween 20 (PBST) at room temperature for 10 minutes each time, with agitation.

The pins were then incubated at room temperature for 1 hour with the secondary antibody, horseradish peroxidase-streptavidin conjugate (Zymed Laboratories, Inc., South San Francisco, Calif.) diluted 1:2500 with PBST. They were washed again as described above.

Substrate buffer was prepared by combining 200 ml 1.0M. disodium hydrogen orthophosphate solution with 160 ml 1.0M. citric acid solution, diluting the mixture with 1640 ml deionized water, and adjusting to pH 4.0 using either citric acid or sodium hydroxide solutions. Substrate solution was prepared by dissolving 10 mg 2,2'-azino-bis(3-ethylbenzthiazoline-6-sulfonic acid) diammonium salt in 20 ml substrate buffer and adding 6 microliters 30% hydrogen peroxide. The mimotope pins were incubated at room temperature with this solution, using microtiter plates containing 150 microliters per well. When color development appeared to be appropriate for measurement by an ELISA plate reader, the pin block was removed and the plate was read at a wavelength of 450 nm. The pin block was then disrupted by the procedure described above.

The data were entered into the Pin Technology™ computer program, which performed statistical analysis and evaluation and furnished a print-out of the results identifying the strongest binding epitopes. Briefly, the 25% of the wells having the lowest optical density readings were assumed to represent background in each experiment. The mean value and the standard deviation of these readings were calculated. Significant recognition of peptides by antisera was attributed to the pins corresponding to those wells showing absorbance readings greater than the sum of the background mean and three standard deviations from the mean.

Human ZPA epitopes were examined for reactivity with mouse anti-human ZP antiserum prepared as described above. Peptides of 15 amino acids in length were synthesized beginning with amino acid number 1 as illustrated in SEQ ID NO. 43. Successive peptides having a 7-amino acid overlap with the preceding peptide of the series were synthesized. The following peptides were shown to bind mouse anti-human ZP antiserum: 1–15, 9–23, 25–39, 33–47, 65–79, 81–95, 89–103, 97–111, 105–119, 113–127, 121–135, 129–143, 145–159, 153–167, 161–175, 193–207, 209–223, 217–231, 225–239, 241–255, 249–263, 273–287, 281–295, 289–303, 305–319, 313–327, 321–335, 329–343, 337–351, 345–359, 385–399, 393–407, 401–415, 409–423, 417–431, 425–439, 441–455, 449–463, 457–471, 481–495, 489–503, 497–511, 505–519, 513–527, 521–535, 537–551, 545–559, 561–575, 569–583, 577–591, 585–599, 601–615, 609–623, 617–631, 625–639, 633–647, 641–655, 665–679, 697–711, 705–719, 713–727, 721–735, and 729–743.

Similarly, human ZPB epitopes were mapped using mouse anti-human ZP antiserum. In these experiments, 15 amino acid peptides were synthesized beginning with amino acid number 1 as set out in SEQ ID NO. 41. The overlap between successive peptides in this case was 9 amino acids. The following peptides were shown to bind mouse anti-human ZP antiserum: 7–21, 25–39, 31–45, 49–63, 67–81, 73–87, 79–93, 91–105, 103–117, 121–135, 193–207, 205–219, 211–225, 217–231, 223–237, 229–243, 253–267, 259–273, 265–279, 283–297, 289–303, 295–309, 301–315, 307–321, 313–327, 319–333, 343–357, 349–363, 355–369, 367–381, 373–387, 379–393, 385–399, 403–417, 409–423, 415–429, 421–435, 433–447, 439–453, 445–459, 451–465, 481–495, 487–501, 499–513, 505–519, 511–525, 523–537, 529–543, and 547–561.

Human ZPC epitopes were mapped using mouse anti-human ZP antiserum. In these experiments, the 15 amino acid peptides were synthesized beginning with amino acid number 1 as set out in Chamberlin et al., *Proc. Nat'l Acad. Sci. U.S.A.* 87:6014–6018 (1990) which is incorporated herein by reference. The overlap between successive peptides was 10 amino acids. The following peptides were shown to bind mouse anti-human ZP antiserum: 21–35, 51–65, 116–130, 146–160, 151–165, 181–195, 241–255, 251–265, 271–285, 296–310, 321–335, 401–415, and 411–425.

Canine ZPC epitopes were mapped using rabbit anti-canine ZP antiserum. In these experiments, the 15 amino acid peptides were synthesized beginning at amino acid number 1 set out in SEQ ID NO. 10. The overlap between successive peptides was 5 amino acids. The following peptides were shown to bind rabbit anti-canine ZP antiserum: 51–65, 61–75, 81–95, 131–145, 181–195, and 301–315.

Feline ZPC epitopes were mapped using rabbit anti-feline ZP antiserum. In these experiments, the 15 amino acid peptides were synthesized beginning at amino acid number 1 as set out in SEQ ID NO. 18. The overlap between successive peptides was 5 amino acids. The following peptides were shown to bind rabbit anti-feline ZP: 36–50, 46–60, 56–70, 76–90, 96–110, 106–120, 116–130, 126–140, 136–150, 146–160, 156–170, 186–200, 196–210, 246–260, 266–280, 276–290, 286–300, 296–310, 316–330, 326–340, 336–350, 346–360, 376–390, 396–410, and 406–420.

Bovine ZPC epitopes were mapped using rabbit anti-bovine ZP antiserum. In these experiments, the overlapping 15 amino acid peptides were synthesized beginning at amino acid number 1 as set out in SEQ ID NO. 24. The overlap between peptides was 10 amino acids. The following peptides were shown to be reactive with rabbit anti-bovine ZP antiserum: 1–15, 31–45, 51–65, 56–70, 61–75, 76–90, 106–120, 111–125, 116–130, 121–135, 131–145, 136–150, 141–155, 146–160, 151–165, 161–175, 181–195, 186–200, 191–205, 196–210, 201–215, 206–220, 216–230, 226–240, 241–255, 246–260, 261–275, 266–280, 271–285, 276–290, 291–305, 296–310, 301–315, 316–330, 321–335, 326–340, 331–345, 336–350, 341–355, 356–370, 361–375, 376–390, 381–395, 386–400, 396–410, 401–415, and 406–420.

EXAMPLE 18

Immunization of Dogs with Recombinant ZPC Proteins

Dogs were immunized with various preparations of recombinant canine ZPC. The plasmid pZ169 bacterial expression vector (FIG. 5) was constructed as follows. The parent vector pZ98 (described in Example 9) was digested with the restriction enzymes PvuI and Ban HI, and the large fragment was gel purified. Into this vector was ligated a fragment created by annealing the following oligonucleotides:

```
5' CGCCCTTCCCAGCAACTGCACCATCACCACCATGGG 3'
   (SEQ ID NO. 50); and
5' GATCCCCATGGTGGTGGTGATGGTGCAGTTGCTGGGAAGGGCGAT 3'
   (SEQ ID NO. 51).
```

These oligonucleotides create a fragment with PvuI and BamHI ends, and codes for the hexapeptide sequence $His_6$. This intermediate vector was digested with the restriction enzymes BamHI and EcoRI, and the large fragment was gel purified. Into this vector was ligated a fragment created by annealing the following oligonucleotides:

```
5' GATCCCTCGAGCCACCATCACCACCATCATG 3'
    (SEQ ID NO. 52); and
5' AATTCATGATGGTGGTGATGGTGGCTCGAGG 3'
    (SEQ ID NO. 53).
```

These oligonucleotides create a fragment with BamHI and EcoRI ends and an XhoI site just downstream of the BamHI site, and which codes for the hexapeptide sequence $His_6$. This new vector was named pZ88, and contains unique BamHI and XhoI cloning sites between two $His_6$ sequences. To create pZ169, the pZ88 vector was digested with the restriction enzymes BamHI and XhoI, and the large fragment was gel purified. Into this vector was ligated a fragment generated by performing a PCR (polymerase chain reaction) of the canine ZPC cDNA using the following oligonucleotides:

```
5' CCCGGATCCGCAGACCATCTGGCCAACTGAG 3'
    (SEQ ID NO. 54); and
5' GCGCTCGAGGGCATATGGCTGCCAGTGTG 3'
    (SEQ ID NO. 55).
```

Figure 5:
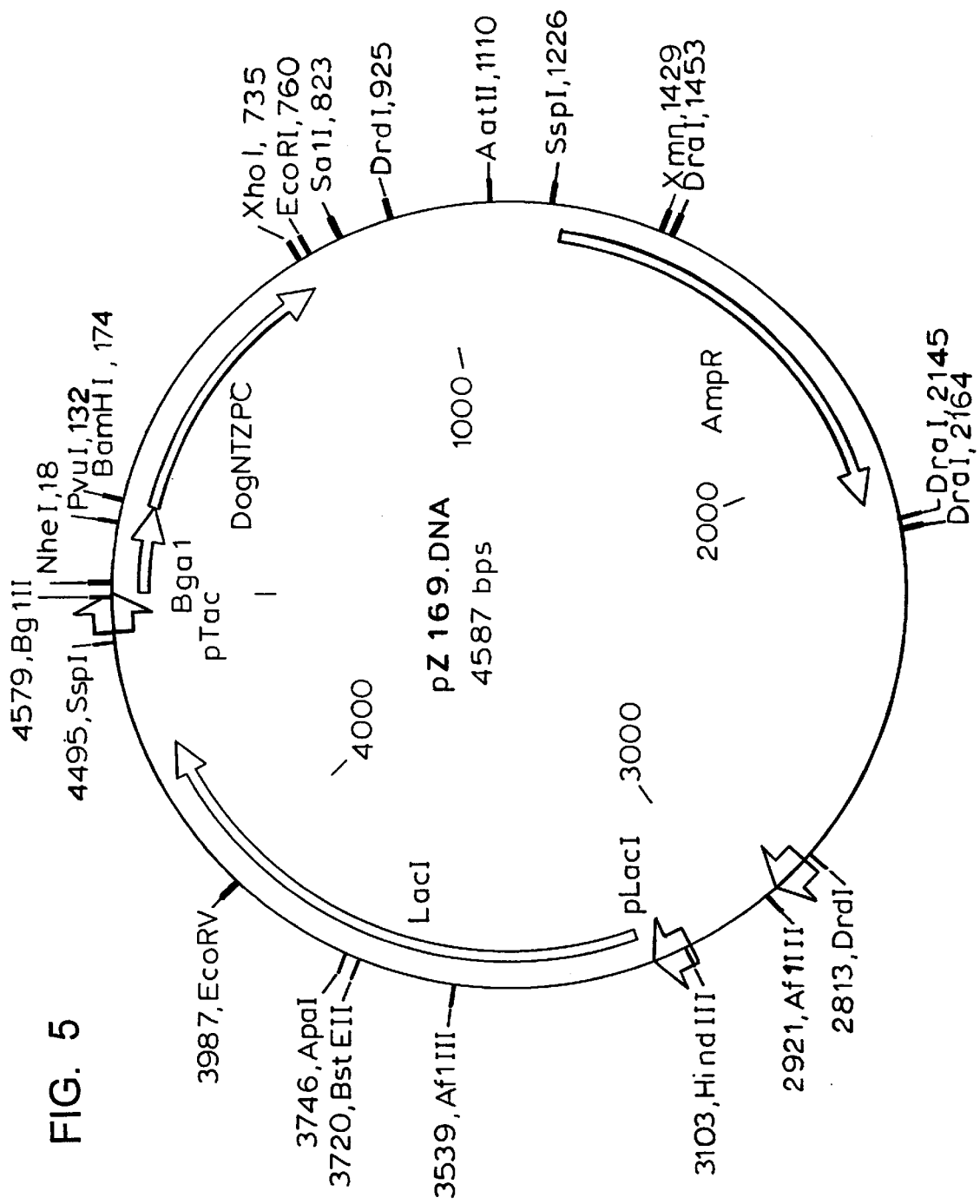
FIG. 5 is a diagrammatic representation of the plasmid vector pZ169.

This PCR creates a fragment containing amino acids 23–207 of the canine ZPC sequence, with BamHI and XhoI ends. This new vector is named pZ169, (FIG. 5) and produces a protein containing amino acids 1–56 of the *E. coil* β-galactosidase sequence, $His_6$, amino acids 23–207 of the canine ZPC sequence, $His_6$, and amino acids 1006–1023 of the *E. coli* β-galactosidase sequence. This protein is referred to as N-terminal canine ZPC. In FIG. 5, pTAC refers to the tac promoter described above; AmpR refers to an ampicillin resistance marker, ori is an *E. coli* origin of replication sequences and pLacI is the laci promoter which drives expression of the laci gene.

Recombinant canine ZPC was produced and purified as described in Example 9. A baculovirus expression vector pZ145 was constructed as follows. The parent vector pBlue-Bac2 (purchased from Invitrogen Corporation, San Diego, Calif.) was digested with the restriction enzymes NheI and BamHI, and the large fragment was gel purified. Into this vector was ligated a fragment generated by a PCR of the porcine ZPC cDNA using the following oligonucleotide:

```
5' CGCGCTAGCAGATCTATGGCGCCGAGCTGGAGGTTC 3'
    (SEQ ID NO. 56); and
5' CGCGGATCCTATTAATGGTGGTGATGGTGGTGACTAGTGGACCCTTCCA 3'
    (SEQ ID NO. 57).
```

This PCR creates a fragment with NheI and BamHI ends, and contains amino acids 27–350 of the porcine ZPC sequence followed by an SpeI site and the hexapeptide $His_6$. This new vector is named pZ147. To create the pZ145 vector, pZ147 is digested with NheI and SpeI and the large fragment is gel purified (this removes the pig ZPC sequence). Into this vector was ligated a fragment generated by a PCR of the canine ZPC cDNA using the following oligonucleotides:

```
5' CCCGCTAGCAGATCTATGGGGCTGAGCTATGGAATTTTC 3'
    (SEQ ID NO. 58); and
5' CGCACTAGTTGACCCCTCTATACCATGATCACTA 3'
    (SEQ ID NO. 59).
```

Figure 6:
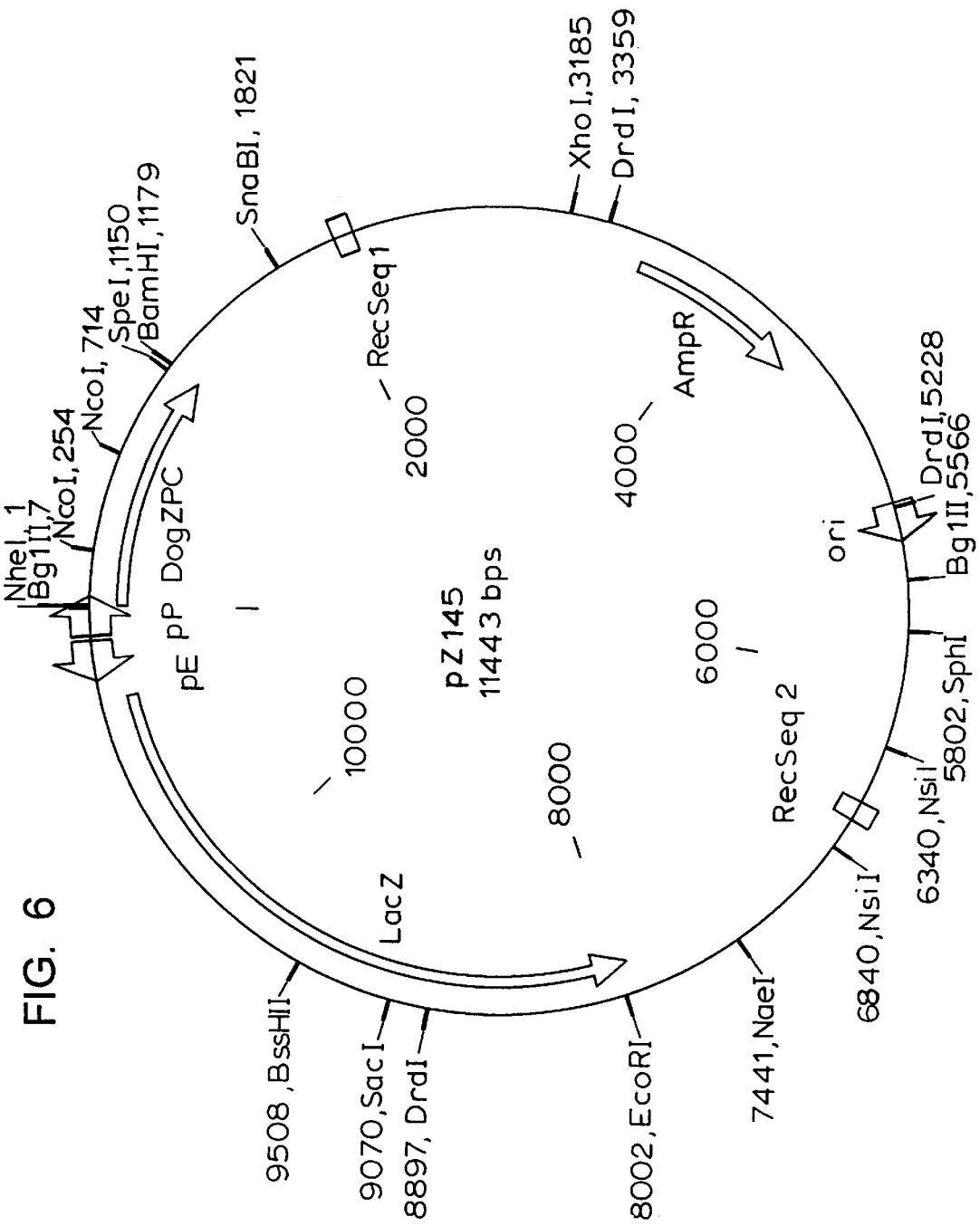
FIG. 6 is a diagrammatic representation of the plasmid vector pZ145.

This PCR creates a fragment with NheI and SpeI ends, and contains amino acids 1–379 of the canine sequence. Transformants of this ligation were screened for the presence of the inserted NheI/SpeI fragment in the correct orientation (since the NheI and SpeI sticky ends are identical). This new vector is named pZ145, (FIG. 6) and produces a protein containing amino acids 1–379 of the DZPC sequence followed by $His_6$. This protein is referred to as baculo-canine ZPC. In FIG. 6, pP represents the baculovirus polyhedrin promoter, AmpR represents an ampicillin resistance marker, LacZ represents the gene for β-galactosidase, pE is a constituitive promoter which drives the expression of LacZ and ori is the *E. coli* origin of replication.

Recombinant baculovirus derived canine ZPC was produced by co-transfecting insect SF9 cells with pZ145 and *Autographica californica* multiply enveloped nuclear polyhedrosis virus (AcMNPV) using methods well known in the art as described in the MAXBAC™ kit purchased from Invitrogen, San Diego, Calif. Recombinant canine ZPC produced in SF9 cells was prepared from cotransfected SF9 cells as follows. Cotransfected cells were harvested and pelleted by centrifugation and recombinant canine ZPC was purified as was described in Example 9 for purification from a cell pellet. Recombinant canine ZPC may also be isolated from the culture medium and purified on a Ni-column as described in Example 9.

Other expression vectors which are capable of expressing zona pellucida encoding nucleotide sequences under the control of a variety of regulatory sequences are within the scope of the present invention and are readily constructed using methods well known in the art.

Recombinant zona pellucida proteins may also be modified to increase their potential antigenicity by a variety of methods well known in the art. For example, a recombinant dog ZPC was modified by palmitylation was prepared as follows. Approximately 1 mg of recombinant ZPC produced using the plasmid pZ169 as described above was brought to a final concentration of 8M urea (total volume 0.2–0.3 mls.). A palmitylation solution ($Pl_2O$/TEA) was then prepared by adding palmitic anhydride to triethylamine to give a final concentration of palmitic anhydride of 20 mg/ml of triethylamine.

Approximately 10 μl of $Pl_2O$/TEA solution was added to 1 mg of recombinant canine ZPC in 8M urea (described above). The mixture was allowed to stand at room temperature for a least two hours after which the preparation was ready for mixture with GMDP/oil adjuvant.

Chitosan modification is another useful modification of canine ZPC for the practice of the present invention. Briefly, 1.5 ml of sterile mineral oil was added to 1.5 ml of recombinant canine ZPC solution prepared as described above using the plasmid pZ169 (2 mg/ml ZPC, 3 mg total is 8M urea) was mixed with 5 drops of Arlacel A (mannide monooleate, Sigma, St, Louis, Mo.). Subsequently, 0.75 ml of Chitosan (2% wt/vol. is 0.5M sodium acetate, pH 5.0) was added, and the mixture was sonicated for 10–20 seconds, followed by the addition of 0.045 ml of 50% NaOH and another round of sonication for 10–20 seconds. Finally, 10 μl of 10 mg/ml GMDP/8M urea was added.

A group of three dogs was immunized five times each at one-month intervals with subcutaneous injections of 1 mg doses of the N-terminal canine ZPC modified by the addition of chitosan prepared as described above. Immunized dogs developed antibody titers of 1:8000–1:16000 against heat solubilized dog zona pellucida (self-titers) using methods described above. The estrus cycle of the dogs showing self-titers was anovulatory and prolonged (4–6 weeks instead of the normal 10-day to 14-day cycle for normal dogs). Of the three immunized dogs, two have experienced their first estrus; one of the two dogs exhibited estrus six months after the first immunization and was bred and found to be infertile. The second of the two dogs experienced estrus and remained infertile nine months after the first immunization. The third dog has yet to experience estrus more than nine months after immunization.

Another group of four dogs were immunized three times at one-month intervals using 1 mg doses of palmitylated canine ZPC (prepared as described above) in GMDP/oil adjuvant administered subcutaneously. These animals achieved self-titers (against heat solubilized dog zona pellucida) of 1:4000–1:8000. Nearly seven months after immunization, two of the four dogs experienced estrus and remain infertile. The remaining two dogs have yet to experience estrus.

Another set of dogs was immunized 3 times at one-month intervals, using subcutaneous injections of 1 mg of recombinant canine ZPC produced using pZ166, (a plasmid similar to pZ169 but containing a DNA sequence encoding amino acids 23–379 of the canine ZPC protein) in GMDP/oil adjuvant. These animals failed to develop self-titers and became pregnant after breeding. Similarly, dogs immunized with canine ZPC fragments produced using the baculovirus system failed to induce infertility.

EXAMPLE 19

Vaccination of Cows and Cats with Recombinant Zona Pellucida Proteins

Preliminary studies were undertaken to assess the ability of recombinant zona pellucida proteins to induce infertility in cows and cats.

Cows were injected with 3 or more doses (in GMDP (250 μg) oil adjuvant) of 1 mg of a variety of recombinantly derived ZPC proteins from canine and porcine sources including canine ZPC produced using the plasmid pZ169 as shown in FIG. 5. Recombinant proteins were administered in an unmodified form and in palmitylated and chitosan modified forms. None of the ZP protein preparations induced self-titers or infertility in the vaccinated cows. Further studies are underway using different recombinant preparations of zona pellucida proteins and differing dosage regimens in attempts to induce self-titers and infertility in cows.

Similarly, cats were vaccinated with the following recombinant zona pellucida proteins: a mixture of recombinant feline ZPA, ZPB, and ZPC; porcine ZPC produced using pZ156 as described above and shown in FIG. 3; and canine ZPC produced using the plasmid pZ169 described above and shown in FIG. 5. Cats vaccinated using these ZP protein preparations produced antibody to the vaccine proteins, but produced no self-titers and were consequently fertile. Studies are ongoing to determine the effects of modifying the recombinant zona pellucida proteins in attempts to stimulate the production of self-titers and to induce infertility.

Studies are also ongoing to select other recombinantly derived zona pellucida protein fragments for testing as possible immunocontraceptives.

Numerous modifications in variations in the practice of the invention as illustrated in the above examples are expected to occur to those of ordinary skill in the art. Consequently, the illustrative examples are not intended to limit the scope of the invention as set out in the appended claims.

We claim:

1. An isolated DNA encoding a ZPC polyptide, the DNA being selected from the group consisting of DNA set out in SEQ ID NOS 5, 7, 11, 17, and 23.

2. A vector which comprises a DNA according to claim 1.

3. A procaryotic or eucaryotic host cell stably transformed or transfected with a vector according to claim 2.

4. A process for the production of a mammalian ZPC polypeptide, said process comprising:
   (a) growing, under suitable nutrient conditions, procaryotic or eucaryotic host cells according to claim 3; and
   (b) isolating the ZPC polypeptide produced therefrom.

5. An isolated DNA encoding a ZPC polypeptide said polypeptide comprising an amino acid sequence selected from the group consisting of SEQ ID NOS. 6, 8, 12, 18, and 24.

6. A vector which comprises a DNA according to claim 5.

7. A procaryotic or eucaryotic host cell stably transformed or transfected with a vector according to claim 6.

8. A process for the production of a mammalian ZPC polypeptide, said process comprising:
   (a) growing, under suitable nutrient conditions, procaryotic or eucaryotic host cells according to claim 7; and
   (b) isolating the ZPC polypeptide produced therefrom.

\* \* \* \* \*

UNITED STATES PATENT AND TRADEMARK OFFICE
CERTIFICATE OF CORRECTION

PATENT NO. : 5,837,497

DATED : November 17, 1998

INVENTOR(S) : Jeffrey D. Harris, Kuang T. Hsu, and Joseph S. Podolski

It is certified that error appears in the above-identified patent and that said Letters Patent is hereby corrected as shown below:

On the title page, in the "Inventors" field please delete "The Woodlands, Tex." and insert --, Kuang T. Hsu, and Joseph S. Podolski, all of The Woodlands, Tex.-- therefor.

Signed and Sealed this

Twenty-eighth Day of September, 1999

Attest:

Q. TODD DICKINSON

*Attesting Officer*  *Acting Commissioner of Patents and Trademarks*